US012637428B2

(12) United States Patent
Sime et al.

(10) Patent No.: US 12,637,428 B2
(45) Date of Patent: May 26, 2026

(54) ISOQUINOLINE DERIVATIVES AS SIK2 INHIBITORS

(71) Applicant: Cancer Research Technology Limited, London (GB)

(72) Inventors: Mairi Sime, Glasgow (GB); Justin Bower, Glasgow (GB); Duncan McArthur, Glasgow (GB); Angelo Pugliese, Glasgow (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 1005 days.

(21) Appl. No.: 17/773,197

(22) PCT Filed: Oct. 30, 2020

(86) PCT No.: PCT/GB2020/052744
§ 371 (c)(1),
(2) Date: Apr. 29, 2022

(87) PCT Pub. No.: WO2021/084264
PCT Pub. Date: May 6, 2021

(65) Prior Publication Data

US 2023/0045929 A1 Feb. 16, 2023

(30) Foreign Application Priority Data

Oct. 31, 2019 (GB) ...................................... 1915831

(51) Int. Cl.
*C07D 217/26* (2006.01)
*C07D 401/04* (2006.01)
*C07D 401/12* (2006.01)
*C07D 405/12* (2006.01)

(52) U.S. Cl.
CPC ......... *C07D 217/26* (2013.01); *C07D 401/04* (2013.01); *C07D 401/12* (2013.01); *C07D 405/12* (2013.01)

(58) Field of Classification Search
CPC .. C07D 217/26; C07D 401/04; C07D 401/12; C07D 405/12
See application file for complete search history.

(56) References Cited

U.S. PATENT DOCUMENTS

| | | | |
|---|---|---|---|
| 2004/0204427 | A1 | 10/2004 | Chen et al. |
| 2019/0315752 | A1 | 10/2019 | Gray et al. |

FOREIGN PATENT DOCUMENTS

| | | | | |
|---|---|---|---|---|
| CN | 104418860 | A | 3/2015 | |
| EP | 2 746 283 | A1 | 6/2014 | |
| WO | WO 99/61444 | A2 | 12/1999 | |
| WO | WO 00/24744 | A1 | 5/2000 | |
| WO | WO 01/29042 | A1 | 4/2001 | |
| WO | WO 2004/041821 | A1 | 5/2004 | |
| WO | WO 2004/041822 | A1 | 5/2004 | |
| WO | WO-2006039718 | A2 * | 4/2006 | ................ A61P 1/04 |
| WO | WO 2007/136465 | A2 | 11/2007 | |
| WO | WO 2008/122614 | A1 | 10/2008 | |
| WO | WO 2012/080284 | A2 | 6/2012 | |
| WO | WO 2013/113669 | A1 | 8/2013 | |
| WO | WO 2013/136070 | A1 | 9/2013 | |
| WO | WO 2018/035061 | A1 | 2/2018 | |
| WO | WO 2018/160774 | A1 | 9/2018 | |
| WO | WO 2018/198077 | A2 | 11/2018 | |
| WO | WO 2021/084265 | A1 | 5/2021 | |
| WO | WO 2021/084266 | A1 | 5/2021 | |

OTHER PUBLICATIONS

Ferguson et al., "Kinase inhibitors: the road ahead," Nature Reviews, vol. 17, May 2018, pp. 353-376.
Gao et al., "SIK2 promotes reprogramming of glucose metabolism through PI3K/AKT/HIF-1α pathway and Drp1-mediated mitochondrial fission in ovarian cancer," Cancer Letters, vol. 469, 2020, pp. 89-101.
Lin et al., "Discovery and Optimization of 2-Amino-4-methylquinazoline Derivatives as Highly Potent Phosphatidylinositol 3-Kinase Inhibitors for Cancer Treatment," Journal of Medicinal Chemistry, vol. 61, Jun. 21, 2018, pp. 6087-6109.
Sun et al., "The potent roles of salt-inducible kinases (SIKs) in metabolic homeostasis and tumorigenesis," Signal Transduction and Targeted Therapy, vol. 5, No. 150, 2020, pp. 1-15.
Sundberg et al., "Small-molecule screening identifies inhibition of salt-inducible kinases as a therapeutic strategy to enhance immunoregulatory functions of dendritic cells, " PNAS, vol. 111, No. 34, Aug. 26, 2014, pp. 12468-12473.
Wein et al., "SIKs control osteocyte responses to parathyroid hormone," Nature Communications, Oct. 19, 2016, pp. 1-17 (19 pages total).

* cited by examiner

*Primary Examiner* — Renee Claytor
*Assistant Examiner* — Christopher Lindsay Johnson
(74) *Attorney, Agent, or Firm* — Birch, Stewart, Kolasch & Birch, LLP

(57) ABSTRACT

Provided are compounds of the Formula I, and salts and solvates thereof: (I) wherein $R^1$, $R^2$, $R^3$, $X^1$, $X^2$, $X^3$ and Z are defined in the specification. The compounds are inhibitors of salt-inducible kinase (SIK), particular SIK2, and are useful in therapy, particularly in the treatment of a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder.

(I)

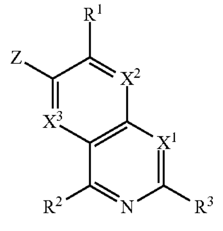

18 Claims, No Drawings

ISOQUINOLINE DERIVATIVES AS SIK2 INHIBITORS

INTRODUCTION

Provided herein are compounds of Formula I as defined herein and salts or solvates thereof.

The compounds of Formula I and their salts and solvates inhibit salt-inducible kinases (SIK), in particular SIK2, and may be used to treat diseases or conditions mediated, at least in part, by aberrant SIK activity.

The present application further provides pharmaceutical compositions comprising at least one compound of Formula I and/or a pharmaceutically acceptable salt or solvate thereof and a pharmaceutically acceptable excipient.

The present application also provides methods of treating a disease or condition mediated, at least in part, by aberrant SIK activity (for instance, a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder) comprising administering to a subject in need a compound of Formula I and/or a pharmaceutically acceptable salt or solvate thereof.

BACKGROUND OF THE INVENTION

Protein kinases play a central role in cellular activation processes. Aberrant kinase activity has been observed in many diseases states including benign and malignant proliferative disorders as well as diseases resulting from inappropriate activation of the immune or nervous system.

Salt-inducible kinase (SIK) is a serine/threonine protein kinase that belongs to the sucrose non-fermenting 1/AMP-activated protein kinase (SNF1/AMPK) family. The SIK family comprises three isoforms, namely, SIK1, SIK2, and SIK3, all of which may act as metabolic transmitters.

SIK2 modulates various biological functions and acts as a signal transmitter in various pathways. SIK2 has been shown to function in diverse biological processes, including gluconeogenesis, neuronal survival, melanogenesis, hepatic steatosis, and centrosome splitting (1-5). SIK2 is also implicated in the progression of cancer (1, 6-8) and the expression of SIK2 has been found to be significantly higher in multiple types of tumors. SIK expression is significantly different from that in adjacent tissues in cancers such as breast cancer, lung cancer, melanoma, primary liver cancer, and ovarian cancer, (1, 3, 5, 9-11).

WO 2018/009544 describes small molecule inhibitors of SIK2 in vitro. Furthermore, other small molecule inhibitors have shown promise in anticancer models (12-14).

However, there is a need for further small molecule inhibitors of SIK, and in particular SIK2, in order to realise a therapeutically effective drug for treatment of diseases caused by aberrant activity of SIK, in particular SIK2.

The present invention provides alternative and/or improved compounds which inhibit SIK2.

SUMMARY OF THE INVENTION

In one aspect, the present invention provides a compound of Formula I as defined herein, and/or a salt or solvate thereof.

In another aspect, the present invention provides a pharmaceutical composition which comprises a compound of Formula I as defined herein, or a pharmaceutically acceptable salt or solvate thereof, and one or more pharmaceutically acceptable excipients.

In another aspect, the present invention provides a compound of Formula I as defined herein, or a pharmaceutically acceptable salt or solvate thereof, or a pharmaceutical composition as defined herein, for use in therapy.

In another aspect, the present invention provides a compound of Formula I as defined herein, or a pharmaceutically acceptable salt or solvate thereof, or a pharmaceutical composition as defined herein, for use in the treatment of a disease or condition associated with aberrant activity of salt-inducible kinase (SIK).

In another aspect, the present invention provides a compound of Formula I as defined herein, or a pharmaceutically acceptable salt or solvate thereof, or a pharmaceutical composition as defined herein, for use in the treatment of a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder.

In another aspect, the present invention provides a compound of Formula I as defined herein, or a pharmaceutically acceptable salt or solvate thereof, or a pharmaceutical composition as defined herein, for use in the treatment of a cancer.

In another aspect, the present invention provides the use of a compound of Formula I as defined herein, or a pharmaceutically acceptable salt or solvate thereof, in the manufacture of a medicament for the treatment of a disease or condition associated with aberrant activity of salt-inducible kinase (SIK).

In another aspect, the present invention provides the use of a compound of Formula I as defined herein, or a pharmaceutically acceptable salt or solvate thereof, in the manufacture of a medicament for the treatment of a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder.

In another aspect, the present invention provides the use of a compound of Formula I as defined herein, or a pharmaceutically acceptable salt or solvate thereof, in the manufacture of a medicament for the treatment of a cancer.

In another aspect, the present invention provides a method of treating a disease or condition associated with aberrant activity of salt-inducible kinase (SIK), said method comprising administering to a subject in need thereof an effective amount of a compound of Formula I as defined herein, or a pharmaceutically acceptable salt or solvate thereof.

In another aspect, the present invention provides a method of treating a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder, said method comprising administering to a subject in need thereof an effective amount of a compound of Formula I as defined herein, or a pharmaceutically acceptable salt or solvate thereof.

In another aspect, the present invention provides a method of treating a cancer, said method comprising administering to a subject in need thereof a therapeutically effective amount of a compound of Formula I as defined herein, or a pharmaceutically acceptable salt or solvate thereof, or a pharmaceutical composition as defined herein.

In another aspect, the present invention provides a combination comprising a compound of Formula I, or a pharmaceutically acceptable salt or solvate thereof, as defined herein, with one or more additional therapeutic agents.

Preferred, suitable, and optional features of any one particular aspect of the present invention are also preferred, suitable, and optional features of any other aspect.

DETAILED DESCRIPTION OF THE INVENTION

Definitions

The compounds and intermediates described herein may be named according to either the IUPAC (International Union for Pure and Applied Chemistry) or CAS (Chemical Abstracts Service) nomenclature systems. It should be understood that unless expressly stated to the contrary, the terms "compounds of Formula I" and the more general term "compounds" refer to and include any and all compounds described by and/or with reference to Formula I. It should also be understood that these terms encompasses all stereoisomers, i.e. cis and trans isomers, as well as optical isomers, i.e. R and S enantiomers, of such compounds, in substantially pure form and/or any mixtures of the foregoing in any ratio. This understanding extends to pharmaceutical compositions and methods of treatment that employ or comprise one or more compounds of the Formula I, either by themselves or in combination with additional agents.

Similarly, references to the various sub formulae of formula I (e.g. formula Ia, Ib, Ic, Id . . . IIa . . . IIIa . . . etc.) encompass isomers of the described compounds as listed above, unless specifically described to the contrary.

Unless specified otherwise, atoms are referred to herein by their chemical symbol as appearing in the IUPAC periodic table of the Elements. For example, "C" refers to a carbon atom.

The various hydrocarbon-containing moieties provided herein may be described using a prefix designating the minimum and maximum number of carbon atoms in the moiety, e.g. "($C_{a}$-$_{b}$)" or "$C_a$-$C_b$" or "(a-b)C". For example, $C_a$-$_b$ alkyl indicates an alkyl moiety having the integer "a" to the integer "b" number of carbon atoms, inclusive. Certain moieties may also be described according to the minimum and maximum number of members with or without specific reference to a particular atom or overall structure. For example, the terms "a to b membered ring" or "having between a to b members" refer to a moiety having the integer "a" to the integer "b" number of atoms, inclusive.

"About" when used herein in conjunction with a measurable value such as, for example, an amount or a period of time and the like, is meant to encompass reasonable variations of the value, for instance, to allow for experimental error in the measurement of said value.

As used herein by themselves or in conjunction with another term or terms, "alkyl" and "alkyl group" refer to a branched or unbranched saturated hydrocarbon chain. Unless specified otherwise, alkyl groups typically contain 1-10 carbon atoms, such as 1-6 carbon atoms or 1-4 carbon atoms or 1-3 carbon atoms, and can be substituted or unsubstituted. Representative examples include, but are not limited to, methyl, ethyl, n-propyl, i-propyl, n-butyl, i-butyl, s-butyl, t-butyl, n-pentyl, n-hexyl, n-heptyl, n-octyl, n-nonyl, n-decyl, isopropyl, tert-butyl, isobutyl, etc.

As used herein by themselves or in conjunction with another term or terms, "alkylene" and "alkylene group" refer to a divalent branched or unbranched saturated hydrocarbon chain, i.e. which has two points of attachment to the remainder of the molecule. Unless specified otherwise, alkylene groups typically contain 1-10 carbon atoms, such as 1-6 carbon atoms or 1-3 carbon atoms, and can be substituted or unsubstituted. Representative examples include, but are not limited to, methylene ($-CH_2-$), the ethylene isomers ($-CH(CH_3)-$ and $-CH_2CH_2-$), the propylene isomers ($-CH(CH_3)CH_2-$, $-CH(CH_2CH_3)-$, $-C(CH_3)_3-$, and $-CH_2CH_2CH_2-$), etc.

As used herein by themselves or in conjunction with another term or terms, "alkenyl" and "alkenyl group" refer to a branched or unbranched hydrocarbon chain containing at least one double bond. Unless specified otherwise, alkenyl groups typically contain 2-10 carbon atoms, such as 2-6 carbon atoms or 2-4 carbon atoms, and can be substituted or unsubstituted. Representative examples include, but are not limited to, ethenyl, 3-buten-1-yl, 2-ethenylbutyl, and 3-hexen-1-yl.

As used herein by themselves or in conjunction with another term or terms, "alkynyl" and "alkynyl group" refer to a branched or unbranched hydrocarbon chain containing at least one triple bond. Unless specified otherwise, alkynyl groups typically contain 2-10 carbon atoms, such as 2-6 carbon atoms or 2-4 carbon atoms, and can be substituted or unsubstituted. Representative examples include, but are not limited to, ethynyl, 3-butyn-1-yl, propynyl, 2-butyn-1-yl, and 3-pentyn-1-yl.

As used herein by itself or in conjunction with another term or terms, "aromatic" refers to monocyclic and polycyclic ring systems containing 4n+2 pi electrons, where n is an integer. Aromatic should be understood as referring to and including ring systems that contain only carbon atoms (i.e. "aryl") as well as ring systems that contain at least one heteroatom selected from N, O or S (i.e. "heteroaromatic" or "heteroaryl"). An aromatic ring system can be substituted or unsubstituted.

As used herein by itself or in conjunction with another term or terms, "non-aromatic" refers to a monocyclic or polycyclic ring system having at least one double bond that is not part of an extended conjugated pi system. As used herein, non-aromatic refers to and includes ring systems that contain only carbon atoms as well as ring systems that contain at least one heteroatom selected from N, O or S. A non-aromatic ring system can be substituted or unsubstituted.

As used herein by themselves or in conjunction with another term or terms, "aryl" and "aryl group" refer to phenyl and 7-15 membered bicyclic or tricyclic hydrocarbon ring systems, including bridged, spiro, and/or fused ring systems, in which at least one of the rings is aromatic. Aryl groups can be substituted or unsubstituted. Unless specified otherwise, an aryl group may contain 6 ring atoms (i.e., phenyl) or a ring system containing 9 to 15 atoms, such as 9 to 11 ring atoms, or 9 or 10 ring atoms. Representative examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. Suitably an aryl group is phenyl and naphthyl, suitably phenyl.

As used herein by themselves or in conjunction with another term or terms, "arylene" and "arylene group" refer to a phenylene ($-C_6H_4-$) or to 7 to 15 membered bicyclic or tricyclic hydrocarbon ring systems, including bridged, spiro, and/or fused ring systems, in which at least one of the rings is aromatic. Arylene groups can be substituted or unsubstituted. In some embodiments, an arylene group may contain 6 (i.e., phenylene) ring atoms or be a ring system containing 9 to 15 atoms; such as 9 to 11 ring atoms; or 9 or 10 ring atoms. Arylene groups can be substituted or unsubstituted.

As used herein by themselves or in conjunction with another term or terms, "alkylaryl" and "alkylaryl group" refer to an alkyl group in which a hydrogen atom is replaced by an aryl group, wherein alkyl group and aryl group are as previously defined, such as, for example, benzyl ($C_6H_5CH_2$—). Alkylaryl groups can be substituted or unsubstituted.

As used herein by themselves or in conjunction with another term or terms, "carbocyclic group" and "carbocycle" refer to monocyclic and polycyclic ring systems that contain only carbon atoms in the ring(s), i.e., hydrocarbon ring systems, without regard or reference to aromaticity or degree of unsaturation. Thus, carbocyclic group should be understood as referring to and including ring systems that are fully saturated (such as, for example, a cyclohexyl group), ring systems that are aromatic (such as, for example, a phenyl group), as well as ring systems having fully saturated, aromatic and/or unsaturated portions (such as, for example, cyclohexenyl, 2,3-dihydro-indenyl, and 1,2,3,4-tetrahydronaphthalenyl). The terms carbocyclic and carbocycle further include bridged, fused, and spirocyclic ring systems.

As used herein by themselves or in conjunction with another term or terms, "cycloalkyl" and "cycloalkyl group" refer to a non-aromatic carbocyclic ring system, that may be monocyclic, bicyclic, or tricyclic, saturated or unsaturated, and may be bridged, spiro, and/or fused. A cycloalkyl group may be substituted or unsubstituted. Unless specified otherwise, a cycloalkyl group typically contains from 3 to 12 ring atoms. In some instances a cycloalkyl group may contain 4 to 10 ring atoms (e.g., 4 ring atoms, 5 ring atoms, 6 ring atoms, 7 ring atoms, etc.). Representative examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. Suitably, cycloalkyl groups are selected from cyclopropyl, cyclobutyl, cyclopentyl and cyclohexyl groups.

As used herein by themselves or in conjunction with another term or terms, "alkylcycloalkyl" and "alkylcycloalkyl group" refer to an alkyl group in which a hydrogen atom is replaced by a cycloalkyl group, wherein alkyl group and cycloalkyl group are as previously defined, such as, for example, cyclohexylmethyl ($C_6H_{11}CH_2$—). Alkylcycloalkyl groups can be substituted or unsubstituted.

As used herein by themselves or in conjunction with another term or terms, "haloalkyl" and "haloalkyl group" refer to alkyl groups in which one or more hydrogen atoms are replaced by halogen atoms. Haloalkyl includes both saturated alkyl groups as well as unsaturated alkenyl and alkynyl groups. Representative examples include, but are not limited to, $—CF_3$, $—CHF_2$, $—CH_2F$, $—CF_2CF_3$, $—CHFCF_3$, $—CH_2CF_3$, $—CF_2CH_3$, $—CHFCH_3$, $—CF_2CF_2CF_3$, $—CF_2CH_2CH_3$, $—CF{=}CF_2$, $—CCl{=}CH_2$, $—CBr{=}CH_2$, $—CI{=}CH_2$, $—C{\equiv}C—CF_3$, $—CHFCH_2CH_3$ and $—CHFCH_2CF_3$. Haloalkyl groups can be substituted or unsubstituted. Suitably, a haloalkyl group is selected from $CHF_2$ and $CF_3$, suitably $CF_3$.

As used herein by themselves or in conjunction with another term or terms, "haloalkoxy" and "haloalkoxy group" refer to alkoxy groups (i.e. O-alkyl groups) in which one or more hydrogen atoms are replaced by halogen atoms. Haloalkoxy includes both saturated alkoxy groups as well as unsaturated alkenyl and alkynyl groups. Representative examples include, but are not limited to, $—OCF_3$, $—OCHF_2$, $—OCH_2F$, $—OCF_2CF_3$, $—OCHFCF_3$, $—OCH_2CF_3$, $—OCF_2CH_3$, $—OCHFCH_3$, $—OCF_2CF_2CF_3$, $—OCF_2CH_2CH_3$, $—OCF{=}CF_2$, $—OCCl{=}CH_2$, $—OCBr{=}CH_2$, $—OCHFCH_2CH_3$ and $—OCHFCH_2CF_3$. Haloalkoxy groups can be substituted or unsubstituted. Suitably, a haloalkyoxy group is selected from $—OCHF_2$ and $—OCF_3$, suitably $—OCF_3$.

As used herein by themselves or in conjunction with another term or terms, "halo" and "halogen" include fluorine, chlorine, bromine and iodine atoms and substituents.

As used herein by themselves or in conjunction with another term or terms, "heteroaryl" and "heteroaryl group" refer to (a) 5 and 6 membered monocyclic aromatic rings, which contain, in addition to carbon atom(s), at least one heteroatom, such as nitrogen, oxygen or sulfur, and (b) 7 to 15 membered bicyclic and tricyclic rings, which contain, in addition to carbon atom(s), at least one heteroatom, such as nitrogen, oxygen or sulfur, and in which at least one of the rings is aromatic. In some instances, a heteroaryl group can contain two or more heteroatoms, which may be the same or different. Heteroaryl groups can be substituted or unsubstituted, and may be bridged, spiro, and/or fused. In some instances, a heteroaryl group may contain 5, 6, or 8 to 15 ring atoms. In other instances, a heteroaryl group may contain 5 to 10 ring atoms, such as 5, 6, 9, or 10 ring atoms. Representative examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.$0^{2,7}$]dodeca-2(7),3,5-trienyl, 12-oxa-10-aza-tricyclo[6.3.1.$0^{2,7}$]dodeca-2(7),3,5-trienyl, 12-aza-tricyclo[7.2.1.$0^{2,7}$]dodeca-2(7),3,5-trienyl, 10-aza-tricyclo[6.3.2.$0^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. Suitably, a heteroaryl is a 5- or 6-membered heteroaryl ring comprising one, two or three heteroatoms selected from N, O or S.

As used herein by themselves or in conjunction with another term or terms, "alkylheteroaryl" and "alkylheteroaryl group" refer to an alkyl group in which a hydrogen atom is replaced by a heteroaryl group, wherein alkyl group and heteroaryl group are as previously defined. Alkylheteroaryl groups can be substituted or unsubstituted. Where carbon numbers are provided, e.g. ($C_{n-m}$)alkylheteroaryl, the range refers to the whole group. Suitably, the constituent alkyl group has 1-6 carbons, suitable 1-3 carbons.

As used herein by themselves or in conjunction with another term or terms, "heterocyclic group" and "heterocycle" refer to monocyclic and polycyclic ring systems that contain carbon atoms and at least one heteroatom selected from nitrogen, oxygen, sulfur or phosphorus in the ring(s), without regard or reference to aromaticity or degree of unsaturation.

Thus, a heterocyclic group should be understood as referring to and including ring systems that are fully saturated (such as, for example, a piperidinyl group), ring systems that are aromatic (such as, for example, a pyrindinyl group), as well as ring systems having fully saturated, aromatic and/or unsaturated portions (such as, for example, 1,2,3,6-tetrahydropyridinyl and 6,8-dihydro-5H-[1,2,4]triazolo[4,3-a]pyrizinyl). The terms heterocyclic and heterocycle further include bridged, fused, and spirocyclic ring systems.

As used herein by themselves or in conjunction with another term or terms, "heterocycloalkyl" and "heterocycloalkyl group" refer to 3 to 15 membered monocyclic, bicyclic, and tricyclic non-aromatic ring systems, which contain, in addition to carbon atom(s), at least one heteroatom, such as nitrogen, oxygen, sulfur or phosphorus. Heterocycloalkyl groups may be fully saturated or contain unsaturated portions and may be bridged, spiro, and/or fused ring systems. In some instances a heterocycloalkyl group may contain at least two or heteroatoms, which may be the same or different. Heterocycloalkyl groups can be substituted or unsubstituted. In some instances a heterocycloalkyl group may contain from 3 to 10 ring atoms or from 3 to 7 ring atoms or from 5 to 7 ring atoms, such as 5 ring atoms, 6 ring atoms, or 7 ring atoms. Representative examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide, 7-oxabicyclo[2.2.1]heptanyl, 6,8-dihydro-5H-[1,2,4]triazolo[4,3-a]pyrazin-7-yl, 6,8-dihydro-5H-imidazo[1,5-a]pyrazin-7-yl, 6,8-dihydro-5H-imidazo[1,2-a]pyrazin-7-yl, 5,6,8,9-tetrahydro-[1,2,4]triazolo[4,3-d][1,4]diazepin-7-yl and 6,8-dihydro-5H-[1,2,4]triazolo[4,3-a]pyrazin-7-yl. Suitably, a heterocyclylalkyl group as defined herein is a monocyclic, bicyclic or spiro heterocyclyl group comprising one, two or three heteroatoms selected from N, O or S.

As used herein by themselves or in conjunction with another term or terms, "heterocycloalkylene" and "heterocycloalkylene group" refer to 3 to 15 membered monocyclic, bicyclic, or tricyclic non-aromatic ring systems, which contain, in addition to carbon atom(s), at least one heteroatom, such as nitrogen, oxygen, sulfur or phosphorus. Heterocycloalkylene groups may be fully saturated or contain unsaturated portions and may be bridged, spiro, and/or fused. Heterocycloalkylene groups can be substituted or unsubstituted. In some instances, a heterocycloalkylene group may contain from 3 to 10 ring atoms; such as from 3 to 7 ring atoms. In other instances a heterocycloalkylene group may contain from 5 to 7 ring atoms, such as 5 ring atoms, 6 ring atoms, or 7 ring atoms.

As used herein by themselves or in conjunction with another term or terms, "alkylheterocycloalkyl" and "alkylheterocycloalkyl group" refer to an alkyl group in which a hydrogen atom is replaced by a heterocycloalkyl group, wherein alkyl group and heterocycloalkyl group are as previously defined, such as, for example, pyrrolidinylmethyl ($C_aH_8NCH_2$—). Alkylheteroycloalkyl groups can be substituted or unsubstituted. Where carbon numbers are provided, e.g. ($C_n$-$_m$)alkylheterocycloalkyl, the range refers to the whole group. Suitably, the constituent alkyl group has 1-6 carbons, suitable 1-3 carbons.

As used herein by itself or in conjunction with another term or terms, "pharmaceutically acceptable" refers to materials that are generally chemically and/or physically compatible with other ingredients (such as, for example, with reference to a formulation), and/or is generally physiologically compatible with the recipient (such as, for example, a subject) thereof.

As used herein by itself or in conjunction with another term or terms, "pharmaceutical composition" refers to a composition that can be used to treat a disease, condition, or disorder in a subject, including a human.

As used herein by itself or in conjunction with another term or terms, "pseudohalogen" refers to —OCN, —SCN, —$CF_3$, and —CN.

As used herein by themselves or in conjunction with another term or terms, "subject(s)" and "patient(s)", suitably refer to mammals, in particular humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s).

As used herein by themselves or in conjunction with another term or terms, "therapeutic" and "therapeutically effective amount" refer to an amount a compound, composition or medicament that (a) inhibits or causes an improvement in a particular disease, condition or disorder; (b) attenuates, ameliorates or eliminates one or more symptoms of a particular disease, condition or disorder; (c) or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c). It should be understood that in, for example, a human or other mammal, a therapeutically effective amount can be determined experimentally in a laboratory or clinical setting, or a therapeutically effective amount may be the amount required by the guidelines of the United States Food and Drug Administration (FDA) or equivalent foreign regulatory body, for the particular disease and subject being treated. It should be appreciated that determination of proper dosage forms, dosage amounts, and routes of administration is within the level of ordinary skill in the pharmaceutical and medical arts.

As used herein whether by themselves or in conjunction with another term or terms, "treating", "treated" and "treatment", refer to and include prophylactic, ameliorative, palliative, and curative uses and results. In some embodiments, the terms "treating", "treated", and "treatment" refer to curative uses and results as well as uses and results that diminish or reduce the severity of a particular condition, characteristic, symptom, disorder, or disease described herein. For example, treatment can include diminishment of several symptoms of a condition or disorder or complete eradication of said condition or disorder. It should be understood that the term "prophylactic" as used herein is not absolute but rather refers to uses and results where the administration of a compound or composition diminishes the likelihood or seriousness of a condition, symptom, or disease state, and/or delays the onset of a condition, symptom, or disease state for a period of time.

As used herein, a "therapeutically active agent", whether used alone or in conjunction with another term or terms, refers to any compound, i.e. a drug, that has been found to be useful in the treatment of a disease, disorder or condition and is not described by Formula I.

It should be understood that a therapeutically active agent may not be approved by the FDA or an equivalent foreign regulatory body.

A "therapeutically effective amount" means the amount of a compound that, when administered to a subject or patient for treating a disease, is sufficient to effect such treatment for the disease. The "therapeutically effective amount" will vary depending on the compound, the disease and its severity and the age, weight, etc., of the subject or patient to be treated. 

A wavy bond (  ) is used herein to show a point of attachment. For instance, to show how group L of L-A bonds to the remainder of the molecule.

A bond terminating inside a cyclic structure and not terminating at an atom of the ring structure represents that the bond may be connected to any of the atoms in the ring structure where allowed by valency.

As used herein by themselves or in conjunction with another term or terms, "stable" and "chemically stable" refer to a compound that is sufficiently robust to be isolated from a reaction mixture with a useful degree of purity. The present application is directed solely to the preparation of stable compounds. When lists of alternative substituents include members which, owing to valency requirements, chemical stability, or other reasons, cannot be used to substitute a particular group, the list is intended to be read in context to include only those members of the list that are suitable for substituting the particular group. For example, when considering the degree of optional substitution of a particular moiety, it should be understood that the number of substituents does not exceed the valency appropriate for that moiety. For example, if group R is a methyl group ($—CH_3$), it can be optionally substituted by 1 to 3 substituents.

In one aspect the present invention relates to:

1. A compound of formula I, or a salt or solvate thereof:

(I)

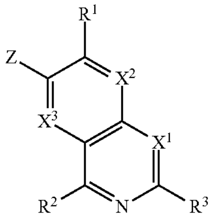

wherein:

$X^2$ is selected from C-L-A and $CR^5$; where $R^5$ is selected from the group consisting of hydrogen, CN, $C(O)NH_2$, $C(O)NHR^f$, $C(O)N(R^f)_2$ and $N(R^{p1})C(O)R^f$, where each $R^f$ is independently selected from $C_{1-6}$ alkyl which is optionally substituted with one or more groups selected from halogen, OH, $NH_2$, NHMe, $NMe_2$, and $C_{1-3}$ alkoxy, and $R^{p1}$ is selected from hydrogen, $C_{1-3}$ alkyl and $C_{1-3}$ haloalkyl;

$X^1$ is selected from $CR^4$, C-L-A, and N; where $R^4$ is selected from the group consisting of hydrogen, halogen, CN, $C(O)NH_2$, $C(O)NHR^m$, $C(O)N(R^m)_2$, $N(R^{p2})C(O)R^m$, where each $R^m$ is independently selected from $C_{1-6}$ alkyl which is optionally substituted with one or more groups selected from halogen, OH, $NH_2$, NHMe, $NMe_2$, and $C_{1-3}$ alkoxy, and $R^{p2}$ is selected from hydrogen, $C_{1-3}$ alkyl and $C_{1-3}$ haloalkyl;

$X^3$ is selected from $CR^6$ and N; where $R^6$ is selected from hydrogen, halogen, OH, CN, $NH_2$ and $C_{1-3}$ alkyl;

with the proviso that one of $X^1$ or $X^2$ must be C-L-A; only one of $X^1$ and $X^2$ can be C-L-A; and only one of $X^1$ and $X^3$ can be N;

L is selected from the group consisting of a direct bond, $—N(R^g)(CH_2)_x—$, $—O(CH_2)_x—$, $—S(CH_2)_x—$, $—S(=O)_2(CH_2)_x—$, $—S(=O)(CH_2)_x—$, $—OS(=O)(CH_2)_x—$, $—OS(=O)_2(CH_2)_x—$, $—OS(=O)_2O(CH_2)_x—$, $—S(=O)NR^g(CH_2)_x—$, $—OS(=O)_2NR^g(CH_2)_x—$; $—(CH_2)_x—$, $—C(O)(CH_2)_x—$, $—C(O)N(R^g)(CH_2)_x—$, $—N(R^g)C(O)(CH_2)_x—$, $—N(R^g)C(O)N(R^g)(CH_2)_x—$, $—N(R^g)C(O)O(CH_2)_x—$, $—OC(O)N(R^g)(CH_2)_x—$, $—N(R^g)S(O)_2O(CH_2)_x—$, $—N(R^g)S(O)_2(CH_2)_x—$; where each $R^g$ is independently selected from hydrogen, $C_{1-3}$ alkyl and $C_{1-3}$ haloalkyl; and where $_x$ is a number selected from 0 to 3;

A is selected from the group consisting of 3-15 membered heterocycloalkyl and $C_{3-12}$-cycloalkyl wherein each 3-15 membered heterocycloalkyl and $C_{3-12}$-cycloalkyl is optionally substituted by one or more substituents Re, where Re is selected from hydrogen, halogen, CN, =O, $(CH_2)_yOH$, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

Z is selected from $C_{6-15}$ aryl and 5-15 membered heteroaryl, wherein said $C_{6-15}$ aryl and 5-15 membered heteroaryl are optionally and independently substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, OS(o)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN;

$R^1$ is selected from the group consisting of hydrogen, $C_{1-3}$ alkyl, and halogen;

$R^2$ is selected from the group consisting of hydrogen; $C_{1-3}$ alkyl and $NH_2$; and $R^3$ is selected from the group consisting of hydrogen, —$NH_2$, —$NHR^a$, —$NR^aR^b$, —N($R^{a1}$)C(O)$R^c$, —N($R^{a1}$)C(O)$OR^d$, —N($R^{a1}$)S(O)$_2OR^d$, —N($R^{a1}$)S(O)$_2R^d$, —C(O)$NHR^a$, —C(O)$NR^aR^b$, —C(O)$R^c$, C(O)$OR^d$, —OC(O)$R^c$, —OH, —$OR^d$, where each of $R^a$, $R^b$, $R^c$ and $R^d$ are independently selected from $C_{1-6}$ alkyl and $C_3$-$C_6$ cycloalkyl wherein said $C_{1-6}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; and each $R^{a1}$ is independently selected from H or $C_{1-3}$ alkyl.

The invention is described further by way of the following numbered paragraphs:

2. A compound of formula I, or a salt or solvate thereof, according to paragraph 1 with the proviso that the compound is not one of the following compounds:

5-piperazin-1-yl-7-pyridin-4-yl-isoquinoline;

6-phenyl-8-(pyrrolidine-3-yl)quinazoline;

4-methyl-3-(4-morpholinoisoquinolin-7-yl)benzamide;

Methyl 4-methyl-3-(4-((S)-3-methylmorpholino)isoquinolin-7-yl)benzoate;

6-(5-Fluoro-6-methoxypyridin-3-yl)-4-methyl-8-((tetrahydro-2H-pyran-4-yl)oxy)quinazolin-2-amine;

6-{6-Methoxypyridin-3-yl)-4-methyl-8-((tetrahydro-2H-pyran-4-yl)oxy)quinazolin-2-amine;

N—N-diethyl-4-(4-(3-(piperidin-1-yl)propylamino)-1,7-naphthyridin-2-yl)benzamide; and N-(1-methylcyclopropyl)-7-(pyridine-4-yl)isoquinolin-5-amine.

3. A compound of formula I, or a salt or solvate thereof, according to any one of paragraphs 1 and 2 with the proviso that when $X^1$ is N, $X^2$ is C-L-A or $CR^5$, $X^3$ is CH, $R^1$ and $R^3$ are H and Z is 3-fluorophenyl, then $R^2$ is not $NH_2$.

4. A compound of formula I, or a salt or solvate thereof, according to any one of the preceding paragraphs with the proviso that when $X^2$ is CH, $X^3$ is CH or N, $R^1$ and $R^3$ are H and Z is 3-fluorophenyl, then $R^2$ is not $NH_2$.

5. A compound of formula I, or a salt or solvate thereof, according to any one of the preceding paragraphs with the proviso that when $X^1$ is CH, $R^1$, $R^2$ and $R^3$ are H and $X^3$ is N, then Z is not pyrid-4-yl.

6. A compound of formula I, or a salt or solvate thereof, according to any one of the preceding paragraphs wherein $X^1$ is selected from $CR^4$ and C-L-A.

7. A compound of formula I, or a salt or solvate thereof, according to any one of paragraphs 1 to 5 wherein $X^1$ is N.

8. A compound of formula I, or a salt or solvate thereof, according to any one of the preceding paragraphs wherein $X^2$ is C-L-A.

9. A compound of formula I, or a salt or solvate thereof, according to any one of paragraphs 1 to 5 wherein $X^1$ is selected from $CR^4$ and $X^2$ is selected from C-L-A.

10. A compound of formula I, or a salt or solvate thereof, according to any one of the preceding paragraphs wherein $X^3$ is $CR^6$.

11. A compound of formula I, or a salt or solvate thereof, according to any one of paragraphs 1 to 9 wherein $X^3$ is N.

12. A compound of paragraph 1, or a salt or solvate thereof, according to any one of sub-formulae Ia, Ib, Ic, Id or Ie:

(Ia)

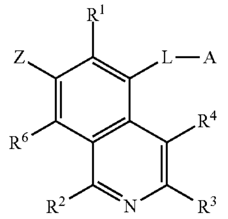

(Ib)

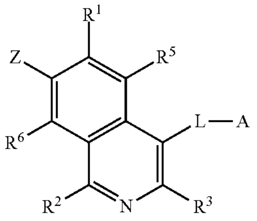

-continued (Ic)

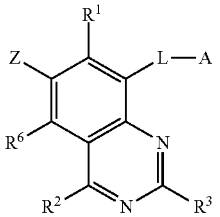

(Id)

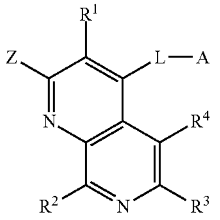

(Ie)

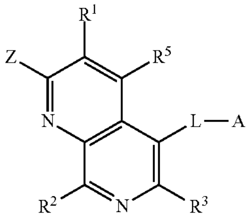

13. A compound of paragraph 12, or a salt or solvate thereof, according to one of sub-formulae Ia, Ib, Ic or Id.
14. A compound of paragraph 12, or a salt or solvate thereof, according to one of sub-formulae Ia or Ib.
15. A compound of paragraph 12, or a salt or solvate thereof, according to sub-formula Ia.
16. A compound of paragraph 12, or a salt or solvate thereof, according to one of sub-formula Ic, Id or Ie.
17. A compound according to any one of the preceding paragraphs wherein L is selected from the group consisting of a direct bond, —N($R^g$)($CH_2$)$_x$—, —O($CH_2$)$_x$—, —S($CH_2$)$_x$—, —S(=O)$_2$($CH_2$)$_x$—, —S(=O)($CH_2$)$_x$—, —OS(=O)($CH_2$)$_x$—, —OS(=O)$_2$ ($CH_2$)$_x$—, —S(=O)N$R^g$($CH_2$)$_x$—, —($CH_2$)$_x$—, —C(O)($CH_2$)$_x$—, —C(O)N($R^g$)($CH_2$)$_x$—, —N($R^g$)C(O)($CH_2$)$_x$—, —N($R^g$)C(O)N($R^g$)($CH_2$)$_x$—, —N($R^g$)S(O)$_2$($CH_2$)$_x$—; where each $R^g$ is independently selected from hydrogen, $C_{1-3}$ alkyl and $C_{1-3}$ haloalkyl; and where $_x$ is a number selected from 0 to 3;
18. A compound according to any one of the preceding paragraphs, or a salt or solvate thereof, wherein L is selected from the group consisting of direct bond, —N($R^g$)($CH_2$)$_x$—, —O($CH_2$)$_x$—, —C(O)N($R^g$)($CH_2$)$_x$—, and —N($R^g$)C(O)($CH_2$)$_x$—; where each $R^g$ is independently selected from hydrogen, $C_{1-3}$ alkyl and $C_{1-3}$ haloalkyl and x is a number selected from 0 to 3;
19. A compound according to any one of the preceding paragraphs, or a salt or solvate thereof, wherein L is selected from the group consisting of direct bond, —N($R^g$)($CH_2$)$_x$—, —O($CH_2$)$_x$—, C(O)NH($CH_2$)$_x$, and N($R^g$)C(O)($CH_2$)$_x$; where x is a number selected from 0 and 3;
20. A compound according to any one of the preceding paragraphs, or a salt or solvate thereof, wherein L is selected from the group consisting of direct bond, —NH—, —NH$CH_2$, O, C(O)NH— and —NHC(O)—.
21. A compound according to any one of the preceding paragraphs, or a salt or solvate thereof, wherein L is selected from the group consisting of direct bond, —NH— and C(O)NH—.
22. A compound according to any one of the preceding paragraphs, or a salt or solvate thereof, wherein L is selected from the group consisting of a direct bond and —NH—.
23. A compound according to any one of the preceding paragraphs, or a salt or solvate thereof, wherein $R^g$ is selected from the group consisting of a hydrogen, methyl and ethyl.
24. A compound according to any one of the preceding paragraphs, or a salt or solvate thereof, wherein $R^g$ is hydrogen.
25. A compound according to any one of the preceding paragraphs, or a salt or solvate thereof, wherein x is 0 or 1.
26. A compound according to any one of the preceding paragraphs, or a salt or solvate thereof, wherein A is selected from the group consisting of 4-11 membered heterocycloalkyl and $C_{3-7}$-cycloalkyl wherein each 4-11 membered heterocycloalkyl and $C_{3-7}$-cycloalkyl is optionally substituted by one or more substituents $R^e$, where $R^e$ is selected from hydrogen, halogen, CN, =O, ($CH_2$)$_y$OH, $C_{1-4}$ alkyl, ($CH_2$)$_y$$C_{1-4}$ alkoxy, ($CH_2$)$_y$$C_{1-4}$ haloalkyl, ($CH_2$)$_y$$C_{1-4}$ haloalkoxy, ($CH_2$)$_y$$NH_2$, ($CH_2$)$_y$NH$R^q$, ($CH_2$)$_y$N($R^q$)$_2$, ($CH_2$)$_y$NHCO($R^q$), ($CH_2$)$_y$CON$H_2$, ($CH_2$)$_y$CONH($R^q$), and ($CH_2$)$_y$CON($R^q$)$_2$, and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where y is a number between 0 and 3.
27. A compound according to any one of the preceding paragraphs, or a salt or solvate thereof, wherein A is selected from the group consisting of 4-7 membered heterocycloalkyl and $C_{3-7}$-cycloalkyl wherein each 4-7 membered heterocycloalkyl and $C_{3-7}$-cycloalkyl is optionally substituted by one or more substituents $R^e$, where $R^e$ is selected from hydrogen, halogen, CN, =O, ($CH_2$)$_y$OH, $C_{1-4}$ alkyl, ($CH_2$)$_y$$C_{1-4}$ alkoxy, ($CH_2$)$_y$$C_{1-4}$ haloalkyl, ($CH_2$)$_y$$C_{1-4}$ haloalkoxy, ($CH_2$)$_y$$NH_2$, ($CH_2$)$_y$NH$R^q$, ($CH_2$)$_y$N($R^q$)$_2$, ($CH_2$)$_y$NHCO($R^q$), ($CH_2$)$_y$CON$H_2$, ($CH_2$)$_y$CONH($R^q$), and ($CH_2$)$_y$CON($R^q$)$_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.
28. A compound according to any one of the preceding paragraphs, or a salt or solvate thereof, wherein A is selected from the group consisting of 4-7 membered heterocycloalkyl and $C_{3-7}$-cycloalkyl wherein each 4-7 membered heterocycloalkyl and $C_{3-7}$-cycloalkyl is optionally substituted by one or more substituents $R^e$, where $R^e$ is selected from hydrogen, halogen, CN, =O, ($CH_2$)$_y$OH, $C_{1-4}$ alkyl, ($CH_2$)$_y$$C_{1-4}$ alkoxy, ($CH_2$)$_y$$C_{1-4}$ haloalkyl, ($CH_2$)$_y$$C_{1-4}$ haloalkoxy, ($CH_2$)$_y$$NH_2$, ($CH_2$)$_y$NH$R^q$, ($CH_2$)$_y$N($R^q$)$_2$, ($CH_2$)$_y$CON$H_2$, ($CH_2$)$_y$CONH($R^q$), and ($CH_2$)$_y$CON($R^q$)$_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.
29. A compound according to any one of the preceding paragraphs, or a salt or solvate thereof, wherein A is selected from the group consisting of 4-7 membered heterocycloalkyl and $C_{3-6}$-cycloalkyl wherein each 4-7 membered heterocycloalkyl and $C_{3-6}$-cycloalkyl is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where $_y$ is a number between 0 and 3.

30. A compound according to any one of the preceding paragraphs, or a salt or solvate thereof, wherein A is selected from azetidinyl, oxetanyl, cyclobutyl, pyrrolidinyl, cyclopentyl, tetrahydrofuranyl, piperidinyl, piperazinyl, morpholinyl, cyclohexyl, tetrahydropyran, azepanyl, diazepanyl and cycloheptane, each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

31. A compound according to any one of the preceding paragraphs, or a salt or solvate thereof, wherein A is selected from azetidinyl, cyclobutyl, pyrrolidinyl, cyclopentyl, piperidinyl, piperazinyl, morpholinyl, cyclohexyl, azepanyl, diazepanyl and cycloheptane, each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where $_y$ is a number between 0 and 3.

32. A compound according to any one of the preceding paragraphs, or a salt or solvate thereof, wherein A is selected from azetidinyl, cyclobutyl, pyrrolidinyl, cyclopentyl, piperidinyl, piperazinyl, morpholinyl, and cyclohexyl, each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

33. A compound according to any one of the preceding paragraphs, or a salt or solvate thereof, wherein A is selected from azetidinyl, cyclobutyl, pyrrolidinyl, cyclopentyl, piperidinyl, piperazinyl, morpholinyl, and cyclohexyl, each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where y is a number between 0 and 3.

34. A compound according to any one of paragraphs 1 to 25, or a salt or solvate thereof, wherein A is selected from azetidinyl, cyclobutyl, pyrrolidinyl, cyclopentyl, piperidinyl, cyclohexyl and azepanyl each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

35. A compound according to any one of paragraphs 1 to 16, or a salt or solvate thereof, wherein L is a —NH— and A is selected from azetidinyl, cyclobutyl, pyrrolidinyl, cyclopentyl, piperidinyl, cyclohexyl and azepanyl each of which is optionally substituted by one or more substituents $R^e$, where $R^e$ is selected from hydrogen, halogen, CN, =O, $(CH_2)_yOH$, $C_{1-4}$ alkyl, $(CH_2)_yC_{1-4}$ alkoxy, $(CH_2)_yC_{1-4}$ haloalkyl, $(CH_2)_yC_{1-4}$ haloalkoxy, $(CH_2)_yNH_2$, $(CH_2)_yNHR^q$, $(CH_2)_yN(R^q)_2$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

36. A compound according to any one of paragraphs 1 to 16, or a salt or solvate thereof, wherein L-A is selected from the group consisting of:

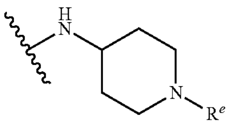
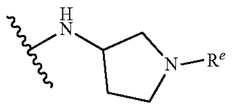
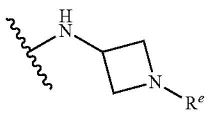
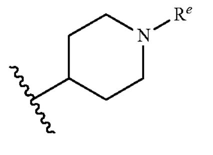
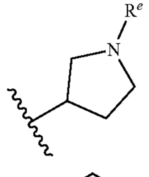
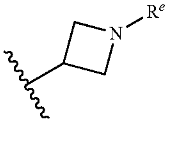
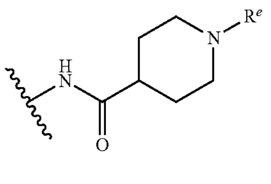
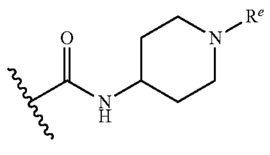

-continued

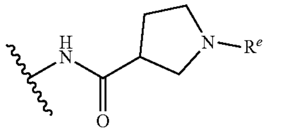
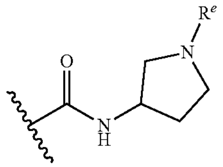
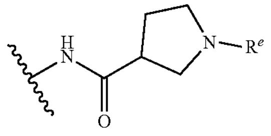
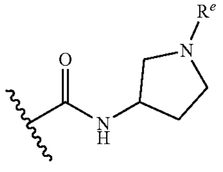
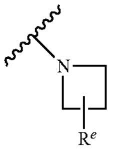
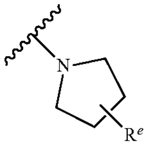
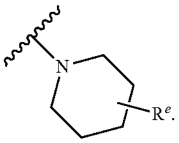

37. A compound according to paragraph 36, or a salt or solvate thereof, wherein L-A is selected from the group consisting of:

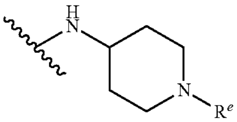
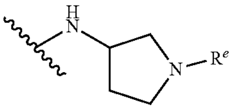
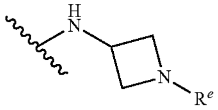
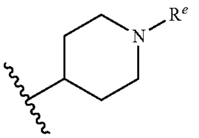
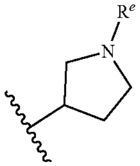
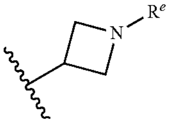
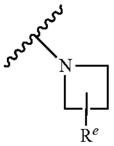
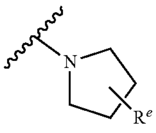
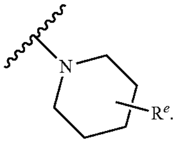

38. A compound according to paragraph 36, or a salt or solvate thereof, wherein L-A is selected from the group consisting of:

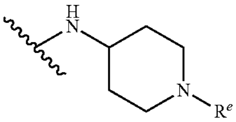
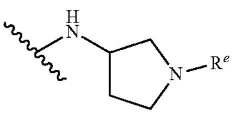
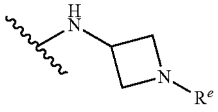
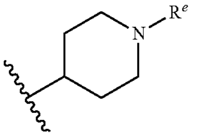

-continued

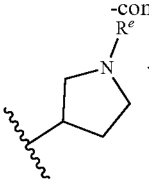
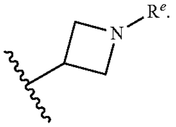

39. A compound according to paragraph 36, or a salt or solvate thereof, wherein L-A is selected from the group consisting of:

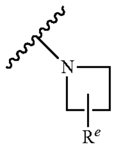
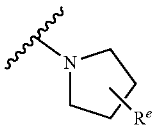
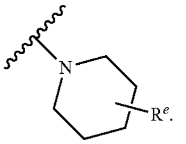

40. A compound according to paragraph 36, or a salt or solvate thereof, wherein L-A is selected from the group consisting of:

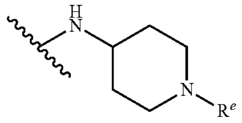
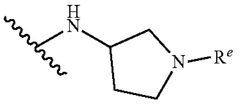
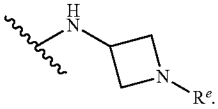

41. A compound according to any one of the preceding paragraphs, or a salt or solvate thereof, wherein Z is selected from $C_{6-15}$ aryl and 5-12 membered heteroaryl, wherein said $C_{6-15}$ aryl and 5-12 membered heteroaryl are optionally and independently substituted with one or more RX groups, where Rx is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^jR^k$, —C(O)C(=O)$R^h$, —N$R^jR^k$, —N$R^j$C(=O)$R^h$, —N$R^j$C(=O)O$R^k$, —N$R^j$C(=O)N$R^jR^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —S(=O)$R^h$, OS(=O)$_2R^h$, —OS(=O)$_2$O$R^j$, —S(=O)N$R^jR^k$, —OS(=O)$_2$N$R^jR^k$, —S(=O)$_2$ N$R^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterarly, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

42. A compound according to paragraph 41, or a salt or solvate thereof, wherein Z is selected from $C_{6-15}$ aryl and 5-12 membered heteroaryl, wherein said $C_{6-15}$ aryl and 5-12 membered heteroaryl are optionally and independently substituted with one or more RX groups, where Rx is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$haloalkoxy, $C_{3-6}$ cycloalkyl, $NR^jR^k$, $C_{1-6}$ alkyl, O—$C_{1-3}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

43. A compound according to paragraph 42, or a salt or solvate thereof, wherein Z is selected from $C_{1-5}$ aryl and 5-12 membered heteroaryl, wherein said $C_{6-15}$ aryl and 5-12 membered heteroaryl are optionally and independently substituted with one or more RX groups, where Rx is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

44. A compound according to any one of paragraphs 1 to 40, or a salt or solvate thereof, wherein Z is selected from $C_{6-15}$ aryl and 5-11 membered heteroaryl, wherein said $C_{6-15}$ aryl and 5-11 membered heteroaryl are optionally and independently substituted with one or more $R^x$ groups, where $R^x$ is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

45. A compound according to paragraph 44, or a salt or solvate thereof, wherein Z is selected from $C_{6-15}$ aryl and 5-11 membered heteroaryl, wherein said $C_{6-15}$ aryl and 5-11 membered heteroaryl are optionally and independently substituted with one or more RX groups, where $R^x$ is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

46. A compound according to paragraph 45, or a salt or solvate thereof, wherein Z is selected from $C_{6-15}$ aryl and 5-11 membered heteroaryl, wherein said $C_{6-15}$ aryl and 5-11 membered heteroaryl are optionally and independently substituted with one or more RX groups, where $R^x$ is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$OR^j$, —C(O)C(═O)$R^h$, —$NR^jR^k$, —$NR^j$C(═O)$OR^k$, —OR, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

47. A compound according to any one of paragraphs 1 to 40, or a salt or solvate thereof, wherein Z is selected from $C_{6-15}$ aryl and 5-6 membered heteroaryl, wherein said $C_{6-15}$ aryl and 5-6 membered heteroaryl are optionally and independently substituted with one or more RX groups, where RX is selected from hydroxyl, ═O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)$OR^j$, —C(═O)$NR^jR^k$, —C(O)C(═O)$R^h$, —$NR^jR^k$, —$NR^j$C(═O)$R^h$, —$NR^j$C(═O)$OR^k$, —$NR^j$C(═O)$NR^jR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$, —S(═O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

48. A compound according to paragraph 47, or a salt or solvate thereof, wherein Z is selected from $C_{6-15}$ aryl and 5-6 membered heteroaryl, wherein said $C_{6-15}$ aryl and 5-6 membered heteroaryl are optionally and independently substituted with one or more RX groups, where $R^x$ is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)$OR^j$, —C(O)C(═O)$R^h$, —$NR^jR^k$, —$NR^j$C(═O)$OR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

49. A compound according to paragraph 48, or a salt or solvate thereof, wherein Z is selected from $C_{6-15}$ aryl and 5-6 membered heteroaryl, wherein said $C_{6-15}$ aryl and 5-6 membered heteroaryl are optionally and independently substituted with one or more RX groups, where $R^x$ is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(═O)$OR^j$, —C(O)C(═O)$R^h$, —$NR^jR^k$, —$NR^j$C(═O)$OR^k$, —$OR^j$, —$SR^j$, —OC (=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

50. A compound according to any one of paragraphs 1 to 40, or a salt or solvate thereof, wherein Z is selected from $C_{6-11}$ aryl and 5-11 membered heteroaryl, wherein said $C_{6-11}$ aryl and 5-11 membered heteroaryl are optionally and independently substituted with one or more $R^x$ groups, where $R^x$ is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

51. A compound according to paragraph 50, or a salt or solvate thereof, wherein Z is selected from $C_{6-11}$ aryl and 5-11 membered heteroaryl, wherein said $C_{6-11}$ aryl and 5-11 membered heteroaryl are optionally and independently substituted with one or more RX groups, where $R^x$ is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

52. A compound according to paragraph 51, or a salt or solvate thereof, wherein Z is selected from $C_{6-11}$ aryl and 5-11 membered heteroaryl, wherein said $C_{6-11}$ aryl and 5-11 membered heteroaryl are optionally and independently substituted with one or more RX groups, where $R^x$ is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^1$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

53. A compound according to any one of paragraphs 1 to 40, or a salt or solvate thereof, wherein Z is selected from $C_{6-11}$ aryl and 5-6 membered heteroaryl, wherein said $C_{6-11}$ aryl and 5-6 membered heteroaryl are optionally and independently substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^jR^k$, —C(O)C(=O)$R^h$, —N$R^jR^k$, —N$R^j$C(=O)$R^h$, —N$R^j$C(=O)O$R^k$, —N$R^j$C(=O)N$R^jR^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$, —S(=O)$_2$N$R^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

54. A compound according to paragraph 53, or a salt or solvate thereof, wherein Z is selected from $C_{6-11}$ aryl and 5-6 membered heteroaryl, wherein said $C_{6-11}$ aryl and 5-6 membered heteroaryl are optionally and independently substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^jR^k$, —N$R^j$C(=O)O$R^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

55. A compound according to paragraph 54, or a salt or solvate thereof, wherein Z is selected from $C_{6-11}$ aryl and 5-6 membered heteroaryl, wherein said $C_{6-11}$ aryl and 5-6 membered heteroaryl are optionally and independently substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(=O)O$R^j$, —C(O)C(=O)$R^h$, —N$R^jR^k$, —N$R^j$C(=O)O$R^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^1$, —S(=O)N$R^jR^k$, —OS(=O)$_2$N$R^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

56. A compound according to any one of paragraphs 1 to 40, or a salt or solvate thereof, wherein Z is selected from phenyl and 5-11 membered heteroaryl, wherein said phenyl and 5-11 membered heteroaryl are optionally and independently substituted with one or more RX groups, where $R^x$ is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^jR^k$, —C(O)C(=O)$R^h$, —N$R^jR^k$, —N$R^j$C(=O)$R^h$, —N$R^j$C(=O)O$R^k$, —N$R^j$C(=O)N$R^jR^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$, —S(=O)$_2$N$R^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

57. A compound according to paragraph 56, or a salt or solvate thereof, wherein Z is selected from phenyl and 5-11 membered heteroaryl, wherein said phenyl and 5-11 membered heteroaryl are optionally and independently substituted with one or more RX groups, where $R^x$ is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)$OR^j$, —C(O)C(═O)$R^h$, —$NR^jR^k$, —$NR^j$C(═O)$OR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$haloalkyl, $C_{1-6}$haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

58. A compound according to paragraph 57, or a salt or solvate thereof, wherein Z is selected from phenyl and 5-11 membered heteroaryl, wherein said phenyl and 5-11 membered heteroaryl are optionally and independently substituted with one or more RX groups, where $R^x$ is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(═O)$OR^j$, —C(O)C(═O)$R^h$, —$NR^jR^k$, —$NR^j$C(═O)$OR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

59. A compound according to any one of paragraphs 1 to 40, or a salt or solvate thereof, wherein Z is selected from phenyl and 5-6 membered heteroaryl, wherein said phenyl and 5-6 membered heteroaryl are optionally and independently substituted with one or more RX groups, where RX is selected from hydroxyl, ═O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)$OR^j$, —C(═O)$NR^jR^k$, —C(O)C(═O)$R^h$, —$NR^jR^k$, —$NR^j$C(═O)$R^h$, —$NR^j$C(═O)$OR^k$, —$NR^j$C(═O)$NR^jR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$, —S(═O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

60. A compound according to paragraph 59, or a salt or solvate thereof, wherein Z is selected from phenyl and 5-6 membered heteroaryl, wherein said phenyl and 5-6 membered heteroaryl are optionally and independently substituted with one or more RX groups, where RX is selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)$OR^j$, —C(O)C(═O)$R^h$, —$NR^jR^k$, —$NR^j$C(═O)$OR^k$, —$OR^j$, —$SR^j$, —OC(═O)$R^h$, —OC(═O)$NR^jR^k$, —OC(═O)$OR^j$, —S(═O)$_2R^h$, —S(═O)$R^h$, —OS(═O)$R^h$, —OS(═O)$_2R^h$, —OS(═O)$_2OR^j$, —S(═O)$NR^jR^k$, —OS(═O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

61. A compound according to paragraph 60, or a salt or solvate thereof, wherein Z is selected from phenyl and 5-6 membered heteroaryl, wherein said phenyl and 5-6 membered heteroaryl are optionally and independently substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, OS(=O)$R^h$, —OS(=O)$_2$ $R^h$, —OS(=O)$_2OR^j$, —S(=O)$NR^jR^k$, —OS(=O)$_2$ $NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

62. A compound according to any one of paragraphs 1 to 40, or a salt or solvate thereof, wherein Z is a phenyl, wherein said phenyl is optionally substituted with one or more $R^x$ groups, where $R^x$ is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

63. A compound according to paragraph 62, or a salt or solvate thereof, wherein Z is a phenyl, wherein said phenyl is optionally substituted with one or more RX groups, where RX is selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

64. A compound according to paragraph 63, or a salt or solvate thereof, wherein Z is a phenyl, wherein said phenyl is optionally substituted with one or more $R^x$ groups, where $R^x$ is selected from hydroxyl, =O, halogen, CN, $C_{1-6}$haloalkyl, $C_{1-6}$haloalkoxy, $C_{1-6}$ alkyl, $C_{1-6}$alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

65. A compound according to any one of paragraphs 1 to 40, or a salt or solvate thereof, wherein Z is selected from:

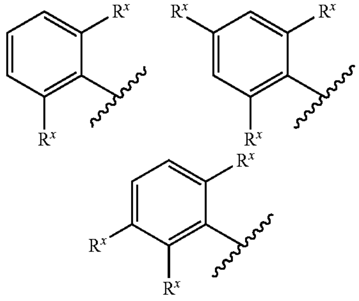

where $R^x$ is selected from hydroxyl, =O, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

66. A compound according to any one of paragraphs 1 to 40, or a salt or solvate thereof, wherein Z is selected from:

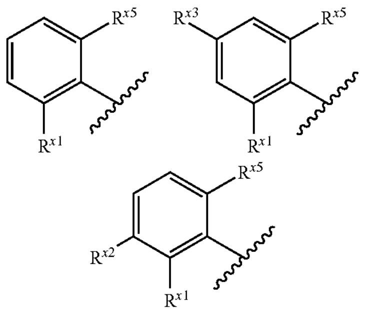

where $R^{x1}$, $R^{x3}$ and $R^{x5}$ are independently selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, OS(=O)$_2R^h$, —OS(=O)$_2$ $OR^j$, —S(=O)$NR^jR^k$, —OS(=O)$_2NR^jR^k$, —S(=O)$_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where $R^{x2}$ is selected from hydroxyl, =O, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$NR^j$C(=O)$OR^k$, —SRI, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

67. A compound according to any one of paragraphs 1 to 40, or a salt or solvate thereof, wherein Z is selected from:

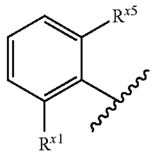
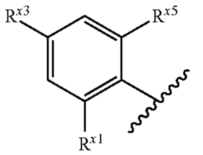
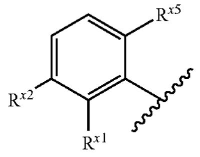

where $R^{x1}$, $R^{x3}$ and $R^{x5}$ are independently selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —O$R^j$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

where $R^{x2}$ is selected from hydroxyl, =O, halogen, CN, $C_{1-6}$ haloalkyl, $C_{1-6}$haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —SRI, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

68. A compound according to any one of paragraphs 1 to 40, or a salt or solvate thereof, wherein Z is selected from:

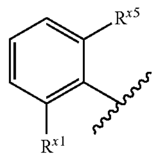
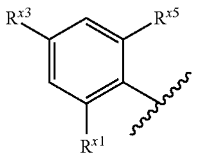
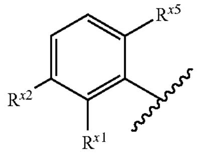

where $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —O$R^j$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

where $R^{x2}$ is selected from hydroxyl, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —S$R^j$, —OC(=O)$R^h$, —OC(=O)O$R^j$, —S(=O)$_2$$R^h$, —S(=O)$R^h$, —OS(=O)$R^h$, —OS(O)$_2$$R^h$, —OS(=O)$_2$O$R^j$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

69. A compound according to any one of paragraphs 1 to 40, or a salt or solvate thereof, wherein Z is selected from:

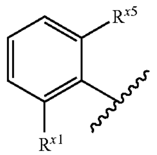
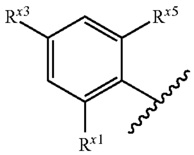
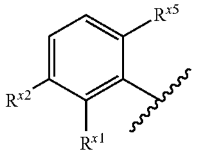

where $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —$NR^jR^k$, —$NR^jC(=O)OR^k$, —$OR^j$, —$SR^j$, —$OC(=O)R^h$, —$OC(=O)NR^jR^k$, —$OC(=O)OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where $R^{x2}$ is selected from hydroxyl, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

70. A compound according to any one of paragraphs 1 to 40, or a salt or solvate thereof, wherein Z is selected from:

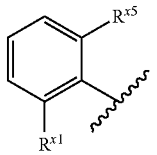
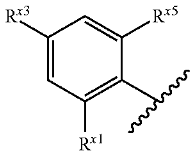

-continued

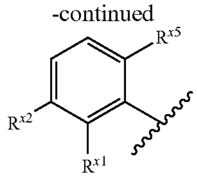

where $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —$NR^jR^k$, —$NR^jC(=O)OR^k$, —$OR^j$, —$SR^j$, —$OC(=O)R^h$, —$OC(=O)NR^jR^k$, —$OC(=O)OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where $R^{x2}$ is selected from hydroxyl, halogen, CN, $C_{1-6}$ haloalkyl, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$haloalkoxy, $C_{3-6}$ cycloalkyl, $NR^jR^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

71. A compound according to any one of paragraphs 1 to 40, or a salt or solvate thereof, wherein Z is selected from:

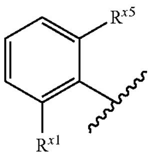

where $R^{x1}$ and $R^{x5}$ are independently selected from hydroxyl, halogen, CN, $C_{1-6}$haloalkyl, $C_{1-6}$ haloalkoxy, $C_{1-6}$ alkyl and $C_{1-6}$ alkoxy.

72. A compound according to any one of paragraphs 1 to 40, or a salt or solvate thereof, wherein Z is selected from:

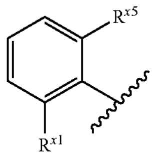

where $R^{x1}$ and $R^{x5}$ are independently selected from halogen, CN, $C_{1-6}$ haloalkyl, $C_{1-6}$ haloalkoxy, $C_{1-6}$ alkyl and $C_{1-6}$ alkoxy.

73. A compound according to any one of paragraphs 1 to 40, or a salt or solvate thereof, wherein Z is selected from:

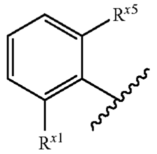

where $R^{x1}$ and $R^{x5}$ are independently selected from halogen, CN, $C_{1-6}$ alkyl and $C_{1-6}$ alkoxy.

74. A compound according to any one of paragraphs 1 to 40, or a salt or solvate thereof, wherein Z is selected from:

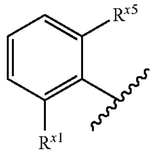

where $R^{x1}$ and $R^{x5}$ are independently selected from halogen and $C_{1-6}$ alkyl.

75. A compound according to any one of paragraphs 1 to 40, or a salt or solvate thereof, wherein Z is selected from:

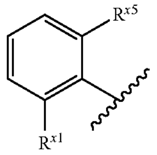

where $R^{x1}$ and $R^{x5}$ are independently selected from halogen and $C_{1-3}$ alkyl.

76. A compound according to any one of the preceding paragraphs, or a salt or solvate thereof, wherein Z is selected from:

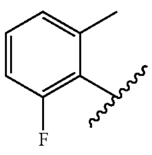 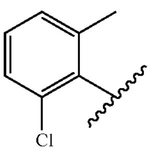

77. A compound of paragraph 1, or a salt or solvate thereof, according to one of sub-formulae If, Ig or Ih:

(If)

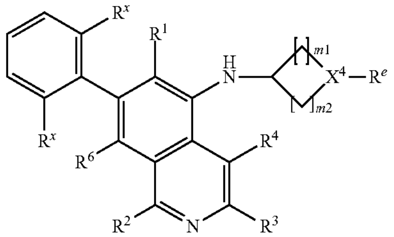

(Ig)

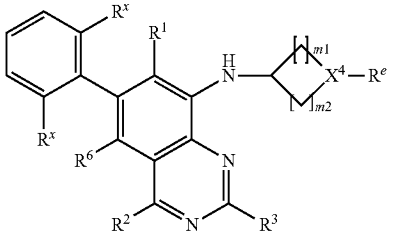

(Ih)

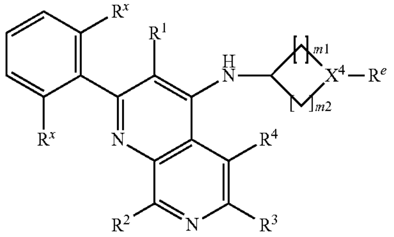

wherein $X^4$ is selected from nitrogen and CH;

m1 and m2 are numbers independently selected from 1 and 2;

$R^1$ is selected from the group consisting of hydrogen, $C_{1-3}$ alkyl, and halogen;

$R^2$ is selected from the group consisting of hydrogen; $C_{1-3}$ alkyl and $NH_2$; and $R^3$ is selected from the group consisting of hydrogen, $—NH_2$, $—NHR^a$, $—NR^aR^b$, $—N(R^{a1})C(O)R^c$, $—N(R^{a1})C(O)OR^d$, $—N(R^{a1})S(O)_2OR^d$, $—N(R^{a1})S(O)_2R^d$, $—C(O)NHR^a$, $—C(O)NR^aR^b$, $—C(O)R^c$, $C(O)OR^d$, $—OC(O)R^1$, —OH, $—OR^d$, where each of $R^a$, $R^b$, $R^c$ and $R^d$ are independently selected from $C_{1-6}$ alkyl and $C_3$-$C_6$ cycloalkyl wherein said $C_{1-6}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from H or $C_{1-3}$ alkyl.

$R^4$ is selected from the group consisting of hydrogen, halogen, CN, $C(O)NH_2$, $C(O)NHR'''$, $C(O)N(R''')_2$, $N(R^{p2})C(O)R'''$, where each $R'''$ is independently selected from $C_{1-6}$ alkyl which is optionally substituted with one or more groups selected from halogen, OH, $NH_2$, NHMe, $NMe_2$, and $C_{1-3}$ alkoxy, and $R^{p2}$ is selected from hydrogen, $C_{1-3}$ alkyl and $C_{1-3}$ haloalkyl;

$R^6$ is selected from hydrogen, halogen, OH, CN, $NH_2$ and $C_{1-3}$ alkyl;

$R^e$ is selected from hydrogen, halogen, CN, =O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

$R^x$ is selected from hydroxyl, =O, halogen, CN, $C_{1-3}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —NRIC(=O)$R^h$, —$NR^j$C(=O)$OR^k$, —NRIC(=O)$NR^jR^k$, —$OR^j$, —$SR^j$, —OC(=O)$R^h$, —OC(=O)$NR^jR^k$, —OC(=O)$OR^j$, —S(=O)$_2R^h$, —S(=O)$R^h$, —OS(=O)$R^h$, —OS(=O)$_2R^h$, —OS(=O)$_2OR^j$, —S(=O)$NR^jR^k$, —OS(=O)$_2NR^jR^k$, —S(=O)$_2NR^jR^k$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

78. A compound according to paragraph 77, or a salt or solvate thereof, of sub-formula If.

79. A compound according to paragraph 77, or a salt or solvate thereof, of sub-formula Ig or Ih.

80. A compound according to paragraph 77, or a salt or solvate thereof, of sub-formula Ig.

81. A compound according to paragraph 77, or a salt or solvate thereof, of sub-formula Ih.

82. A compound according to any one of paragraphs 77 to 81, or a salt or solvate thereof, wherein $X^4$ is nitrogen.

83. A compound according to any one of paragraphs 77 to 81, or a salt or solvate thereof, wherein $X^4$ is CH.

84. A compound according to any one of paragraphs 77 to 83, or a salt or solvate thereof, wherein m1 and m2 are both 1.

85. A compound according to any one of paragraphs 77 to 83, or a salt or solvate thereof, wherein one of m1 and m2 is 1 and the other is two.

86. A compound according to any one of paragraphs 77 to 83, or a salt or solvate thereof, wherein m1 and m2 are both 2.

87. A compound according to paragraph 77 to 81, or a salt or solvate thereof, wherein m1 and m2 are both 2 and $X^4$ is nitrogen.

88. A compound according to any one of the preceding paragraphs, or a salt or solvate thereof, wherein $R^3$ is selected from the group consisting of —$NH_2$, —$NHR^a$, —$NR^aR^b$, —NHC(O)$R^c$, —$N(R^{a1})C(O)OR^d$, —$N(R^{a1})S(O)_2OR^d$, —$N(R^{a1})S(O)_2R^d$, —C(O)$NHR^a$, —C(O)$NR^aR^b$, C(O)$OR^d$, —OC(O)$R^c$, —OH, and —$OR^d$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

89. A compound according to any one of the preceding paragraphs, or a salt or solvate thereof, wherein $R^3$ is selected from the group consisting of —$NH_2$, —$NHR^a$, —$NR^aR^b$, —NHC(O)$R^C$, —$N(R^{a1})C(O)OR^d$, —$N(R^{a1})S(O)_2OR^d$, —$N(R^{a1})S(O)_2R^d$, —OC(O)$R^c$, —OH, and —$OR^d$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

90. A compound according to any one of the preceding paragraphs, or a salt or solvate thereof, wherein $R^3$ is selected from the group consisting of —$NH_2$, —$NHR^a$, —$NR^aR^b$, —$N(R^{a1})C(O)R^c$, —$N(R^{a1})C(O)OR^d$, —$N(R^{a1})S(O)_2OR^d$, —$N(R^{a1})S(O)_2R^d$, —C(O)$NHR^a$, and —C(O)$NR^aR^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

91. A compound according to any one of the preceding paragraphs, or a salt or solvate thereof, wherein $R^3$ is selected from the group consisting of —$NH_2$, —$NHR^a$, and —$NR^aR^b$, —$N(R^{a1})C(O)R^c$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

92. A compound according to any one of the preceding paragraphs, or a salt or solvate thereof, wherein $R^3$ is selected from the group consisting of —$NH_2$, —$NHR^a$, and —$NR^aR^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

93. A compound according to any one of the preceding paragraphs, or a salt or solvate thereof, wherein $R^3$ is selected from the group consisting of hydrogen, —$NH_2$, —$NHR^a$, —$NR^aR^b$, —N($R^{a1}$)C(O)$R^c$, —N($R^{a1}$)C(O)O$R^d$, —N($R^{a1}$)S(O)$_2$O$R^d$, —N($R^{a1}$)S(O)$_2R^d$, —C(O)NH$R^a$, and —C(O)N$R^aR^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

94. A compound according to any one of the preceding paragraphs, or a salt or solvate thereof, wherein $R^3$ is selected from the group consisting of hydrogen, —$NH_2$, —$NHR^a$, —$NR^aR^b$, and —N($R^{a1}$)C(O)$R^c$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

95. A compound according to any one of the preceding paragraphs, or a salt or solvate thereof, wherein $R^3$ is selected from the group consisting of hydrogen, —$NH_2$, —$NHR^a$, and —$NR^aR^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$ and each $R^{a1}$ is independently selected from hydrogen and $C_{1-3}$ alkyl.

96. A compound according to any one of the preceding paragraphs, or a salt or solvate thereof, wherein $R^a$, $R^b$, $R^c$ and $R^d$ are independently selected from $C_{1-4}$ alkyl wherein said $C_{1-4}$ alkyl is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$.

97. A compound according to any one of the preceding paragraphs, or a salt or solvate thereof, wherein $R^a$, $R^b$, $R^c$ and $R^d$ are independently selected from methyl or ethyl; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$.

98. A compound according to any one of the preceding paragraphs, or a salt or solvate thereof, wherein $R^3$ is —$NH_2$ or hydrogen.

99. A compound according to any one of the preceding paragraphs wherein $R^{a1}$ is independently selected from hydrogen, methyl and ethyl.

100. A compound according to any one of the preceding paragraphs wherein $R^{a1}$ is independently selected from hydrogen and methyl.

101. A compound according to any one of the preceding paragraphs wherein $R^{a1}$ is hydrogen.

102. A compound according to any one of the preceding paragraphs, or a salt or solvate thereof, wherein $R^e$ is selected from hydrogen, halogen, CN, =O, $(CH_2)_y$OH, $C_{1-4}$ alkyl, $(CH_2)_yC_{1-4}$ alkoxy, $(CH_2)_yNH_2$, $(CH_2)_yNHR^q$, $(CH_2)_yN(R^q)_2$, $(CH_2)_y$NHCO($R^q$), $(CH_2)_y$CONH$_2$, $(CH_2)_y$CONH($R^q$), and $(CH_2)_y$CON$(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where $_y$ is a number between 0 and 3.

103. A compound according to any one of the preceding paragraphs, or a salt or solvate thereof, wherein $R^e$ is selected from hydrogen, =O, $(CH_2)_y$OH, $C_{1-4}$ alkyl, $(CH_2)_yC_{1-4}$ alkoxy, $(CH_2)_yNH_2$, $(CH_2)_yNHR^q$, $(CH_2)_yN(R^q)_2$, $(CH_2)_y$NHCO($R^q$), $(CH_2)_y$CONH$_2$, $(CH_2)_y$CONH($R^q$), and $(CH_2)_y$CON$(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

104. A compound according to any one of the preceding paragraphs, or a salt or solvate thereof, wherein $R^e$ is selected from hydrogen, =O, $(CH_2)_yOH$, $C_{1-4}$ alkyl, $(CH_2)_yNH_2$, $(CH_2)_yNHR^q$, $(CH_2)_yN(R^q)_2$, $(CH_2)_yNHCO(R^q)$ and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

105. A compound according to any one of the preceding paragraphs, or a salt or solvate thereof, wherein $R^e$ is selected from hydrogen, =O, $(CH_2)_yOH$, $C_{1-4}$ alkyl, $(CH_2)_yNH_2$, $(CH_2)_yNHR^q$, and $(CH_2)_yN(R^q)_2$; and where each $R^q$ is independently selected from $C_{1-4}$ alkyl which is optionally substituted with one or more groups selected from halogen, OH, $NH_2$, NHMe, $NMe_2$, and $C_{1-3}$alkoxy; and where $_y$ is a number between 0 and 3.

106. A compound according to any one of the preceding paragraphs, or a salt or solvate thereof, wherein $R^e$ is selected from hydrogen, =O, $(CH_2)_yOH$, $C_{1-4}$ alkyl, $(CH_2)_yNH_2$, $(CH_2)_yNHR^q$, and $(CH_2)_yN(R^q)_2$; and where each $R^q$ is independently selected from $C_{1-4}$ alkyl which is optionally substituted with one or more groups selected from OH, $NH_2$, NHMe, $NMe_2$, and $C_{1-3}$ alkoxy; and where $_y$ is a number between 0 and 3.

107. A compound according to any one of the preceding paragraphs, or a salt or solvate thereof, wherein y is 0 or 1.

108. A compound according to any one of the preceding paragraphs, or a salt or solvate thereof, wherein $R^e$ is selected from hydrogen, $C_{1-4}$ alkyl, $NH_2$, $NH(C_{1-4}$ alkyl), and N $(C_{1-4}$ alkyl$)_2$.

109. A compound according to any one of the preceding paragraphs, or a salt or solvate thereof, wherein $R^e$ is selected from hydrogen, methyl, ethyl, $NH_2$, NHMe, and $NMe_2$.

110. A compound according to any one of the preceding paragraphs, or a salt or solvate thereof, wherein $R^q$ is selected from methyl or ethyl which is optionally substituted with one or more groups selected from halogen, OH, $NH_2$, NHMe, $NMe_2$, and $C_{1-3}$alkoxy.

111. A compound according to any one of the preceding paragraphs, or a salt or solvate thereof, wherein $R^q$ is selected from methyl or ethyl which is optionally substituted with one or more groups selected from halogen, OH and $C_{1-3}$ alkoxy.

112. A compound according to any one of paragraphs 1 to 40, 65 and 77 to 111, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(=O)$NR^jR^k$, —C(O)C(=O)$R^h$, —$NR^jR^k$, —$NR^j$C(=O)$R^h$, —$NR^j$C(=O)$OR^k$, —$NR^j$C(=O)$NR^jR^k$, —$OR^j$, —$SR^j$, —OC(=O)$R^h$, —OC(=O)$NR^jR^k$, and —OC(=O)$OR^j$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$ is independently selected from $C_{1-6}$ alkyl optionally substituted by one or more groups selected from halogen, $C_{1-6}$alkoxy, $NH_2$, $NH(C_{1-3}$ alkyl) and $N(C_{1-3}$ alkyl$)_2$;

where each $R^j$ and $R^K$ are independently selected from hydrogen, $C_{1-6}$ haloalkyl, $C_{3-6}$ cycloalkyl, phenyl, benzyl and $C_{1-6}$ alkyl wherein said $C_{1-6}$ haloalkyl, $C_{3-6}$ cycloalkyl, phenyl, benzyl and $C_{1-6}$ alkyl are optionally substituted with one or more groups selected from halogen, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

113. A compound according to paragraph 112, or a salt or solvate thereof, wherein RX is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, and —OC(=O)$OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$ is independently selected from $C_{1-6}$ alkyl optionally substituted by one or more groups selected from halogen, $C_{1-6}$alkoxy, $NH_2$, $NH(C_{1-3}$ alkyl) and $N(C_{1-3}$ alkyl$)_2$;

where each $R^j$ and $R^K$ are independently selected from hydrogen, $C_{1-6}$ haloalkyl, $C_{3-6}$ cycloalkyl, phenyl, benzyl and $C_{1-6}$ alkyl wherein said $C_{1-6}$ haloalkyl, $C_{3-6}$ cycloalkyl, phenyl, benzyl and $C_{1-6}$ alkyl are optionally substituted with one or more groups selected from halogen, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

114. A compound according to paragraph 113, or a salt or solvate thereof, wherein RX is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(=O)$OR^j$, —C(O)C(=O)$R^h$, —$NR^jR^k$, —$NR^j$C(=O)$OR^k$, —$OR^j$, —$SR^j$, —OC(=O)$R^h$, —OC(=O)$NR^jR^k$, and —OC(=O)$OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$ is independently selected from $C_{1-6}$ alkyl optionally substituted by one or more groups selected from $C_{1-6}$alkoxy, $NH_2$, $NH(C_{1-3}$ alkyl) and $N(C_{1-3}$ alkyl$)_2$;

where each $R^j$ and $R^K$ are independently selected from hydrogen, $C_{1-6}$ haloalkyl, $C_{3-6}$ cycloalkyl, phenyl, benzyl and $C_{1-6}$ alkyl wherein said $C_{1-6}$ haloalkyl, $C_{3-6}$ cycloalkyl, phenyl, benzyl and $C_{1-6}$ alkyl are optionally substituted with one or more groups selected from $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

115. A compound according to any one of paragraphs 1 to 40, 65 and 77 to 111, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)O$R^j$, —C(═O)N$R^jR^k$, —N$R^jR^k$, —N$R^j$C(═O)$R^h$, —O$R^j$, and —S$R^j$; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

116. A compound according to paragraph 115, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(═O)$R^h$, —C(═O)O$R^j$, —N$R^jR^k$, —O$R^j$, and —S$R^j$; where said $C_{1-6}$ alkyl, $C_{1-6}$alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

117. A compound according to paragraph 116, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —C(═O)O$R^j$, —N$R^jR^k$, —O$R^j$, and —S$R^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

118. A compound according to any one of paragraphs 1 to 40, 65 and 77 to 111, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, $C_{6-11}$ aryl, heteroaryl, —C(═O)$R^h$, —C(═O)O$R^j$, —C(═O)N$R^jR^k$, —N$R^jR^k$, —N$R^j$C(═O)$R^h$, —O$R^j$, and —S$R^j$; where said $C_{1-6}$ alkyl, $C_{2-6}$alkenyl, $C_{2-6}$ alkynyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, halogen, ═O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heterary1, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

119. A compound according to paragraph 118, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl, —C(═O)$R^h$, —C(═O)O$R^j$, —N$R^jR^k$, —O$R^j$, and —S$R^j$; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

120. A compound according to paragraph 119, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl, —C(=O)$OR^j$, —$NR^jR^k$, —$OR^j$, and —$SR^j$; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

121. A compound according to any one of paragraphs 1 to 40, 65 and 77 to 111, or a salt or solvate thereof, wherein RX is selected from hydroxyl, halogen, CN, $C_{1-6}$ haloalkyl, $C_{1-6}$ haloalkoxy, $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, $C_{6-11}$ aryl, heteroaryl; where said $C_{1-6}$ alkyl, $C_{2-6}$ alkenyl, $C_{2-6}$ alkynyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

122. A compound according to paragraph 121, or a salt or solvate thereof, wherein RX is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

123. A compound according to paragraph 122, or a salt or solvate thereof, wherein RX is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

124. A compound according to any one of paragraphs 1 to 40, 65 and 77 to 111, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

125. A compound according to paragraph 124, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, $C_{6-11}$ aryl, heteroaryl; where said $C_{1-6}$ alkyl, $C_{1-6}$ alkoxy, $C_{3-6}$ cycloalkyl, 3-10 membered heterocycloalkyl, $C_{6-11}$ aryl, and heteroaryl and are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

126. A compound according to any one of paragraphs 1 to 40, 65 and 77 to 111, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, and $C_{1-6}$ alkoxy where said $C_{1-6}$ alkyl and $C_{1-6}$ alkoxy, are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

127. A compound according to paragraph 126, or a salt or solvate thereof, wherein $R^x$ is selected from hydroxyl, halogen, CN, $C_{1-6}$ haloalkyl, $C_{1-6}$ haloalkoxy, $C_{1-6}$ alkyl, and $C_{1-6}$ alkoxy where said $C_{1-6}$ alkyl and $C_{1-6}$ alkoxy, are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

128. A compound according to any one of paragraphs 1 to 40, 65 and 77 to 111, or a salt or solvate thereof, wherein RX is selected from halogen, CN, $C_{1-6}$ haloalkyl and $C_{1-6}$ alkyl, and where said $C_{1-6}$ alkyl is optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

129. A compound according to paragraph 128, or a salt or solvate thereof, wherein $R^x$ is selected from halogen, CN, $C_{1-6}$ haloalkyl and $C_{1-6}$ alkyl, and where said $C_{1-6}$ alkyl is optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-3}$ alkyl wherein said $C_{3-6}$ cycloalkyl, phenyl, benzyl, 5-6 membered heteraryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

130. A compound according to any one of paragraphs 1 to 40, 65 and 77 to 129, or a salt or solvate thereof, wherein $R^x$ is selected from halogen, CN, $C_{1-6}$ haloalkyl and $C_{1-6}$ alkyl.

131. A compound according to paragraph 130, or a salt or solvate thereof, wherein RX is selected from fluoro, chloro, CN, $CF_3$, methyl and ethyl.

132. A compound according to paragraph 130, or a salt or solvate thereof, wherein $R^x$ is selected from fluoro, chloro and methyl.

133. A compound according to any one of the preceding paragraphs, or a salt or solvate thereof, wherein $R^h$ is independently selected from $C_{1-3}$ alkyl optionally substituted by one or more groups selected from halogen, $C_{1-6}$ alkoxy, $NH_2$, $NH(C_{1-3}$ alkyl) and $N(C_{1-3}$ alkyl$)_2$.

134. A compound according to any one of the preceding paragraphs, or a salt or solvate thereof, wherein $R^h$ is independently selected from $C_{1-3}$ alkyl optionally substituted by one or more groups selected from halogen, OMe, $NH_2$, NH(Me) and $N(Me)_2$.

135. A compound according to any one of the preceding paragraphs, or a salt or solvate thereof, wherein $R^h$ is independently selected from methyl and ethyl optionally substituted by one or more groups selected from halogen, OMe, $NH_2$, NH(Me) and $N(Me)_2$.

136. A compound according to any one of the preceding paragraphs, or a salt or solvate thereof, wherein $R^j$ and $R^K$ are independently selected from hydrogen, $C_{1-3}$ haloalkyl, $C_{3-6}$ cycloalkyl, phenyl, benzyl and $C_{1-3}$ alkyl wherein said $C_{1-3}$ haloalkyl, $C_{3-6}$ cycloalkyl, phenyl, benzyl and $C_{1-3}$ alkyl are optionally substituted with one or more groups selected from halogen, OMe, $NH_2$, NH(Me) and $N(Me)_2$; or $R^j$ and $R^K$ when attached to the same atom and together with the atom to which they are attached combine to provide a 3-6 membered heterocycloalkyl which is optionally substituted by one or more groups selected from halogen, hydroxy, $C_{1-3}$ alkyl, $C_{1-3}$ alkoxy, =O and CN.

137. A compound according to any one of the preceding paragraphs, or a salt or solvate thereof, wherein $R^j$ and $R^K$ are independently selected from hydrogen, $CF_3$, and $C_{1-3}$ alkyl wherein said $C_{1-3}$ alkyl is optionally substituted with one or more groups selected from halogen, OMe, $NH_2$, NH(Me) and $N(Me)_2$; or $R^j$ and $R^K$ when attached to the same atom and together with the atom to which they are attached combine to provide a 3-6 membered heterocycloalkyl which is optionally substituted by one or more groups selected from halogen, hydroxy, $C_{1-3}$ alkyl, $C_{1-3}$alkoxy, =O and CN.

138. A compound according to any one of the preceding paragraphs, or a salt or solvate thereof, wherein $R^j$ and $R^K$ are independently selected from hydrogen, methyl and ethyl; or $R^j$ and $R^K$ when attached to the same atom and together with the atom to which they are attached combine to provide a 3-6 membered heterocycloalkyl which is optionally substituted by one or more groups selected from halogen, hydroxy, methyl, ethyl, OMe, =O and CN.

139. A compound according to any one of the preceding paragraphs, or a salt or solvate thereof, wherein $R^j$ and $R^K$ are independently selected from hydrogen and methyl.

140. A compound according to any one of the preceding paragraphs, or a salt or solvate thereof, wherein $R^1$ is selected from the group consisting of hydrogen, methyl, ethyl and halogen.

141. A compound according to any one of the preceding paragraphs, or a salt or solvate thereof, wherein $R^1$ is selected from the group consisting of hydrogen, methyl, fluoro and chloro.

142. A compound according to any one of the preceding paragraphs, or a salt or solvate thereof, wherein $R^1$ is hydrogen or fluoro.

143. A compound according to any one of the preceding paragraphs, or a salt or solvate thereof, wherein $R^1$ is hydrogen.

144. A compound according to any one of the preceding paragraphs, or a salt or solvate thereof, wherein $R^2$ is hydrogen, methyl or ethyl.

145. A compound according to any one of the preceding paragraphs, or a salt or solvate thereof, wherein $R^2$ is hydrogen.

146. A compound according to any one of the preceding paragraphs, or a salt or solvate thereof, wherein $R^6$ is selected from hydrogen, halogen, OH, CN, $NH_2$, methyl and ethyl.

147. A compound according to any one of the preceding paragraphs, or a salt or solvate thereof, wherein $R^6$ is selected from hydrogen, fluoro, chloro, OH, CN, $NH_2$, methyl and ethyl.

148. A compound according to any one of the preceding paragraphs, or a salt or solvate thereof, wherein $R^6$ is selected from hydrogen, fluoro, chloro, methyl and ethyl.

149. A compound according to any one of the preceding paragraphs, or a salt or solvate thereof, wherein $R^6$ is selected from hydrogen, fluoro and methyl.

150. A compound according to any one of the preceding paragraphs, or a salt or solvate thereof, wherein $R^6$ is hydrogen.

151. A compound according to any one of the preceding paragraphs, or a salt or solvate thereof, wherein $R^4$ is selected from the group consisting of hydrogen, halogen, CN, $C(O)NH_2$, $C(O)NHR^m$, $C(O)N(R^m)_2$, where each $R^m$ is independently selected from $C_{1-4}$ alkyl which is optionally substituted with one or more groups selected from halogen, OH, $NH_2$, NHMe, $NMe_2$, and $C_{1-3}$ alkoxy.

152. A compound according to any one of the preceding paragraphs, or a salt or solvate thereof, wherein $R^4$ is selected from the group consisting of hydrogen, halogen, CN.

153. A compound according to any one of the preceding paragraphs, or a salt or solvate thereof, wherein $R^4$ is selected from the group consisting of hydrogen, fluoro, chloro, and CN.

154. A compound according to any one of the preceding paragraphs, or a salt or solvate thereof, wherein $R^4$ is hydrogen.

155. A compound according to any one of the preceding paragraphs, or a salt or solvate thereof, wherein $R^m$ is independently selected from methyl and ethyl each of which is optionally substituted with one or more groups selected from halogen, OH, $NH_2$, NHMe, $NMe_2$, and OMe.

156. A compound according to any one of the preceding paragraphs, or a salt or solvate thereof, wherein $R^m$ is independently selected from methyl and ethyl.

157. A compound according to any one of the preceding paragraphs, or a salt or solvate thereof, wherein $R^{p2}$ is hydrogen or methyl.

158. A compound according to any one of the preceding paragraphs, or a salt or solvate thereof, wherein $R^5$ is selected from the group consisting of hydrogen, halogen, CN, $C(O)NH_2$, $C(O)NHR^f$, $C(O)N(R^f)_2$, where each $R^f$ is independently selected from $C_{1-4}$ alkyl which is optionally substituted with one or more groups selected from halogen, OH, $NH_2$, NHMe, $NMe_2$, and $C_{1-3}$ alkoxy.

159. A compound according to any one of the preceding paragraphs, or a salt or solvate thereof, wherein $R^5$ is selected from the group consisting of hydrogen, halogen, CN.

160. A compound according to any one of the preceding paragraphs, or a salt or solvate thereof, wherein $R^5$ is selected from the group consisting of hydrogen, fluoro, chloro, and CN.

161. A compound according to any one of the preceding paragraphs, or a salt or solvate thereof, wherein $R^5$ is hydrogen.

162. A compound according to any one of the preceding paragraphs, or a salt or solvate thereof, wherein $R^f$ is independently selected from methyl and ethyl each of which is optionally substituted with one or more groups selected from halogen, OH, $NH_2$, NHMe, $NMe_2$, and OMe.

163. A compound according to any one of the preceding paragraphs, or a salt or solvate thereof, wherein $R^f$ is independently selected from methyl and ethyl.

164. A compound according to any one of the preceding paragraphs, or a salt or solvate thereof, wherein $R^{p1}$ is hydrogen or methyl.

165. A compound of paragraph 1, or a salt or solvate thereof, according to one of sub-formulae IIa, IIb, IIc, IId, IIe, IIf, IIg, IIh and IIi:

(IIa)

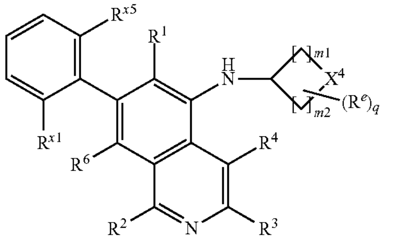

(IIb)

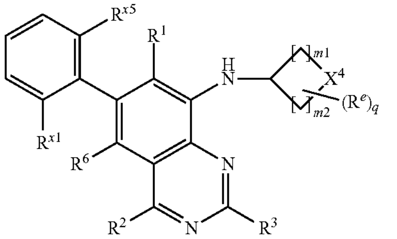

(IIc)

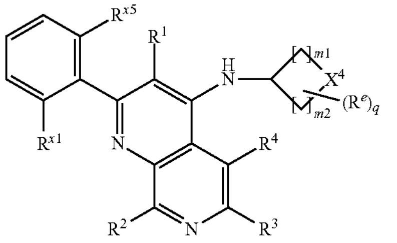

(IId)

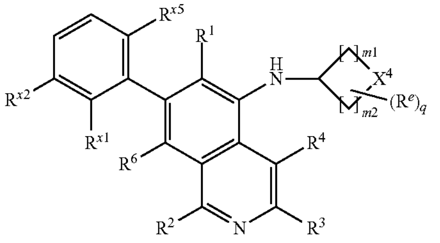

-continued (IIe)

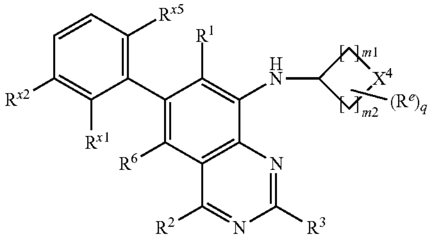

(IIf)

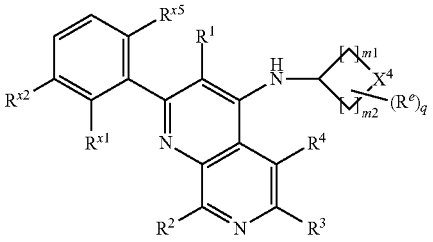

(IIg)

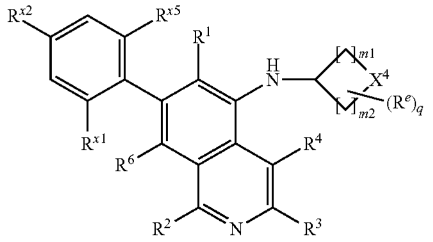

(IIh)

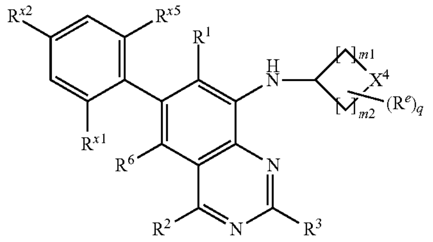

(IIi)

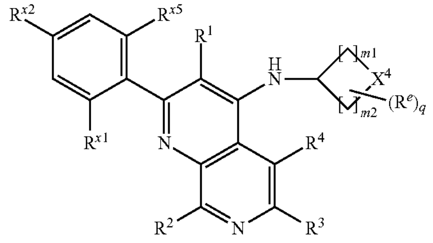

wherein $X^4$ is selected from nitrogen and CH;

m1 and m2 are numbers independently selected from 1, 2, 3 and 4;

q is a number independently selected from 1, 2 and 3;

$R^1$ is selected from the group consisting of hydrogen, $C_{1-3}$ alkyl, and halogen;

$R^2$ is selected from the group consisting of hydrogen; $C_{1-3}$ alkyl and $NH_2$;

$R^3$ is selected from the group consisting of hydrogen, —$NH_2$, —$NHR^a$, —$NR^aR^b$, —$N(R^{a1})C(O)R^c$, —$N(R^{a1})C(O)OR^d$, —$N(R^{a1})S(O)_2OR^d$, —$N(R^{a1})S(O)_2R^d$, —$C(O)NHR^a$, —$C(O)NR^aR^b$, —$C(O)R^c$, $C(O)OR^d$, —$O(O)R^c$, —OH, —$OR^d$, where each of $R^a$, $R^b$, $R^c$ and $R^d$ are independently selected from $C_{1-6}$ alkyl and $C_3$-$C_6$ cycloalkyl wherein said $C_{1-6}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from H or $C_{1-3}$ alkyl.

$R^4$ is selected from the group consisting of hydrogen, halogen, CN, $C(O)NH_2$, $C(O)NHR^m$, $C(O)N(R^m)_2$, $N(R^{p2})C(O)R^m$, where each $R^m$ is independently selected from $C_{1-4}$ alkyl which is optionally substituted with one or more groups selected from halogen, OH, $NH_2$, NHMe, $NMe_2$, and $C_{1-3}$ alkoxy, and $R^{p2}$ is selected from hydrogen, $C_{1-3}$ alkyl and $C_{1-3}$ haloalkyl;

$R^6$ is selected from hydrogen, halogen, OH, CN, $NH_2$ and $C_{1-3}$ alkyl;

$R^e$ is selected from hydrogen, halogen, CN, =O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

$R^{x1}$, $R^{x3}$ and $R^{x5}$ are independently selected from hydroxyl, =O, halogen, CN, $C_{1-6}$haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^jR^k$, —C(O)C(=O)$R^h$, —N$R^jR^k$, —NRIC(=O)$R^h$, —N$R^j$C(=O)O$R^k$, —NRIC(=O)N$R^jR^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$, —S(=O)$_2$N$R^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl; and $R^{x2}$ is selected from hydroxyl, =O, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^jR^k$, —N$R^j$C(=O)O$R^k$, —SRI, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

166. A compound according to paragraph 165, or a salt or solvate thereof, selected from a compound of:

sub-formulae IIa, IIb or IIc; or sub-formulae IId, IIe or IIf; or sub-formulae IIg, IIh or IIi.

167. A compound according to paragraph 165, or a salt or solvate thereof, selected from a compound of:

sub-formulae IIa, IId or IIg; or sub-formulae IIb, IIe or IIh; or sub-formulae IIc, IIf or IIi.

168. A compound according to any one of paragraphs 165 to 167, or a salt or solvate thereof, wherein $R^1$ is selected from the group consisting of hydrogen, methyl, ethyl and halogen.

169. A compound according to any one of paragraphs 165 to 168, or a salt or solvate thereof, wherein $R^1$ is hydrogen or fluoro.

170. A compound according to any one of paragraphs 165 to 169, or a salt or solvate thereof, wherein $R^2$ is hydrogen, methyl or ethyl.

171. A compound according to any one of paragraphs 165 to 170, or a salt or solvate thereof, wherein $R^6$ is selected from hydrogen, halogen, OH, CN, $NH_2$, methyl and ethyl.

172. A compound according to any one of paragraphs 165 to 171, or a salt or solvate thereof, wherein $R^6$ is selected from hydrogen, fluoro, chloro, methyl and ethyl.

173. A compound according to any one of paragraphs 165 to 172, or a salt or solvate thereof, wherein $R^6$ is selected from hydrogen, fluoro and methyl.

174. A compound according to any one of paragraphs 165 to 173, or a salt or solvate thereof, wherein $R^4$ is selected from the group consisting of hydrogen, halogen, CN, $C(O)NH_2$, $C(O)NHR^m$, $C(O)N(R^m)_2$, where each $R^m$ is independently selected from $C_{1-4}$ alkyl which is optionally substituted with one or more groups selected from halogen, OH, $NH_2$, NHMe, $NMe_2$, and $C_{1-3}$ alkoxy.

175. A compound according to any one of paragraphs 165 to 174, or a salt or solvate thereof, wherein $R^4$ is selected from the group consisting of hydrogen, halogen, CN.

176. A compound according to any one of paragraphs 165 to 175, or a salt or solvate thereof, wherein $R^4$ is selected from the group consisting of hydrogen, fluoro, chloro, and CN.

177. A compound of paragraph 1, or a salt or solvate thereof, according to one of sub-formulae IIIa, IIIb, IIIc, IIId, IIIe, IIIf, IIIg, IIIh and IIIi:

(IIIa)

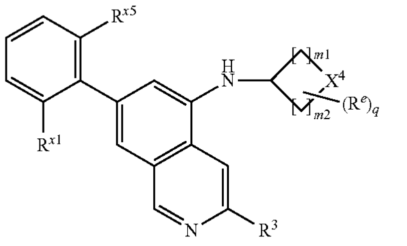

(IIIb)

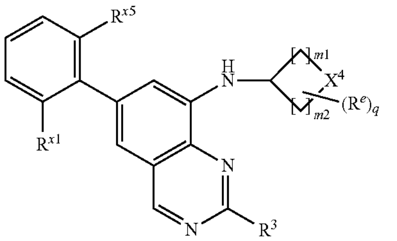

(IIIc)

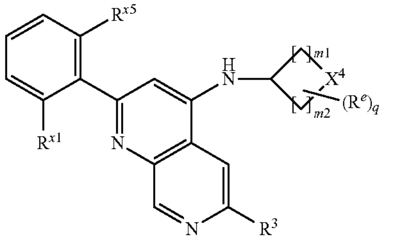

(IIId)

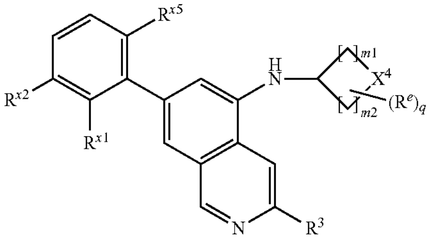

(IIIe)

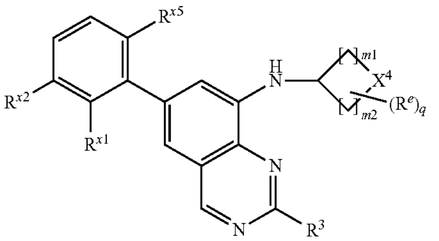

(IIIf)

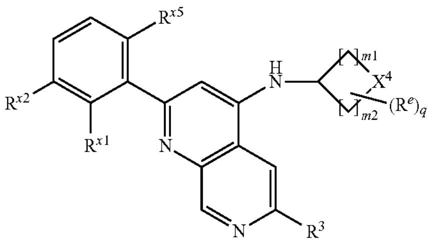

-continued (IIIg)

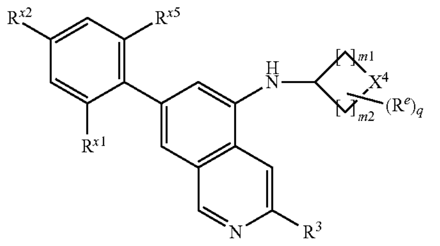

(IIIh)

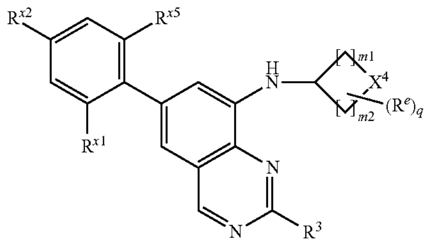

(IIIi)

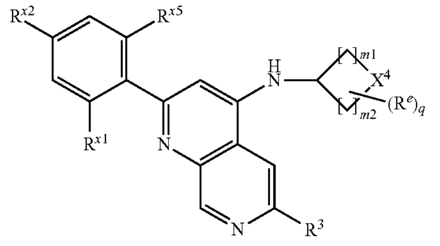

wherein $X^4$ is selected from nitrogen and CH;

m1 and m2 are numbers independently selected from 1, 2, 3 and 4;

q is a number independently selected from 1, 2 and 3;

$R^3$ is selected from the group consisting of hydrogen, —$NH_2$, —$NHR^a$, —$NR^aR^b$, —$N(R^{a1})C(O)R^c$, —$N(R^{a1})C(O)OR^d$, —$N(R^{a1})S(O)_2OR^d$, —$N(R^{a1})S(O)_2R^d$, —$C(O)NHR^a$, —$C(O)NR^aR^b$, —$C(O)R^c$, $C(O)OR^d$, —$OC(O)R^c$, —OH, —$OR^d$, where each of $R^a$, $R^b$, $R^c$ and $R^d$ are independently selected from $C_{1-6}$ alkyl and $C_3$-$C_6$ cycloalkyl wherein said $C_{1-6}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from H or $C_{1-3}$ alkyl.

$R^e$ is selected from hydrogen, halogen, CN, ═O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

where $R^{x1}$, $R^{x3}$ and $R^{x5}$ are independently selected from hydroxyl, ═O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)O$R^j$, —C(═O)N$R^j$$R^k$, —C(O)C(═O)$R^h$, —N$R^j$$R^k$, —N$R^j$C(═O)$R^h$, —N$R^j$C(═O)O$R^k$, —N$R^j$C(═O)N$R^j$$R^k$, —O$R^j$, —S$R^j$, —OC(═O)$R^h$, —OC(═O)N$R^j$$R^k$, —OC(═O)O$R^j$, —S(═O)$_2R^h$, —S(═O)$R^h$, —OS(═O)$R^h$, —OS(═O)$_2R^h$, —OS(═O)$_2$O$R^j$, —S(═O)N$R^j$$R^k$, —OS(═O)$_2$N$R^j$$R^k$, —S(═O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

where $R^{x2}$ is selected from hydroxyl, ═O, halogen, CN, $C_{1-6}$haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)O$R^j$, —C(O)C(═O)$R^h$, —N$R^j$$R^k$, —N$R^j$C(═O)O$R^k$, —SRI, —OC(═O)$R^h$, —OC(═O)N$R^j$$R^k$, —OC(═O)O$R^j$, —S(═O)$_2R^h$, —S(═O)$R^h$, —OS(═O)$R^h$, —OS(═O)$_2R^h$, —OS(═O)$_2$O$R^j$, —S(═O)N$R^j$$R^k$, —OS(═O)$_2$N$R^j$$R^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, ═O and CN.

178. A compound according to paragraph 177, or a salt or solvate thereof, selected from a compound of:
sub-formulae IIIa, IIIb or IIIc; or
sub-formulae IIId, IIIe or IIIf; or
sub-formulae IIIg, IIIh or IIIi.

179. A compound according to paragraph 177, or a salt or solvate thereof, selected from a compound of:
sub-formulae IIIa, IIId or IIIg; or
sub-formulae IIIb, IIIe or IIIh; or
sub-formulae IIIc, IIIf or IIIi.

180. A compound according to any one of paragraphs 165 to 179, or a salt or solvate thereof, wherein $R^3$ is selected from the group consisting of —$NH_2$, —NH$R^a$, —N$R^a$$R^b$, —NHC(O)$R^c$, —N($R^{a1}$)C(O)O$R^d$, —N($R^{a1}$)S(O)$_2$O$R^d$, —N($R^{a1}$)S(O)$_2R^d$, —C(O)NH$R^a$, —C(O)N$R^a$$R^b$, C(O)O$R^d$, —OC(O)$R^c$, —OH, and —O$R^d$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

181. A compound according to any one of paragraphs 165 to 179, or a salt or solvate thereof, wherein $R^3$ is selected from the group consisting of —$NH_2$, —NH$R^a$, —N$R^a$$R^b$, —NHC(O)$R^c$, —N($R^{a1}$)C(O)O$R^d$, —N($R^{a1}$)S(O)$_2$O$R^d$, —N($R^{a1}$)S(O)$_2R^d$, OC(O)$R^c$, —OH, and —O$R^d$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

182. A compound according to any one of paragraphs 165 to 179, or a salt or solvate thereof, wherein $R^3$ is selected from the group consisting of —$NH_2$, —NH$R^a$, —N$R^a$$R^b$, —N($R^{a1}$)C(O)$R^c$, —N($R^{a1}$)C(O)O$R^d$, —N($R^{a1}$)S(O)$_2$O$R^d$, —N($R^{a1}$)S(O)$_2R^d$, —C(O)NH$R^a$, and —C(O)N$R^a$$R^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

183. A compound according to any one of paragraphs 165 to 179, or a salt or solvate thereof, wherein $R^3$ is selected from the group consisting of —$NH_2$, —NH$R^a$, —N$R^a$$R^b$ and —N($R^{a1}$)C(O)$R^c$, where each of $R^a$, $R^b$, and $R^c$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, NH($C_{1-3}$ alkyl) and N($C_{1-3}$ alkyl)$_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, NH($C_{1-3}$ alkyl) and N($C_{1-3}$ alkyl)$_2$; and each $R^{a1}$ is independently selected from hydrogen and $C_{1-3}$ alkyl.

184. A compound according to any one of paragraphs 165 to 179, or a salt or solvate thereof, wherein $R^3$ is selected from the group consisting of —$NH_2$, —$NHR^a$ and —$NR^aR^b$, where each of $R^a$ and $R^b$, are independently selected from $C_{1-4}$ alkyl and $C_3$—C cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$; or $R^1$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

185. A compound according to any one of paragraphs 165 to 179, or a salt or solvate thereof, wherein $R^3$ is selected from the group consisting of hydrogen, —$NH_2$, —$NHR^a$, —$NR^aR^b$, —$N(R^{a1})C(O)R^c$, —$N(R^{a1})C(O)OR^d$, —$N(R^{a1})S(O)_2OR^d$, —$N(R^{a1})S(O)_2R^d$, —$C(O)NHR^a$, and —$C(O)NR^aR^b$, where each of $R^a$, $R^b$, $R^c$ and $R^d$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

186. A compound according to any one of paragraphs 165 to 179, or a salt or solvate thereof, wherein $R^3$ is selected from the group consisting of hydrogen, —$NH_2$, —$NHR^a$, —$NR^aR^b$, —$N(R^{a1})C(O)R^c$, where each of $R^a$, $R^b$ and $R^c$ are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$; and each $R^{a1}$ is independently selected from hydrogen and $C_{1-3}$ alkyl.

187. A compound according to any one of paragraphs 165 to 179, or a salt or solvate thereof, wherein $R^3$ is selected from the group consisting of hydrogen, —$NH_2$, —$NHR^a$, and —$NR^aR^b$, where each of $R^a$ and $R^b$, are independently selected from $C_{1-4}$ alkyl and $C_3$-$C_6$ cycloalkyl wherein said $C_{1-4}$ alkyl and $C_3$-$C_6$ cycloalkyl are optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$alkoxy, $C_{1-3}$haloalkyl, $C_{1-3}$haloalkoxy, $NH_2$, $NH(C_{1-3}$ alkyl) and $N(C_{1-3}$ alkyl$)_2$ and each $R^{a1}$ is independently selected from hydrogen and $C_{1-3}$ alkyl.

188. A compound according to any one of paragraphs 165 to 187, or a salt or solvate thereof, wherein $R^a$, $R^b$, $R^c$ and $R^d$ are independently selected from $C_{1-4}$ alkyl wherein said $C_{1-4}$ alkyl is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$.

189. A compound according to any one of paragraphs 165 to 187, or a salt or solvate thereof, wherein $R^a$, $R^b$, $R^c$ and $R^d$ are independently selected from methyl or ethyl; or $R^a$ and $R^b$ when attached to the same atom and together with the atom to which they are attached combine to provide a 3-7 membered heterocycloalkyl which is optionally substituted by one or more groups selected from OH, halogen, CN, $C_{1-3}$ alkyl, $C_{1-3}$ alkoxy, $C_{1-3}$ haloalkyl, $C_{1-3}$ haloalkoxy, $NH_2$, $NH(C_{1-3}$ alkyl) and $N(C_{1-3}$ alkyl$)_2$.

190. A compound according to any one of paragraphs 165 to 189 wherein $R^{a1}$ is independently selected from hydrogen, methyl and ethyl.

191. A compound according to any one of paragraphs 165 to 189 wherein $R^{a1}$ is independently selected from hydrogen and methyl.

192. A compound according to any one of paragraphs 165 to 189 wherein $R^{a1}$ is hydrogen.

193. A compound according to any one of paragraphs 165 to 187, or a salt or solvate thereof, wherein $R^3$ is hydrogen or —$NH_2$.

194. A compound of paragraph 1, or a salt or solvate thereof, according to one of sub-formulae IVa, IVb, IVc, IVd, IVe, IVf, IVg, IVh and IVi:

(IVa)

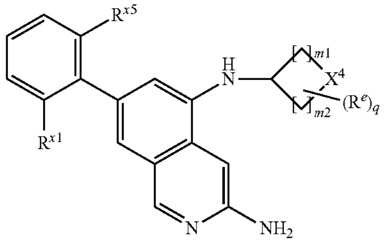

(IVb)

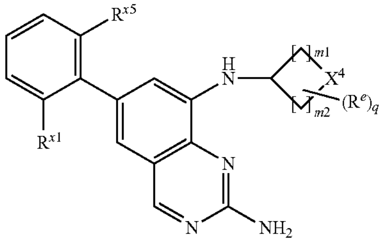

-continued (IVc)

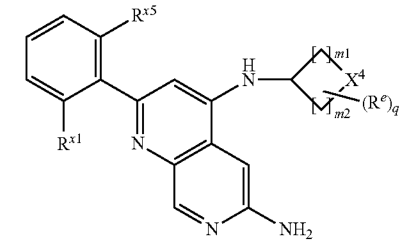

(IVd)

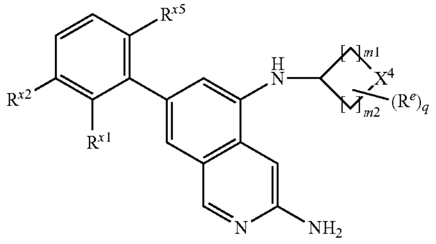

(IVe)

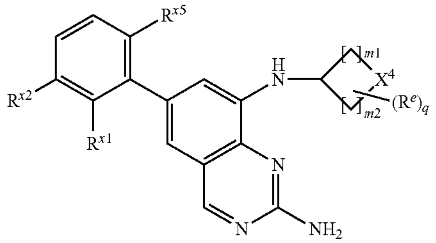

(IVf)

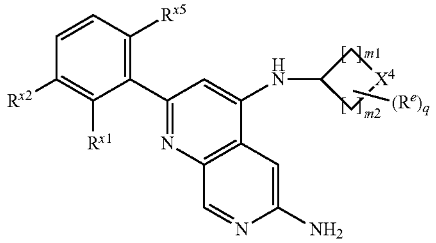

(IVg)

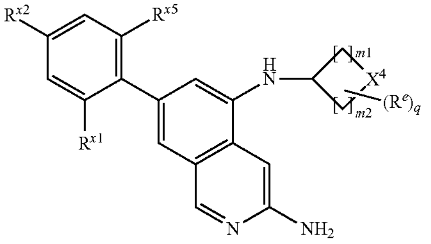

(IVh)

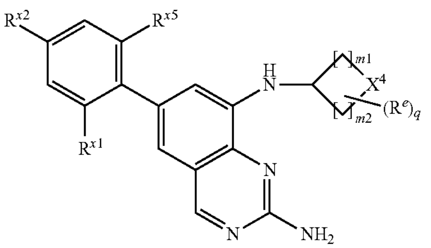

-continued (IVi)

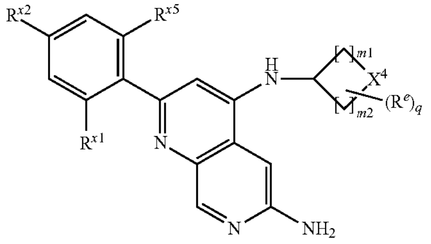

wherein $X^4$ is selected from nitrogen and CH;

m1 and m2 are numbers independently selected from 1, 2, 3 and 4;

q is a number independently selected from 1, 2 and 3;

$R^e$ is selected from hydrogen, halogen, CN, ═O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

$R^{x1}$, $R^{x3}$ and $R^{x5}$ are independently selected from hydroxyl, ═O, halogen, CN, $C_{1-6}$haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)O$R^j$, —C(═O)N$R^jR^k$, —C(O)C(═O)$R^h$, —N$R^jR^k$, —N$R^j$C(═O)$R^h$, —N$R^j$C(═O)O$R^k$, —N$R^j$C(═O)N$R^jR^k$, —O$R^j$, —S$R^j$, —OC(═O)$R^h$, —OC(═O)N$R^jR^k$, —OC(═O)O$R^j$, —S(═O)$_2R^h$, —S(═O)$R^h$, —OS(═O)$R^h$, —OS(═O)$_2R^h$, —OS(═O)$_2$O$R^j$, —S(═O)N$R^jR^k$, —OS(═O)$_2$N$R^jR^k$, —S(═O)$_2$N$R^jR^k$; where said $C_{1-6}$ alkyl, $C_{1-6}$alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$haloalkyl, $C_{1-6}$haloalkoxy, $C_{3-6}$ cycloalkyl, N$R^jR^k$, $C_{1-6}$ alkyl, O—$C_{1-6}$ alkyl, and phenyl; and $R^{x2}$ is selected from hydroxyl, ═O, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(═O)$R^h$, —C(═O)O$R^j$, —C(O)C(═O)$R^h$, —N$R^jR^k$, —N$R^j$C(═O)O$R^k$, —SRI, —OC(═O)$R^h$, —OC(═O)N$R^jR^k$, —OC(═O)O$R^j$, —S(═O)$_2R^h$, —S(═O)$R^h$, —OS(═O)$R^h$, —OS(═O)$_2R^h$, —OS(═O)$_2$O$R^j$, —S(═O)N$R^jR^k$, —OS(═O)$_2$N$R^jR^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, ═O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, $NH(C_{1-3}$ alkyl) and $N(C_{1-3}$ alkyl$)_2$; or $R^J$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

195. A compound according to paragraph 194, or a salt or solvate thereof, selected from a compound of:

sub-formulae IVa, IVb or IVc; or sub-formulae IVd, IVe or IVf; or sub-formulae IVg, IVh or IVi.

196. A compound according to paragraph 194, or a salt or solvate thereof, selected from a compound of:

sub-formulae IVa, IVd or IVg; or sub-formulae IVb, IVe or IVh; or sub-formulae IVc, IVf or IVi.

197. A compound of paragraph 1, or a salt or solvate thereof, according to one of sub-formulae Va, Vb, Vc, Vd, Ve, Vf, Vg, Vh and Vi:

(Va)

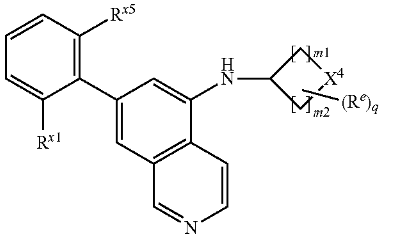

(Vb)

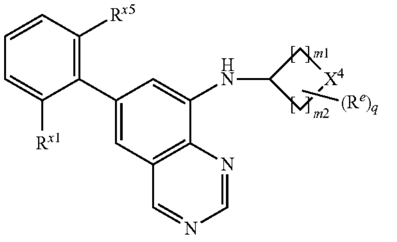

(Vc)

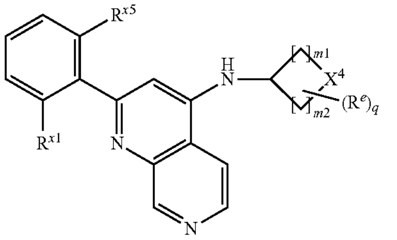

(Vd)

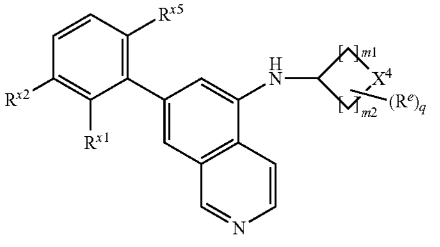

-continued (Ve)

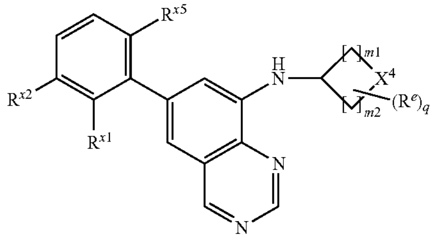

(Vf)

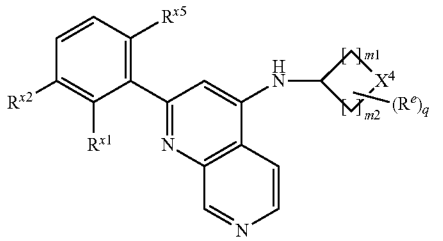

(Vg)

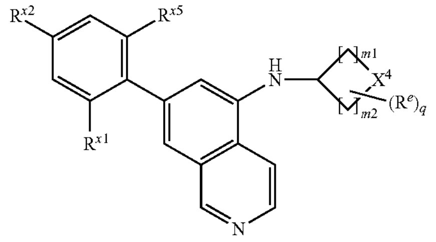

(Vh)

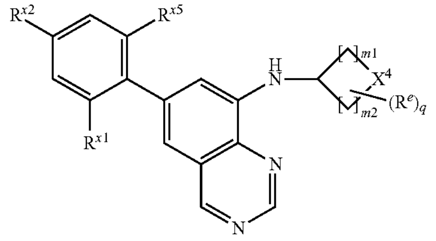

(Vi)

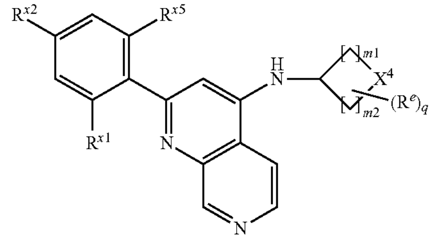

wherein $X^4$ is selected from nitrogen and CH;

m1 and m2 are numbers independently selected from 1, 2, 3 and 4;

q is a number independently selected from 1, 2 and 3;

$R^e$ is selected from hydrogen, halogen, CN, =O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

$R^{x1}$, $R^{x3}$ and $R^{x5}$ are independently selected from hydroxyl, =O, halogen, CN, $C_{1-6}$haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl $—C(=O)R^h$, $—C(=O)OR^j$, $—C(=O)NR^jR^k$, $—C(O)C(=O)R^h$, $—NR^jR^k$, $—NR^jC(=O)R^h$, $—NR^jC(=O)OR^k$, $—NR^jC(=O)NR^jR^k$, $—OR^j$, $—SR^j$, $—OC(=O)R^h$, $—OC(=O)NR^jR^k$, $—OC(=O)OR^j$, $—S(=O)_2R^h$, $—S(=O)R^h$, $—OS(=O)R^h$, $—OS(=O)_2R^h$, $—OS(=O)_2OR^j$, $—S(=O)NR^jR^k$, $—OS(=O)_2NR^jR^k$, $—S(=O)_2NR^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$haloalkoxy, $C_{3-6}$ cycloalkyl, $NR^jR^k$, $C_{1-6}$ alkyl, O—$C_{1-6}$ alkyl, and phenyl; and $R^{x2}$ is selected from hydroxyl, =O, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl $—C(=O)R^h$, $—C(=O)OR^j$, $—C(O)C(=O)R^h$, $—NR^jR^k$, $—NR^jC(=O)OR^k$, —SRI, $—OC(=O)R^h$, $—OC(=O)NR^jR^k$, $—OC(=O)OR^j$, $—S(=O)_2R^h$, $—S(=O)R^h$, $—OS(=O)R^h$, $—OS(=O)_2R^h$, $—OS(=O)_2OR^j$, $—S(=O)NR^jR^k$, $—OS(=O)_2NR^jR^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

198. A compound according to paragraph 197, or a salt or solvate thereof, selected from a compound of:
sub-formulae Va, Vb or Vc; or
sub-formulae Vd, Ve or Vf; or
sub-formulae Vg, Vh or Vi.

199. A compound according to paragraph 197, or a salt or solvate thereof, selected from a compound of:
sub-formulae Va, Vd or Vg; or
sub-formulae Vb, Ve or Vh; or
sub-formulae Vc, Vf or Vi.

200. A compound according to any one of paragraphs 165 to 199, or a salt or solvate thereof, wherein $X^4$ is nitrogen.

201. A compound according to any one of paragraphs 165 to 199, or a salt or solvate thereof, wherein $X^4$ is CH.

202. A compound according to any one of paragraphs 165 to 201, or a salt or solvate thereof, wherein m1 and m2 are independently selected from 1, 2 and 3; suitably selected from 1 and 2.

203. A compound according to any one of paragraphs 165 to 201, or a salt or solvate thereof, wherein m1 and m2 are both 2.

204. A compound according to any one of paragraphs 165 to 201, or a salt or solvate thereof, wherein one of m1 and m2 is 1 and the other is 3.

205. A compound according to any one of paragraphs 165 to 201, or a salt or solvate thereof, wherein one of m1 and m2 is 1 and the other is 4.

206. A compound according to any one of paragraphs 165 to 201, or a salt or solvate thereof, wherein one of m1 and m2 is 1 and the other is 2.

207. A compound according to any one of paragraphs 165 to 201, or a salt or solvate thereof, wherein one of m1 and m2 is 2 and the other is 3.

208. A compound according to any one of paragraphs 165 to 201, or a salt or solvate thereof, wherein m1 and m2 are both 1.

209. A compound according to paragraphs 165 to 199, or a salt or solvate thereof, wherein m1 and m2 are both 2 and $X^4$ is nitrogen.

210. A compound according to any one of paragraphs 165 to 209, or a salt or solvate thereof, wherein q is 1 or 2.

211. A compound according to any one of paragraphs 165 to 210, or a salt or solvate thereof, wherein q is 1.

212. A compound according to any one of paragraphs 165 to 211, or a salt or solvate thereof, wherein $R^e$ is selected from hydrogen, halogen, CN, =O, $(CH_2)_yOH$, $C_{1-4}$ alkyl, $(CH_2)_yC_{1-4}$ alkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

213. A compound according to any one of paragraphs 165 to 211, or a salt or solvate thereof, wherein $R^e$ is selected from hydrogen, =O, $(CH_2)_yOH$, $C_{1-4}$ alkyl, $(CH_2)_yC_{1-4}$ alkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

214. A compound according to any one of paragraphs 165 to 211, or a salt or solvate thereof, wherein $R^e$ is selected from hydrogen, =O, $(CH_2)_yOH$, $C_{1-4}$ alkyl, $(CH_2)_yNH_2$, $(CH_2)_yNHR^q$, $(CH_2)_yN(R^q)_2$, $(CH_2)_yNHCO(R^q)$ and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3.

215. A compound according to any one of paragraphs 165 to 211, or a salt or solvate thereof, wherein $R^e$ is selected from hydrogen, =O, $(CH_2)_yOH$, $C_{1-4}$ alkyl, $(CH_2)_yNH_2$, $(CH_2)_yNHR^q$, and $(CH_2)_yN(R^q)_2$, and where each $R^q$ is independently selected from $C_{1-4}$ alkyl which is optionally substituted with one or more groups selected from OH, $NH_2$, NHMe, $NMe_2$, and $C_{1-3}$ alkoxy; and where $_y$ is a number between 0 and 3.

216. A compound according to any one of paragraphs 165 to 215, or a salt or solvate thereof, wherein $_y$ is 0 or 1.

217. A compound according to any one of paragraphs 165 to 216, or a salt or solvate thereof, wherein $R^e$ is selected from hydrogen, $C_{1-4}$ alkyl, $NH_2$, NH($C_{1-4}$ alkyl), and N ($C_{1-4}$ alkyl)$_2$.

218. A compound according to any one of paragraphs 165 to 217, or a salt or solvate thereof, wherein $R^e$ is selected from hydrogen, methyl, ethyl, $NH_2$, NHMe, and $NMe_2$.

219. A compound according to any one of paragraphs 165 to 216, or a salt or solvate thereof, wherein $R^q$ is selected from methyl and ethyl which is optionally substituted with one or more groups selected from halogen, OH, $NH_2$, NHMe, $NMe_2$, and $C_{1-3}$ alkoxy.

220. A compound according to any one of paragraphs 165 to 216, or a salt or solvate thereof, wherein $R^q$ is selected from methyl or ethyl which is optionally substituted with one or more groups selected from halogen, OH and $C_{1-3}$ alkoxy.

221. A compound according to any one of paragraphs 165 to 220, or a salt or solvate thereof, wherein $R^{x1}$, $R^{x3}$ and $R^{x5}$ are independently selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-5}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^j$$R^k$, —C(O)C(=O)$R^h$, —N$R^j$$R^k$, —N$R^j$C(=O)$R^h$, —N$R^j$C(=O)O$R^k$, —N$R^j$C(=O)N$R^j$$R^k$, —O$R^j$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, OS(o)$_2$$R^h$, —OS(=O)$_2$O$R^j$, —S(=O)N$R^j$$R^k$, —OS(=O)$_2$N$R^j$$R^k$, —S(=O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

wherein $R^{2x}$ is selected from hydroxyl, =O, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{1-6}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-3}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl; and where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

222. A compound according to any one of paragraphs 165 to 220, or a salt or solvate thereof, wherein $R^{x1}$, $R^{x3}$ and $R^{x5}$ are independently selected from hydroxyl, =O, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —O$R^j$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

wherein $R^{x2}$ is selected from hydroxyl, =O, halogen, CN, $C_{1-5}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl; and where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

223. A compound according to any one of paragraphs 165 to 220, or a salt or solvate thereof, wherein $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(O)C(=O)$R^h$, —N$R^j$$R^k$, —N$R^j$C(=O)O$R^k$, —O$R^j$, —S$R^j$, —OC(=O)$R^h$, —OC(=O)N$R^j$$R^k$, —OC(=O)O$R^j$, —S(=O)$_2$$R^h$, —S(=O)$R^h$, —OS(=O)$R^h$, —OS(=O)$_2$$R^h$, —OS(=O)$_2$O$R^j$, —S(=O)N$R^j$$R^k$, —OS(=O)$_2$N$R^j$$R^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^j$$R^k$, $C_{1-6}$ alkyl, O—$C_{1-6}$ alkyl, and phenyl;

wherein $R^{x2}$ is selected from hydroxyl, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)$OR^j$, —C(O)C(=O)$R^h$, —$NR^jR^k$, —$SR^j$, —OC(=O)$R^h$, —OC(=O)$OR^j$, —S(=O)$_2R^h$, —S(=O)$R^h$, —OS(=O)$R^h$, —OS(=O)$_2R^h$, —OS(=O)$_2OR^j$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl; and where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

224. A compound according to any one of paragraphs 165 to 220, or a salt or solvate thereof, wherein $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

wherein $R^{x2}$ is selected from hydroxyl, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl; and where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN.

225. A compound according to any one of paragraphs 165 to 220, or a salt or solvate thereof, wherein $R^{x1}$, $R^{x3}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —$NR^jR^k$, —$NR^j$C(=O)$OR^k$, —$OR^j$, —$SR^j$, —OC(=O)$R^h$, —OC(=O)$NR^jR^k$, —OC(=O)$OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

wherein $R^{x2}$ is selected from hydroxyl, halogen, CN, $C_{1-6}$ haloalkyl, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl; and where each $R^h$, $R^j$ and $R^K$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, NH($C_{1-3}$ alkyl) and N($C_{1-3}$ alkyl)$_2$; or $R^j$ and $R^K$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$alkoxy.

226. A compound according to any one of paragraphs 165 to 220, or a salt or solvate thereof, wherein $R^{x1}$ and $R^{x5}$ are independently selected from hydroxyl, halogen, CN, $C_{1-6}$ haloalkyl, $C_{1-6}$ haloalkoxy, $C_{1-6}$ alkyl and $C_{1-6}$ alkoxy.

227. A compound according to any one of paragraphs 165 to 220, or a salt or solvate thereof, wherein $R^{x1}$ and $R^{x5}$ are independently selected from halogen, CN, $C_{1-6}$ haloalkyl, $C_{1-6}$ haloalkoxy, $C_{1-6}$ alkyl and $C_{1-6}$ alkoxy.

228. A compound according to any one of paragraphs 165 to 220, or a salt or solvate thereof, wherein $R^{x1}$ and $R^{x5}$ are independently selected from halogen, CN, $C_{1-6}$ alkyl and $C_{1-6}$ alkoxy.

229. A compound according to any one of paragraphs 165 to 220, or a salt or solvate thereof, wherein $R^{x1}$ and $R^{x5}$ are independently selected from halogen and $C_{1-6}$ alkyl.

230. A compound according to any one of paragraphs 165 to 220, or a salt or solvate thereof, wherein $R^{x1}$ and $R^{x5}$ are independently selected from fluoro, chloro and methyl.

231. A compound, or a salt or solvate thereof, selected from:

| Example | Structure | Name |
|---|---|---|
| E1 | 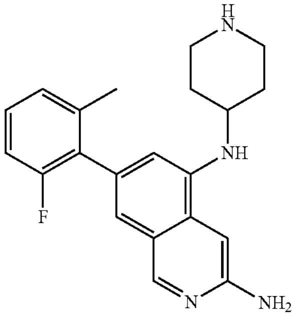 [SMILES: Cc1cccc(F)c1-c1cc(NC2CCNCC2)c2cc(N)ncc2c1] | 7-(2-fluoro-6-methyl-phenyl)-N5-(4-piperidyl)isoquinoline-3,5-diamine |
| E2 | 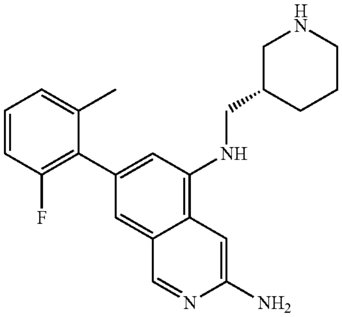 [SMILES: Cc1cccc(F)c1-c1cc(NC[C@H]2CCCNC2)c2cc(N)ncc2c1] | 7-(2-fluoro-6-methyl-phenyl)-N5-[[(3S)-3-piperidyl]methyl]isoquinoline-3,5-diamine |
| E3 | 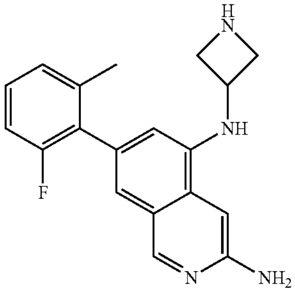 [SMILES: Cc1cccc(F)c1-c1cc(NC2CNC2)c2cc(N)ncc2c1] | N5-(azetidin-3-yl)-7-(2-fluoro-6-methyl-phenyl)isoquinoline-3,5-diamine |
| E4 | 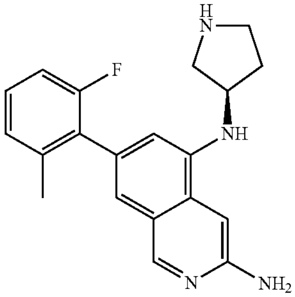 [SMILES: Cc1cccc(F)c1-c1cc(N[C@@H]2CCNC2)c2cc(N)ncc2c1] | 7-(2-fluoro-6-methyl-phenyl)-N5-[(3R)-pyrrolidin-3-yl]isoquinoline-3,5-diamine |
| E5 | 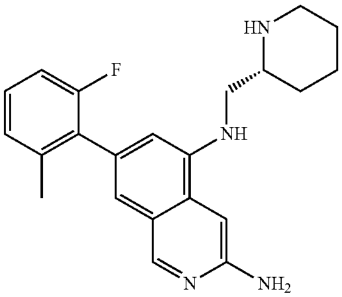 [SMILES: Cc1cccc(F)c1-c1cc(NC[C@H]2CCCCN2)c2cc(N)ncc2c1] | 7-(2-fluoro-6-methyl-phenyl)-N5-[[(2R)-2-piperidyl]methyl]isoquinoline-3,5-diamine |

-continued

| Example | Structure | Name |
|---|---|---|
| E6 | 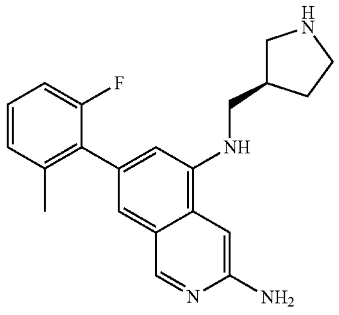 [SMILES: Cc1cccc(F)c1-c1cc(NC[C@@H]2CCNC2)c2cc(N)ncc2c1] | 7-(2-fluoro-6-methyl-phenyl)-N5-[[(3R)-pyrrolidin-3-yl]methyl]isoquinoline-3,5-diamine |
| E7 | 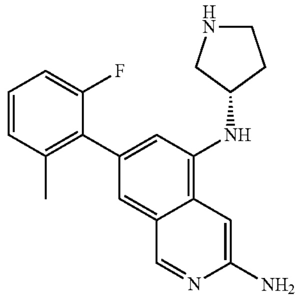 [SMILES: Cc1cccc(F)c1-c1cc(N[C@H]2CCNC2)c2cc(N)ncc2c1] | 7-(2-fluoro-6-methyl-phenyl)-N5-[(3S)-pyrrolidin-3-yl]isoquinoline-3,5-diamine |
| E8 | 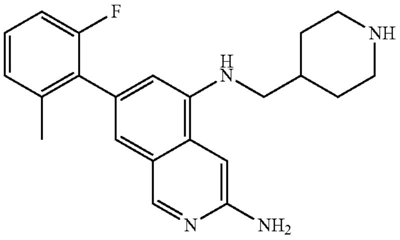 | 7-(2-fluoro-6-methyl-phenyl)-N5-(4-piperidylmethyl)isoquinoline-3,5-diamine |
| E9 | 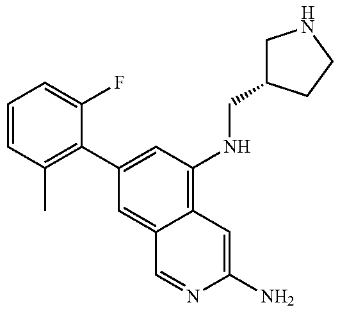 [SMILES: Cc1cccc(F)c1-c1cc(NC[C@H]2CCNC2)c2cc(N)ncc2c1] | 7-(2-fluoro-6-methyl-phenyl)-N5-[[(3S)-pyrrolidin-3-yl]methyl]isoquinoline-3,5-diamine |
| E10 | 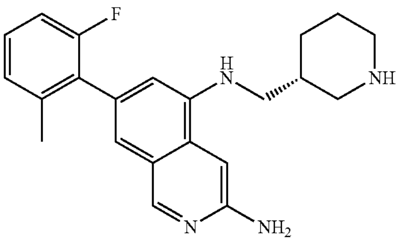 [SMILES: Cc1cccc(F)c1-c1cc(NC[C@@H]2CCCNC2)c2cc(N)ncc2c1] | 7-(2-fluoro-6-methyl-phenyl)-N5-[[(3R)-3-piperidyl]methyl]isoquinoline-3,5-diamine |

-continued

| Example | Structure | Name |
|---|---|---|
| E11 | 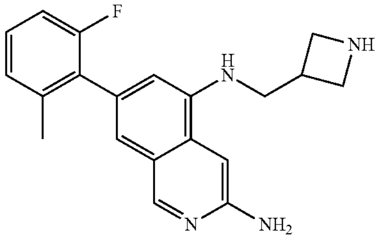 [SMILES: Cc1cccc(F)c1-c1cc(NCC2CNC2)c2cc(N)ncc2c1] | N5-(azetidin-3-ylmethyl)-7-(2-fluoro-6-methyl-phenyl)isoquinoline-3,5-diamine |
| E12 | 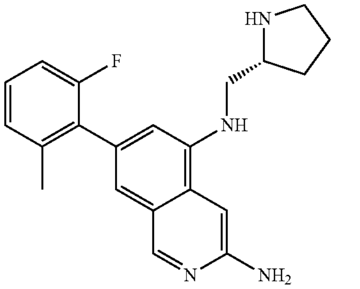 [SMILES: Cc1cccc(F)c1-c1cc(NC[C@H]2CCCN2)c2cc(N)ncc2c1] | 7-(2-fluoro-6-methyl-phenyl)-N5-[[(2R)-pyrrolidin-2-yl]methyl]isoquinoline-3,5-diamine |
| E13 | 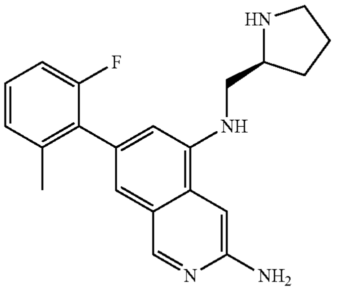 [SMILES: Cc1cccc(F)c1-c1cc(NC[C@@H]2CCCN2)c2cc(N)ncc2c1] | 7-(2-fluoro-6-methyl-phenyl)-N5-[[(2S)-pyrrolidin-2-yl]methyl]isoquinoline-3,5-diamine |
| E14 | 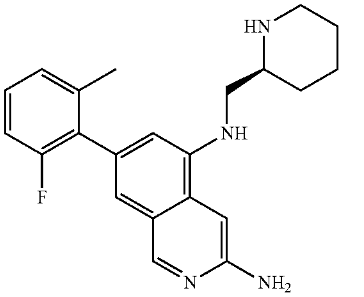 [SMILES: Cc1cccc(F)c1-c1cc(NC[C@@H]2CCCCN2)c2cc(N)ncc2c1] | 7-(2-fluoro-6-methyl-phenyl)-N5-[[(2S)-2-piperidyl]methyl]isoquinoline-3,5-diamine |
| E15 | 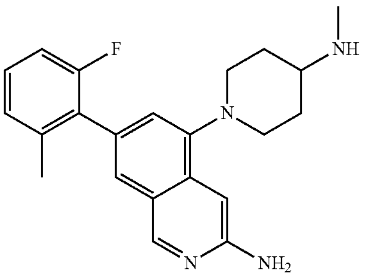 [SMILES: CNC1CCN(c2cc(-c3c(C)cccc3F)cc3cnc(N)cc23)CC1] | 7-(2-fluoro-6-methyl-phenyl)-5-[4-(methylamino)-1-piperidyl]isoquinolin-3-amine |

-continued
| Example | Structure | Name |
|---|---|---|
| E16 | 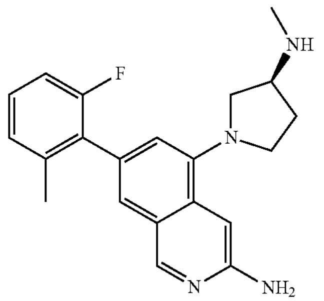 [SMILES: CN[C@H]1CCN(c2cc(-c3c(C)cccc3F)cc3cnc(N)cc23)C1] | 7-(2-fluoro-6-methyl-phenyl)-5-[(3S)-3-(methylamino)pyrrolidin-1-yl]isoquinolin-3-amine |
| E17 | 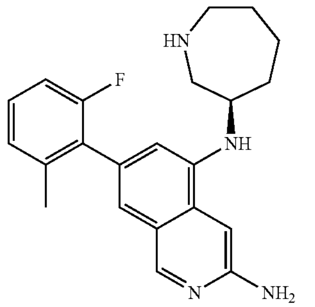 [SMILES: Cc1cccc(F)c1-c1cc(N[C@@H]2CCCCNC2)c2cc(N)ncc2c1] | N5-[(3R)-azepan-3-yl]-7-(2-fluoro-6-methyl-phenyl)isoquinoline-3,5-diamine |
| E18 | 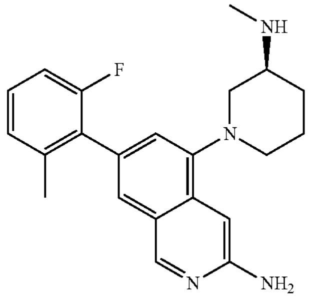 [SMILES: CN[C@H]1CCCN(c2cc(-c3c(C)cccc3F)cc3cnc(N)cc23)C1] | 7-(2-fluoro-6-methyl-phenyl)-5-[(3S)-3-(methylamino)-1-piperidyl]isoquinolin-3-amine |
| E19 | 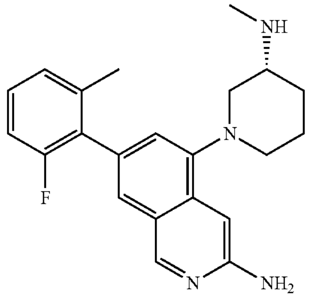 [SMILES: CN[C@@H]1CCCN(c2cc(-c3c(C)cccc3F)cc3cnc(N)cc23)C1] | 7-(2-fluoro-6-methyl-phenyl)-5-[(3R)-3-(methylamino)-1-piperidyl]isoquinolin-3-amine |
| E20 | 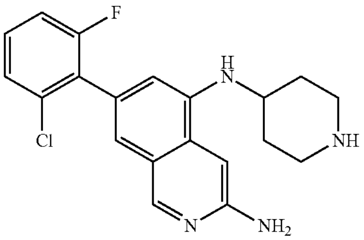 [SMILES: Nc1cc2c(NC3CCNCC3)cc(-c3c(F)cccc3Cl)cc2cn1] | 7-(2-chloro-6-fluoro-phenyl)-N5-(4-piperidyl)isoquinoline-3,5-diamine |

-continued

| Example | Structure | Name |
|---|---|---|
| E21 | 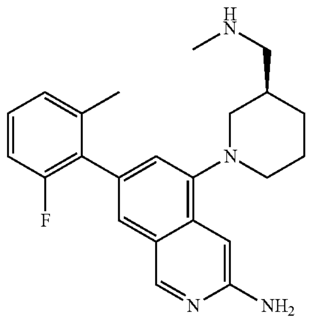 [SMILES: CNC[C@H]1CCCN(c2cc(-c3c(C)cccc3F)cc3cnc(N)cc23)C1] | 7-(2-fluoro-6-methyl-phenyl)-5-[(3R)-3-(methylaminomethyl)-1-piperidyl]isoquinolin-3-amine |
| E22 | 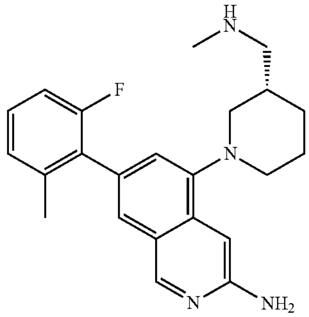 [SMILES: CNC[C@@H]1CCCN(c2cc(-c3c(C)cccc3F)cc3cnc(N)cc23)C1] | 7-(2-fluoro-6-methyl-phenyl)-5-[(3S)-3-(methylaminomethyl)-1-piperidyl]isoquinolin-3-amine |
| E23 | 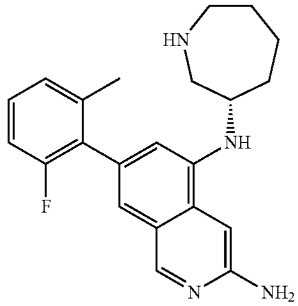 [SMILES: Cc1cccc(F)c1-c1cc(N[C@H]2CCCCNC2)c2cc(N)ncc2c1] | N5-[(3S)-azepan-3-yl]-7-(2-fluoro-6-methyl-phenyl)isoquinoline-3,5-diamine |
| E24 | 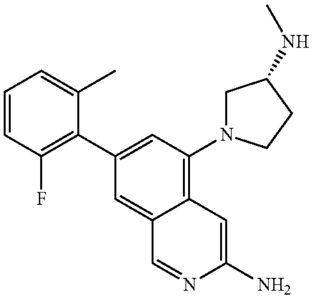 [SMILES: CN[C@@H]1CCN(c2cc(-c3c(C)cccc3F)cc3cnc(N)cc23)C1] | 7-(2-fluoro-6-methyl-phenyl)-5-[(3R)-3-(methylamino)pyrrolidin-1-yl]isoquinolin-3-amine |
| E25 | 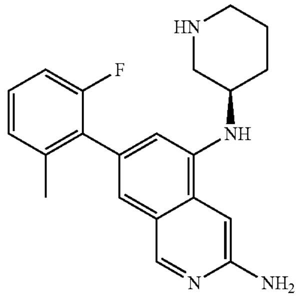 [SMILES: Cc1cccc(F)c1-c1cc(N[C@@H]2CCCNC2)c2cc(N)ncc2c1] | 7-(2-fluoro-6-methyl-phenyl)-N5-[(3R)-3-piperidyl]isoquinoline-3,5-diamine |

-continued
| Example | Structure | Name |
|---|---|---|
| E26 | 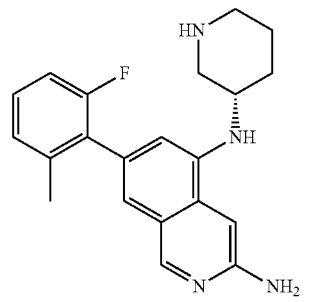 [SMILES: Cc1cccc(F)c1-c1cc(N[C@H]2CCCNC2)c2cc(N)ncc2c1] | 7-(2-fluoro-6-methyl-phenyl)-N5-[(3S)-3-piperidyl]isoquinoline-3,5-diamine |
| E27 | 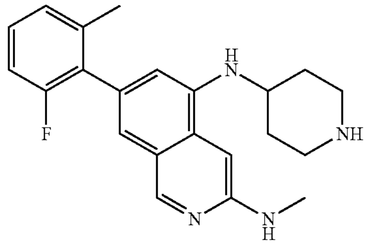 | 7-(2-fluoro-6-methyl-phenyl)-N3-methyl-N5-(4-piperidyl)isoquinoline-3,5-diamine |
| E28 | 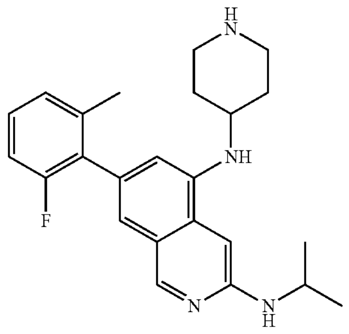 [SMILES: Cc1cccc(F)c1-c1cc(NC2CCNCC2)c2cc(NC(C)C)ncc2c1] | 7-(2-fluoro-6-methyl-phenyl)-N3-isopropyl-N5-(4-piperidyl)isoquinoline-3,5-diamine |
| E29 | 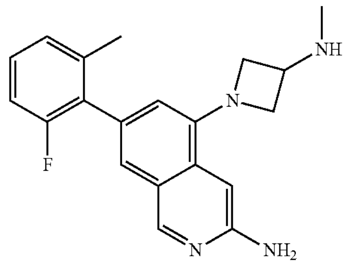 [SMILES: CNC1CN(c2cc(-c3c(C)cccc3F)cc3cnc(N)cc23)C1] | 7-(2-fluoro-6-methyl-phenyl)-5-[3-(methylamino)azetidin-1-yl]isoquinolin-3-amine |
| E30 | 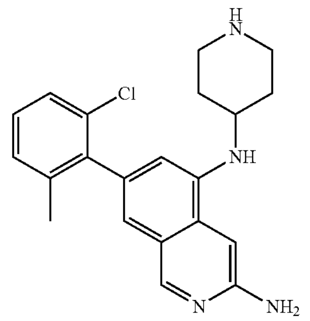 [SMILES: Cc1cccc(Cl)c1-c1cc(NC2CCNCC2)c2cc(N)ncc2c1] | 7-(2-chloro-6-methyl-phenyl)-N5-(4-piperidyl)isoquinoline-3,5-diamine |

-continued

| Example | Structure | Name |
|---|---|---|
| E31 | 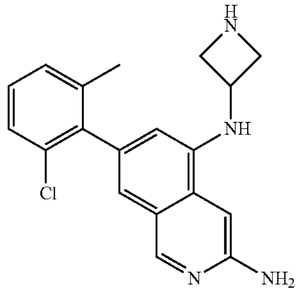 [SMILES: Cc1cccc(Cl)c1-c1cc(NC2CNC2)c2cc(N)ncc2c1] | N5-(azetidin-3-yl)-7-(2-chloro-6-methyl-phenyl)isoquinoline-3,5-diamine |
| E32 | 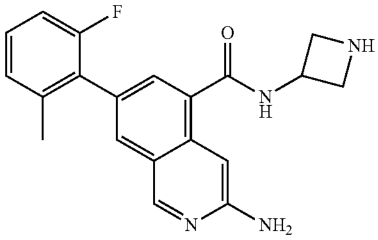 [SMILES: Cc1cccc(F)c1-c1cc(C(=O)NC2CNC2)c2cc(N)ncc2c1] | 3-amino-N-(azetidin-3-yl)-7-(2-fluoro-6-methyl-phenyl)isoquinoline-4-carboxamide |
| E33 | 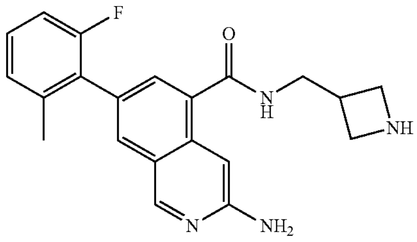 [SMILES: Cc1cccc(F)c1-c1cc(C(=O)NCC2CNC2)c2cc(N)ncc2c1] | 3-amino-N-(azetidin-3-ylmethyl)-7-(2-fluoro-6-methyl-phenyl)isoquinoline-4-carboxamide |
| E34 | 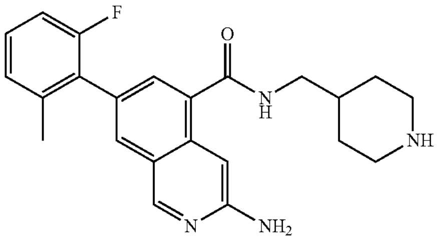 [SMILES: Cc1cccc(F)c1-c1cc(C(=O)NCC2CCNCC2)c2cc(N)ncc2c1] | 3-amino-7-(2-fluoro-6-methyl-phenyl)-N-(4-piperidylmethyl)isoquinoline-4-carboxamide |
| E35 | 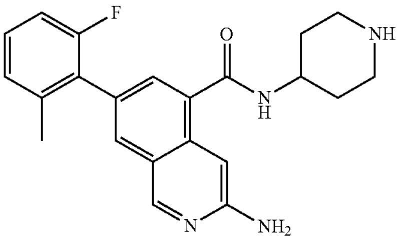 [SMILES: Cc1cccc(F)c1-c1cc(C(=O)NC2CCNCC2)c2cc(N)ncc2c1] | 3-amino-7-(2-fluoro-6-methyl-phenyl)-N-(4-piperidyl)isoquinoline-4-carboxamide |
| E36 | 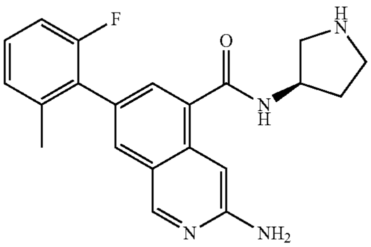 [SMILES: Cc1cccc(F)c1-c1cc(C(=O)N[C@@H]2CCNC2)c2cc(N)ncc2c1] | 3-amino-7-(2-fluoro-6-methyl-phenyl)-N-[(3R)-pyrrolidin-3-yl]isoquinoline-4-carboxamide |

-continued

| Example | Structure | Name |
|---|---|---|
| E37 | 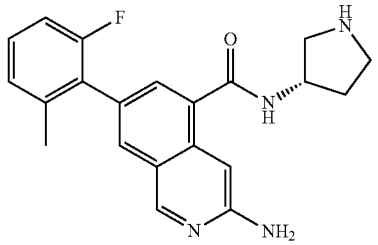 [SMILES: Cc1cccc(F)c1-c1cc(C(=O)N[C@H]2CCNC2)c2cc(N)ncc2c1] | 3-amino-7-(2-fluoro-6-methyl-phenyl)-N-[(3S)-pyrrolidin-3-yl]isoquinoline-4-carboxamide |
| E38 | 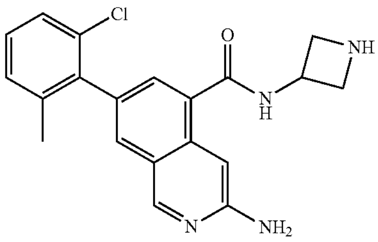 [SMILES: Cc1cccc(Cl)c1-c1cc(C(=O)NC2CNC2)c2cc(N)ncc2c1] | 3-amino-N-(azetidin-3-yl)-7-(2-chloro-6-methyl-phenyl)isoquinoline-4-carboxamide |
| E39 | 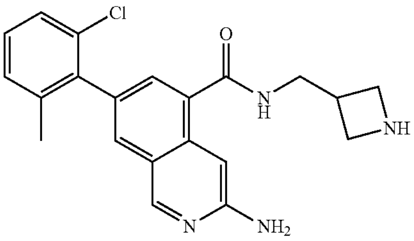 [SMILES: Cc1cccc(Cl)c1-c1cc(C(=O)NCC2CNC2)c2cc(N)ncc2c1] | 3-amino-N-(azetidin-3-ylmethyl)-7-(2-chloro-6-methyl-phenyl)isoquinoline-4-carboxamide |
| E40 | 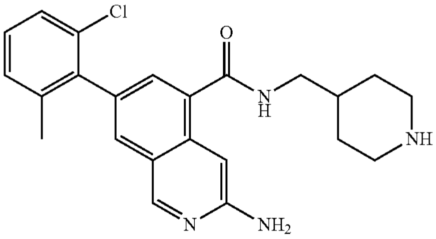 [SMILES: Cc1cccc(Cl)c1-c1cc(C(=O)NCC2CCNCC2)c2cc(N)ncc2c1] | 3-amino-7-(2-chloro-6-methyl-phenyl)-N-(4-piperidylmethyl)isoquinoline-4-carboxamide |
| E41 | 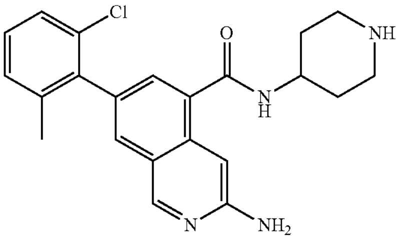 [SMILES: Cc1cccc(Cl)c1-c1cc(C(=O)NC2CCNCC2)c2cc(N)ncc2c1] | 3-amino-7-(2-chloro-6-methyl-phenyl)-N-(4-piperidyl)isoquinoline-4-carboxamide |
| E42 | 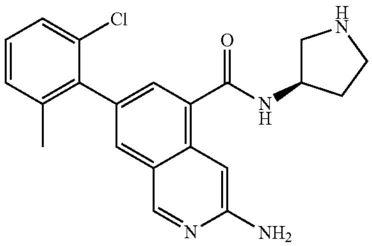 [SMILES: Cc1cccc(Cl)c1-c1cc(C(=O)N[C@@H]2CCNC2)c2cc(N)ncc2c1] | 3-amino-7-(2-chloro-6-methyl-phenyl)-N-[(3R)-pyrrolidin-3-yl]isoquinoline-4-carboxamide |

-continued

| Example | Structure | Name |
| --- | --- | --- |
| E43 | 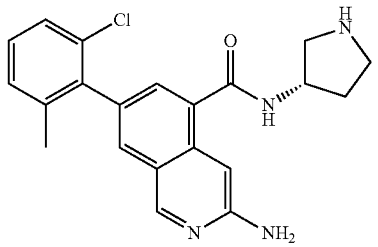 [SMILES: Cc1cccc(Cl)c1-c1cc(C(=O)N[C@H]2CCNC2)c2cc(N)ncc2c1] | 3-amino-7-(2-chloro-6-methyl-phenyl)-N-[(3S)-pyrrolidin-3-yl]isoquinoline-4-carboxamide |
| E44 | 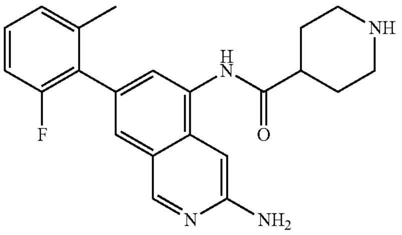 [SMILES: Cc1cccc(F)c1-c1cc(NC(=O)C2CCNCC2)c2cc(N)ncc2c1] | N-[3-amino-7-(2-fluoro-6-methyl-phenyl)-5-isoquinolyl]piperidine-4-carboxamide |
| E45 | 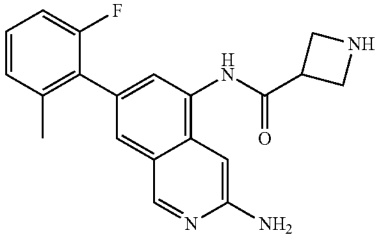 [SMILES: Cc1cccc(F)c1-c1cc(NC(=O)C2CNC2)c2cc(N)ncc2c1] | N-[3-amino-7-(2-fluoro-6-methyl-phenyl)-5-isoquinolyl]azetidine-3-carboxamide |
| E46 | 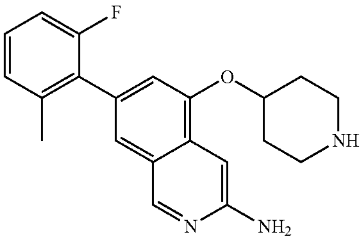 [SMILES: Cc1cccc(F)c1-c1cc(OC2CCNCC2)c2cc(N)ncc2c1] | 7-(2-fluoro-6-methyl-phenyl)-5-(4-piperidyloxy)isoquinolin-3-amine |
| E47 | 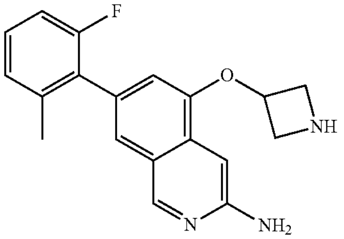 [SMILES: Cc1cccc(F)c1-c1cc(OC2CNC2)c2cc(N)ncc2c1] | 5-(azetidin-3-yloxy)-7-(2-fluoro-6-methyl-phenyl)isoquinolin-3-amine |
| E48 | 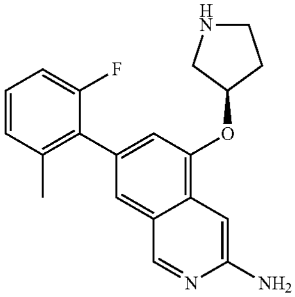 [SMILES: Cc1cccc(F)c1-c1cc(O[C@@H]2CCNC2)c2cc(N)ncc2c1] | 7-(2-fluoro-6-methyl-phenyl)-5-[(3R)-pyrrolidin-3-yl]oxy-isoquinolin-3-amine |

-continued
| Example | Structure | Name |
|---|---|---|
| E49 | 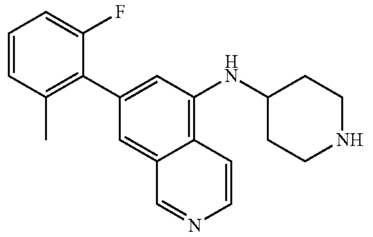 [SMILES: Cc1cccc(F)c1-c1cc(NC2CCNCC2)c2ccncc2c1] | 7-(2-fluoro-6-methyl-phenyl)-N-(4-piperidyl)isoquinolin-5-amine |
| E50 | 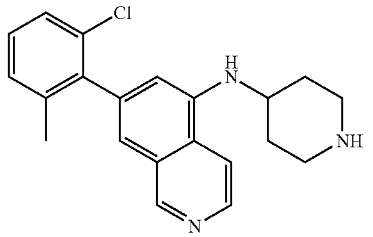 | 7-(2-chloro-6-methyl-phenyl)-N-(4-piperidyl)isoquinolin-5-amine |
| E51 | 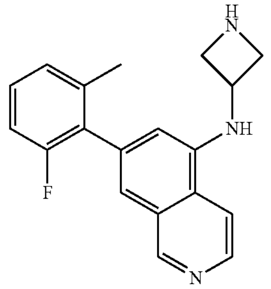 [SMILES: Cc1cccc(F)c1-c1cc(NC2CNC2)c2ccncc2c1] | N-(azetidin-3-yl)-7-(2-fluoro-6-methyl-phenyl)isoquinolin-5-amine |
| E52 | 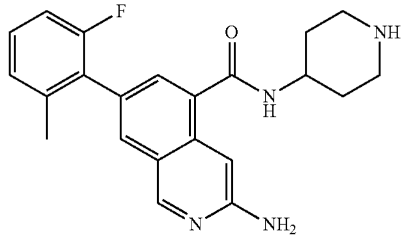 [SMILES: Cc1cccc(F)c1-c1cc(C(=O)NC2CCNCC2)c2cc(N)ncc2c1] | 3-amino-7-(2-fluoro-6-methyl-phenyl)-N-(4-piperidyl)isoquinoline-5-carboxamide |
| E53 | 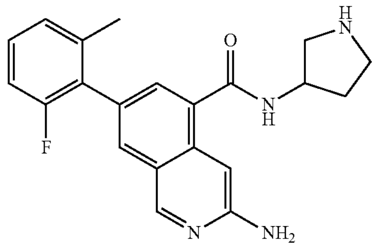 [SMILES: Cc1cccc(F)c1-c1cc(C(=O)NC2CCNC2)c2cc(N)ncc2c1] | 3-amino-7-(2-fluoro-6-methyl-phenyl)-N-pyrrolidin-3-yl-isoquinoline-5-carboxamide |

-continued

| Example | Structure | Name |
| --- | --- | --- |
| E54 | 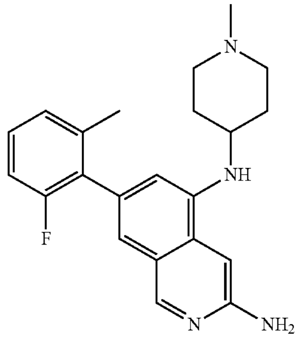 [SMILES: Cc1cccc(F)c1-c1cc(NC2CCN(C)CC2)c2cc(N)ncc2c1] | 7-(2-fluoro-6-methyl-phenyl)-N5-(1-methyl-4-piperidyl)isoquinoline-3,5-diamine |
| E55 | 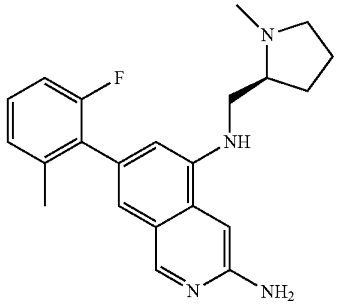 [SMILES: Cc1cccc(F)c1-c1cc(NC[C@@H]2CCCN2C)c2cc(N)ncc2c1] | 7-(2-fluoro-6-methyl-phenyl)-N5-[[(2S)-1-methylpyrrolidin-2-yl]methyl]isoquinoline-3,5-diamine |
| E56 | 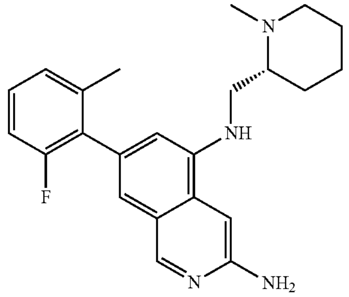 [SMILES: Cc1cccc(F)c1-c1cc(NC[C@H]2CCCCN2C)c2cc(N)ncc2c1] | 7-(2-fluoro-6-methyl-phenyl)-N5-[[(2R)-1-methyl-2-piperidyl]methyl]isoquinoline-3,5-diamine |
| E57 | 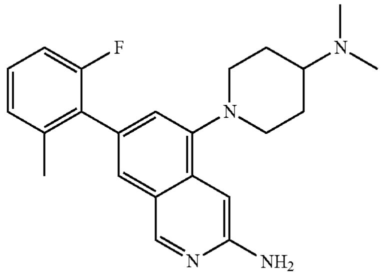 [SMILES: Cc1cccc(F)c1-c1cc(N2CCC(N(C)C)CC2)c2cc(N)ncc2c1] | 5-[4-(dimethylamino)-1-piperidyl]-7-(2-fluoro-6-methyl-phenyl)isoquinolin-3-amine |
| E58 | 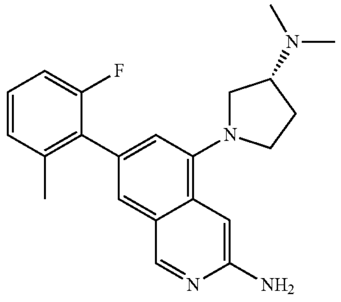 [SMILES: Cc1cccc(F)c1-c1cc(N2CC[C@@H](N(C)C)C2)c2cc(N)ncc2c1] | 5-[(3R)-3-(dimethylamino)pyrrolidin-1-yl]-7-(2-fluoro-6-methyl-phenyl)isoquinolin-3-amine |

-continued

| Example | Structure | Name |
|---|---|---|
| E59 | 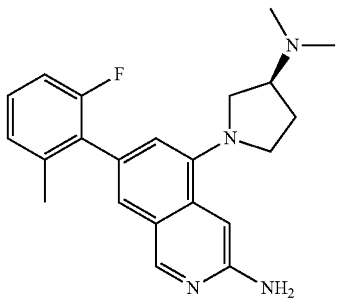 [SMILES: Cc1cccc(F)c1-c1cc(N2CC[C@H](N(C)C)C2)c2cc(N)ncc2c1] | 5-[(3S)-3-(dimethylamino)pyrrolidin-1-yl]-7-(2-fluoro-6-methyl-phenyl)isoquinolin-3-amine |
| E60 | 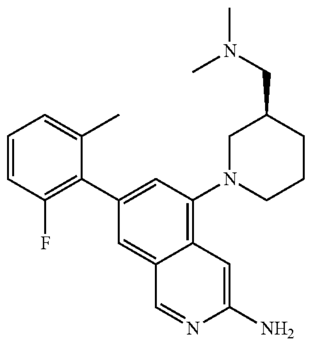 [SMILES: Cc1cccc(F)c1-c1cc(N2CCC[C@H](CN(C)C)C2)c2cc(N)ncc2c1] | 5-[(3R)-3-[(dimethylamino)methyl]-1-piperidyl]-7-(2-fluoro-6-methyl-phenyl)isoquinolin-3-amine |
| E61 | 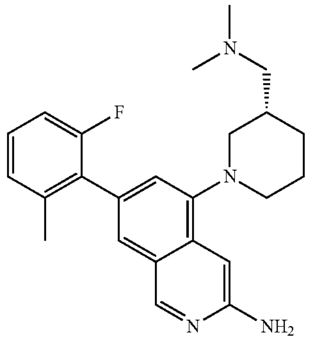 [SMILES: Cc1cccc(F)c1-c1cc(N2CCC[C@@H](CN(C)C)C2)c2cc(N)ncc2c1] | 5-[(3S)-3-[(dimethylamino)methyl]-1-piperidyl]-7-(2-fluoro-6-methyl-phenyl)isoquinolin-3-amine |
| E62 | 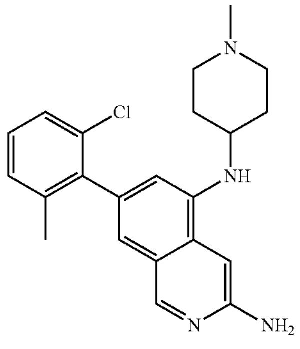 [SMILES: Cc1cccc(Cl)c1-c1cc(NC2CCN(C)CC2)c2cc(N)ncc2c1] | 7-(2-chloro-6-methyl-phenyl)-N5-(1-methyl-4-piperidyl)isoquinoline-3,5-diamine |
| E63 | 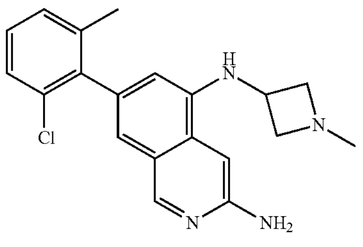 [SMILES: Cc1cccc(Cl)c1-c1cc(NC2CN(C)C2)c2cc(N)ncc2c1] | 7-(2-chloro-6-methyl-phenyl)-N5-(1-methylazetidin-3-yl)isoquinoline-3,5-diamine |

-continued
| Example | Structure | Name |
|---|---|---|
| E64 | 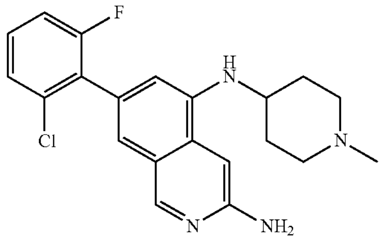 [SMILES: CN1CCC(Nc2cc(-c3c(F)cccc3Cl)cc3cnc(N)cc23)CC1] | 7-(2-chloro-6-fluoro-phenyl)-N5-(1-methyl-4-piperidyl)isoquinoline-3,5-diamine |
| E65 | 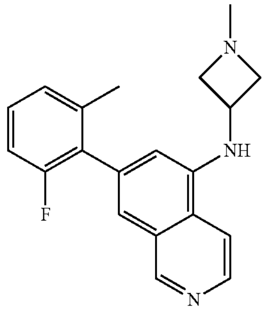 [SMILES: Cc1cccc(F)c1-c1cc(NC2CN(C)C2)c2ccncc2c1] | 7-(2-fluoro-6-methyl-phenyl)-N-(1-methylazetidin-3-yl)isoquinolin-5-amine |
| E66 | 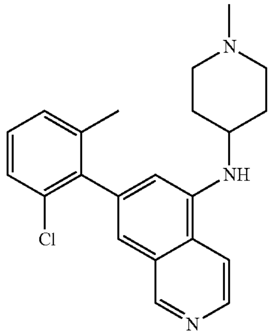 | 7-(2-chloro-6-methyl-phenyl)-N-(1-methyl-4-piperidyl)isoquinolin-5-amine |
| E67 | 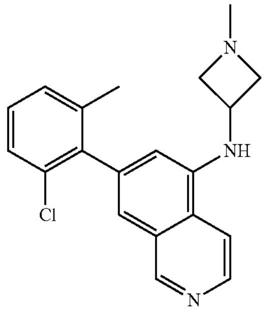 [SMILES: Cc1cccc(Cl)c1-c1cc(NC2CN(C)C2)c2ccncc2c1] | 7-(2-chloro-6-methyl-phenyl)-N-(1-methylazetidin-3-yl)isoquinolin-5-amine |
| E68 | 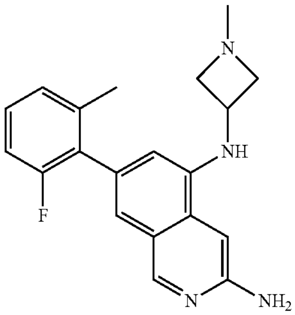 [SMILES: Cc1cccc(F)c1-c1cc(NC2CN(C)C2)c2cc(N)ncc2c1] | 7-(2-fluoro-6-methyl-phenyl)-N5-(1-methylazetidin-3-yl)isoquinoline-3,5-diamine |

-continued

| Example | Structure | Name |
| --- | --- | --- |
| E69 | 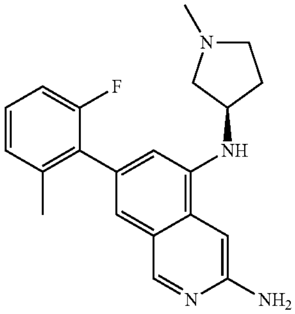 [SMILES: Cc1cccc(F)c1-c1cc(N[C@@H]2CCN(C)C2)c2cc(N)ncc2c1] | 7-(2-fluoro-6-methyl-phenyl)-N5-[(3R)-1-methylpyrrolidin-3-yl]isoquinoline-3,5-diamine |
| E70 | 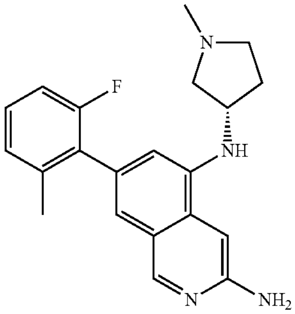 [SMILES: Cc1cccc(F)c1-c1cc(N[C@H]2CCN(C)C2)c2cc(N)ncc2c1] | 7-(2-fluoro-6-methyl-phenyl)-N5-[(3S)-1-methylpyrrolidin-3-yl]isoquinoline-3,5-diamine |
| E71 | 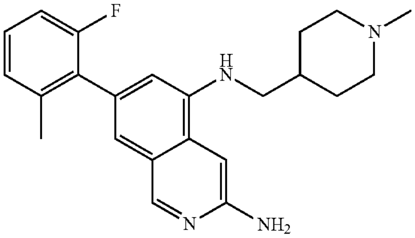 [SMILES: Cc1cccc(F)c1-c1cc(NCC2CCN(C)CC2)c2cc(N)ncc2c1] | 7-(2-fluoro-6-methyl-phenyl)-N5-[(1-methyl-4-piperidyl)methyl]isoquinoline-3,5-diamine |
| E72 | 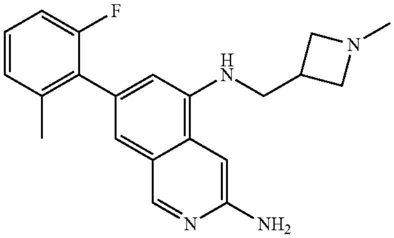 [SMILES: Cc1cccc(F)c1-c1cc(NCC2CN(C)C2)c2cc(N)ncc2c1] | 7-(2-fluoro-6-methyl-phenyl)-N5-[(1-methylazetidin-3-yl)methyl]isoquinoline-3,5-diamine |
| E73 | 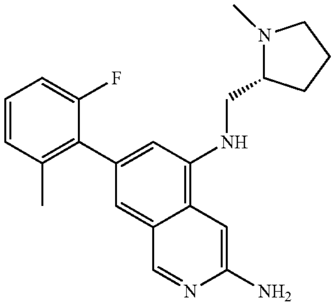 [SMILES: Cc1cccc(F)c1-c1cc(NC[C@H]2CCCN2C)c2cc(N)ncc2c1] | 7-(2-fluoro-6-methyl-phenyl)-N5-[[(2R)-1-methylpyrrolidin-2-yl]methyl]isoquinoline-3,5-diamine |

-continued
| Example | Structure | Name |
|---|---|---|
| E74 | 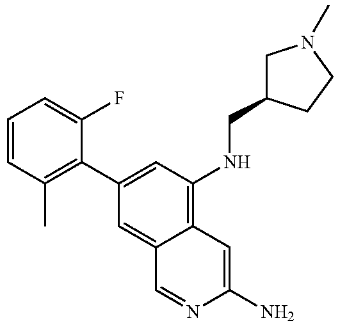 [SMILES: Cc1cccc(F)c1-c1cc(NC[C@@H]2CCN(C)C2)c2cc(N)ncc2c1] | 7-(2-fluoro-6-methyl-phenyl)-N5-[[(3S)-1-methylpyrrolidin-3-yl]methyl]isoquinoline-3,5-diamine |
| E75 | 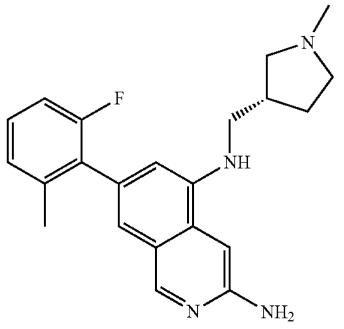 [SMILES: Cc1cccc(F)c1-c1cc(NC[C@H]2CCN(C)C2)c2cc(N)ncc2c1] | 7-(2-fluoro-6-methyl-phenyl)-N5-[[(3 R)-1-methylpyrrolidin-3-yl]methyl]isoquinoline-3,5-diamine |
| E76 | 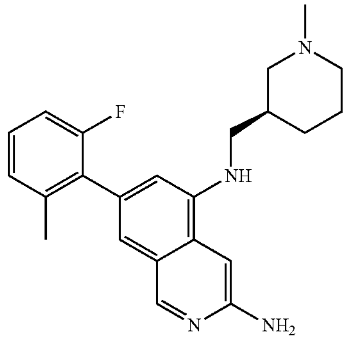 [SMILES: Cc1cccc(F)c1-c1cc(NC[C@@H]2CCCN(C)C2)c2cc(N)ncc2c1] | 7-(2-fluoro-6-methyl-phenyl)-N5-[[(3S)-1-methyl-3-piperidyl]methyl]isoquinoline-3,5-diamine |
| E77 | 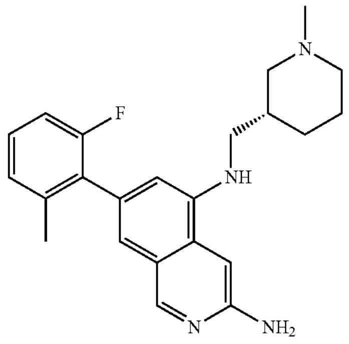 [SMILES: Cc1cccc(F)c1-c1cc(NC[C@H]2CCCN(C)C2)c2cc(N)ncc2c1] | 7-(2-fluoro-6-methyl-phenyl)-N5-[[(3R)-1-methyl-3-piperidyl]methyl]isoquinoline-3,5-diamine |

-continued

| Example | Structure | Name |
| --- | --- | --- |
| E78 | 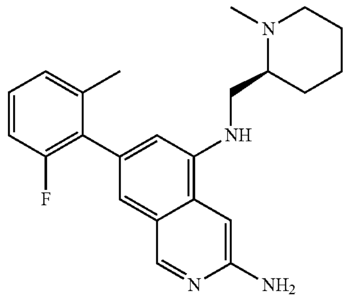 [SMILES: Cc1cccc(F)c1-c1cc(NC[C@@H]2CCCCN2C)c2cc(N)ncc2c1] | 7-(2-fluoro-6-methyl-phenyl)-N5-[[(2S)-1-methyl-2-piperidyl]methyl]isoquinoline-3,5-diamine |
| E79 | 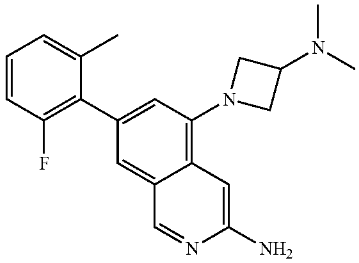 [SMILES: Cc1cccc(F)c1-c1cc(N2CC(N(C)C)C2)c2cc(N)ncc2c1] | 5-[3-(dimethylamino)azetidin-1-yl]-7-(2-fluoro-6-methyl-phenyl)isoquinolin-3-amine |
| E80 | 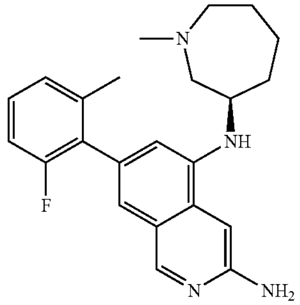 [SMILES: Cc1cccc(F)c1-c1cc(N[C@@H]2CCCCN(C)C2)c2cc(N)ncc2c1] | 7-(2-fluoro-6-methyl-phenyl)-N5-[(3R)-1-methylazepan-3-yl]isoquinoline-3,5-diamine |
| E81 | 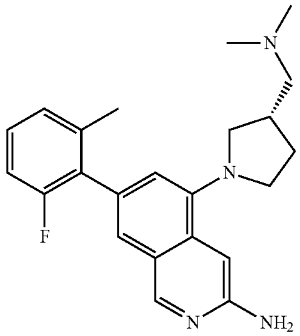 [SMILES: Cc1cccc(F)c1-c1cc(N2CC[C@@H](CN(C)C)C2)c2cc(N)ncc2c1] | 5-[(3S)-3-[(dimethylamino)methyl]pyrrolidin-1-yl]-7-(2-fluoro-6-methyl-phenyl)isoquinolin-3-amine |
| E82 | 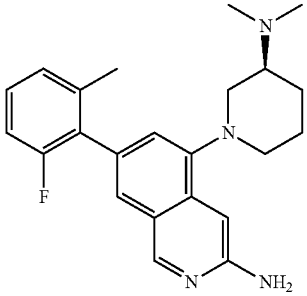 [SMILES: Cc1cccc(F)c1-c1cc(N2CCC[C@H](N(C)C)C2)c2cc(N)ncc2c1] | 5-[(3S)-3-(dimethylamino)-1-piperidyl]-7-(2-fluoro-6-methyl-phenyl)isoquinolin-3-amine |

-continued

| Example | Structure | Name |
|---|---|---|
| E83 | 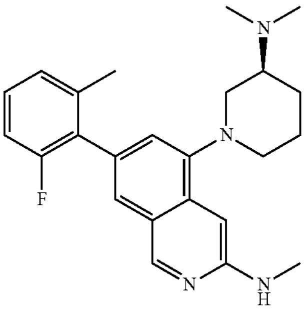 [SMILES: CNc1cc2c(N3CCC[C@H](N(C)C)C3)cc(-c3c(C)cccc3F)cc2cn1] | 5-[(3S)-3-(dimethylamino)-1-piperidyl]-7-(2-fluoro-6-methyl-phenyl)-N-methyl-isoquinolin-3-amine |
| E84 | 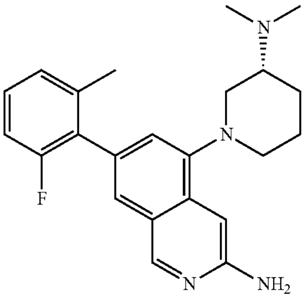 [SMILES: Cc1cccc(F)c1-c1cc(N2CCC[C@@H](N(C)C)C2)c2cc(N)ncc2c1] | 5-[(3R)-3-(dimethylamino)-1-piperidyl]-7-(2-fluoro-6-methyl-phenyl)isoquinolin-3-amine |
| E85 | 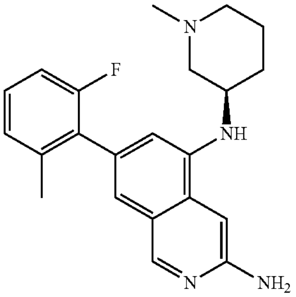 [SMILES: Cc1cccc(F)c1-c1cc(N[C@@H]2CCCN(C)C2)c2cc(N)ncc2c1] | 7-(2-fluoro-6-methyl-phenyl)-N5-[(3R)-1-methyl-3-piperidyl]isoquinoline-3,5-diamine |
| E86 | 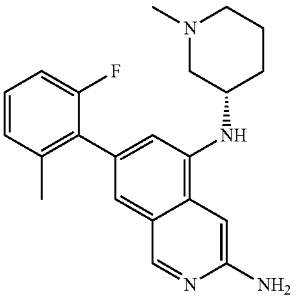 [SMILES: Cc1cccc(F)c1-c1cc(N[C@H]2CCCN(C)C2)c2cc(N)ncc2c1] | 7-(2-fluoro-6-methyl-phenyl)-N5-[(3S)-1-methyl-3-piperidyl]isoquinoline-3,5-diamine |
| E87 | 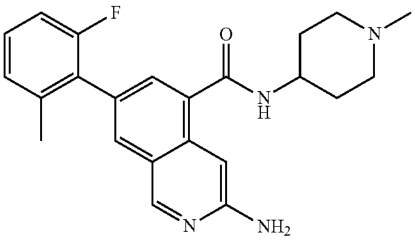 [SMILES: Cc1cccc(F)c1-c1cc(C(=O)NC2CCN(C)CC2)c2cc(N)ncc2c1] | 3-amino-7-(2-fluoro-6-methyl-phenyl)-N-(1-methyl-4-piperidyl)isoquinoline-4-carboxamide |

-continued

| Example | Structure | Name |
|---|---|---|
| E88 | 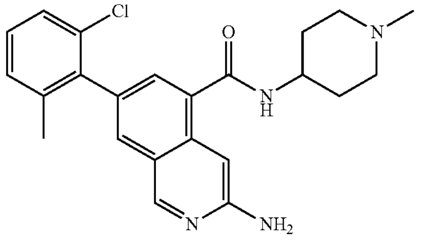 [SMILES: Cc1cccc(Cl)c1-c1cc(C(=O)NC2CCN(C)CC2)c2cc(N)ncc2c1] | 3-amino-7-(2-chloro-6-methyl-phenyl)-N-(1-methyl-4-piperidyl)isoquinoline-4-carboxamide |
| E89 | 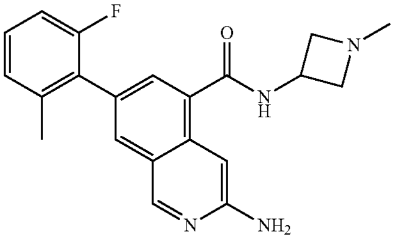 [SMILES: Cc1cccc(F)c1-c1cc(C(=O)NC2CN(C)C2)c2cc(N)ncc2c1] | 3-amino-7-(2-fluoro-6-methyl-phenyl)-N-(1-methylazetidin-3-yl)isoquinoline-4-carboxamide |
| E90 | 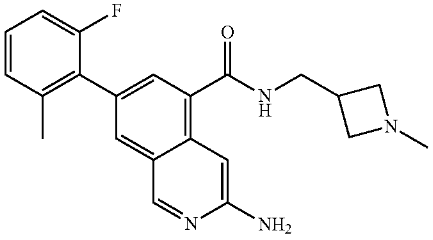 [SMILES: Cc1cccc(F)c1-c1cc(C(=O)NCC2CN(C)C2)c2cc(N)ncc2c1] | 3-amino-7-(2-fluoro-6-methyl-phenyl)-N-[(1-methylazetidin-3-yl)methyl]isoquinoline-4-carboxamide |
| E91 | 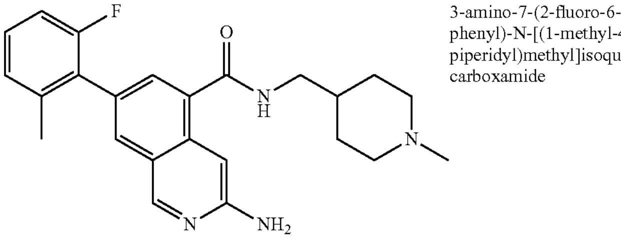 | 3-amino-7-(2-fluoro-6-rnethyl-phenyl)-N-[(1-methyl-4-piperidyl)methyl]isoquinoline-4-carboxamide |
| E92 | 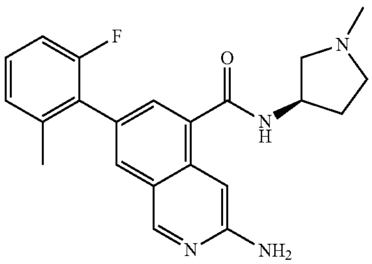 [SMILES: Cc1cccc(F)c1-c1cc(C(=O)N[C@@H]2CCN(C)C2)c2cc(N)ncc2c1] | 3-amino-7-(2-fluoro-6-methyl-phenyl)-N-[(3R)-1-methylpyrrolidin-3-yl]isoquinoline-4-carboxamide |
| E93 | 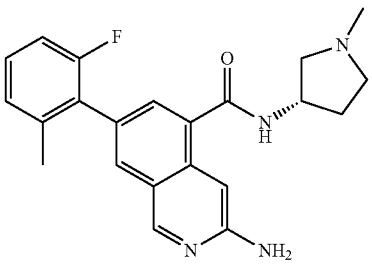 [SMILES: Cc1cccc(F)c1-c1cc(C(=O)N[C@H]2CCN(C)C2)c2cc(N)ncc2c1] | 3-amino-7-(2-fluoro-6-methyl-phenyl)-N-[(3S)-1-methylpyrrolidin-3-yl]isoquinoline-4-carboxamide |

-continued

| Example | Structure | Name |
| --- | --- | --- |
| E94 | 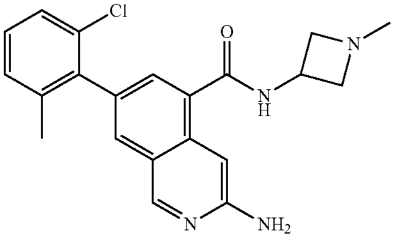 [SMILES: Cc1cccc(Cl)c1-c1cc(C(=O)NC2CN(C)C2)c2cc(N)ncc2c1] | 3-amino-7-(2-chloro-6-methyl-phenyl)-N-(1-methylazetidin-3-yl)isoquinoline-4-carboxamide |
| E95 | 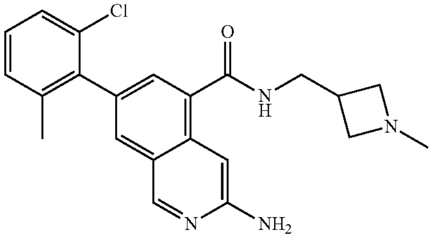 [SMILES: Cc1cccc(Cl)c1-c1cc(C(=O)NCC2CN(C)C2)c2cc(N)ncc2c1] | 3-amino-7-(2-chloro-6-methyl-phenyl)-N-[(1-methylazetidin-3-yl)methyl]isoquinoline-4-carboxamide |
| E96 | 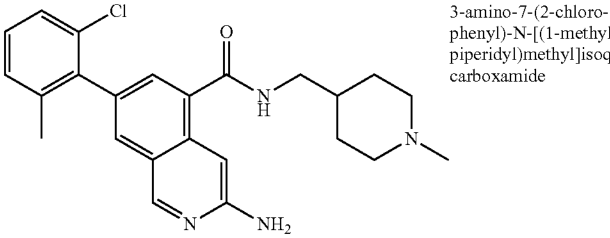 | 3-amino-7-(2-chloro-6-methyl-phenyl)-N-[(1-methyl-4-piperidyl)methyl]isoquinoline-4-carboxamide |
| E97 | 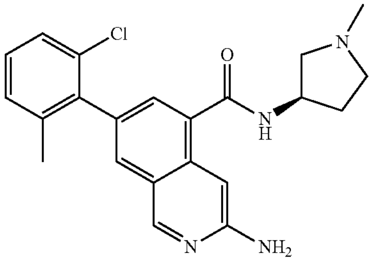 [SMILES: Cc1cccc(Cl)c1-c1cc(C(=O)N[C@@H]2CCN(C)C2)c2cc(N)ncc2c1] | 3-amino-7-(2-chloro-6-methyl-phenyl)-N-[(3R)-1-methylpyrrolidin-3-yl]isoquinoline-4-carboxamide |
| E98 | 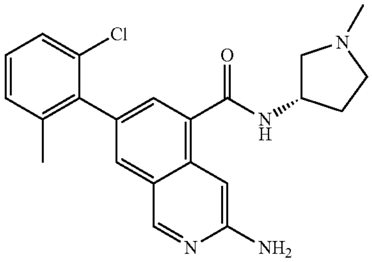 [SMILES: Cc1cccc(Cl)c1-c1cc(C(=O)N[C@H]2CCN(C)C2)c2cc(N)ncc2c1] | 3-amino-7-(2-chloro-6-methyl-phenyl)-N-[(3S)-1-methylpyrrolidin-3-yl]isoquinoline-4-carboxamide |
| E99 | 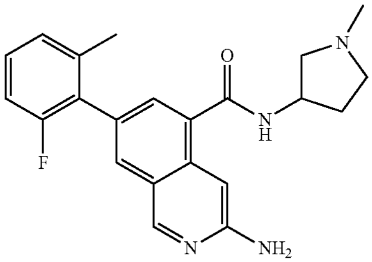 [SMILES: Cc1cccc(F)c1-c1cc(C(=O)NC2CCN(C)C2)c2cc(N)ncc2c1] | 3-amino-7-(2-fluoro-6-methyl-phenyl)-N-(1-methylpyrrolidin-3-yl)isoquinoline-5-carboxamide |

-continued

| Example | Structure | Name |
|---|---|---|
| E100 | 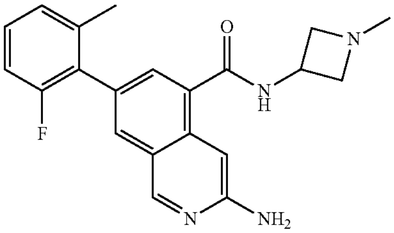 [SMILES: Cc1cccc(F)c1-c1cc(C(=O)NC2CN(C)C2)c2cc(N)ncc2c1] | 3-amino-7-(2-fluoro-6-methyl-phenyl)-N-(1-methylazetidin-3-yl)isoquinoline-5-carboxamide |
| E101 | 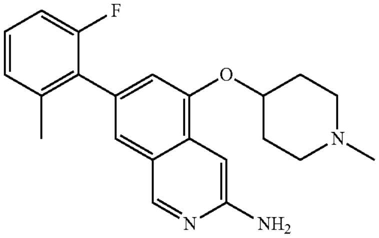 [SMILES: Cc1cccc(F)c1-c1cc(OC2CCN(C)CC2)c2cc(N)ncc2c1] | 7-(2-fluoro-6-methyl-phenyl)-5-[(1-methyl-4-piperidyl)oxy]isoquinolin-3-amine |
| E102 | 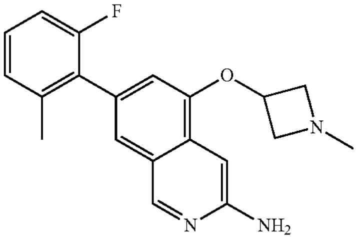 [SMILES: Cc1cccc(F)c1-c1cc(OC2CN(C)C2)c2cc(N)ncc2c1] | 7-(2-fluoro-6-methyl-phenyl)-5-(1-methylazetidin-3-yl)oxy-isoquinolin-3-amine |
| E103 | 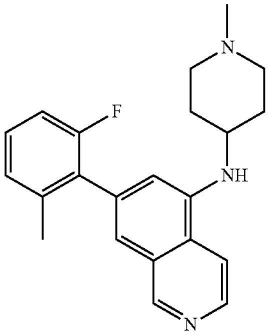 [SMILES: Cc1cccc(F)c1-c1cc(NC2CCN(C)CC2)c2ccncc2c1] | 7-(2-fluoro-6-methyl-phenyl)-N-(1-methyl-4-piperidyl)isoquinolin-5-amine |
| E104 | 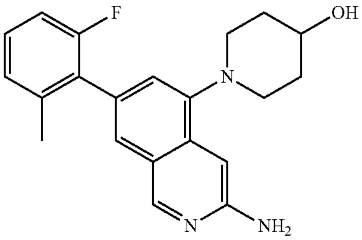 [SMILES: Cc1cccc(F)c1-c1cc(N2CCC(O)CC2)c2cc(N)ncc2c1] | 1-[3-amino-7-(2-fluoro-6-methyl-phenyl)-5-isoquinolyl]piperidin-4-ol |
| E105 | 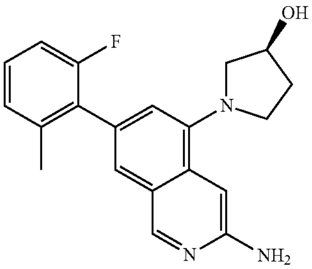 [SMILES: Cc1cccc(F)c1-c1cc(N2CC[C@H](O)C2)c2cc(N)ncc2c1] | (3S)-1-[3-amino-7-(2-fluoro-6-methyl-phenyl)-5-isoquinolyl]pyrrolidin-3-ol |

-continued
| Example | Structure | Name |
| --- | --- | --- |
| E106 | 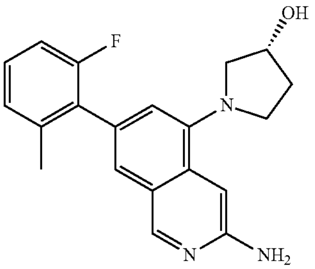 [SMILES: Cc1cccc(F)c1-c1cc(N2CC[C@@H](O)C2)c2cc(N)ncc2c1] | (3R)-1-[3-amino-7-(2-fluoro-6-methyl-phenyl)-5-isoquinolyl]pyrrolidin-3-ol |
| E107 | 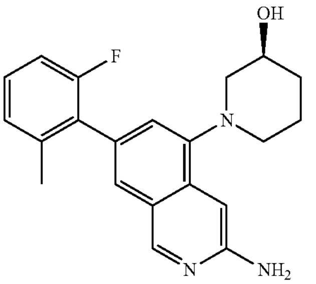 [SMILES: Cc1cccc(F)c1-c1cc(N2CCC[C@H](O)C2)c2cc(N)ncc2c1] | (3S)-1-[3-amino-7-(2-fluoro-6-methyl-phenyl)-5-isoquinolyl]piperidin-3-ol |
| E108 | 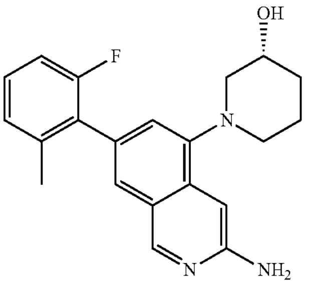 [SMILES: Cc1cccc(F)c1-c1cc(N2CCC[C@@H](O)C2)c2cc(N)ncc2c1] | (3R)-1-[3-amino-7-(2-fluoro-6-methyl-phenyl)-5-isoquinolyl]piperidin-3-ol |
| E109 | 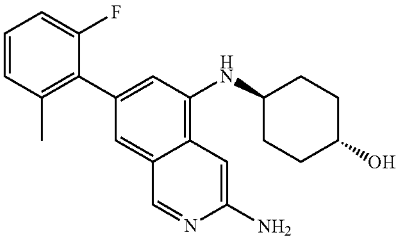 [SMILES: Cc1cccc(F)c1-c1cc(N[C@H]2CC[C@H](O)CC2)c2cc(N)ncc2c1] | 4-[[3-amino-7-(2-fluoro-6-methyl-phenyl)-5-isoquinolyl]amino]cyclohexanol |
| E110 | 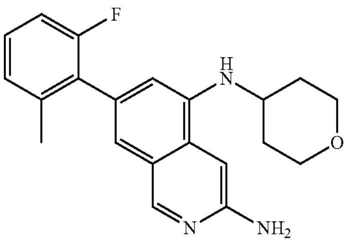 [SMILES: Cc1cccc(F)c1-c1cc(NC2CCOCC2)c2cc(N)ncc2c1] | 7-(2-fluoro-6-methyl-phenyl)-N5-tetrahydropyran-4-yl-isoquinoline-3,5-diamine |

-continued

| Example | Structure | Name |
|---|---|---|
| E111 | 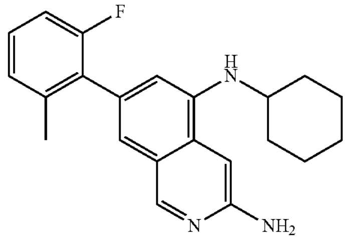 [SMILES: Cc1cccc(F)c1-c1cc(NC2CCCCC2)c2cc(N)ncc2c1] | N5-cyclohexyl-7-(2-fluoro-6-methyl-phenyl)isoquinoline-3,5-diamine |
| E112 | 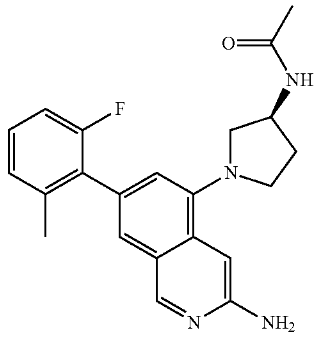 [SMILES: CC(=O)N[C@H]1CCN(c2cc(-c3c(C)cccc3F)cc3cnc(N)cc23)C1] | N-[(3S)-1-[3-amino-7-(2-fluoro-6-methyl-phenyl)-5-isoquinolyl]pyrrolidin-3-yl]acetamide |
| E113 | 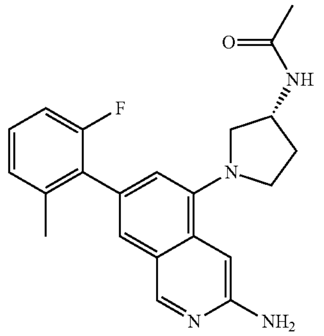 [SMILES: CC(=O)N[C@@H]1CCN(c2cc(-c3c(C)cccc3F)cc3cnc(N)cc23)C1] | N-[(3R)-1-[3-amino-7-(2-fluoro-6-methyl-phenyl)-5-isoquinolyl]pyrrolidin-3-yl]acetamide |
| E114 | 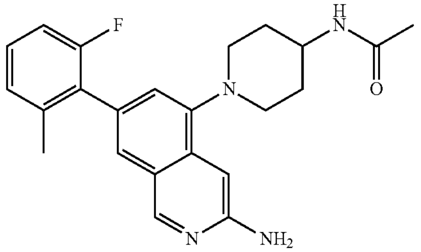 [SMILES: CC(=O)NC1CCN(c2cc(-c3c(C)cccc3F)cc3cnc(N)cc23)CC1] | N-[1-[3-amino-7-(2-fluoro-6-methyl-phenyl)-5-isoquinolyl]-4-piperidyl]acetamide |
| E115 | 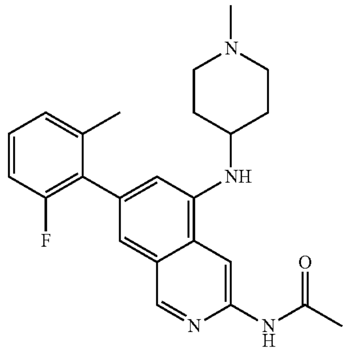 [SMILES: CC(=O)Nc1cc2c(NC3CCN(C)CC3)cc(-c3c(C)cccc3F)cc2cn1] | N-[7-(2-fluoro-6-methyl-phenyl)-5-[(1-methyl-4-piperidyl)amino]-3-isoquinolyl]acetamide |

-continued

| Example | Structure | Name |
| --- | --- | --- |
| E116 | 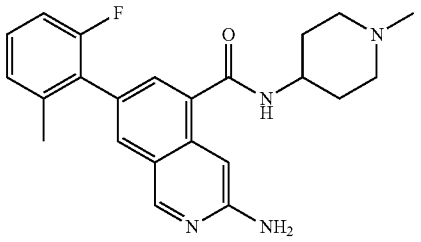 [SMILES: Cc1cccc(F)c1-c1cc(C(=O)NC2CCN(C)CC2)c2cc(N)ncc2c1] | 3-amino-7-(2-fluoro-6-methyl-phenyl)-N-(1-methyl-4-piperidyl)isoquinoline-5-carboxamide |
| E117 | 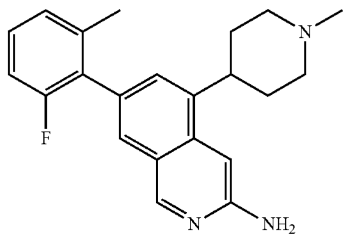 [SMILES: Cc1cccc(F)c1-c1cc(C2CCN(C)CC2)c2cc(N)ncc2c1] | 7-(2-fluoro-6-methyl-phenyl)-5-(1-methyl-4-piperidyl)isoquinolin-3-amine |
| E118 | 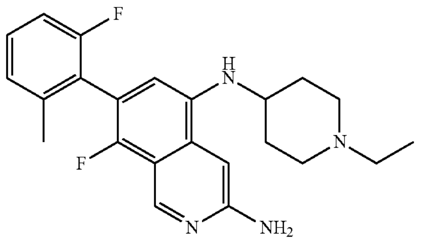 [SMILES: CCN1CCC(Nc2cc(-c3c(C)cccc3F)c(F)c3cnc(N)cc23)CC1] | N5-(1-ethyl-4-piperidyl)-8-fluoro-7-(2-fluoro-6-methyl-phenyl)isoquinoline-3,5-diamine |
| E119 | 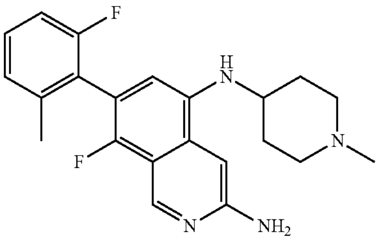 [SMILES: Cc1cccc(F)c1-c1cc(NC2CCN(C)CC2)c2cc(N)ncc2c1F] | 8-fluoro-7-(2-fluoro-6-methyl-phenyl)-N5-(1-methyl-4-piperidyl)isoquinoline-3,5-diamine |
| E120 | 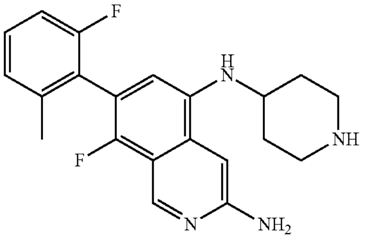 [SMILES: Cc1cccc(F)c1-c1cc(NC2CCNCC2)c2cc(N)ncc2c1F] | 8-fluoro-7-(2-fluoro-6-methyl-phenyl)-N5-(4-piperidyl)isoquinoline-3,5-diamine |
| E121 | 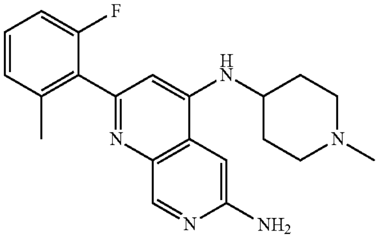 [SMILES: Cc1cccc(F)c1-c1cc(NC2CCN(C)CC2)c2cc(N)ncc2n1] | 2-(2-Fluoro-6-methyl-phenyl)-N4-(1-methyl-4-piperidyl)-1,7-naphthyridine-4,6-diamine |

-continued

| Example | Structure | Name |
|---|---|---|
| E122 | 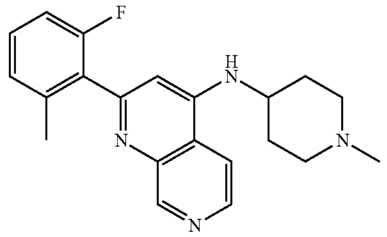 [SMILES: Cc1cccc(F)c1-c1cc(NC2CCN(C)CC2)c2ccncc2n1] | 2-(2-Fluoro-6-methyl-phenyl)-N-(1-methyl-4-piperidyl)-1,7-naphthyridin-4-amine |
| E123 | 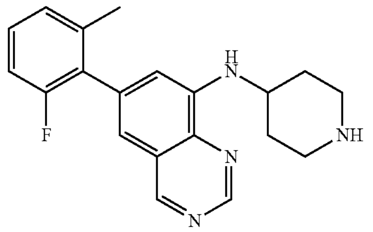 [SMILES: Cc1cccc(F)c1-c1cc(NC2CCNCC2)c2ncncc2c1] | 6-(2-Fluoro-6-methyl-phenyl)-N-(4-piperidyl)quinazolin-8-amine |
| E124 | 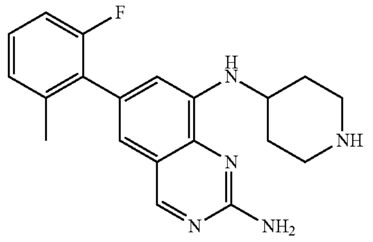 | 6-(2-Fluoro-6-methyl-phenyl)-N8-(4-piperidyl)quinazoline-2,8-diamine |
| E125 | 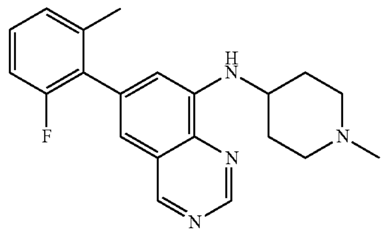 [SMILES: Cc1cccc(F)c1-c1cc(NC2CCN(C)CC2)c2ncncc2c1] | 6-(2-Fluoro-6-methyl-phenyl)-N-(1-methyl-4-piperidyl)quinazolin-8-amine |
| E126 | 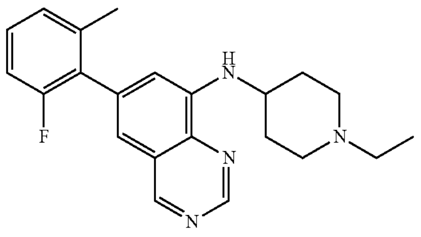 [SMILES: CCN1CCC(Nc2cc(-c3c(C)cccc3F)cc3cncnc23)CC1] | N-(1-Ethyl-4-piperidyl)-6-(2-fluoro-6-methyl-phenyl)quinazolin-8-amine |
| E127 | 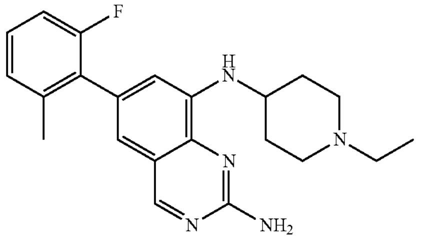 [SMILES: CCN1CCC(Nc2cc(-c3c(C)cccc3F)cc3cnc(N)nc23)CC1] | N8-(1-Ethyl-4-piperidyl)-6-(2-fluoro-6-methyl-phenyl)quinazoline-2,8-diamine |

232. A compound, or a salt or solvate thereof, selected from:

| Example | Structure | Name |
|---|---|---|
| E128 | 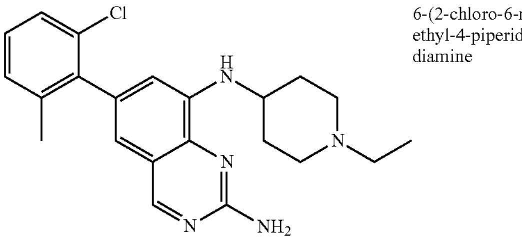 | 6-(2-chloro-6-methyl-phenyl)-N8-(1-ethyl-4-piperidyl)quinazoline-2,8-diamine |
| E129 | 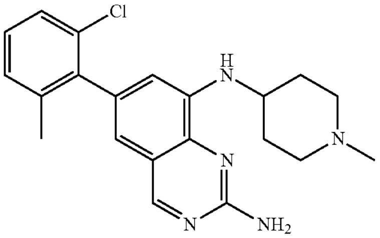 [SMILES: Cc1cccc(Cl)c1-c1cc(NC2CCN(C)CC2)c2nc(N)ncc2c1] | 6-(2-chloro-6-methyl-phenyl)-N8-(1-methyl-4-piperidyl)quinazoline-2,8-diamine |
| E130 | 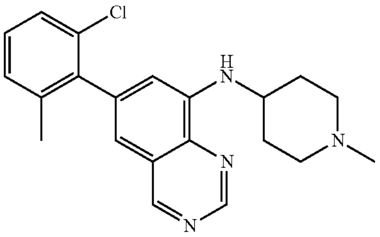 [SMILES: Cc1cccc(Cl)c1-c1cc(NC2CCN(C)CC2)c2ncncc2c1] | 6-(2-chloro-6-methyl-phenyl)-N-(1-methyl-4-piperidyl)quinazolin-8-amine |
| E131 | 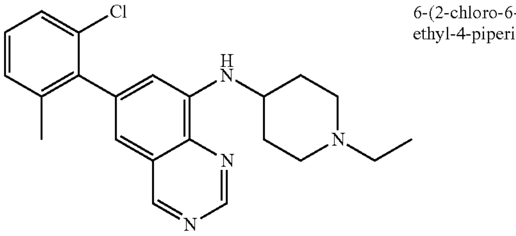 | 6-(2-chloro-6-methyl-phenyl)-N-(1-ethyl-4-piperidyl)quinazolin-8-amine |
| E132 | 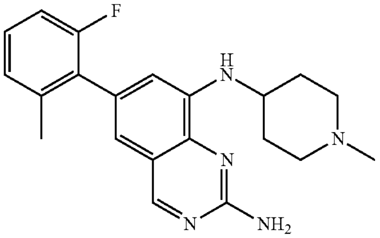 [SMILES: Cc1cccc(F)c1-c1cc(NC2CCN(C)CC2)c2nc(N)ncc2c1] | 6-(2-fluoro-6-methyl-phenyl)-N8-(1-methyl-4-piperidyl)quinazoline-2,8-diamine |
| E133 | 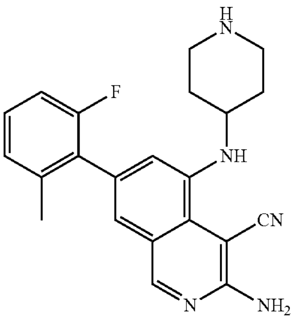 [SMILES: Cc1cccc(F)c1-c1cc(NC2CCNCC2)c2c(C#N)c(N)ncc2c1] | 3-amino-7-(2-fluoro-6-methyl-phenyl)-5-(4-piperidylamino)isoquinoline-4-carbonitrile |

-continued

| Example | Structure | Name |
|---|---|---|
| E134 | 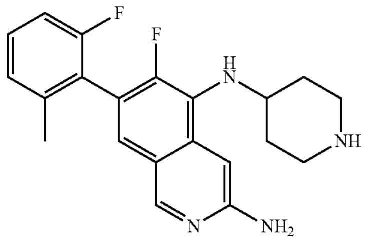 [SMILES: Cc1cccc(F)c1-c1cc2cnc(N)cc2c(NC2CCNCC2)c1F] | 6-fluoro-7-(2-fluoro-6-methyl-phenyl)-N5-(4-piperidyl)isoquinoline-3,5-diamine |
| E135 | 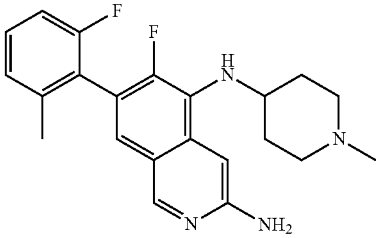 [SMILES: Cc1cccc(F)c1-c1cc2cnc(N)cc2c(NC2CCN(C)CC2)c1F] | 6-fluoro-7-(2-fluoro-6-methyl-phenyl)-N5-(1-methyl-4-piperidyl)isoquinoline-3,5-diamine |
| E136 | 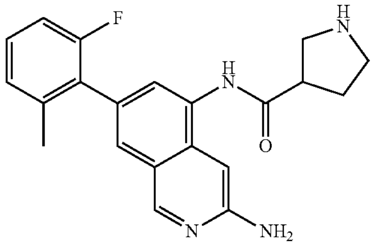 [SMILES: Cc1cccc(F)c1-c1cc(NC(=O)C2CCNC2)c2cc(N)ncc2c1] | N-[3-amino-7-(2-fluoro-6-methyl-phenyl)-5-isoquinolyl]pyrrolidine-3-carboxamide |
| E137 | 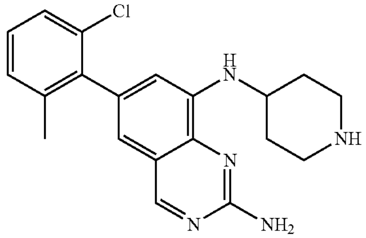 [SMILES: Cc1cccc(Cl)c1-c1cc(NC2CCNCC2)c2nc(N)ncc2c1] | 6-(2-chloro-6-methyl-phenyl)-N8-(4-piperidyl)quinazoline-2,8-diamine |
| E138 | 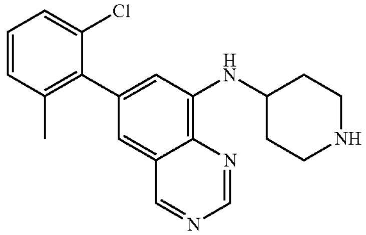 [SMILES: Cc1cccc(Cl)c1-c1cc(NC2CCNCC2)c2ncncc2c1] | 6-(2-chloro-6-methyl-phenyl)-N-(4-piperidyl)quinazolin-8-amine |

233. A compound according to any one of the preceding paragraphs as a pharmaceutically acceptable salt.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Salts and Solvates

The compounds (including final products and intermediates) described herein may be isolated and used per se or may be isolated in the form of a salt, suitably pharmaceutically acceptable salts. It should be understood that the terms “salt(s)” and “salt form(s)” used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more.

Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or approved by the FDA or equivalent foreign regulatory body for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In one embodiment, the compounds of Formula I and sub-formulae thereof are isolated as pharmaceutically acceptable salts.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of the Formula I and sub-formulae thereof may exist in solvated as well as unsolvated forms such as, for example, hydrated forms. It is to be understood that the invention encompasses all such solvated forms that possess the biological activity described herein.

Polymorphs

It is also to be understood that certain compounds of the Formula I and sub-formulae thereof may exhibit polymorphism, and that the invention encompasses all such forms that possess the biological activity described herein.

N-Oxides

Compounds of the Formula I and sub-formulae thereof containing an amine function may also form N-oxides. A reference herein to a compound of the Formula I and sub-formulae thereof that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, $4^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

Tautomers

Compounds of the Formula I and sub-formulae thereof may exist in a number of different tautomeric forms and references to compounds of the Formula I and sub-formulae thereof include all such forms. For the avoidance of doubt, where a compound can exist in one of several tautomeric forms, and only one is specifically described or shown, all others are nevertheless embraced by Formula I and sub-formulae thereof. Examples of tautomeric forms include keto-, enol-, and enolate-forms, as in, for example, the following tautomeric pairs: keto/enol (illustrated below), pyrimidone/hydroxypyrimidine, imine/enamine, amide/imino alcohol, amidine/amidine, nitroso/oxime, thioketone/enethiol, and nitro/aci-nitro.

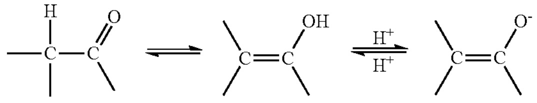

keto enol enolate

Isomers

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

Certain compounds of Formula I and sub-formulae thereof may have one or more asymmetric centres and therefore can exist in a number of stereoisomeric configurations. Consequently, such compounds can be synthesized and/or isolated as mixtures of enantiomers and/or as individual (pure) enantiomers, and, in the case of two or more asymmetric centres, single diastereomers and/or mixtures of diastereomers. It should be understood that the present application includes all such enantiomers and diastereomers and mixtures thereof in all ratios.

Isotopes

The compounds of the present invention are described herein using structural formulas that do not specifically recite the mass numbers or the isotope ratios of the constituent atoms. As such it is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^{1}H$, $^{2}H$, and $^{3}H$; etc. Preferably, the constituent atoms in the compounds of the present invention are present in their naturally occurring ratios of isotope forms.

Prodrugs and Metabolites

The compounds of Formula I and sub-formulae thereof may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula I and in-vivo cleavable amide derivatives that may be formed at a carboxy group or an amino group in a compound of the Formula I and sub-formulae thereof.

Accordingly, the present invention includes those compounds of the Formula I and sub-formulae thereof as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I and sub-formulae thereof may be a synthetically-produced compound or a metabolically-produced compound.

A suitable pharmaceutically acceptable pro-drug of a compound of the Formula I and sub-formulae thereof is one that is based on reasonable medical judgement as being suitable for administration to the human or animal body without undesirable pharmacological activities and without undue toxicity.

Various forms of pro-drug have been described, for example in the following documents:— a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews,* 8, 1-38 (1992);
e) H. Bundgaard, et al., *Journal of Pharmaceutical Sciences,* 77, 285 (1988);
f) N. Kakeya, et al., *Chem. Pharm. Bull.,* 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I and sub-formulae thereof that possesses a carboxy group is, for example, an in vivo cleavable ester thereof. An in vivo cleavable ester of a compound of the Formula I containing a carboxy group is, for example, a pharmaceutically acceptable ester which is cleaved in the human or animal body to produce the parent acid. Suitable pharmaceutically acceptable esters for carboxy include $C_{1-6}$ alkyl esters such as methyl, ethyl and tert-butyl, $C_{1-6}$ alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$ alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$ alkoxycarbonyloxy-$C_{1-6}$ alkyl esters such as methoxycarbonyloxymethyl and 1-methoxycarbonyloxyethyl esters.

A suitable pharmaceutically acceptable pro-drug of a compound of the Formula I and sub-formulae thereof that possesses a hydroxy group is, for example, an in vivo cleavable ester or ether thereof. An in vivo cleavable ester or ether of a compound of the Formula I and sub-formulae thereof containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula I and sub-formulae thereof that possesses a carboxy group is, for example, an in vivo cleavable amide thereof, for example an amide formed with an amine such as ammonia, a $C_{1-4}$alkylamine such as methylamine, a ($C_{1-4}$ alkyl)$_2$amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$ alkylamine such as benzylamine and amino acids such as glycine or an ester thereof.

A suitable pharmaceutically acceptable pro-drug of a compound of the Formula I and sub-formulae thereof that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$ alkyl)piperazin-1-ylmethyl.

The in vivo effects of a compound of the Formula I and sub-formulae thereof may be exerted in part by one or more metabolites that are formed within the human or animal body after administration of a compound of the Formula I and sub-formulae thereof. As stated hereinbefore, the in vivo effects of a compound of the Formula I and sub-formulae thereof may also be exerted byway of metabolism of a precursor compound (a pro-drug).

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the person skilled in the art. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I as defined herein, or a pharmaceutically acceptable salt or solvate thereof, or a pharmaceutical composition as defined herein, for use in therapy.

In another aspect, the present invention provides a compound of Formula I as defined herein, or a pharmaceutically acceptable salt or solvate thereof, or a pharmaceutical composition as defined herein, for use in the treatment of treatment of a disease or condition associated with aberrant activity of salt-inducible kinase (SIK).

In another aspect, the present invention provides the use of a compound of Formula I as defined herein, or a pharmaceutically acceptable salt or solvate thereof, in the manufacture of a medicament for the treatment of a disease or condition associated with aberrant activity of salt-inducible kinase (SIK).

In another aspect, the present invention provides a method of treating a disease or condition associated with aberrant activity of salt-inducible kinase (SIK), said method comprising administering to a subject in need thereof an effective amount of a compound of Formula I as defined herein, or a pharmaceutically acceptable salt or solvate thereof.

Unless stated otherwise reference to the treatment of a disease or condition associated with aberrant activity of salt-inducible kinase (SIK) is intended to encompass diseases or conditions associated with aberrant activity of one or more of SIK1, SIK2 and SIK3. Suitably, the disease or condition is associated with aberrant activity of SIK2.

In another aspect, the present invention provides a compound of Formula I as defined herein, or a pharmaceutically acceptable salt or solvate thereof, or a pharmaceutical composition as defined herein, for use in the treatment of a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder.

In another aspect, the present invention provides the use of a compound of Formula I as defined herein, or a pharmaceutically acceptable salt or solvate thereof, in the manufacture of a medicament for the treatment of a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder.

In another aspect, the present invention provides a method of treating a proliferative disorder, a benign neoplasm, pathological angiogenesis, an inflammatory disease or condition, a musculoskeletal disease or condition, an autoimmune disease, a haematological disease or condition, a neurological disease or condition, a psychiatric disorder, or a metabolic disorder, said method comprising administering to a subject in need thereof an effective amount of a compound of Formula I as defined herein, or a pharmaceutically acceptable salt or solvate thereof.

The terms "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g. of connective tissues), and atherosclerosis. Any type of cell may be treated, including but not limited to, lung, colon, breast, ovarian, prostate, liver, pancreas, brain, blood and skin.

In one embodiment, the proliferative disorder is cancer, suitably a cancer selected from lung, colon, breast, ovarian, prostate, liver, pancreas, brain, blood and skin cancer.

In one embodiment, the proliferative disorder is cancer, suitably a cancer selected from breast, brain, blood and ovarian cancer.

In one embodiment, the proliferative disorder is cancer, suitably a cancer selected from blood and ovarian cancer.

In one embodiment, the proliferative disorder is hematopoietic tumour, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); and myelofibrosis.

The benign neoplasm may be, for example, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign neoplasm may be endometrial implants or a keratocystic odontogenic tumor.

In another aspect, the present invention provides a compound of Formula I as defined herein, or a pharmaceutically acceptable salt or solvate thereof, or a pharmaceutical composition as defined herein, for use in the treatment of a cancer.

In another aspect, the present invention provides the use of a compound of Formula I as defined herein, or a pharmaceutically acceptable salt or solvate thereof, in the manufacture of a medicament for the treatment of a cancer.

In another aspect, the present invention provides a method of treating a cancer, said method comprising administering to a subject in need thereof a therapeutically effective amount of a compound of Formula I as defined herein, or a pharmaceutically acceptable salt or solvate thereof, or a pharmaceutical composition as defined herein.

The cancer may be non-metastatic or metastatic and which may be a solid tumour or a haematological ("liquid") cancer. The cancer may, for example, be selected from:

(1) Carcinoma, including for example tumours derived from stratified squamous epithelia (squamous cell carcinomas) and tumours arising within organs or glands (adenocarcinomas). Examples include breast, colon, lung, prostate, ovary. esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma (SCLC) and non-small cell carcinoma of the lung (NSCLC), lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

In a particular embodiment a compound of the invention, or a pharmaceutically acceptable salt thereof may be for use in the treatment of a cancer selected from cancer selected from lung, colon, breast, ovarian, prostate, liver, pancreas, brain, blood and skin cancer.

In one embodiment, the cancer is selected from breast, brain, blood and ovarian cancer.

In one embodiment, the cancer is selected from blood and ovarian cancer.

In one embodiment, the cancer is a leukemia. Suitably the leukemia is selected from chronic myeloid leukaemia (CML), acute myeloid leukaemia (AML), chronic lymphocytic leukaemia (CLL) and acute lymphoblastic leukaemia (ALL).

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

In one embodiment, the compounds described herein are for use in treating an acute or chronic autoimmune and/or inflammatory condition. In one embodiment, the compounds described herein are for use in treating one or more of the following: rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment, the compounds described herein are for use in the treatment a inflammatory disorder such as rheumatoid arthritis, osteoarthritis, acute gout, psoriasis, systemic lupus erythematosus, multiple sclerosis or inflammatory bowel disease (Crohn's disease and Ulcerative colitis).

Routes of Administration

The compounds of the invention or pharmaceutical compositions comprising these compounds may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The compounds of the invention and salts, solvates thereof defined hereinbefore may be applied as a sole therapy or may involve, in addition to the compound of the invention, one or more additional therapeutic agents, e.g. an anti-tumour agent.

In the context of cancer treatment, in addition to the compound of the invention therapy may involve conventional surgery or radiotherapy or chemotherapy. Such chemotherapy may include one or more of the following categories of anti-tumour agents:— other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

vascular damaging agents such as Combretastatin A4 and compounds disclosed in International Patent Applications WO 99/02166, WO 00/40529, WO 00/41669, WO 01/92224, WO 02/04434 and WO 02/08213;

an endothelin receptor antagonist, for example zibotentan (ZD4054) or atrasentan;

antisense therapies, for example those which are directed to the targets listed above, such as ISIS 2503, an anti-ras antisense;

gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

Herein, where the term “combination” is used it is to be understood that this refers to simultaneous, separate or sequential administration. In one aspect of the invention “combination” refers to simultaneous administration. In another aspect of the invention “combination” refers to separate administration. In a further aspect of the invention “combination” refers to sequential administration. Where the administration is sequential or separate, the delay in administering the second component should not be such as to lose the beneficial effect of the combination. In one embodiment, a combination refers to a combination product.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Chemistry

The following examples are provided solely to illustrate the present invention and are not intended to limit the scope of the invention, as described herein.

The compounds of the invention may be prepared using synthetic techniques that are known in the art (as illustrated by the examples herein).

Several methods for the chemical synthesis of the compounds of the present application are described herein. These and/or other well-known methods may be modified and/or adapted in various ways in order to facilitate the synthesis of additional compounds within the scope of the present application and claims. Such alternative methods and modifications should be understood as being within the spirit and scope of this application and claims. Accordingly, it should be understood that the methods set forth in the following descriptions, schemes and examples are intended for illustrative purposes and are not to be construed as limiting the scope of the disclosure.

Synthesis and Characterisation

Abbreviations

AcOH Acetic acid
BINAP 2,2'-bis(diphenylphosphino)-1,1'-binaphthalene
BOC tert-butyloxycarbonyl
Bn Benzyl
t-BuBrettPhos 2-(Di-tert-butylphosphino)-2',4',6'-triisopropyl-3,6-dimethoxy-1,1'-biphenyl
t-BuXPhos 2-Di-tert-butylphosphino-2',4',6'-triisopropylbiphenyl
Cbz Carboxybenzyl
CVs Column volumes
DAD Diode Array Detector
DCE Dichloroethane
DCM Dichloromethane
DEA Diethanolamine
DIPEA N,N-Diisopropylethylamine
DMA N,N-Dimethylacetamide
DMAP 4-Dimethylaminopyridine
DMF N,N-Dimethylformamide
DMSO Dimethylsulfoxide
DMSO-$d_6$ Deuterated dimethylsulfoxide
ES Electrospray (ionisation)
Et Ethyl
EtOAc Ethyl acetate
EtOH Ethanol
HATU 1-[Bis(dimethylamino)methylene-1H-1,2,3-triazolo[4,5-b]pyridinium-3-oxide-hexafluorophosphate
HPLC High performance liquid chromatography
LCMS Liquid chromatography mass spectrometry
Me Methyl
MeCN Acetonitrile
MeOH Methanol
Ms Mesyl
n-BuLi n-Butyllithium
NMP N-Methyl-2-pyrrolidone
$Pd(PPhs)_4$ Tetrakis(triphenylphosphine)palladium(0)
Pet. ether Petroleum ether
Rt Retention time (minutes)
RT Room temperature
RuPhos 2-Dicyclohexylphosphino-2',6'-diisopropoxybiphenyl
SCX Strong cation exchange (column)
SDQ Single Quadrupole Detector
SEM [2-(Trimethylsilyl)ethoxy]methyl acetal
TBDPS tert-butyldiphenylsilyl
TFA Trifluoroacetic acid
TH F Tetrahydrofuran
TH P Tetrahydropyran
TLC Thin layer chromatography
TRT Trityl
Ts Tosyl
w/w % weight per weight

Material and Methods

Reagents were purchased from commercial sources and used as received. All solvents were of reagent grade unless otherwise stated, with anhydrous equivalents being sourced from external suppliers. All reactions were performed under an inert atmosphere of nitrogen unless otherwise stated. Brine refers to a saturated aqueous solution of sodium chloride.

$^1$H NMR spectra were obtained in solutions of chloroform-d, methanol-$d^4$ or DMSO-$d^6$ at 25° C. using a 400 MHz spectrometer with chemical shifts given in parts per million (ppm).

High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass.

Where intermediates were prepared as an inseparable mixture of regiosiomers, the desired intermediate is drawn and named, but data is quoted for both regioisomers. The corresponding examples were purified as single regioisomers and characterized as such.

TABLE 1

LCMS Method codes (Flow expressed in mL/min; column temperature (T) in ° C.; Run time in minutes).

| Method code | Instrument | Column | Mobile phase | Gradient | Flow Column T | Run time |
|---|---|---|---|---|---|---|
| 1 | Shimadzu: LC-MS2020 - SPD-M20A and Alltech 3300ELSD | SunFire C18 5 μm 50*4.6 mm | A: HCOOH 0.1% in water, B: HCOOH 0.1% in $CH_3CN$ | 90% A for 0.4 min, to 5% A in 1.2 min, to 1% A in 1.0 min. | 2.0 40 | 2.6 |
| 2 | Waters UPLC-QDa- PDA Detector | ACQUITY UPLC BEH C18 1.7 μm 2.1*50 mm | A: HCOOH 0.1% in water, B: HCOOH 0.1% in $CH_3CN$ | 90% A for 0.1 min, to 5% A in 1.1 min, hold 5% A in 0.8 min. | 0.6 50 | 2.0 |
| 3 | Agilent G6120B G1315D DADVL Detector and G4260B ELSD | Xbridge C18 5 μm 150*4.6 mm | A: $NH_4OH$ 0.1% in water, B: NH4OH 0.1% in $CH_3CN$ | 90% A for 1.0 min, to 5% A in 10.0 min, hold 5% A in 2.0 min. | 2.0 40 | 2.6 |

TABLE 2

Preparative HPLC Method codes (Flow expressed in mL/min).

| Method code | Instrument | Column | Mobile phase | Gradient | Trigger | Flow |
|---|---|---|---|---|---|---|
| 1 | Waters 2767/Qda | SunFire 19*250 mm 10 um | A: $CF_3COOH$ 0.1% in water, B: $CH_3CN$ | Changed with different compounds | 254 nm | 2.6 |
| 2 | Waters 2767/Qda | SunFire 19*250 mm 10 um | A: NH4OH 0.1% in water, B: $CH_3CN$ | Changed with different compounds | 254 nm | 2.6 |
| 3 | Waters 2767/Qda | SunFire 19*250 mm 10 um | A: $NH_4HCO_3$ 0.1% in water, B: $CH_3CN$ | Changed with different compounds | 2.6 | 2.6 |

Preparation 1 (P1)

2-(2-Fluoro-6-methyl-phenyl)-4,4,5,5-tetramethyl-1,3,2-dioxaborolane

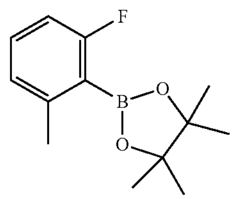 [SMILES: Cc1cccc(F)c1B1OC(C)(C)C(C)(C)O1]

A round-bottom flask equipped with a magnetic stir bar was charged with 1-fluoro-2-iodo-3-methylbenzene (20.0 g, 84.7 mmol), $K_2CO_3$ (24.6 g, 178.0 mmol), 4,4,4',4',5,5,5',5'-octamethyl-2,2'-bi(1,3,2-dioxaborolane) (43.0 g, 169.4 mmol), $Pd(dppf)Cl_2$ (2.5 g), 1,4-dioxane (200 mL) and $H_2O$ (20 mL). This mixture was heated to 100° C. and stirred overnight under an atmosphere of argon. LCMS showed the major product was the desired.

The reaction was cooled to room temperature, and then filtered. The filtrate was concentrated in vacuo and diluted with EtOAc (300 mL). The solution was washed with water, brine, dried over $Na_2SO_4$, and concentrated. The oil was chromatographed [$SiO_2$, Pet. ether] to afford 2-(2-fluoro-6- methyl-phenyl)-4,4,5,5-tetramethyl-1,3,2-dioxaborolane (P1) as light yellow oil (12.5 g).

$^1$H NMR (400 MHz, DMSO-$d_6$): δ: ppm 7.33 (m, 1H), 7.01 (d, J=7.6 Hz, 1H), 6.92 (t, J=8.4 Hz 1H), 2.37 (s, 3H), 1.31 (s, 12H)

The following compounds were prepared in a similar manner to 2-(2-fluoro-6-methyl-phenyl)-4,4,5,5-tetramethyl-1,3,2-dioxaborolane (P1) using the appropriately substituted aryl iodide and 4,4,4',4',5,5,5',5'-octamethyl-2,2'-bi (1,3,2-dioxaborolane):

| Preparation | Structure | Name | $^1$H NMR Data ($CDCl_3$) |
|---|---|---|---|
| P2 | 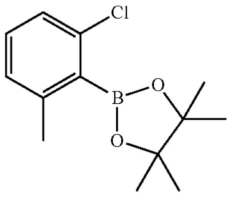 [SMILES: Cc1cccc(Cl)c1B1OC(C)(C)C(C)(C)O1] | 2-(2-chloro-6-methyl-phenyl)-4,4,5,5-tetramethyl-1,3,2-dioxaborolane | 7.26 (s, 1H) 7.12-7.15 (m, 2H) 7.00-7.02 (m, 1H) 2.37 (s, 1H) 1.41 (s, 12H) |

Preparation 3 (P3)

2-(2-Chloro-6-fluoro-phenyl)-4,4,5,5-tetramethyl-1,3,2-dioxaborolane

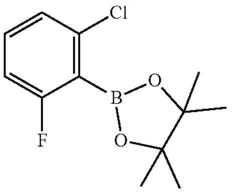 [SMILES: CC1(C)OB(c2c(F)cccc2Cl)OC1(C)C]

(2-Chloro-6-fluoro-phenyl)boronic acid (2.26 g, 12.96 mmol) and pinacol (1.84 g, 15.55 mmol) were dissolved in $PhCH_3$ (22 mL) and the solution was heated to 110° C. overnight. The organics were extracted into EtOAc, washed with brine, dried over $Na_2SO_4$ and concentrated under reduced pressure. The residue was chromatographed to give 2-(2-chloro-6-fluoro-phenyl)-4,4,5,5-tetramethyl-1,3,2-dioxaborolane (P3) (2.9 g).

$^1$H NMR (400 MHz, DMSO-$d_6$): δ: ppm 7.48 (m, 1H), 7.29 (d, J=7.6 Hz, 1H), 7.17 (t, J=8.4 Hz 1H), 1.33 (s, 12H).

Preparation 4 (P4)

(3-Bromo-5-chloro-phenyl)methanamine

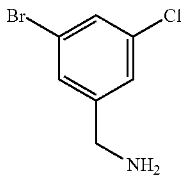

To a mixture of 3-bromo-5-chloro-benzonitrile (50.0 g, 0.231 mol) in THF (500 mL) was added $BH_3$/THF (350 mL, 1M) at 0° C. under an atmosphere of argon. The mixture was stirred at 50° C. for 1 hour. After this time, HCl (120 mL, 6M) was added to the mixture at 0° C. and the mixture was stirred at 50° C. for 30 minutes. Water (200 mL) was added and the organics were extracted into EtOAc. The aqueous layer was adjusted to pH ~7-8 by addition of $Na_2CO_3$. The organics were extracted into further EtOAc before being concentrated under reduced pressure provide (3-bromo-5-chloro-phenyl)methanamine (P4) as a yellow oil (27.7 g), LCMS $ES^+$ 222 [M+H]+, Rt=0.800 mins (Method 1).

The following compounds were prepared in a similar manner to (3-bromo-5-chloro-phenyl)methanamine (P4) using the appropriate benzonitrile:

| Preparation | Structure | Name | $^1$H NMR Data DMSO-$d_6$ |
|---|---|---|---|
| P5 | 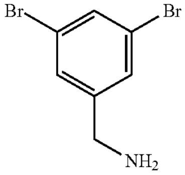 | (3,5-dibromophenyl) methanamine | 7.63 (s, 1H) 7.56 (s, 2H) 3.69 (s, 2H) 1.99 (br s, 2H) |

Preparation 6 (P6)

N-[(3-Bromo-5-chloro-phenyl)methyl]-2,2-diethoxy-acetamidine

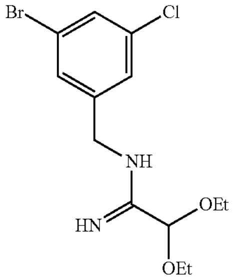 [SMILES: CCOC(OCC)C(=N)NCc1cc(Cl)cc(Br)c1]

A mixture of (3-bromo-5-chloro-phenyl)methanamine (P4) (10.0 g, 45.35 mmol) and methyl 2,2-diethoxyacetimidate (9.50 g, 58.96 mmol) was stirred at room temperature under an atmosphere of argon overnight. The mixture was concentrated under reduced pressure and the crude material (16.0 g) was used directly in the next step without further purification.

Preparation 7 (P7)

(Z)-1-(3,5-Dibromophenyl)-N-(2,2-dimethoxyethyl) methanimine

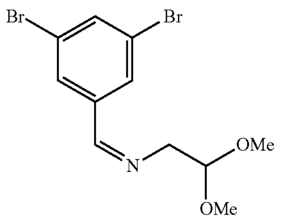 [SMILES: COC(C/N=C\c1cc(Br)cc(Br)c1)OC]

To a solution of 3,5-dibromobenzaldehyde (6.100 g, 23.40 mmol) in EtOH (60 mL) stirred at room temperature was added 2,2-dimethoxyethanamine (3.20 g, 30.42 mmol). The resulting mixture was stirred at 30° C. for 3 hours. After this time, the solution was concentrated under reduced pressure and the residue was washed with Pet. ether to give (Z)-1-(3,5-dibromophenyl)-N-(2,2-dimethoxyethyl)methanimine (P7) (4.500 g).

$^1$H NMR (400 MHz, $CDCl_3$): δ: ppm 8.16 (s, 1H), 7.82 (s, 1H), 7.81 (s, 1H), 7.70 (t, J=1.6 Hz, 1H), 4.67 (t, J=5.2 Hz, 1H), 3.77 (d, J=4.4 Hz, 2H), 3.42 (s, 6H)

Preparation 8 (P8)

7-Bromo-5-chloro-isoquinolin-3-amine

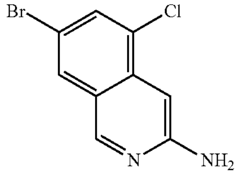 [SMILES: Nc1cc2c(Cl)cc(Br)cc2cn1]

N-[(3-Bromo-5-chloro-phenyl)methyl]-2,2-diethoxy-acetamidine (P6) (44.0 g, 0.125 mol) was added to conc. $H_2SO_4$ (150 mL) dropwise at 0° C. and the mixture was stirred at 80° C. for 2 hours. After this time, the mixture was added to ice-water slowly and the pH adjusted to 8 by addition of NaOH aq. solution (12M). A precipitate formed which was filtered, washed with water and Pet. ether, and dried. The resulting residue was chromatographed [$SiO_2$] to provide 7-bromo-5-chloro-isoquinolin-3-amine (P8) and 5-bromo-7-chloro-isoquinolin-3-amine as a mixture of regioisomers (17.4 g) which was used directly in subsequent steps without further purification, LCMS ES$^+$ 257 [M+H]$^+$, Rt=0.48 mins (Method 2)

Preparation 9 (P9)

5,7-Dibromoisoquinolin-3-amine

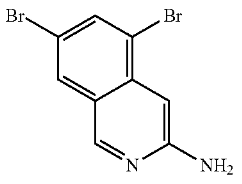 [SMILES: Nc1cc2c(Br)cc(Br)cc2cn1]

To a solution of (3,5-dibromophenyl)methanamine (P5) (3.00 g, 14.3 mmol) in MeOH was added methyl 2,2-diethoxyacetimidate (2.10 g, 13.6 mmol) and the solution was stirred at 60° C. overnight. After this time, the reaction mixture was concentrated under reduced pressure. $H_2SO_4$ (15 mL) was added to the residue and the mixture was stirred at room temperature for 3 hours. The mixture was adjusted to pH 8 using NaOH (aq. soln. 12M). The organics were extracted into EtOAc and subsequently concentrated under reduced pressure. The residue was chromatographed [$SiO_2$] to give 5,7-dibromoisoquinolin-3-amine (P9) (2.40 g) LCMS ES$^+$ 301, 303, 305 [M+H]$^+$, Rt=0.98 mins (Method 2).

$^1$H NMR (400 MHz, DMSO-$d_6$): δ: ppm 8.83 (s, 1H), 8.12 (s, 1H), 7.94 (s, 1H), 6.75 (s, 1H), 6.46 (s, 2H)

Preparation 10 (P10)

5,7-Dibromoisoquinoline

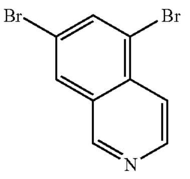

To a mixture of (Z)-1-(3,5-dibromophenyl)-N-(2,2-dimethoxyethyl)methanimine (P7) (7.00 g, 207.7 mmol) in DCM (10 mL) was added $H_2SO_4$ (60 mL) at 0° C. The mixture was stirred at 80° C. for 5 hours. The reaction mixture was quenched with ice and NaOH (aq. soln., 2M) was added until pH=6-7. The organics were extracted with EtOAc, washed with brine, dried over $Na_2SO_4$ and concentrated under reduced pressure. The residue was chromatographed [$SiO_2$, Pet. ether:EtOAc, 10:1] to give 5,7-dibromoisoquinoline (P10) (3.10 g), LCMS ES$^+$ 286, 288 [M+H]+, Rt=1.655 mins (Method 1).

Preparation 11 (P11)

7-(4,4,5,5-Tetramethyl-1,3,2-dioxaborolan-2-yl)isoquinolin-3-amine

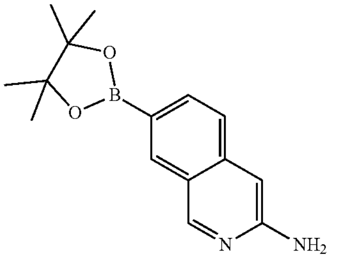 [SMILES: CC1(C)OB(c2ccc3cc(N)ncc3c2)OC1(C)C]

To a solution of 7-bromoisoquinolin-3-amine (1.00 g, 4.48 mmol) in DMSO (10 mL) was added 4,4,5,5-tetramethyl-2-(4,4,5,5-tetramethyl-1,3,2-dioxaborolan-2-yl)-1,3,2-dioxaborolane (1.20 g, 4.71 mmol), potassium acetate (1.70 g, 17.92 mmol) and $Pd(PPh_3)_2Cl_2$ (0.400 g). Argon was bubbled through the solution and the resulting solution was stirred at 100° C. overnight. After this time, the organics were extracted with DCM, washed with water, dried over $Na_2SO_4$ and concentrated under reduced pressure. The resulting residue was chromatographed [$SiO_2$, Pet. ether: EtOAc, 1:1] to give 7-(4,4,5,5-tetramethyl-1,3,2-dioxaborolan-2-yl)isoquinolin-3-amine (P11) (0.51 g), LCMS $ES^+$ 271 [M+H]+, Rt=1.621 mins (Method 3).

Preparation 12 (P12)

7-(2-Fluoro-6-methyl-phenyl)isoquinolin-3-amine

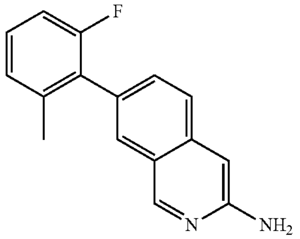 [SMILES: Cc1cccc(Cl)c1-c1ccc2cc(N)ncc2c1]

To a solution of 7-(4,4,5,5-tetramethyl-1,3,2-dioxaborolan-2-yl)isoquinolin-3-amine (P11) (0.51 g, 1.89 mmol) in 1,4-dioxane (5 mL) was added 1-fluoro-2-iodo-3-methyl-benzene (0.446 g, 1.89 mmol), water (1 mL), $Cs_2CO_3$ (1.20 g, 3.78 mmol) and $Pd(dppf)Cl_2$ (0.139 g). Argon was bubbled through the solution and the mixture was stirred at 100° C. for 2 hours. The organics were extracted into EtOAc, washed with water, dried over $Na_2SO_4$ and concentrated under reduced pressure. The resulting residue was chromatographed [$SiO_2$, Pet.Ether:EtOAc, 2:1] to give 7-(2- fluoro-6-methyl-phenyl)isoquinolin-3-amine (P12), (0.480 g), LCMS $ES^+$253 $[M+H]^+$, Rt=1.127 mins (Method 1).

The following compounds were prepared in a similar manner to 7-(2-fluoro-6-methyl-phenyl)isoquinolin-3-amine (P12) using 7-(4,4,5,5-tetramethyl-1,3,2-dioxaborolan-2-yl)isoquinolin-3-amine (P11) and the appropriate aryl halide:

| Preparation | Structure | Name | LCMS Data |
|---|---|---|---|
| P13 | 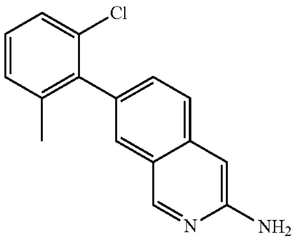 | 7-(2-chloro-6-methyl-phenyl)isoquinolin-3-amine | $ES^+$ 269, 271 $[M + H]^+$, Rt = 1.107 mins (Method 1) |

Preparation 14 (P14)

5-Bromo-7-(2-fluoro-6-methyl-phenyl)isoquinoline

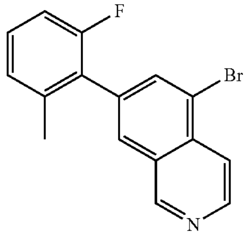 [SMILES: Cc1cccc(F)c1-c1cc(Br)c2ccncc2c1]

To a solution of 5,7-dibromoisoquinoline (P9) (1.10 g, 3.84 mmol), 2-(2-fluoro-6-methyl-phenyl)-4,4,5,5-tetramethyl-1,3,2-dioxaborolane (0.990 g, 4.23 mmol) and $Pd(dppf)Cl_2$ (0.280 g, 0.384 mmol) in dioxane/$H_2O$ (50 mL/5 mL) was added $Cs_2CO_3$ (2.50 g, 7.68 mmol). The mixture was stirred at 25° C. for 3 hours. After this time, the mixture was filtered and concentrated under reduced pressure. The residue was chromatographed [$SiO_2$, Pet. ether: EtOAc 10%-50%] to give 5-bromo-7-(2-fluoro-6-methyl-phenyl)isoquinoline and 7-bromo-5-(2-fluoro-6-methyl-phenyl)isoquinoline As a mixture of regioisomers (P14) (0.600 g), LCMS $ES^+$ 316 $[M+H]^+$, Rt=1.715, 1.835 mins (Method 1).

The following compounds were prepared in a similar manner to 5-bromo-7-(2-fluoro-6-methyl-phenyl)isoquinoline (P14) using 5,7-dibromoisoquinoline (P9) and the appropriate boronic ester:

| Preparation | Structure | Name | LCMS Data |
|---|---|---|---|
| P15 | 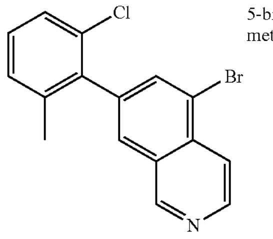 | 5-bromo-7-(2-chloro-6-methyl-phenyl)isoquinoline | $ES^+$ 334 $[M + H]^+$, Rt = 1.813, 1.943 mins (Method 1) |

Preparation 16 (P16)

4-bromo-7-(2-fluoro-6-methyl-phenyl)isoquinolin-3-amine

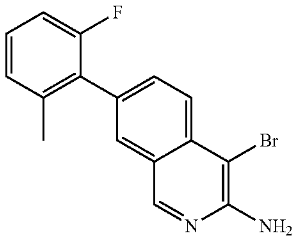

To a solution of 7-(2-fluoro-6-methyl-phenyl)isoquinolin-3-amine (P12) (0.48 g, 1.45 mmol) in DCM (5 mL) at 0° C. was added N-bromosuccinimide (0.258 g, 1.45 mmol). The solution was allowed to warm to room temperature and stirred at room temperature overnight.

The mixture was washed with water, dried over $Na_2SO_4$, and concentrated under reduced pressure. The resulting residue was chromatographed [$SiO_2$, Pet. ether:EtOAc, 5:1] to afford 4-bromo-7-(2-fluoro-6-methyl-phenyl)isoquinolin-3-amine (P16) (0.390 g), LCMS $ES^+$ 331, 333 $[M+H]^+$, Rt=1.787 mins (Method 1).

The following compounds were prepared in a similar manner to 4-bromo-7-(2-fluoro-6-methyl-phenyl)isoquinolin-3-amine (P16) using the appropriate amino 7-aryl-isoquinolin-3-amine and N-bromosuccinimide:

| Preparation | Precursor | Structure | Name | LCMS Data |
|---|---|---|---|---|
| P17 | P13 | 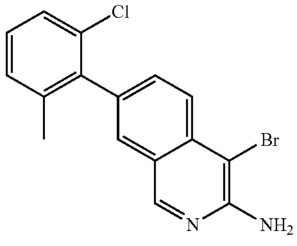 | 4-bromo-7-(2-chloro-6-methyl-phenyl)isoquinolin-3-amine | $ES^+$ 346 $[M + H]^+$, Rt = 1.933 mins (Method 1) |

Preparation 18 (P18)

Methyl 3-amino-7-(2-fluoro-6-methyl-phenyl)isoquinoline-4-carboxylate

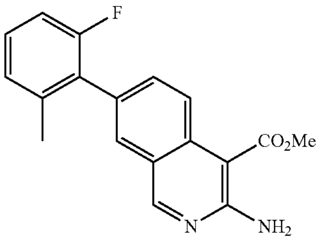 [SMILES: COC(=O)c1c(N)ncc2cc(-c3c(C)cccc3F)ccc12]

To a solution of 4-bromo-7-(2-fluoro-6-methyl-phenyl)isoquinolin-3-amine (P16) (0.050 g, 0.151 mmol) in DMF (1 mL) was added $Pd(PPh_3)_2Cl_2$ (0.010 g, 0.015 mmol), $Na_2CO_3$ (0.032 g, 0.302 mmol) and MeOH (1 mL). CO (gas) was bubbled through the solution and the resulting mixture was stirred at 100° C. overnight. The organics were extracted into EtOAc, washed with brine, dried over $Na_2SO_4$ and concentrated under reduced pressure. The resulting residue was chromatographed [$SiO_2$, Pet. ether:EtOAc, 3:1] to give methyl 3-amino-7-(2-fluoro-6-methyl-phenyl)isoquinoline-4-carboxylate (P18) (0.050 g), LCMS $ES^+$ 311 $[M+H]^+$, Rt=1.687 mins (Method 1).

The following compounds were prepared in a similar manner to methyl 3-amino-7-(2-fluoro-6-methyl-phenyl)isoquinoline-4-carboxylate (P18) using the appropriate amino 4-bromo-7-aryl-isoquinolin-3-amine:

| Preparation | Precursor | Structure | Name | LCMS Data |
|---|---|---|---|---|
| P19 | P17 | 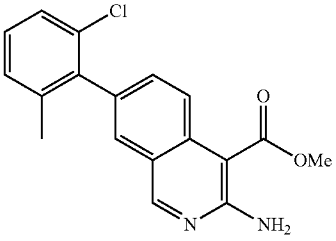 [SMILES: COC(=O)c1c(N)ncc2cc(-c3c(C)cccc3Cl)ccc12] | methyl 3-amino-7-(2-chloro-6-methyl-phenyl)isoquinoline-4-carboxylate | $ES^+$ 327 $[M + H]^+$, Rt = 1.860 mins (Method 1) |

Preparation 20 (P20)

3-Amino-7-(2-fluoro-6-methyl-phenyl)isoquinoline-4-carboxylic acid

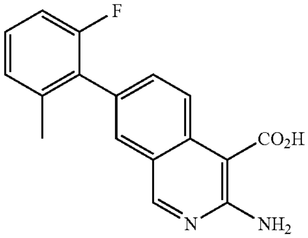

To a solution of methyl 3-amino-7-(2-fluoro-6-methyl-phenyl)isoquinoline-4-carboxylate (P18) (0.050 g) in MeOH (4 mL) was added NaOH (aq. soln., 4N, 2 mL) and the solution was stirred at 70° C. for 2 hours. The solution was concentrated under reduced pressure before the residue was dissolved in water and neutralised using HCl (aq. soln., 4N). The organics were extracted with EtOAc, dried over $Na_2SO_4$ and concentrated under reduced pressure to give 3-amino-7-(2-fluoro-6-methyl-phenyl)isoquinoline-4-carboxylic acid (P20) (0.040 g), LCMS $ES^-$ 295 $[M-H]^-$, Rt=1.355 mins (Method 1).

The following compounds were prepared in a similar manner to methyl 3-amino-7-(2-fluoro-6-methyl-phenyl) isoquinoline-4-carboxylic acid (P20) using the appropriate amino 4-bromo-7-aryl-isoquinolin-4-carboxylate:

Preparation 22 (P22)

5-Chloro-7-(2-fluoro-6-methyl-phenyl)isoquinolin-3-amine

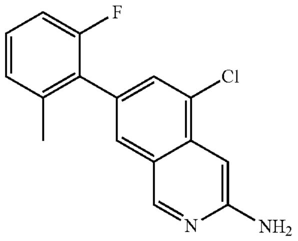

A round-bottom flask equipped with a magnetic stir bar was charged with a mixture of 7-bromo-5-chloro-isoquinolin-3-amine and 5-bromo-7-chloro-isoquinolin-3-amine (P8) (3.00 g, 11.65 mmol), 2-(2-fluoro-6-methyl-phenyl)-4,4,5,5-tetramethyl-1,3,2-dioxaborolane (P1) (7.20 g, 30.5 mmol), $Cs_2CO_3$ (11.4 g, 34.9 mmol), Pd(dppf)$Cl_2$ (0.300 g), dioxane (30 mL) and $H_2O$ (3 mL). This mixture was heated to 100° C. and stirred for overnight under an atmosphere of argon. After this time, the reaction mixture was cooled to room temperature and filtered. The filtrate was concentrated under reduced pressure and diluted with EtOAc (60 mL). The solution was washed with water, brine, dried over $Na_2SO_4$, concentrated and chromatographed to give 5-chloro-7-(2-fluoro-6-methyl-phenyl)isoquinolin-3-amine (P22) and 7-chloro-5-(2-fluoro-6-methyl-phenyl)isoquinolin-3-amine as a mixture of regioisomers which was used directly in subsequent steps without further purification LCMS $ES^+$ 287 $[M+H]^+$, Rt=8.931, 9.279 mins (extended Method 1).

| Preparation | Precursor | Structure | Name | LCMS Data |
|---|---|---|---|---|
| P21 | P19 | 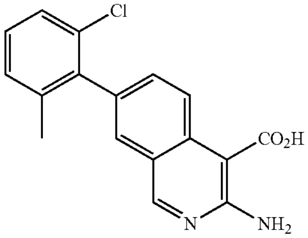 [SMILES: Cc1cccc(Cl)c1-c1ccc2c(C(=O)O)c(N)ncc2c1] | 3-amino-7-(2-chloro-6-methyl-phenyl)isoquinoline-4-carboxylic acid | $ES^-$ 313 $[M - H]^-$, Rt = 1.472 mins (Method 1) |

Preparation 22a (P22a)

4-bromo-5-chloro-7-(2-fluoro-6-methyl-phenyl)isoquinolin-3-amine

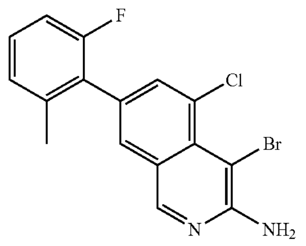

A mixture of 5-chloro-7-(2-fluoro-6-methyl-phenyl)isoquinolin-3-amine (P22) and 7-chloro-5-(2-fluoro-6-methyl-phenyl)isoquinolin-3-amine regioisomers (3.30 g, 11.51 mmol), $Et_3N$ (0.349 g, 3.45 mmol), AcOH (0.069 g, 1.5 mmol) in DMF (30.0 mL) was stirred at 0° C. N-Bromosuccinimide (2.46 g, 13.81 mmol) was added and the mixture was stirred at 0° C. for 30 minutes. After this time $H_2O$ (50.0 mL) was added. The organics were extracted using EtOAc (3×30 mL) and washed with brine. The combined organics were dried over $Na_2SO_4$, filtered and concentrated under reduced pressure. The residue was chromatographed [$SiO_2$, Pet. ether:EtOAc, 5:1] to give a mixture of 4-bromo-5-chloro-7-(2-fluoro-6-methyl-phenyl)isoquinolin-3-amine and 4-bromo-7-chloro-5-(2-fluoro-6-methyl-phenyl)isoquinolin-3-amine (P22a) (2.3 g).

$^1H$ NMR (400 MHz, DMSO-de): δ: ppm 8.97 (s, 1H), 7.95 (s, 1H), 7.71 (s, 1H), 7.34-7.37 (m, 1H), 7.14-7.21 (m, 2H), 6.73 (s, 2H), 2.20 (s, 3H).

Preparation 22b (P22b)

3-amino-5-chloro-7-(2-fluoro-6-methyl-phenyl)isoquinoline-4-carbonitrile

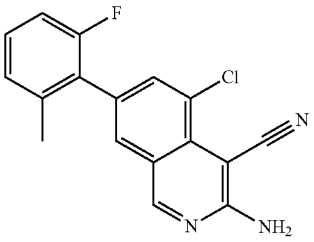 [SMILES: Cc1cccc(F)c1-c1cc(Cl)c2c(C#N)c(N)ncc2c1]

A mixture of 4-bromo-5-chloro-7-(2-fluoro-6-methyl-phenyl)isoquinolin-3-amine and 4-bromo-7-chloro-5-(2-fluoro-6-methyl-phenyl)isoquinolin-3-amine (P22a) (1.20 g, 3.28 mmol) and CuCN (0.354 g, 3.94 mmol) in NMP (6.0 mL) was heated at 150° C. in the microwave for 1 hour. After this time, the mixture was cooled to room temperature and $H_2O$ (6.0 mL) was added. The organics were extracted into EtOAc (3×5.0 mL) and washed with brine. The combined organics were dried over $Na_2SO_4$, filtered and concentrated under reduced pressure. The residue was chromatographed [$SiO_2$, Pet. ether:EtOAc, 7:1] to give 3-amino-5-chloro-7-(2-fluoro-6-methyl-phenyl)isoquinoline-4-carbonitrile (P22b) (0.40 g)

$^1H$ NMR (400 MHz, DMSO-$d_6$): δ: ppm 9.15 (s, 1H), 7.97 (s, 1H), 7.90 (s, 1H), 7.48 (bs, 2H), 7.35-7.40 (m, 1H), 7.14-7.22 (m, 2H), 2.19 (s, 3H)

Preparation 23 (P23)

5-Bromo-7-(2-fluoro-6-methyl-phenyl)isoquinolin-3-amine

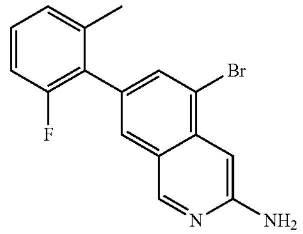 [SMILES: Cc1cccc(F)c1-c1cc(Br)c2cc(N)ncc2c1]

To a solution of 5,7-dibromoisoquinolin-3-amine (P9) (1.00 g, 3.3 mmol) in 1,4-dioxane (15 mL) was added 2-(2-fluoro-6-methyl-phenyl)-4,4,5,5-tetramethyl-1,3,2-dioxaborolane (P1) (0.800 g, 3.4 mmol). Pd (dppf)$Cl_2$ (0.100 g), $Cs_2CO_3$ (2.14 g, 6.6 mmol) and $H_2O$ (1.0 mL) were added and the mixture was stirred at 100° C. for 2 hours. The mixture was allowed to cool room temperature. The organics were extracted into EtOAc and the solution concentrated under reduced pressure. The resulting residue was purified using preparative HPLC (Method 2) to give 5-bromo-7-(2-fluoro-6-methyl-phenyl)isoquinolin-3-amine and 7-bromo-5-(2-fluoro-6-methyl-phenyl)isoquinolin-3-amine as a mixture of regioisomers (P23) (0.350 g) which was used in subsequent steps without further purification, LCMS $ES^+$ 331, 333 $[M+H]^+$, Rt=1.22, 1.26 mins (Method 2).

The following compounds were prepared as a mixture of regioisomers in a similar manner to 5-bromo-7-(2-fluoro-6-methyl-phenyl)isoquinolin-3-amine (P23) and 7-bromo-5-(2-fluoro-6-methyl-phenyl)isoquinolin-3-amine using 5,7-dibromoisoquinolin-3-amine (P9) and the appropriate boronic ester:

| Preparation | Structure | Name | LCMS Data |
|---|---|---|---|
| P24 | 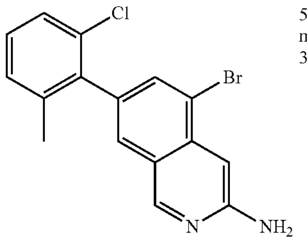 | 5-bromo-7-(2-chloro-6-methyl-phenyl)isoquinolin-3-amine | $ES^+$ 347 $[M + H]^+$, Rt = 1.29, 1.33 mins (Method 2) |

Preparation 25 (P25)

Methyl 3-amino-7-(2-fluoro-6-methyl-phenyl)isoquinoline-5-carboxylate

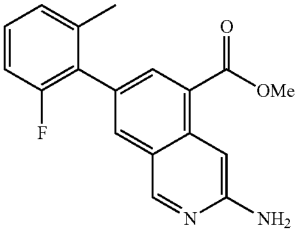 [SMILES: COC(=O)c1cc(-c2c(C)cccc2F)cc2cnc(N)cc12]

To a solution of 5-bromo-7-(2-fluoro-6-methyl-phenyl)isoquinolin-3-amine and 7-bromo-5-(2-fluoro-6-methyl-phenyl)isoquinolin-3-amine regioisomeric mixture (P23) (0.055 g, 1.67 mmol) in MeOH (6.0 mL) was added $Et_3N$ (0.378 g, 3.34 mmol) and $Pd(dppf)Cl_2$ (0.122 g, 0.67 mmol). The mixture was stirred at 100° C. under an atmosphere of CO for 16 hours. The reaction mixture was allowed to cool to room temperature. Water (3 mL) was added, the mixture was filtered and the organics were extracted into EtOAc (3×5 mL). The organics were washed with brine, dried over $Na_2SO_4$, filtered and concentrated under reduced pressure. The residue was chromatographed [$SiO_2$, EtOAc] to give methyl 3-amino-7-(2-fluoro-6-methyl-phenyl)isoquinoline-5-carboxylate and methyl 3-amino-5-(2-fluoro-6-methyl-phenyl)isoquinoline-7-carboxylate as a mixture of regioisomers (P25), (0.365 g), LCMS $ES^+$ 311 $[M+H]^+$, Rt=1.620 mins (Method 1)

Preparation 26 (P26)

3-Amino-7-(2-fluoro-6-methyl-phenyl)isoquinoline-5-carboxylic acid

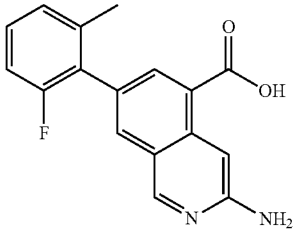 [SMILES: Cc1cccc(F)c1-c1cc(C(=O)O)c2cc(N)ncc2c1]

To a solution of methyl 3-amino-7-(2-fluoro-6-methyl-phenyl)isoquinoline-5-carboxylate and methyl 3-amino-5-(2-fluoro-6-methyl-phenyl)isoquinoline-7-carboxylate as a mixture of regioisomers (P25), (0.365 g, 1.18 mmol) in MeOH/H2O (20:1, 4.0 mL) was added LiOH (0.141 g, 5.9 mmol). The mixture was stirred at room temperature for 2 hours. HCl (1M aq. soln.) was added to the solution until pH=7. The organics were extracted with EtOAc (6×5 mL) and concentrated under reduced pressure to give 3-amino-7-(2-fluoro-6-methyl-phenyl)isoquinoline-5-carboxylic acid and 3-amino-5-(2-fluoro-6-methyl-phenyl)isoquinoline-7-carboxylic acid as a mixture of regioisomers (P26) (0.312 g), LCMS $ES^+$ 296 $[M+H]^+$, Rt=0.893 mins (Method 1).

Preparation 27 (P27)

5-Chloro-7-(2-fluoro-6-methyl-phenyl)-N-methyl-isoquinolin-3-amine

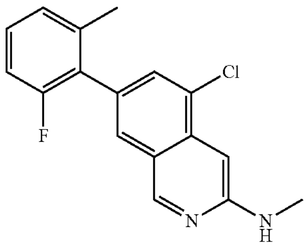 [SMILES: CNc1cc2c(Cl)cc(-c3c(C)cccc3F)cc2cn1]

To a solution of 5-chloro-7-(2-fluoro-6-methyl-phenyl)isoquinolin-3-amine and 7-chloro-5-(2-fluoro-6-methyl-phenyl)isoquinolin-3-amine mixture of regioisomers (P22) (0.150 g, 0.52 mmol) in THF (5 mL) was added paraformaldehyde (0.078 g, 2.62 mmol) and MeOH (3 drops). The solution was stirred at room temperature for 1 hour before $NaBH_3CN$ (0.198 g, 3.14 mmol) was added and the solution was stirred at 60° C. overnight. Paraformaldehyde (0.039 g) and $NaBH_3CN$ (0.100 g) were added and the solution was stirred at 60° C. for a further 5 hours. The reaction was repeated (5×30 mg regioisomer mixture used). The batches were combined and chromatographed to give 5-chloro-7-(2-fluoro-6-methyl-phenyl)-N-methyl-isoquinolin-3-amine and 7-chloro-5-(2-fluoro-6-methyl-phenyl)-N-methyl-isoquinolin-3-amine as a mixture of regiosiomers (P27) (0.189 g), LCMS $ES^+$ 301, 303 $[M+H]^+$, Rt=1.18, 1.32 mins (Method 2).

Preparation 28 (P28)

5-Chloro-7-(2-fluoro-6-methyl-phenyl)-N-isopropyl-isoquinolin-3-amine

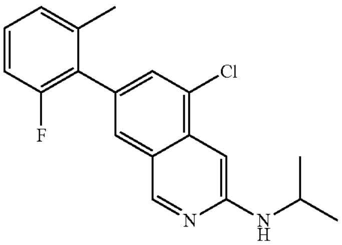 [SMILES: Cc1cccc(F)c1-c1cc(Cl)c2cc(NC(C)C)ncc2c1]

A solution of a solution of 5-chloro-7-(2-fluoro-6-methyl-phenyl)isoquinolin-3-amine and 7-chloro-5-(2-fluoro-6-methyl-phenyl)isoquinolin-3-amine mixture of regioisomers (P22) (0.400 g, 1.39 mmol) in MeOH (5 mL) was added acetone (5 mL) and the solution was stirred at room temperature for 1 hour. $NaBH_3CN$ (0.352 g, 5.59 mmol) and acetic acid (a few drops) were added and the solution was stirred overnight. The reaction was repeated (3×30 mg regioisomer mixture used). The batches were combined and chromatographed [$SiO_2$, Pet. ether:EtOAc, 5:1] to give 5-chloro-7-(2-fluoro-6-methyl-phenyl)-N-isopropyl-isoquinolin-3-amine and 7-chloro-5-(2-fluoro-6-methyl-phenyl)-

N-isopropyl-isoquinolin-3-amine as a mixture of regioisomers (P28) (0.292 g), LCMS $ES^+$ 329 $[M+H]^+$, Rt=1.65, 1.76 mins (Method 2).

Preparation 29 (P29)

3-Amino-7-(2-fluoro-6-methyl-phenyl)isoquinolin-5-ol

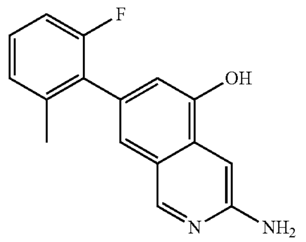

To a solution of 5-chloro-7-(2-fluoro-6-methyl-phenyl)isoquinolin-3-amine (regioisomeric mixture) (P22) (0.200 g, 5.22 mmol), t-BuXPhos (0.020 g) in 1,4-dioxane (6 mL) and water (2 mL) was added KOH (0.292 g, 5.22 mmol). $Pd2(dba)_3$ (0.020 g) was added and the resulting mixture was heated in the microwave at 100° C. for 3 hours. The mixture was diluted with water and the organics were extracted with EtOAc. The combined organics were dried over $MgSO_4$, filtered and concentrated under reduced pressure. The residue was chromatographed to give 3-amino-7-(2-fluoro-6-methyl-phenyl)isoquinolin-5-ol and 3-amino-5-(2-fluoro-6-methyl-phenyl)isoquinolin-7-ol as a mixture of regioisomers (P29), LCMS $ES^+$269 $[M+H]^+$, Rt=1.03 mins (Method 2).

Preparation 30 (P30)

tert-Butyl 3-[(3-amino-7-chloro-5-isoquinolyl)amino]azetidine-1-carboxylate

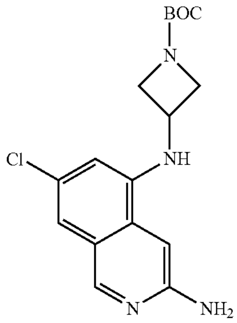 [SMILES: CC(C)(C)OC(=O)N1CC(Nc2cc(Cl)cc3cnc(N)cc23)C1]

To a solution of 7-bromo-5-chloro-isoquinolin-3-amine and 5-bromo-7-chloro-isoquinolin-3-amine regioisomers (P8) (0.500 g, 1.95 mmol) in 1,4-dioxane (5 mL) was added tert-butyl 3-aminoazetidine-1-carboxylate (0.435 g, 2.53 mmol), t-BuONa (0.374 g, 3.90 mmol), $Pd_2(dba)_3$ (0.050 g) and t-BuXPhos (0.050 g). The mixture was stirred at 80° C. overnight before the organics were extracted with EtOAc and concentrated under reduced pressure to give tert-butyl 3-[(3-amino-7-chloro-5-isoquinolyl)amino]azetidine-1-carboxylate and tert-butyl 3-[(3-amino-5-chloro-7-isoquinolyl)amino]azetidine-1-carboxylate (P30) (0.250 g) LCMS ES-349, 351 $[M+H]^+$, Rt=1.34, 1.48 mins (Method 2).

The following compounds were prepared as a mixture of regioisomers in a similar manner to tert-butyl 3-[(3-amino-7-chloro-5-isoquinolyl)amino]azetidine-1-carboxylate (P30) using 7-bromo-5-chloro-isoquinolin-3-amine and 5-bromo-7-chloro-isoquinolin-3-amine regioisomers (P8) and the appropriate amine:

| Preparation | Structure | Name | LCMS Data |
|---|---|---|---|
| P31 | 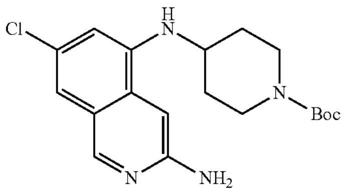 [SMILES: CC(C)(C)OC(=O)N1CCC(Nc2cc(Cl)cc3cnc(N)cc23)CC1] | tert-butyl 4-[(3-amino-7-chloro-5-isoquinolyl)amino]piperidine-1-carboxylate | $ES^+$ 377 $[M + H]^+$, Rt = 0.863, 1.033 mins (Method 1) |
| P32 | 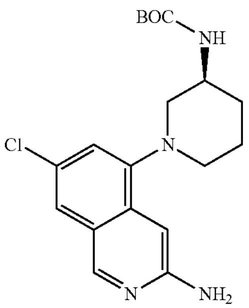 [SMILES: CC(C)(C)OC(=O)N[C@H]1CCCN(c2cc(Cl)cc3cnc(N)cc23)C1] | tert-butyl N-[(3S)-1-(3-amino-7-chloro-5-isoquinolyl)-3-piperidyl]carbamate | $ES^+$ 377, 379 $[M + H]^+$, Rt = 1.01 mins (Method 2) |

Preparation 33 (P33)

7-Chloro-N5-(1-methyl-4-piperidyl)isoquinoline-3,5-diamine

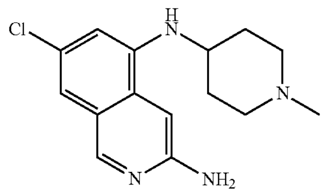 [SMILES: CN1CCC(Nc2cc(Cl)cc3cnc(N)cc23)CC1]

To a solution of 7-bromo-5-chloro-isoquinolin-3-amine and 5-bromo-7-chloro-isoquinolin-3-amine regioisomers (P8) (1.00 g, 3.89 mmol) in 1,4-dioxane (10 mL) was added 1-methylpiperidin-4-amine (0.582 g, 5.06 mmol), t-BuONa (0.747 g, 7.78 mmol), $Pd_2(dba)_3$ (0.100 g), and t-BuXPhos (0.100 g). The mixture was stirred at 80° C. overnight. The reaction mixture was cooled to room temperature, diluted with water and the organics were extracted with EtOAc (3×50 mL). The combined organics were concentrated under reduced pressure and the resulting residue chromatographed [$SiO_2$] to give 7-chloro-N5-(1-methyl-4-piperidyl)isoquinoline-3,5-diamine and 5-chloro-N7-(1-methyl-4-piperidyl) isoquinoline-3,7-diamine as a mixture of regioisomers (P33) (0.260 g), LCMS $ES^+$291, 293 $[M+H]^+$, Rt=0.23, 0.26 mins (Method 2).

Preparation 34 (P34)

Methyl 5-bromo-2-(bromomethyl)-3-nitro-benzoate

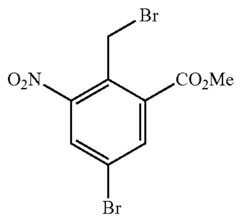 [SMILES: COC(=O)c1cc(Br)cc([N+](=O)[O-])c1CBr]

A mixture of methyl 5-bromo-2-methyl-3-nitro-benzoate (25.00 g, 91.24 mmol), N-bromosuccinimide (16.20 g, 91.01 mmol), benzoyl peroxide (1.10 g, 4.55 mmol), azobisisobutyronitrile (1.50 g, 9.15 mmol) in $CCl_4$ (300 mL) was stirred overnight at 80° C. The mixture was cooled to room temperature, filtered and washed with $CCl_4$. The filtrate was concentrated under reduced pressure and the resulting residue chromatographed to give methyl 5-bromo-2-(bromomethyl)-3-nitro-benzoate (P34) (24.50 g), LCMS $ES^+$ 336 $[(M-Me)+H]^+$, Rt=1.847 mins (Method 1).

Preparation 35 (P35)

Methyl 5-bromo-2-(cyanomethyl)-3-nitro-benzoate

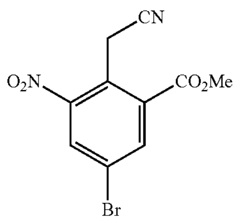 [SMILES: COC(=O)c1cc(Br)cc([N+](=O)[O-])c1CC#N]

A solution of KCN (4.33 g, 0.067 mmol) in MeCN/Water (40 mL) was added to methyl 5-bromo-2-(bromomethyl)-3-nitro-benzoate (P34) (23.50 g, 0.067 mmol) in MeCN/water (200 mL). The reaction mixture was stirred at room temperature for 6 hours. The mixture was diluted with water (200 mL) and the organics were extracted with EtOAc (200 mL). The combined organics were washed with brine, dried over $Na_2SO_4$ and concentrated under reduced pressure. The resulting residue was chromatographed [$SiO_2$, Pet. ether:EtOAc, 5:1] to give methyl 5-bromo-2-(cyanomethyl)-3-nitro-benzoate (P35) (14.20 g), LCMS $ES^+$ 299 $[M+H]^+$, Rt=1.803 mins (Method 1).

Preparation 36 (P36)

Methyl 2-(cyanomethyl)-5-(2-fluoro-6-methyl-phenyl)-3-nitro-benzoate

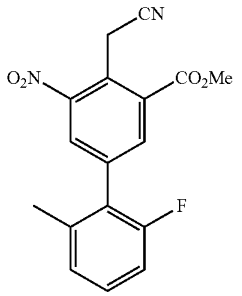 [SMILES: COC(=O)c1cc(-c2c(C)cccc2F)cc([N+](=O)[O-])c1CC#N]

A mixture of methyl 5-bromo-2-(cyanomethyl)-3-nitro-benzoate (P35) (3.20 g, 10.70 mmol), 2-(2-fluoro-6-methyl-phenyl)-4,4,5,5-tetramethyl-1,3,2-dioxaborolane (P1) (3.20 g, 13.80 mmol), $Pd(dppf)C_2$ (0.750 g, 1.07 mmol), $Na_2CO_3$ (2.30 g, 21.40 mmol) in 1,4-dioxane (70 mL) was stirred at 100° C. overnight. The solution was concentrated under reduced pressure and the residue was chromatographed [$SiO_2$, Pet. ether:EtOAc, 4:1] to give methyl 2-(cyanomethyl)-5-(2-fluoro-6-methyl-phenyl)-3-nitro-benzoate (P36) (2.50 g), LCMS $ES^-$ 327 $[M-H]^-$, Rt=1.766 mins (Method 1).

Preparation 37 (P37)

7-(2-Fluoro-6-methyl-phenyl)-3-methoxy-5-nitro-isoquinolin-1-ol

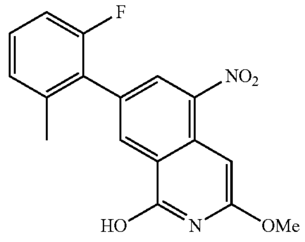 [SMILES: COc1cc2c([N+](=O)[O-])cc(-c3c(C)cccc3F)cc2c(O)n1]

A solution of methyl 2-(cyanomethyl)-5-(2-fluoro-6-methyl-phenyl)-3-nitro-benzoate (P36) (0.210 g, 0.64 mmol) in MeOH (5 mL) was added NaH (60%, 0.064 g, 2.67 mmol) and the reaction mixture was stirred at 80° C. for 3 hours. After this time, the mixture was diluted with water, filtered and the precipitate washed with $Et_2O$. the organics were concentrated under reduced pressure to give 7-(2-fluoro-6-methyl-phenyl)-3-methoxy-5-nitro-isoquinolin-1-ol (P37) (0.120 g), LCMS $ES^+$329 $[M+H]^+$, Rt=1.672 mins (Method 1).

Preparation 38 (P38)

1-Chloro-7-(2-fluoro-6-methyl-phenyl)-3-methoxy-5-nitro-isoquinoline

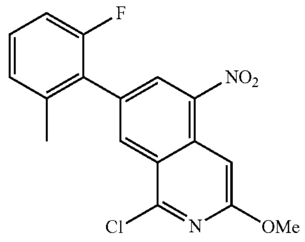 [SMILES: COc1cc2c([N+](=O)[O-])cc(-c3c(C)cccc3F)cc2c(Cl)n1]

A solution of 7-(2-fluoro-6-methyl-phenyl)-3-methoxy-5-nitro-isoquinolin-1-ol (P37) (0.070 g, 0.213 mmol) in $POCl_3$ (2 mL) was stirred overnight at 110° C. The solution was cooled to room temperature and the mixture was poured into water (5 mL). The pH was adjusted with $NaHCO_3$ (aq. soln). The organics were extracted with EtOAc (5 mL), concentrated and the resulting residue chromatographed to give 1-chloro-7-(2-fluoro-6-methyl-phenyl)-3-methoxy-5-nitro-isoquinoline (P38) (0.050 g), LCMS $ES^+$346 $[M+H]^+$, Rt=1.515 mins (Method 1).

Preparation 39 (P39)

7-(2-Fluoro-6-methyl-phenyl)-3-methoxy-isoquinolin-5-amine

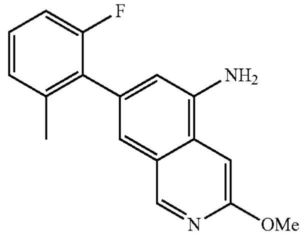 [SMILES: COc1cc2c(N)cc(-c3c(C)cccc3F)cc2cn1]

To a solution of 1-chloro-7-(2-fluoro-6-methyl-phenyl)-3-methoxy-5-nitro-isoquinoline (P38) (0.050 g, 0.15 mmol) in MeOH (15 mL) was added Pd/C (0.020 g) and $Et_3N$ (0.1 mL). the reaction was stirred overnight under an atmosphere of $H_2$ at room temperature. After this time, the mixture was filtered and the organics were concentrated under reduced pressure to give 7-(2-fluoro-6-methyl-phenyl)-3-methoxy-isoquinolin-5-amine (P39) (0.030 g), LCMS $ES^+$ 282 $[M+H]^+$, Rt=1.632 mins (Method 1).

Preparation 40 (P40)

5-Amino-7-(2-fluoro-6-methyl-phenyl)isoquinolin-3-ol

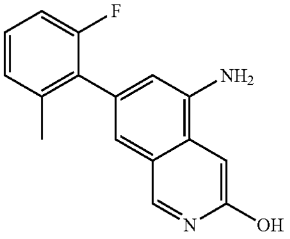 [SMILES: Cc1cccc(F)c1-c1cc(N)c2cc(O)ncc2c1]

A solution of 7-(2-fluoro-6-methyl-phenyl)-3-methoxy-isoquinolin-5-amine (P39) (0.030 g, 0.11 mmol) in acetic acid (0.5 mL) was added HBr (0.2 mL). The solution was stirred at 100° C. for 2 hours. Water was added to the solution and the pH was adjusted to pH 6-7 using $Na_2CO_3$. The organics were extracted with EtOAc and concentrated under reduced pressure. The residue was chromatographed [$SiO_2$, Pet. ether:EtOAc, 1:1] to give 5-amino-7-(2-fluoro-6-methyl-phenyl)isoquinolin-3-ol (P40), (0.020 g), LCMS $ES^+$ 269 $[M+H]^+$, Rt=1.243 mins (Method 1).

Preparation 41 (P41)

[5-Amino-7-(2-fluoro-6-methyl-phenyl)-3-isoquinolyl] trifluoromethanesulfonate

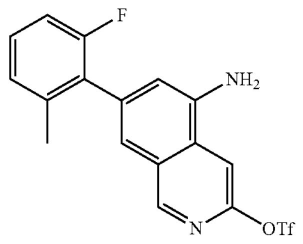 [SMILES: Cc1cccc(F)c1-c1cc(N)c2cc(OS(=O)(=O)C(F)(F)F)ncc2c1]

To a mixture of 5-amino-7-(2-fluoro-6-methyl-phenyl) isoquinolin-3-ol (P40) (0.300 g, 1.12 mmol), $Et_3N$ (0.226 g, 2.24 mmol) in DCM (10 mL) was added N-phenyl-bis (trifluoromethanesulfonimide) (0.480 g, 1.34 mmol). The mixture was stirred overnight. After this time, water was added to the mixture and the organics were extracted using DCM. The combined organics were concentrated under reduced pressure and the residue was chromatographed [$SiO_2$, Pet. ether:EtOAc, 5:1] to give [5-amino-7-(2-fluoro-6-methyl-phenyl)-3-isoquinolyl] trifluoromethanesulfonate (P41) (0.170 g), LCMS $ES^+$ 401 $[M+H]^+$, Rt=1.932 mins (Method 1)

Preparation 42 (P42)

7-(2-Fluoro-6-methyl-phenyl)isoquinolin-5-amine

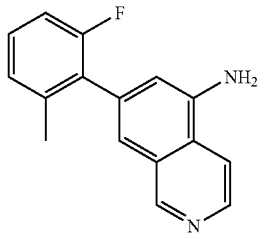 [SMILES: Cc1cccc(F)c1-c1cc(N)c2ccncc2c1]

A mixture of [5-amino-7-(2-fluoro-6-methyl-phenyl)-3-isoquinolyl]trifluoromethanesulfonate (P41) (0.150 g, 0.375 mmol), $Pd(PPh_3)_4$ (0.046 g, 0.038 mmol), formic acid (0.029 g, 0.56 mmol), DIPEA (0.145 g, 1.125 mmol) in NMP (1.5 mL) was stirred at 80° C. for 3 hours. After this time, the mixture was diluted with water (10 mL) and the organics extracted with EtOAc (10 mL). The combined organics were washed with brine (10 mL), dried over $Na_2SO_4$, filtered and concentrated under reduced pressure. The crude residue was chromatographed [$SiO_2$, Pet. ether:EtOAc, 1:1] to give 7-(2-fluoro-6-methyl-phenyl)isoquinolin-5-amine (P42) (0.080 g), LCMS $ES^+$ 401 $[M+H]^+$, Rt=1.932 mins (Method 1).

Preparation 43 (P43)

tert-Butyl 4-[[3-amino-7-(2-fluoro-6-methyl-phenyl)-5-isoquinolyl]amino]piperidine-1-carboxylate

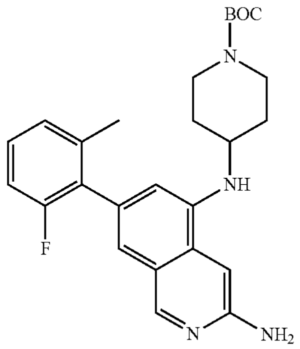 [SMILES: Cc1cccc(F)c1-c1cc(NC2CCN(C(=O)OC(C)(C)C)CC2)c2cc(N)ncc2c1]

To a solution of 5-chloro-7-(2-fluoro-6-methyl-phenyl) isoquinolin-3-amine and 7-chloro-5-(2-fluoro-6-methyl-phenyl)isoquinolin-3-amine mixture (P22) (0.700 g, 2.12 mmol) in 1,4-dioxane (15 mL) was added tert-butyl 4-aminopiperidine-1-carboxylate (0.848 g, 4.24 mmol), t-BuONa (0.407 g, 4.24 mmol), tBuXPhos (0.050 g) and $Pd_2(dba)_3$ (0.050 g). The mixture was degassed by bubbling a stream of argon through. The reaction was heated in a microwave at 11000 for 4 hours in a sealed tube. After this time, the mixture was allowed to cool to room temperature. The organics were extracted into EtOAc, washed with brine, dried over $Na_2SO_4$ and concentrated under reduced pressure. The resulting residue was chromatographed [$SiO_2$] to give tert-butyl 4-[[3-amino-7-(2-fluoro-6-methyl-phenyl)-5-isoquinolyl]amino]piperidine-1-carboxylate (P43) and ter-butyl 4-[[3-amino-5-(2-fluoro-6-methyl-phenyl)-7-isoquinolyl]amino]piperidine-1-carboxylate as a mix of regioisomers which was used directly in subsequent steps without further purification (0.400 g) LCMS $ES^+$ 451 $[M+H]^+$, Rt=1.21 mins (Method 2).

The following compounds were prepared as a mixture of regiosiomers in a similar manner to tert-butyl 4-[[3-amino-7-(2-fluoro-6-methyl-phenyl)-5-isoquinolyl]amino]piperidine-1-carboxylate (P43) using 5-chloro-7-(2-fluoro-6-methyl-phenyl)isoquinolin-3-amine regioisomeric mixture (P22) and the appropriate amine coupling partner:

| Preparation | Structure | Name | LCMS Data |
|---|---|---|---|
| P44 | 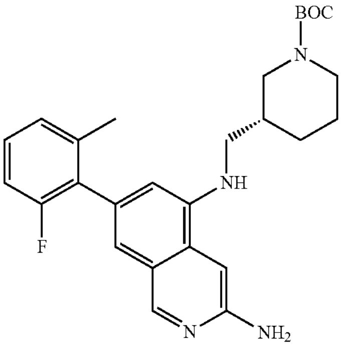 [SMILES: Cc1cccc(F)c1-c1cc(NC[C@H]2CCCN(C(=O)OC(C)(C)C)C2)c2cc(N)ncc2c1] | tert-butyl (3R)-3-[[[3-amino-7-(2-fluoro-6-methyl-phenyl)-5-isoquinolyl]amino]methyl] piperidine-1-carboxylate | ES$^+$ 465 [M + H]$^+$, Rt = 1.34/1.50 mins (Method 2) |
| P45 | 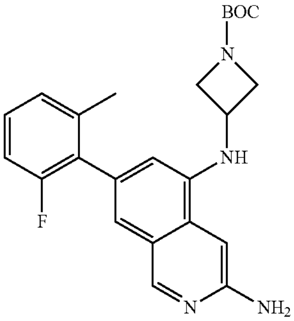 [SMILES: Cc1cccc(F)c1-c1cc(NC2CN(C(=O)OC(C)(C)C)C2)c2cc(N)ncc2c1] | tert-butyl 3-[[3-amino-7-(2-fluoro-6-methyl-phenyl)-5-isoquinolyl]amino] azetidine-1-carboxylate | ES$^+$ 424 [M + H]$^+$, Rt = 0.59/1.04 mins (Method 2) |
| P46 | 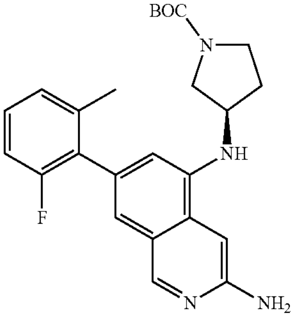 [SMILES: Cc1cccc(F)c1-c1cc(N[C@@H]2CCN(C(=O)OC(C)(C)C)C2)c2cc(N)ncc2c1] | tert-butyl (3R)-3-[[3-amino-7-(2-fluoro-6-methyl-phenyl)-5-isoquinolyl]amino] pyrrolidine-1-carboxylate | ES$^+$ 437 [M + H]$^+$, Rt = 1.18/1.37 mins (Method 2) |
| P47 | 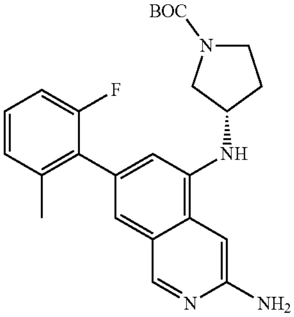 [SMILES: Cc1cccc(F)c1-c1cc(N[C@H]2CCN(C(=O)OC(C)(C)C)C2)c2cc(N)ncc2c1] | tert-butyl (3S)-3-[[3-amino-7-(2-fluoro-6-methyl-phenyl)-5-isoquinolyl]amino] pyrrolidine-1-carboxylate | ES$^+$ 437 [M + H]$^+$, Rt = 1.20/1.24 mins (Method 2) |
| P48 | 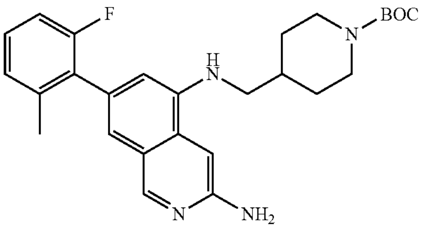 [SMILES: Cc1cccc(F)c1-c1cc(NCC2CCN(C(=O)OC(C)(C)C)CC2)c2cc(N)ncc2c1] | tert-butyl 4-[[[3-amino-7-(2-fluoro-6-methyl-phenyl)-5-isoquinolyl]amino]methyl] piperidine-1-carboxylate | ES$^+$ 465 [M + H]$^+$, Rt = 1.22/1.51 mins (Method 1) |

-continued

| Preparation | Structure | Name | LCMS Data |
|---|---|---|---|
| P49 | 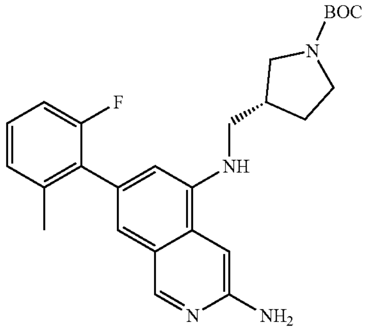 [SMILES: Cc1cccc(F)c1-c1cc(NC[C@H]2CCN(C(=O)OC(C)(C)C)C2)c2cc(N)ncc2c1] | tert-butyl (3R)-3-[[[3-amino-7-(2-fluoro-6-methyl-phenyl)-5-isoquinolyl]amino]methyl]pyrrolidine-1-carboxylate | $ES^+$ 451 $[M + H]^+$, Rt = 0.99/1.29 mins (Method 2) |
| P50 | 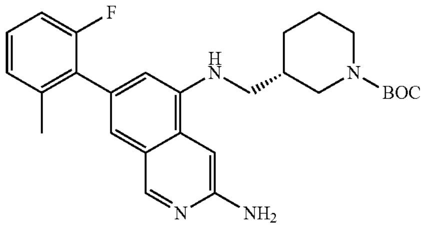 [SMILES: Cc1cccc(F)c1-c1cc(NC[C@@H]2CCCN(C(=O)OC(C)(C)C)C2)c2cc(N)ncc2c1] | tert-butyl (3S)-3-[[[3-amino-7-(2-fluoro-6-methyl-phenyl)-5-isoquinolyl]amino]methyl]piperidine-1-carboxylate | $ES^+$ 465 $[M + H]^+$, Rt = 1.17/1.45 mins (Method 2) |
| P51 | 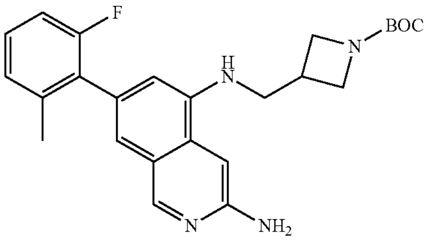 [SMILES: Cc1cccc(F)c1-c1cc(NCC2CN(C(=O)OC(C)(C)C)C2)c2cc(N)ncc2c1] | tert-butyl 3-[[[3-amino-7-(2-fluoro-6-methyl-phenyl)-5-isoquinolyl]amino]methyl]azetidine-1-carboxylate | $ES^+$ 437 $[M + H]^+$, Rt = 1.10/1.27 mins (Method 2) |
| P52 | 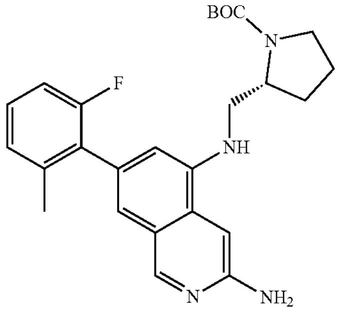 [SMILES: Cc1cccc(F)c1-c1cc(NC[C@H]2CCCN2C(=O)OC(C)(C)C)c2cc(N)ncc2c1] | tert-butyl (2R)-2-[[[3-amino-7-(2-fluoro-6-methyl-phenyl)-5-isoquinolyl]amino]methyl]pyrrolidine-1-carboxylate | $ES^+$ 451 $[M + H]^+$, Rt = 0.57/0.99 mins (Method 2) |
| P53 | 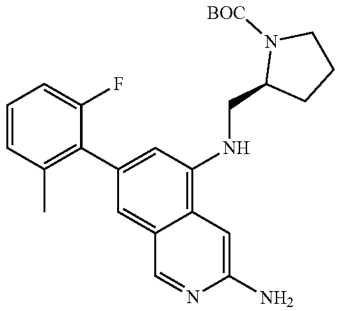 [SMILES: Cc1cccc(F)c1-c1cc(NC[C@@H]2CCCN2C(=O)OC(C)(C)C)c2cc(N)ncc2c1] | tert-butyl (2S)-2-[[[3-amino-7-(2-fluoro-6-methyl-phenyl)-5-isoquinolyl]amino]methyl]pyrrolidine-1-carboxylate | $ES^+$ 451 $[M + H]^+$, Rt = 1.030/1.48 mins (Method 2) |

-continued

| Preparation | Structure | Name | LCMS Data |
| --- | --- | --- | --- |
| P54 | 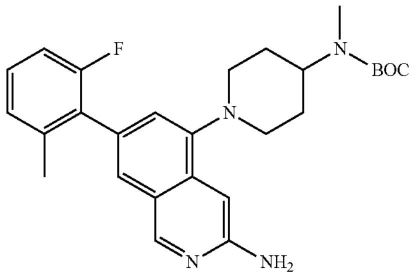 [SMILES: Cc1cccc(F)c1-c1cc(N2CCC(N(C)C(=O)OC(C)(C)C)CC2)c2cc(N)ncc2c1] | tert-butyl N-[1-[3-amino-7-(2-fluoro-6-methyl-phenyl)-5-isoquinolyl]-4-piperidyl]-N-methyl-carbamate | $ES^+$ 465 $[M + H]^+$, Rt = 1.01/1.35 mins (Method 1) |
| P55 | 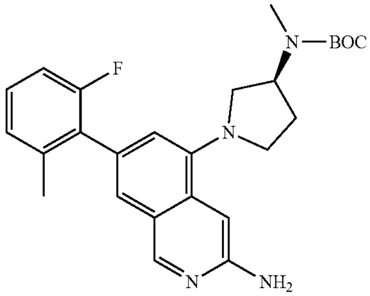 [SMILES: Cc1cccc(F)c1-c1cc(N2CC[C@H](N(C)C(=O)OC(C)(C)C)C2)c2cc(N)ncc2c1] | tert-butyl N-[(3S)-1-[3-amino-7-(2-fluoro-6-methyl-phenyl)-5-isoquinolyl]pyrrolidin-3-yl]-N-methyl-carbamate | $ES^+$ 451 $[M + H]^+$, Rt = 1.17/1.33 mins (Method 2) |
| P56 | 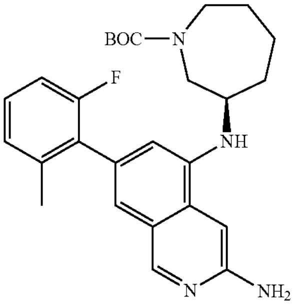 [SMILES: Cc1cccc(F)c1-c1cc(N[C@@H]2CCCCN(C(=O)OC(C)(C)C)C2)c2cc(N)ncc2c1] | tert-butyl (3R)-3-[[3-amino-7-(2-fluoro-6-methyl-phenyl)-5-isoquinolyl]amino] azepane-1-carboxylate | $ES^+$ 465 $[M + H]^+$, Rt = 1.18/1.38 mins (Method 2) |
| P57 | 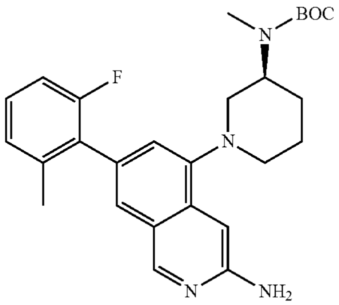 [SMILES: Cc1cccc(F)c1-c1cc(N2CCC[C@H](N(C)C(=O)OC(C)(C)C)C2)c2cc(N)ncc2c1] | tert-butyl N-[(3S)-1-[3-amino-7-(2-fluoro-6-methyl-phenyl)-5-isoquinolyl]-3-piperidyl]-N-methyl-carbamate | $ES^+$ 465 $[M + H]^+$, Rt = 1.27/1.48 mins (Method 2) |
| P58 | 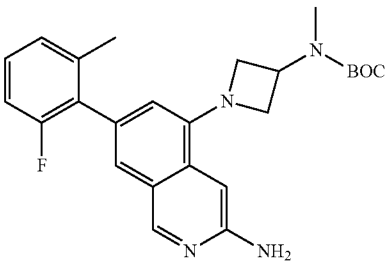 [SMILES: Cc1cccc(F)c1-c1cc(N2CC(N(C)C(=O)OC(C)(C)C)C2)c2cc(N)ncc2c1] | tert-butyl N-[1-[3-amino-7-(2-fluoro-6-methyl-phenyl)-5-isoquinolyl]azetidin-3-yl]-N-methyl-carbamate | $ES^+$ 437 $[M + H]^+$, Rt = 1.14/1.37 mins (Method 2) |

-continued

| Preparation | Structure | Name | LCMS Data |
|---|---|---|---|
| P59 | 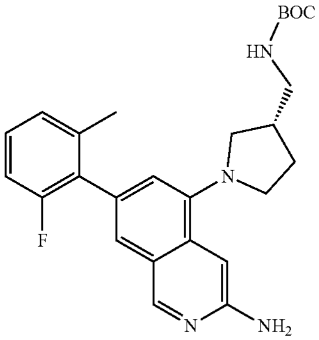 [SMILES: Cc1cccc(F)c1-c1cc(N2CC[C@@H](CNC(=O)OC(C)(C)C)C2)c2cc(N)ncc2c1] | tert-butyl N-[[(3S)-1-[3-amino-7-(2-fluoro-6-methyl-phenyl)-5-isoquinolyl]pyrrolidin-3-yl]methyl]carbamate | $ES^+$ 450 $[M + H]^+$, Rt = 1.13/1.31 mins (Method 2) |
| P60 | 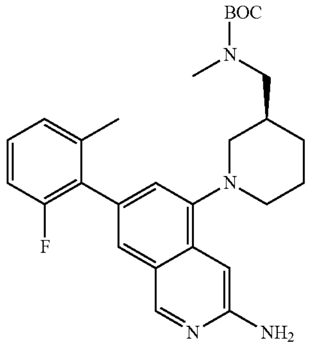 [SMILES: Cc1cccc(F)c1-c1cc(N2CCC[C@H](CN(C)C(=O)OC(C)(C)C)C2)c2cc(N)ncc2c1] | tert-butyl N-[[(3S)-1-[3-amino-7-(2-fluoro-6-methyl-phenyl)-5-isoquinolyl]-3-piperidyl]methyl]-N-methyl-carbamate | $ES^+$ 479 $[M + H]^+$, Rt = 1.30/1.48 mins (Method 2) |
| P61 | 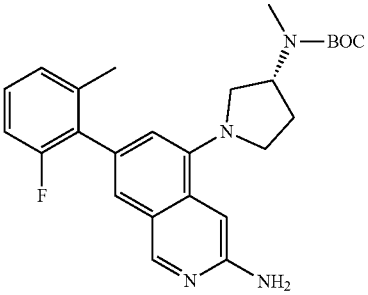 [SMILES: Cc1cccc(F)c1-c1cc(N2CC[C@@H](N(C)C(=O)OC(C)(C)C)C2)c2cc(N)ncc2c1] | tert-butyl N-[(3R)-1-[3-amino-7-(2-fluoro-6-methyl-phenyl)-5-isoquinolyl]pyrrolidin-3-yl]-N-methyl-carbamate | $ES^+$ 451 $[M + H]^+$, Rt = 1.15, 1.32 mins (Method 2) |
| P62 | 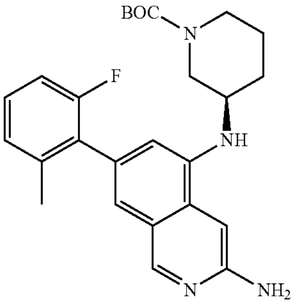 [SMILES: Cc1cccc(F)c1-c1cc(N[C@@H]2CCCN(C(=O)OC(C)(C)C)C2)c2cc(N)ncc2c1] | tert-butyl (3R)-3-[[3-amino-7-(2-fluoro-6-methyl-phenyl)-5-isoquinolyl]amino] piperidine-1-carboxylate | $ES^+$ 451 $[M + H]^+$, Rt = 1.02, 1.26 mins (Method 2) |

-continued

| Preparation | Structure | Name | LCMS Data |
|---|---|---|---|
| P63 | 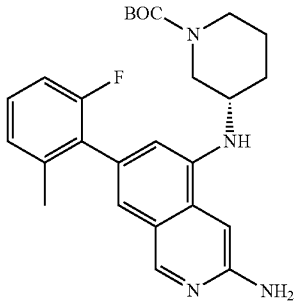 [SMILES: Cc1cccc(F)c1-c1cc(N[C@H]2CCCN(C(=O)OC(C)(C)C)C2)c2cc(N)ncc2c1] | tert-butyl (3S)-3-[[3-amino-7-(2-fluoro-6-methyl-phenyl)-5-isoquinolyl]amino] piperidine-1-carboxylate | $ES^+$ 451 $[M + H]^+$, Rt = 0.57, 0.92 mins (Method 2) |

Preparation 64 (P64)

tert-Butyl 4-[[7-(2-fluoro-6-methyl-phenyl)-3-(methylamino)-5-isoquinolyl]amino]piperidine-1-carboxylate

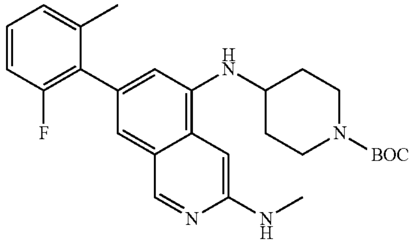 [SMILES: CNc1cc2c(NC3CCN(C(=O)OC(C)(C)C)CC3)cc(-c3c(C)cccc3F)cc2cn1]

To a solution of 5-chloro-7-(2-fluoro-6-methyl-phenyl)-N-methyl-isoquinolin-3-amine and 7-chloro-5-(2-fluoro-6-methyl-phenyl)-N-methyl-isoquinolin-3-amine mixture (P22) (0.150 g, 0.50 mmol) in 1,4-dioxane (10 mL) was added tert-butyl 4-aminopiperidine-1-carboxylate (0.300 g, 1.50 mmol), t-BuONa (0.192 g, 2.00 mmol), $Pd_2(dba)_3$ (0.015 g), and t-BuXPhos (0.015 g). The mixture was stirred at 90° C. under an atmosphere of argon overnight. The mixture was filtered, the solution concentrated under reduced pressure and the residue chromatographed to give tert-butyl 4-[[7-(2-fluoro-6-methyl-phenyl)-3-(methylamino)-5-isoquinolyl]amino]piperidine-1-carboxylate and tert-butyl 4-[[5-(2-fluoro-6-methyl-phenyl)-3-(methylamino)-7-isoquinolyl]amino]piperidine-1-carboxylate as a mixture of regioisomers (P64) (0.054 g), LCMS $ES^+$ 465 $[M+H]^+$, Rt=1.05, 1.37 mins (Method 2).

The following compounds were prepared as a mixture of regioisomers in a similar manner to tert-butyl 4-[[7-(2-fluoro-6-methyl-phenyl)-3-(methylamino)-5-isoquinolyl] amino]piperidine-1-carboxylate (P64) using the appropriate N-alkyl-isoquinolin-3-amine and the appropriate amine coupling partner:

| Preparation | Precursor | Structure | Name | LCMS Data |
|---|---|---|---|---|
| P65 | P28 | 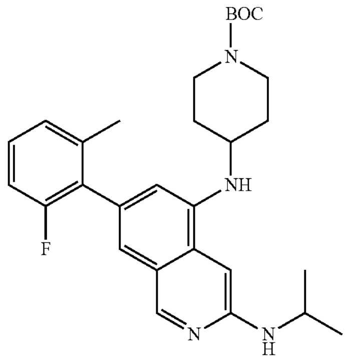 [SMILES: Cc1cccc(F)c1-c1cc(NC2CCN(C(=O)OC(C)(C)C)CC2)c2cc(NC(C)C)ncc2c1] | tert-butyl 4-[[7-(2-fluoro-6-methyl-phenyl)-3-(isopropylamino)-5-isoquinolyl]amino] piperidine-1-carboxylate | $ES^+$ 493 $[M + H]^+$, Rt = 1.01, 1.32 mins (Method 2) |

Preparation 66 (P66)

tert-Butyl N-[[(3R)-1-[3-amino-7-(2-fluoro-6-methyl-phenyl)-5-isoquinolyl]-3-piperidyl]methyl]-N-methyl-carbamate

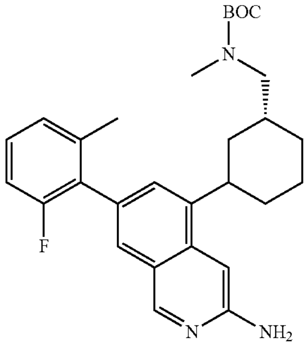 [SMILES: Cc1cccc(F)c1-c1cc(C2CCC[C@@H](CN(C)C(=O)OC(C)(C)C)C2)c2cc(N)ncc2c1]

To a solution of 5-chloro-7-(2-fluoro-6-methyl-phenyl) isoquinolin-3-amine and 7-chloro-5-(2-fluoro-6-methyl-phenyl)isoquinolin-3-amine mixture (P22) (0.300 g, 0.89 mmol) in 1,4-dioxane (12 mL) was added tert-butyl N-methyl-N-[[(3R)-3-piperidyl]methyl]carbamate (0.410 g, 1.79 mmol), t-BuONa (0.170 g, 1.77 mmol), tBuXPhos (0.050 g) and $PdCl_2(PPh_3)_2$ (0.050 g). The mixture was degassed by bubbling a stream of argon through. The reaction was heated at 110° C. for 2 hours in a sealed tube. After this time, the mixture was allowed to cool to room temperature. The organics were extracted into EtOAc, washed with brine, dried over $Na_2SO_4$ and concentrated under reduced pressure. The residue was chromatographed [$SiO_2$, Pet. ether:EtOAc 1:1] to give tert-butyl N-[[(3R)-1-[3-amino-7-(2-fluoro-6-methyl-phenyl)-5-isoquinolyl]-3-piperidyl]methyl]-N-methyl-carbamate and tert-butyl N-[[(3R)-1-[3-amino-5-(2-fluoro-6-methyl-phenyl)-7-isoquinolyl]-3-piperidyl]methyl]-N-methyl-carbamate as a mixture of regioisomers (P66) (0.090 g), LCMS $ES^+$ 478 $[M+H]^+$, Rt=1.24, 1.42 mins (Method 2).

Preparation 67 (P67)

tert-Butyl (2R)-2-[[[3-amino-7-(2-fluoro-6-methyl-phenyl)-5-isoquinolyl]amino]methyl]piperidine-1-carboxylate

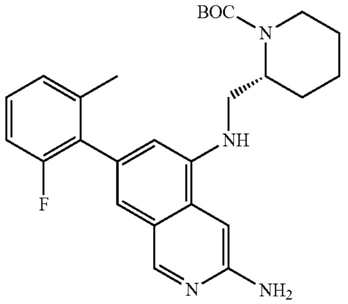 [SMILES: Cc1cccc(F)c1-c1cc(NC[C@H]2CCCCN2C(=O)OC(C)(C)C)c2cc(N)ncc2c1]

To a solution of a mixture of 5-bromo-7-(2-fluoro-6-methyl-phenyl)isoquinolin-3-amine and 7-bromo-5-(2-fluoro-6-methyl-phenyl)isoquinolin-3-amine regioisomers (P23) (0.25 g, 0.15 mmol) in 1,4-dioxane (10 mL) was added tert-butyl (2R)-2-(aminomethyl)piperidine-1-carboxylate (0.48 g, 2.26 mmol), t-BuONa (0.28 g, 3.02 mmol), $Pd_2(dba)_3$ (0.045 g) and t-BuXPhos (0.045 g, 0.11 mmol). The mixture was stirred at 11000 in the microwave for 3.5 hours. After this time, further tert-butyl (2R)-2-(aminomethyl) piperidine-1-carboxylate (0.028 g, 0.13 mmol), t-BuONa (0.010 g, 0.11 mmol), $Pd_2(dba)_r$(0.02 g) was added and the mixture was stirred at 100° C. for a further 5 hours in the microwave. The mixture was chromatographed using preparative HPLC (Method 2) to give tert-butyl (2R)-2-[[[3-amino-7-(2-fluoro-6-methyl-phenyl)-5-isoquinolyl]amino] methyl]piperidine-1-carboxylate (P67) and tert-butyl (2R)-2-[[[3-amino-5-(2-fluoro-6-methyl-phenyl)-7-isoquinolyl] amino]methyl]piperidine-1-carboxylate as a mixture of regioiosmers (0.06 g), LCMS $ES^+$ 465 $[M+H]^+$, Rt=1.66 mins (Method 2).

The following compounds were prepared as a mixture of regiosiomers in a similar manner to ter-butyl (2R)-2-[[[3-amino-7-(2-fluoro-6-methyl-phenyl)-5-isoquinolyl]amino] methyl]piperidine-1-carboxylate (P67) using 5-bromo-7-(2-fluoro-6-methyl-phenyl)isoquinolin-3-amine regioisomeric mixture (P23) and the appropriate amine coupling partner:

| Preparation | Structure | Name | LCMS Data |
|---|---|---|---|
| P68 | 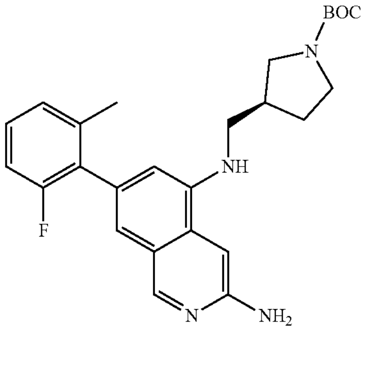 [SMILES: Cc1cccc(F)c1-c1cc(NC[C@@H]2CCN(C(=O)OC(C)(C)C)C2)c2cc(N)ncc2c1] | tert-butyl (3S)-3-[[[3-amino-7-(2-fluoro-6-methyl-phenyl)-5-isoquinolyl]amino]methyl] pyrrolidine-1-carboxylate | $ES^+$ 451 $[M + H]^+$, Rt = 1.22/1.40 mins (Method 2) |

-continued

| Preparation | Structure | Name | LCMS Data |
|---|---|---|---|
| P69 | 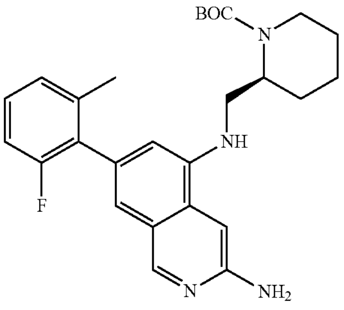 [SMILES: Cc1cccc(F)c1-c1cc(NC[C@@H]2CCCCN2C(=O)OC(C)(C)C)c2cc(N)ncc2c1] | tert-butyl (2S)-2-[[[3-amino-7-(2-fluoro-6-methyl-phenyl)-5-isoquinolyl]amino]methyl] piperidine-1-carboxylate | $ES^+$ 465 $[M + H]^+$, Rt = 1.37/1.54 mins (Method 2) |
| P70 | 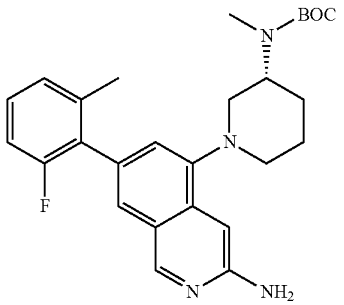 [SMILES: Cc1cccc(F)c1-c1cc(N2CCC[C@@H](N(C)C(=O)OC(C)(C)C)C2)c2cc(N)ncc2c1] | tert-butyl N-[(3R)-1-[3-amino-7-(2-fluoro-6-methyl-phenyl)-5-isoquinolyl]-3-piperidyl]-N-methyl-carbamate | $ES^+$ 465 $[M + H]^+$, Rt = 1.20/1.43 mins (Method 2) |
| P71 | 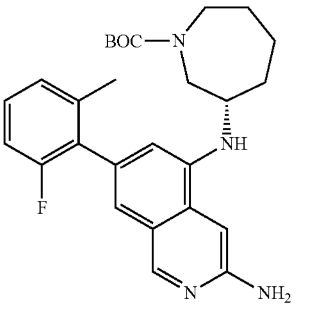 [SMILES: Cc1cccc(F)c1-c1cc(N[C@H]2CCCCN(C(=O)OC(C)(C)C)C2)c2cc(N)ncc2c1] | tert-butyl (3S)-3-[[3-amino-7-(2-fluoro-6-methyl-phenyl)-5-isoquinolyl]amino]azepane-1-carboxylate | $ES^+$ 465 $[M + H]^+$, Rt = 1.11/1.33 mins (Method 2) |

Preparation 72 (P72)

tert-Butyl 4-[[3-amino-7-(2-chloro-6-methyl-phenyl)-5-isoquinolyl]amino]piperidine-1-carboxylate

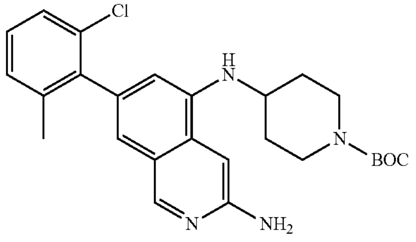 [SMILES: Cc1cccc(Cl)c1-c1cc(NC2CCN(C(=O)OC(C)(C)C)CC2)c2cc(N)ncc2c1]

To a solution of a mixture of 5-bromo-7-(2-chloro-6-methyl-phenyl)isoquinolin-3-amine (P24) and 7-bromo-5-(2-chloro-6-methyl-phenyl)isoquinolin-3-amine (0.38 g, 1.1 mmol) in 1,4-dioxane (10 mL) was added tert-butyl 4-aminopiperidine-1-carboxylate (0.40 g, 2.0 mmol), t-BuONa (0.20 g, 2.0 mmol), t-BuXPhos (0.04 g, 0.094 mmol) and $Pd_2(dba)_3$ (0.040 g). The mixture was heated to 90° C. in the microwave for 75 minutes. After this time, the organics were extracted into EtOAc and concentrated under reduced pressure. The residue was chromatographed [$SiO_2$, EtOAc] to give tert-butyl 4-[[3-amino-7-(2-chloro-6-methyl-phenyl)-5-isoquinolyl]amino]piperidine-1-carboxylate (P72) and tert-butyl 4-[[3-amino-5-(2-chloro-6-methyl-phenyl)-7-isoquinolyl]amino]piperidine-1-carboxylate as a mixture of regioisomers (0.32 g), LCMS $ES^+$ 467, 469 $[M+H]^+$, Rt=1.30 mins (Method 2).

Preparation 73 (P73)

tert-Butyl 3-[[3-amino-7-(2-chloro-6-methyl-phenyl)-5-isoquinolyl]amino]azetidine-1-carboxylate

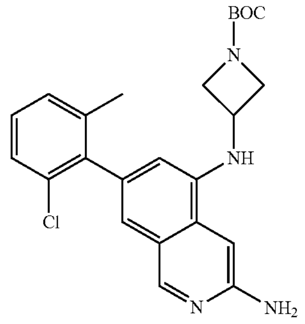

To a solution of tert-butyl 3-[(3-amino-7-chloro-5-isoquinolyl)amino]azetidine-1-carboxylate and tert-butyl 3-[(3-amino-5-chloro-7-isoquinolyl)amino]azetidine-1-carboxylate (P30) regioisomeric mixture (0.250 g, 0.718 mmol) in 1,4-dioxane (8 mL) was added 2-(2-chloro-6-methyl-phenyl)-4,4,5,5-tetramethyl-1,3,2-dioxaborolane (P2) (0.364 g, 1.437 mmol), $K_3PO_4$ (0.305 g, 1.437 mmol), pre-catalyst XPhos-Pd G2 (0.057 g, 0.071 mmol) and water (2 mL). The mixture was stirred at 100° C. overnight. The mixture was concentrated under reduced pressure and chromatographed to give tert-butyl 3-[[3-amino-7-(2-chloro-6-methyl-phenyl)-5-isoquinolyl]amino]azetidine-1-carboxylate and tert-butyl 3-[[3-amino-5-(2-chloro-6-methyl-phenyl)-7-isoquinolyl]amino]azetidine-1-carboxylate as a mixture of regioisomers (P73), LCMS $ES^+$ 439, 441 $[M+H]^+$, Rt=1.51, 1.66 mins (Method 2).

The following compounds were prepared as a mixture of regiosiomers in a similar manner to tert-butyl 3-[[3-amino-7-(2-chloro-6-methyl-phenyl)-5-isoquinolyl]amino]azetidine-1-carboxylate (P73) using the appropriate 3-amino-7-isoquinoline and a boronic ester:

| Preparation | Precursor | Structure | Name | LCMS Data |
|---|---|---|---|---|
| P74 | P31 | 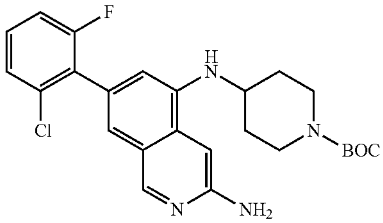 [SMILES: CC(C)(C)OC(=O)N1CCC(Nc2cc(-c3c(F)cccc3Cl)cc3cnc(N)cc23)CC1] | tert-butyl 4-[[3-amino-7-(2-chloro-6-fluoro-phenyl)-5-isoquinolyl]amino]piperidine-1-carboxylate | $ES^+$ 471, 473 $[M + H]^+$, Rt = 1.21/1.38 mins (Method 2) |
| P75 | P32 | 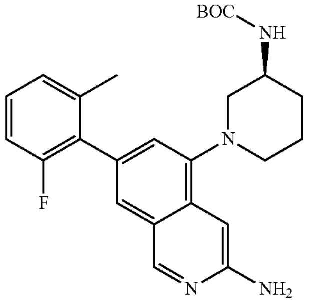 [SMILES: Cc1cccc(F)c1-c1cc(N2CCC[C@H](NC(=O)OC(C)(C)C)C2)c2cc(N)ncc2c1] | tert-butyl N-[(3S)-1-[3-amino-7-(2-fluoro-6-methyl-phenyl)-5-isoquinolyl]-3-piperidyl]carbamate | $ES^+$ 451 $[M + H]^+$, Rt = 1.01, 1.23 mins (Method 2) |

Preparation 75a (P75a)

tert-Butyl 4-[[3-amino-4-cyano-7-(2-fluoro-6-methyl-phenyl)-5-isoquinolyl]amino]piperidine-1-carboxylate

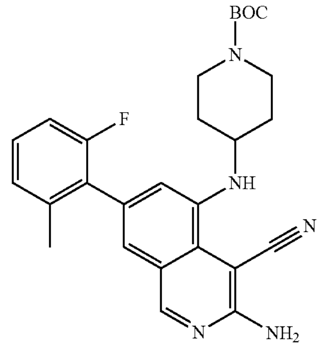 [SMILES: Cc1cccc(F)c1-c1cc(NC2CCN(C(=O)OC(C)(C)C)CC2)c2c(C#N)c(N)ncc2c1]

To a solution of 3-amino-5-chloro-7-(2-fluoro-6-methyl-phenyl)isoquinoline-4-carbonitrile (P22b) (0.150 g, 0.482 mmol), $Pd_2(dba)_3$, t-BuONa (0.116 g, 1.21 mmol), tert-butyl 4-aminopiperidine-1-carboxylate (0.242 g, 1.21 mmol) in xylene (1.5 mL) was added tri-t-butylphosphine (10%, 0.220 g, 0.962 mmol) dropwise. The mixture was stirred overnight at 110° C. under an atmosphere of argon. $H_2O$ (2.0 mL) was added and the mixture was filtered. The organics were extracted with EtOAc (3×3.0 mL), dried over $Na_2SO_4$, filtered and concentrated under reduced pressure. The residue was chromatographed [$SiO_2$, DCM:MeOH 50:1]] to give tert-butyl 4-[[3-amino-4-cyano-7-(2-fluoro-6-methyl-phenyl)-5-isoquinolyl]amino]piperidine-1-carboxylate (P75a) (0.03 g), LCMS $ES^+$ 76 $[M+H]^+$, Rt=1.450 mins (Method 1).

Preparation 76 (P76)

tert-Butyl 3-[[3-amino-7-(2-fluoro-6-methyl-phenyl) isoquinoline-4-carbonyl]amino]azetidine-1-carboxylate

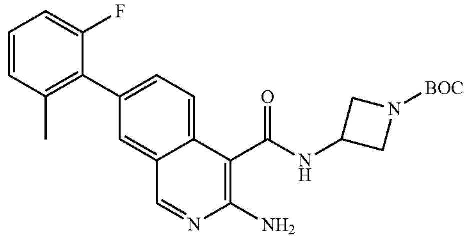

To a solution of 3-amino-7-(2-fluoro-6-methyl-phenyl) isoquinoline-4-carboxylic acid (P20) (0.050 g, 0.168 mmol) in DMF (1 mL) was added tert-butyl 3-aminoazetidine-1-carboxylate (0.035 g, 0.253 mmol), HATU (0.096 g, 0.253 mmol), DIPEA (0.043 g, 0.336 mmol) and the solution was stirred at room temperature overnight. The organics were extracted with EtOAc, washed with brine, dried over $Na_2SO_4$ and concentrated under reduced pressure. The resulting residue was chromatographed to give tert-butyl 3-[[3-amino-7-(2-fluoro-6-methyl-phenyl)isoquinoline-4-carbonyl]amino]azetidine-1-carboxylate (P76), LCMS $ES^+$451 $[M+H]^+$, Rt=1.567 mins (Method 1).

The following compounds were prepared in a similar manner to tert-butyl 3-[[3-amino-7-(2-fluoro-6-methyl-phenyl)isoquinoline-4-carbonyl]amino]azetidine-1-carboxylate (P76) using the appropriate 3-amino-7-aryl-isoquinoline-4-carboxylic acid and amine coupling partner:

| Preparation | Precursor | Structure | Name | LCMS Data |
|---|---|---|---|---|
| P77 | P20 | 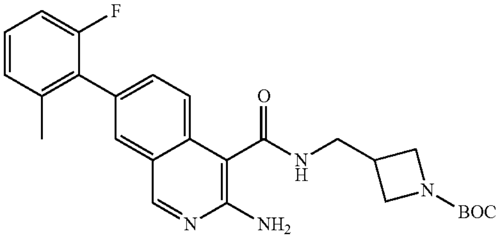 [SMILES: Cc1cccc(F)c1-c1ccc2c(C(=O)NCC3CN(C(=O)OC(C)(C)C)C3)c(N)ncc2c1] | tert-butyl 3-[[[3-amino-7-(2-fluoro-6-methyl-phenyl) isoquinoline-4-carbonyl]amino] methyl] azetidine-1-carboxylate | $ES^+$ 465 $[M + H]^+$, Rt = 1.490 mins (Method 1) |
| P78 | P20 | 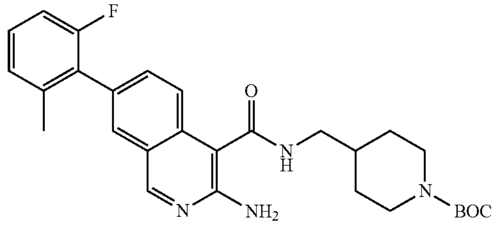 [SMILES: Cc1cccc(F)c1-c1ccc2c(C(=O)NCC3CCN(C(=O)OC(C)(C)C)CC3)c(N)ncc2c1] | tert-butyl 4-[[[3-amino-7-(2-fluoro-6-methyl-phenyl) isoquinoline-4-carbonyl]amino] methyl] piperidine-1-carboxylate | $ES^+$ 493 $[M + H]^+$, Rt = 1.733 mins (Method 1) |

-continued

| Preparation | Precursor | Structure | Name | LCMS Data |
|---|---|---|---|---|
| P79 | P20 | 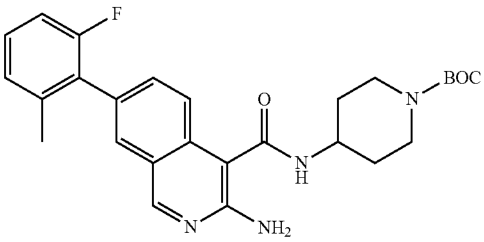 [SMILES: Cc1cccc(F)c1-c1ccc2c(C(=O)NC3CCN(C(=O)OC(C)(C)C)CC3)c(N)ncc2c1] | tert-butyl 4-[[3-amino-7-(2-fluoro-6-methyl-phenyl) isoquinoline-4-carbonyl]amino] piperidine-1-carboxylate | ES+ 479 [M + H]+, Rt = 1.720 mins (Method 1) |
| P80 | P20 | 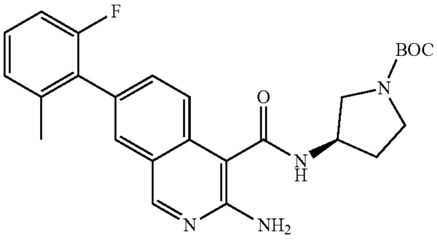 [SMILES: Cc1cccc(F)c1-c1ccc2c(C(=O)N[C@@H]3CCN(C(=O)OC(C)(C)C)C3)c(N)ncc2c1] | tert-butyl (3R)-3-[[3-amino-7-(2-fluoro-6-methyl-phenyl) isoquinoline-4-carbonyl]amino] pyrrolidine-1-carboxylate | ES+ 465 [M + H]+, Rt = 1.38 mins (Method 2) |
| P81 | P20 | 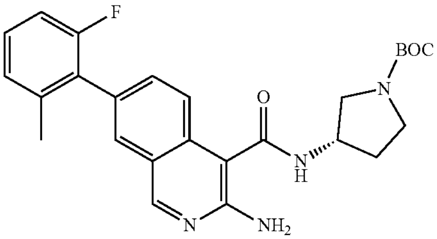 [SMILES: Cc1cccc(F)c1-c1ccc2c(C(=O)N[C@H]3CCN(C(=O)OC(C)(C)C)C3)c(N)ncc2c1] | tert-butyl (3S)-3-[[3-amino-7-(2-fluoro-6-methyl-phenyl) isoquinoline-4-carbonyl]amino] pyrrolidine-1-carboxylate | ES+ 465 [M + H]+, Rt = 1.657 mins (Method 1) |
| P82 | P21 | 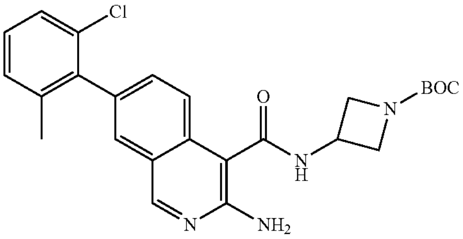 [SMILES: Cc1cccc(Cl)c1-c1ccc2c(C(=O)NC3CN(C(=O)OC(C)(C)C)C3)c(N)ncc2c1] | tert-butyl 3-[[3-amino-7-(2-chloro-6-methyl-phenyl) isoquinoline-4-carbonyl]amino] azetidine-1-carboxylate | ES+ 467 [M + H]+, Rt = 1.593 mins (Method 1) |
| P83 | P21 | 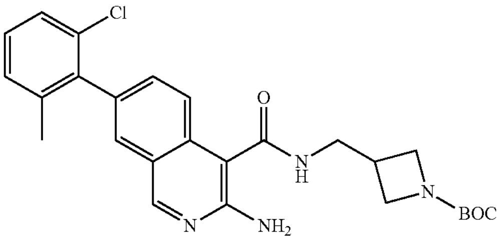 [SMILES: Cc1cccc(Cl)c1-c1ccc2c(C(=O)NCC3CN(C(=O)OC(C)(C)C)C3)c(N)ncc2c1] | tert-butyl 3-[[[3-amino-7-(2-chloro-6-methyl-phenyl) isoquinoline-4-carbonyl]amino] methyl] azetidine-1-carboxylate | ES+ 481 [M + H]+, Rt = 1.580 mins (Method 1) |
| P84 | P21 | 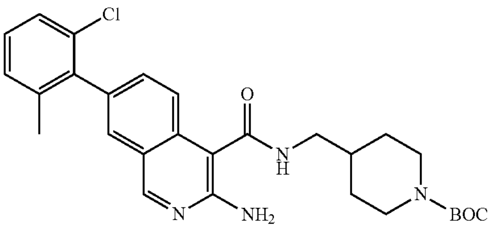 | tert-butyl 4-[[[3-amino-7-(2-chloro-6-methyl-phenyl) isoquinoline-4-carbonyl]amino] methyl] piperidine-1-carboxylate | ES+ 531 [M + Na]+, Rt = 1.52 mins (Method 2) |

-continued

| Preparation | Precursor | Structure | Name | LCMS Data |
|---|---|---|---|---|
| P85 | P21 | 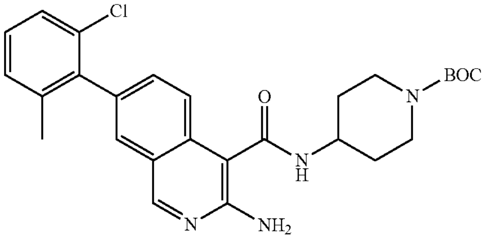 [SMILES: Cc1cccc(Cl)c1-c1ccc2c(C(=O)NC3CCN(C(=O)OC(C)(C)C)CC3)c(N)ncc2c1] | tert-butyl 4-[[3-amino-7-(2-chloro-6-methyl-phenyl) isoquinoline-4-carbonyl]amino] piperidine-1-carboxylate | $ES^+$ 495 [M + H]$^+$, Rt = 1.71 mins (Method 2) |
| P86 | P21 | 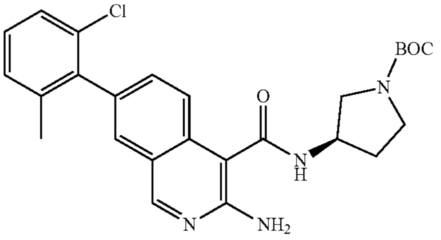 [SMILES: Cc1cccc(Cl)c1-c1ccc2c(C(=O)N[C@@H]3CCN(C(=O)OC(C)(C)C)C3)c(N)ncc2c1] | tert-butyl (3R)-3-[[3-amino-7-(2-chloro-6-methyl-phenyl) isoquinoline-4-carbonyl]amino] pyrrolidine-1-carboxylate | $ES^+$ 481 [M + H]$^+$, Rt = 1.723 mins (Method 1) |
| P87 | P21 | 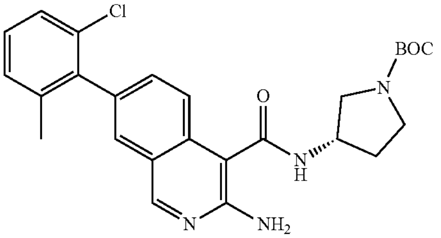 [SMILES: Cc1cccc(Cl)c1-c1ccc2c(C(=O)N[C@H]3CCN(C(=O)OC(C)(C)C)C3)c(N)ncc2c1] | tert-butyl (3S)-3-[[3-amino-7-(2-chloro-6-methyl-phenyl) isoquinoline-4-carbonyl]amino] pyrrolidine-1-carboxylate | $ES^+$ 481 [M + H]$^+$, Rt = 1.707 mins (Method 1) |

Preparation 88 (P88)

tert-Butyl 3-[[3-amino-7-(2-fluoro-6-methyl-phenyl) isoquinoline-5-carbonyl]amino]pyrrolidine-1-carboxylate

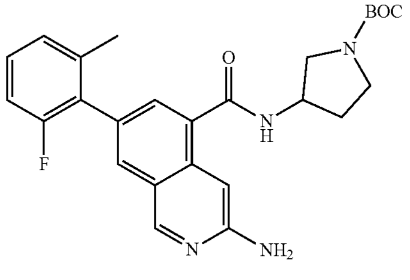 [SMILES: Cc1cccc(F)c1-c1cc(C(=O)NC2CCN(C(=O)OC(C)(C)C)C2)c2cc(N)ncc2c1]

To a solution of 5-bromo-7-(2-fluoro-6-methyl-phenyl) isoquinolin-3-amine (P23) (0.180 g, 0.544 mmol) in DMF (2.0 mL) was added $Et_3N$ (0.110 g, 1.09 mmol), tert-butyl 3-aminopyrrolidine-1-carboxylate (0.203 g, 1.09 mmol) and Pd(dppf)$Cl_2$ (0.040 g, 1.09 mmol). The mixture was stirred at 110° c. for 16 hours under an atmosphere of CO. After this time, the organics were extracted with EtOAc (3×5 mL), washed with brine and concentrate under reduced pressure. The crude residue was purified by preparative HPLC (Method 2) to give tert-butyl 3-[[3-amino-7-(2-fluoro-6-methyl-phenyl)isoquinoline-5-carbonyl]amino]pyrrolidine-1-carboxylate (P88), (0.038 g), LCMS $ES^+$465 [M+H]$^+$ Rt=1.583 mins (Method 1).

Preparation 89 (P89)

tert-Butyl 4-[[3-amino-7-(2-fluoro-6-methyl-phenyl)-5-isoquinolyl]carbamoyl]piperidine-1-carboxylate

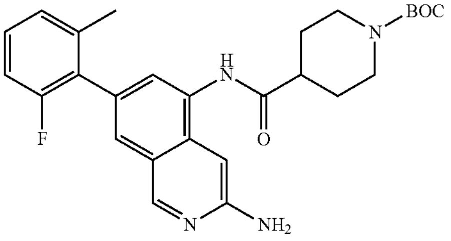 [SMILES: Cc1cccc(F)c1-c1cc(NC(=O)C2CCN(C(=O)OC(C)(C)C)CC2)c2cc(N)ncc2c1]

A solution of 5-bromo-7-(2-fluoro-6-methyl-phenyl)isoquinolin-3-amine and 7-bromo-5-(2-fluoro-6-methyl-phenyl)isoquinolin-3-amine regioisomeric mix (P23) (0.500 g, 1.51 mmol), tert-butyl 4-carbamoylpiperidine-1-carboxylate (0.680 g, 3.02 mmol), CuI (0.031 g, 1.66 mmol), $K_2CO_3$ (0.417 g, 3.02 mmol) and trans-N,N'-dimethylcyclohexane-1,2-diamine (0.236 g, 1.66 mmol) in DMF (10 mL) was stirred at 100° C. for 3 hours. After this time, water (100 mL) was added and the organics were extracted into EtOAc (50 mL×3). The organics were combined, concentrated under reduced pressure and purified using preparative HPLC (Method 2) to give tert-butyl 4-[[3-amino-7-(2-fluoro-6-methyl-phenyl)-5-isoquinolyl]carbamoyl]piperidine-1-carboxylate and tert-butyl 4-[[3-amino-5-(2-fluoro-6-methylphenyl)-7-isoquinolyl]carbamoyl]piperidine-1-carboxylate as a mixture of regioisomers (P89) (0.060 g), LCMS ES$^+$479 $[M+H]^+$, Rt=1.033, 1.193 mins (Method 1).

The following compounds were prepared in a similar manner to tert-butyl 4-[[3-amino-7-(2-fluoro-6-methyl-phenyl)-5-isoquinolyl]carbamoyl]piperidine-1-carboxylate (P89) as a mixture of regioisomers from 5-bromo-7-(2-fluoro-6-methyl-phenyl)isoquinolin-3-amine and 7-bromo-5-(2-fluoro-6-methyl-phenyl)isoquinolin-3-amine regioisomeric mix (P23) and the appropriate amide:

| Preparation | Structure | Name | LCMS Data |
|---|---|---|---|
| P90 | 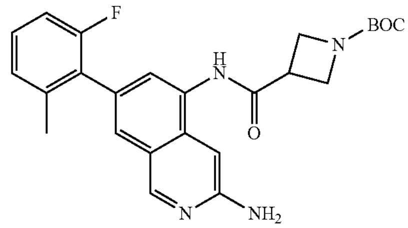 [SMILES: Cc1cccc(F)c1-c1cc(NC(=O)C2CN(C(=O)OC(C)(C)C)C2)c2cc(N)ncc2c1] | tert-butyl 3-[[3-amino-7-(2-fluoro-6-methyl-phenyl)-5-isoquinolyl]carbamoyl] azetidine-1-carboxylate | ES$^+$ 451 $[M + H]^+$, Rt = 1.385, 1.525 mins (Method 1) |
| P90a | 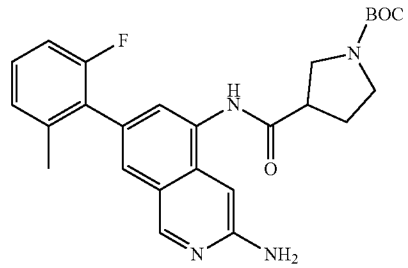 [SMILES: Cc1cccc(F)c1-c1cc(NC(=O)C2CCN(C(=O)OC(C)(C)C)C2)c2cc(N)ncc2c1] | tert-butyl 3-[[3-amino-7-(2-fluoro-6-methyl-phenyl)-5-isoquinolyl]carbamoyl] pyrrolidine-1-carboxylate | ES$^+$ 465 $[M + H]^+$, Rt = 1.142 mins (Method 1) |

Preparation 91 (P91)

tert-Butyl 4-[[3-amino-7-(2-fluoro-6-methyl-phenyl)-5-isoquinolyl]oxy]piperidine-1-carboxylate

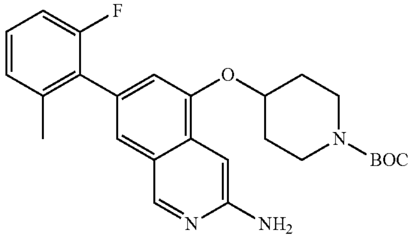 [SMILES: Cc1cccc(F)c1-c1cc(OC2CCN(C(=O)OC(C)(C)C)CC2)c2cc(N)ncc2c1]

To a solution of 3-amino-7-(2-fluoro-6-methyl-phenyl) isoquinolin-5-ol regioisomeric mixture (P29) (0.500 g, 1.86 mmol) in THF (15 mL) was added tert-butyl 4-hydroxypiperidine-1-carboxylate (0.750 g, 3.73 mmol) and $PPh_3$ (0.978 g, 3.73 mmol). The mixture was heated to 50° C. DIAD (1.11 mL, 5.59 mmol) was added dropwise and the mixture was stirred at 50° C. for 1 hour. The mixture was concentrated under reduced pressure and the residue purified by preparative HPLC (Method 2) to give tert-butyl 4-[[3-amino-7-(2-fluoro-6-methyl-phenyl)-5-isoquinolyl]oxy]piperidine-1-carboxylate and tert-butyl 4-[[3-amino-5-(2-fluoro-6-methyl-phenyl)-7-isoquinolyl]oxy]piperidine-1-carboxylate as a mixture of regioisomers (P91) (0.260 g), LCMS ES$^+$ 451 $[M+H]^+$, Rt=1.26 mins (Method 2).

Preparation 92 (P92)

tert-Butyl 3-[[3-amino-7-(2-fluoro-6-methyl-phenyl)-5-isoquinolyl]oxy]azetidine-1-carboxylate

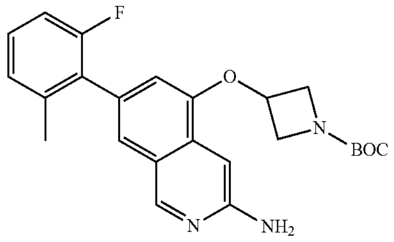 [SMILES: Cc1cccc(F)c1-c1cc(OC2CN(C(=O)OC(C)(C)C)C2)c2cc(N)ncc2c1]

To a solution of 3-amino-7-(2-fluoro-6-methyl-phenyl) isoquinolin-5-ol regioisomeric mixture (P29) (0.050 g, 0.19 mmol) in DMF (3 mL) was added tert-butyl 3-methylsulfonyloxyazetidine-1-carboxylate (0.048 g, 0.19 mmol) and $Cs_2CO_3$ (0.067 g, 0.21 mmol). The mixture was heated to 80° C. When reaction was complete, brine was added and the organics were extracted with EtOAc. The organics were dried over MgSO4, filtered and concentrated under reduced pressure to give tert-butyl 3-[[3-amino-7-(2-fluoro-6-methyl-phenyl)-5-isoquinolyl]oxy]azetidine-1-carboxylate and tert-butyl 3-[[3-amino-5-(2-fluoro-6-methyl-phenyl)-7-isoquinolyl]oxy]azetidine-1-carboxylate as a mixture of regioisomers (P92), LCMS $ES^+$424 $[M+H]^+$, Rt=0.74 mins (Method 2).

Preparation 93 (P93)

tert-Butyl (3S)-3-methylsulfonyloxypyrrolidine-1-carboxylate

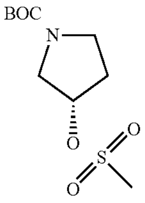

Methanesulfonyl chloride (0.25 mL, 3.21 mmol) and triethylamine (1.1 mL, 8.02 mmol) were added to a solution of tert-butyl (3S)-3-hydroxypyrrolidine-1-carboxylate (0.500 g, 2.67 mmol) in THF (10 mL) under an atmosphere of nitrogen at room temperature. The mixture was stirred at room temperature for 2 hours. After this time, $Na_2CO_3$ (sat. aq. soln.) was added to the mixture and the mixture was diluted with EtOAc. The combined organics were dried over $MgSO_4$, filtered and concentrated under reduced pressure. The residue was chromatographed to give tert-butyl (3S)-3-methylsulfonyloxypyrrolidine-1-carboxylate (P93), LCMS $ES^+$ 210 $[M-(CH3)_2C{=}CH_2]^+$, Rt=1.19 mins (Method 2).

Preparation 94 (P94)

tert-Butyl (3R)-3-[[3-amino-7-(2-fluoro-6-methyl-phenyl)-5-isoquinolyl]oxy]pyrrolidine-1-carboxylate

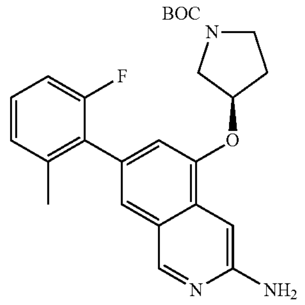 [SMILES: "BOC" ; Cc1cccc(F)c1-c1cc(O[C@@H]2CCNC2)c2cc(N)ncc2c1]

To a solution of 3-amino-7-(2-fluoro-6-methyl-phenyl) isoquinolin-5-ol (0.050 g, 0.19 mmol) (P29) in DMF (3 mL) was added tert-butyl (3S)-3-methylsulfonyloxypyrrolidine-1-carboxylate (0.05 g, 0.19 mmol) and $Cs_2CO_3$ (0.067 g, 0.21 mmol). The mixture was stirred at 80° C. for 2 hours. After this time, brine was added and the organics were extracted with EtOAc. The combined organics were dried over $MgSO_4$, filtered and concentrated under reduced pressure. The residue was purified by preparative HPLC (Method 2) to give tert-butyl (3R)-3-[[3-amino-7-(2-fluoro-6-methyl-phenyl)-5-isoquinolyl]oxy]pyrrolidine-1-carboxylate (P94) (0.056 g), LCMS $ES^+$ 438 $[M+H]^+$, Rt=0.69 mins (Method 2).

Preparation 95 (P95)

tert-Butyl 4-[[3-amino-7-(2-fluoro-6-methyl-phenyl) isoquinoline-5-carbonyl]amino]piperidine-1-carboxylate

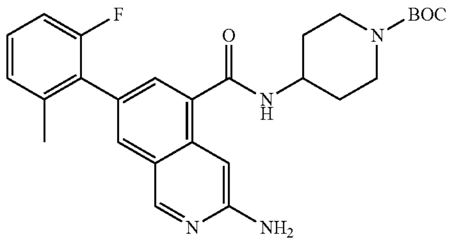 [SMILES: Cc1cccc(F)c1-c1cc(C(=O)NC2CCN(C(=O)OC(C)(C)C)CC2)c2cc(N)ncc2c1]

To a solution of 5-bromo-7-(2-fluoro-6-methyl-phenyl) isoquinolin-3-amine (P23) (0.250 g, 0.756 mmol) in DMF (2.5 mL) was added Pd(dppf)$Cl_2$ (0.056 g, 0.076 mmol), tert-butyl 4-aminopiperidine-1-carboxylate (0.230 g, 1.15 mmol) and $Et_3N$ (0.116 g, 1.15 mmol). The solution was stirred at 110° C. under CO for 16 hours. After this time, the solution was allowed to cool to room temperature and water (3 mL) was added. The organics were extracted with EtOAc (3×5 mL), washed with brine and concentrated under reduced pressure. The crude residue was purified using preparative HPLC (Method 2) to give tert-butyl 4-[[3-amino-7-(2-fluoro-6-methyl-phenyl)isoquinoline-5-carbonyl]amino]piperidine-1-carboxylate (P95) (0.055 g), LCMS $ES^+$ 479 $[M+H]^+$, Rt=1.573 mins (Method 1).

Preparation 96 (P96)

5-[(3S)-3-Amino-1-piperidyl]-7-(2-fluoro-6-methyl-phenyl)isoquinolin-3-amine

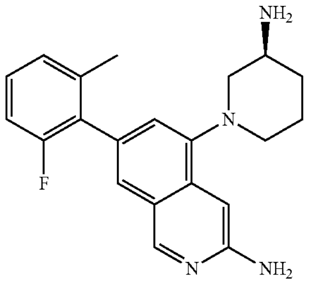 [SMILES: Cc1cccc(F)c1-c1cc(N2CCC[C@H](N)C2)c2cc(N)ncc2c1]

To a solution of tert-butyl N-[(3S)-1-[3-amino-7-(2-fluoro-6-methyl-phenyl)-5-isoquinolyl]-3-piperidyl]carbamate (P75) (0.100 g, 0.22 mmol) in MeOH (10 mL) was added TFA (1 mL). The solution was stirred overnight at room temperature. After this time, the mixture was concentrated under reduced pressure. The residue was neutralised with $Na_2CO_3$ (aq. soln.).

The organics were extracted with EtOAc, washed with brine, dried over $Na_2SO_4$ and concentrated under reduced pressure. The residue was chromatographed to give 5-[(3S)-3-amino-1-piperidyl]-7-(2-fluoro-6-methyl-phenyl)isoquinolin-3-amine (P96) (0.050 g), LCMS $ES^+$351 $[M+H]^+$, Rt=1.14 mins (Method 2).

Preparation 97 (P97)

5-[(3S)-3-(Aminomethyl)pyrrolidin-1-yl]-7-(2-fluoro-6-methyl-phenyl)isoquinolin-3-amine

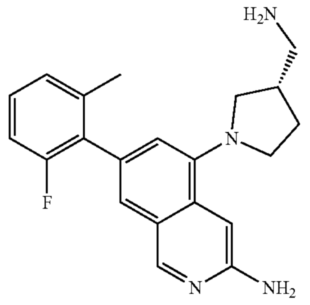 [SMILES: Cc1cccc(F)c1-c1cc(N2CC[C@@H](CN)C2)c2cc(N)ncc2c1]

To a solution of tert-butyl N-[[(3S)-1-[3-amino-7-(2-fluoro-6-methyl-phenyl)-5-isoquinolyl]pyrrolidin-3-yl]methyl]carbamate (P59) (0.180 g, 0.40 mmol) in MeOH (4.0 mL) was added HCl (conc.) (1.0 mL). The solution was stirred at room temperature. The solution was concentrated under reduced pressure and the residue was neutralised using $NaHCO_3$ (aq. soln.) The organics were extracted with EtOAc, dried over $Na_2SO_4$, filtered and concentrated under reduced pressure. The crude residue was chromatographed [$SiO_2$] to give 5-[(3S)-3-(aminomethyl)pyrrolidin-1-yl]-7-(2-fluoro-6-methyl-phenyl)isoquinolin-3-amine (P97) (0.060 g), LCMS $ES^+$ 350 $[M+H]^+$, Rt=1.30, 1.37 mins (Method 2).

Preparation 98 (P98)

tert-Butyl 4-[[7-(2-fluoro-6-methyl-phenyl)-5-isoquinolyl]amino]piperidine-1-carboxylate

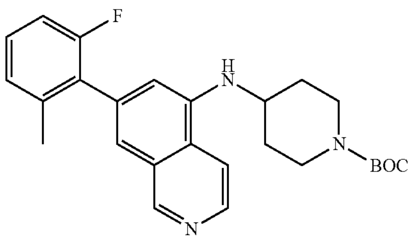 [SMILES: Cc1cccc(F)c1-c1cc(NC2CCN(C(=O)OC(C)(C)C)CC2)c2ccncc2c1]

To a solution of 5-bromo-7-(2-fluoro-6-methyl-phenyl)isoquinoline (P14) (0.500 g, 1.58 mmol), tert-butyl 4-aminopiperidine-1-carboxylate (0.317 g, 1.58 mmol), t-BuX-Phos (0.134 g, 0.316 mmol), $Pd_2(dba)_3$ (0.289 g, 0.316 mmol) in 1,4-dioxane (5 mL) was added t-BuONa (0.455 g, 4.74 mmol). The mixture was heated to 100° C. for 3 hours. The mixture was diluted with water (50 mL) and the organics were extracted with EtOAc. The combined organics were concentrated under reduced pressure and the residue purified by preparative HPLC (Method 2) to give tert-butyl 4-[[7-(2-fluoro-6-methyl-phenyl)-5-isoquinolyl]amino]piperidine-1-carboxylate and tert-butyl 4-[[5-(2-fluoro-6-methyl-phenyl)-7-isoquinolyl]amino]piperidine-1-carboxylate as a mixture of regioisomers (P98), (0.080 g), LCMS $ES^+$ 436 $[M+H]^+$, Rt=0.995, 1.225 mins (Method 1).

The following compounds were prepared in a similar manner to tert-butyl 4-[[7-(2-fluoro-6-methyl-phenyl)-5-isoquinolyl]amino]piperidine-1-carboxylate, as a mixture of regioiomers (Dx), using the appropriate aryl bromide and amine:

| Preparation | Precursor | Structure | Name | LCMS Data |
|---|---|---|---|---|
| P99 | P15 | 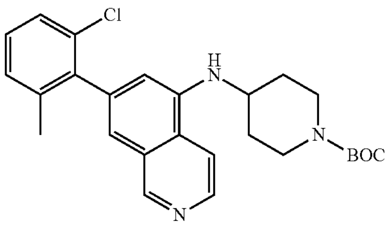 [SMILES: Cc1cccc(Cl)c1-c1cc(NC2CCN(C(=O)OC(C)(C)C)CC2)c2ccncc2c1] | tert-butyl 4-[[7-(2-chloro-6-methyl-phenyl)-5-isoquinolyl]amino]piperidine-1-carboxylate | $ES^+$ 452 $[M + H]^+$, Rt = 0.933, 1.223 mins (Method 1) |

-continued

| Preparation | Precursor | Structure | Name | LCMS Data |
|---|---|---|---|---|
| P100 | P14 | 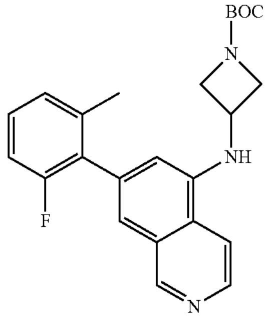 [SMILES: Cc1cccc(F)c1-c1cc(NC2CN(C(=O)OC(C)(C)C)C2)c2ccncc2c1] | tert-butyl 3-[[7-(2-fluoro-6-methyl-phenyl)-5-isoquinolyl]amino]azetidine-1-carboxylate | $ES^+$ 408 $[M + H]^+$, Rt = 1.413 mins (Method 1) |

Preparation 101 (P101)

7-(2-Fluoro-6-methyl-phenyl)-5-(1-methyl-3,6-dihydro-2H-pyridin-4-yl)isoquinolin-3-amine

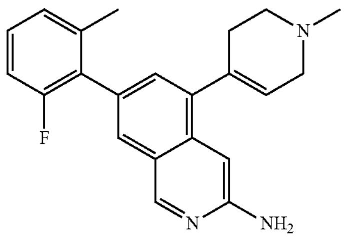 [SMILES: Cc1cccc(F)c1-c1cc(C2=CCN(C)CC2)c2cc(N)ncc2c1]

A mixture of 5-chloro-7-(2-fluoro-6-methyl-phenyl)isoquinolin-3-amine and 7-chloro-5-(2-fluoro-6-methyl-phenyl)isoquinolin-3-amine regioisomers (P23) (0.300 g, 1.04 mmol), 1-methyl-4-(4,4,5,5-tetramethyl-1,3,2-dioxaborolan-2-yl)-3,6-dihydro-2H-pyridine (0.465 g, 2.09 mmol), $Pd(dppf)Cl_2$ (0.076 g, 0.164 mmol), $Cs_2CO_3$ (0.680 g, 2.09 mmol) in dioxane (10 mL) was stirred at 100° C. overnight. After this time, this mixture was cooled to room temperature before being filtered, washing the precipitate with DCM. The organics were combined and concentrated under reduced pressure. The residue was chromatographed [$SiO_2$, DCM:MeOH 15:1] to give 7-(2-fluoro-6-methyl-phenyl)-5-(1-methyl-3,6-dihydro-2H-pyridin-4-yl)isoquinolin-3-amine and 5-(2-fluoro-6-methyl-phenyl)-7-(1-methyl-3,6-dihydro-2H-pyridin-4-yl)isoquinolin-3-amine (P101) (0.150 g), LCMS $ES^+$ 348 $[M+H]^+$, Rt=0.768, 0.865 mins ((Method 1).

Preparation 102 (P102)

5-Bromo-2-fluoro-3-iodo-benzonitrile

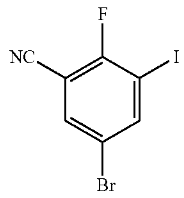 [SMILES: N#Cc1cc(Br)cc(I)c1F]

To a solution of 2,2,6,6-tetramethylpiperidine (2.54 g, 18.00 mmol) in THF (30.0 mL) at −78° C. under an atmosphere of argon was added nBuLi (11.3 mL, 1.6M). The solution was stirred at −30° C. for 1 hour. Diethylzinc was added at −78° C. The solution was stirred for 30 minutes before being allowed to warm to 0° C. for 3 hours. 5-bromo-2-fluoro-benzonitrile (3.00 g, 15.00 mmol) was added at −78° C. and the mixture was stirred at −78° c. for 3 hours. 12 (11.40 g, 45.00 mmol) was added and the solution was stirred at −78° C. for 30 minutes. The mixture was allowed to warm to room temperature and stirred overnight at room temperature. $Na_2SO_3$ (aq. soln.) was added. The organics were extracted with EtOAc (3×30 mL). The combined organics were washed with brine, dried over $Na_2SO_4$, filtered and concentrated under reduced pressure to give 5-bromo-2-fluoro-3-iodo-benzonitrile (P102) (4.00 g).

Preparation 102a (P102a)

3-chloro-4-fluoro-5-iodo-benzoic acid

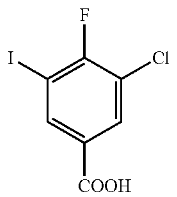 [SMILES: O=C(O)c1cc(Cl)c(F)c(I)c1]

To a solution of 3-chloro-4-fluoro-benzoic acid (20.0 g, 114.6 mmol) in conc $H_2SO_4$ (300 mL) was added NIS (30.9 g, 137.5 mmol). The mixture was stirred at room temperature for 16 hours. After this time, the solution was cooled to room temperature and poured into water (500 mL) at 0° C. The organics were extracted into EtOAc (300 mL×2), washed with $Na_2S_2O_3$ (aq. 300 mL×2), brine (300 mL), dried over $Na_2SO_4$ and concentrated under reduced pressure to give 3-chloro-4-fluoro-5-iodo-benzoic acid (P102a). The material was used without further purification.

$^1H$ NMR (400 MHz, DMSO-$d_6$): δ: ppm 13.43 (bs, 1H), 8.24 (d, J=2 Hz, 1H), 8.03 (d, J=2 Hz, 1H).

Preparation 102b (P102b)

(3-chloro-4-fluoro-5-iodo-phenyl)methanol

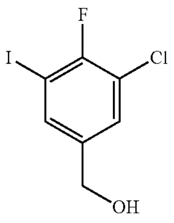 [SMILES: OCc1cc(Cl)c(F)c(I)c1]

To a solution of 3-chloro-4-fluoro-5-iodo-benzoic acid (P102a) (35.0 g, 116.5 mmol) in THF (200 mL) was added $BH_3$/THF (175 mL, 1M in THF) dropwise at room temperature. The mixture was stirred at 50° C. for 2 hours. After this time, the solution was quenched by addition of $NH_4Cl$ (aq. 100 mL) at 0° C. The organics were extracted into EtOAc, washed with $H_2O$ (200 mL), brine (200 mL), dried over $Na_2SO_4$, filtered and concentrated under reduced pressure to give (3-chloro-4-fluoro-5-iodo-phenyl)methanol (P102b) (28.0 g). The crude product was used without further purification in subsequent steps.

$^1H$ NMR (400 MHz, $CDCl_3$): δ: ppm 7.64 (d, J=2 Hz, 1H), 7.37 (d, J=2 Hz, 1H), 4.12 (s, 2H).

Preparation 102c (P102c)

5-(azidomethyl)-1-chloro-2-fluoro-3-iodo-benzene

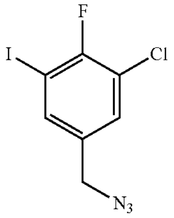 [SMILES: [N-]=[N+]=NCc1cc(Cl)c(F)c(I)c1]

To a solution of (3-chloro-4-fluoro-5-iodo-phenyl)methanol (P102b) (28.0 g, 97.8 mmol) in THF (300 mL) was added DPPA (40.3 g, 146.6 mmol) and DBU (22.3 g, 146.6 mmol) at 0° C. The mixture was stirred at room temperature for 16 hours. After this time, H2O (300 mL) was added to the reaction mixture. The organics were extracted into EtOAc (300 mL×2). The combined organics were washed with $H_2O$ (300 mL), brine (300 mL), dried over $Na_2SO_4$, filtered and concentrated under reduced pressure to give 5-(azidomethyl)-1-chloro-2-fluoro-3-iodo-benzene (P102c) (32.0 g). The material was used directly in subsequent steps without further purification.

$^1H$ NMR (400 MHz, $CDCl_3$): δ: ppm 7.59 (d, J=2 Hz, 1H), 7.34 (d, J=2 Hz, 1H), 4.30 (s, 2H).

Preparation 103 (P103)

(5-Bromo-2-fluoro-3-iodo-phenyl)methanamine

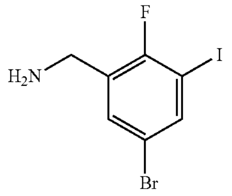 [SMILES: NCc1cc(Br)cc(I)c1F]

To a solution of 5-bromo-2-fluoro-3-iodo-benzonitrile (P102) (4.00 g, 12.27 mmol) in THF (10 mL) at 0° C. under an atmosphere of argon was added borane (18.4 mL, 1M son in THF). The solution was stirred at 50° C. for 3 hours. The mixture was cooled to 0° C. and $NH_4Cl$ (20 mL, aq. soln.) was added dropwise. HCl (10.0 mL, 3M) was added and the solution was stirred at room temperature for 1 hour. The solution was washed with DCM (3×30 mL). The aqueous layer was treated with $K_2CO_3$ to pH 8 and the organics were extracted with EtOAc (3×30 mL). The organics were washed with brine, dried over $Na_2SO_4$, filtered and concentrated under reduced pressure to give (5-bromo-2-fluoro-3-iodo-phenyl)methanamine (P103) (3.05 g) which was used without further purification.

Preparation 103a (P103a)

(3-Chloro-4-fluoro-5-iodo-phenyl)methanamine

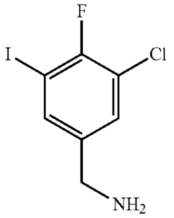 [SMILES: NCc1cc(Cl)c(F)c(I)c1]

To a solution of 5-(azidomethyl)-1-chloro-2-fluoro-3-iodo-benzene (P102c) (32.0 g, 103 mmol) in THF (320 mL) was added $PPh_3$ (32.0 g, 123 mmol) and $H_2O$ (22.1 g, 1.23 mol) at room temperature. The mixture was stirred at 50° C. for 16 hours under an atmosphere of argon. After this time, $H_2O$ (320 mL) was added. The organics were extracted into EtOAc (320 mL×2). The combined organics were washed with $H_2O$ (300 mL), brine (300 mL), dried over $Na_2SO_4$, filtered and concentrated under reduced pressure. The residue was chromatographed [$SiO_2$, DCM:MeOH, 20:1] to give (3-chloro-4-fluoro-5-iodo-phenyl)methanamine (P103a) (50.0 g).

Preparation 104 (P104)

N-[(5-Bromo-2-fluoro-3-iodo-phenyl)methyl]-2,2-diethoxy-acetamidine

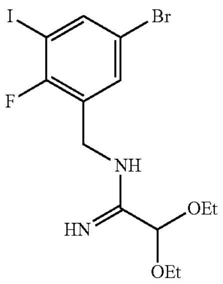 [SMILES: CCOC(OCC)C(=N)NCc1cc(Br)cc(I)c1F]

To a solution of (5-bromo-2-fluoro-3-iodo-phenyl)methanamine (P103) (3.05 g, 9.24 mmol) in EtOH (30 mL) was added methyl 2,2-diethoxyethanimidate (1.79 g, 11.09 mmol) at room temperature. The solution was stirred at room temperature overnight. After this time, the solution was concentrated under reduced pressure to give N-[(5-bromo-2-fluoro-3-iodo-phenyl)methyl]-2,2-diethoxy-acetamidine (P104) (5.80 g) which was used without further purification.

The following compound was prepared in a similar manner to N-[(5-Bromo-2-fluoro-3-iodo-phenyl)methyl]-2,2-diethoxy-acetamidine (P104), using the appropriate aryl bromide and amine:

| Preparation | Precursor | Structure | Name |
| --- | --- | --- | --- |
| P104a | P103a | 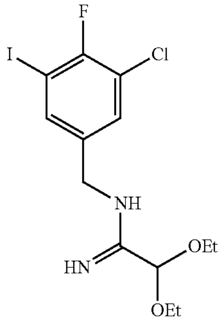 [SMILES: CCOC(OCC)C(=N)NCc1cc(Cl)c(F)c(I)c1] | N-[(3-chloro-4-fluoro-5-iodo-phenyl)methyl]-2,2-diethoxy-acetamidine |

Preparation 105 (P105)

5-Bromo-8-fluoro-7-iodo-isoquinolin-3-amine

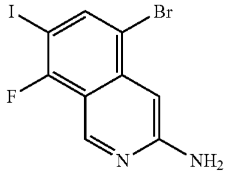 [SMILES: Nc1cc2c(Br)cc(I)c(F)c2cn1]

A solution of N-[(5-bromo-2-fluoro-3-iodo-phenyl)methyl]-2,2-diethoxy-acetamidine (P104) (5.80 g) in $H_2SO_4$ (10 mL, conc.) was stirred at 80° c. for 3 hours. After this time, the solution was cooled to room temperature. The solution was poured into $K_2CO_3$ (10.00 g) in water (50 mL). The organics were extracted with EtOAc (3x30 mL). the combined organics were washed with brine, concentrated under reduced pressure and the residue chromatographed [$SiO_2$, EtOAc in Pet.Ether, 0-25%] to give 5-bromo-8-fluoro-7-iodo-isoquinolin-3-amine (P105) (1.20 g).

$^1$H NMR (400 MHz, DMSO-d6): δ: ppm 8.95 (s, 1H), 8.06 (d, J=6 Hz 1H), 8.762 (d, J=1.2 Hz, 1H), 6.69 (s, 2H).

The following compound was prepared in a similar manner to 5-Bromo-8-fluoro-7-iodo-isoquinolin-3-amine (P105), as a mixture of regioiomers, using the appropriate intermediate:

| Preparation | Precursor | Structure | Name | LCMS Data |
| --- | --- | --- | --- | --- |
| P105a | P104a | 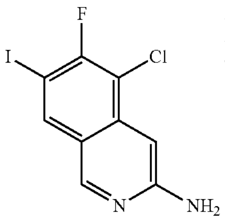 [SMILES: Nc1cc2c(Cl)c(F)c(I)cc2cn1] | 5-chloro-6-fluoro-7-iodo-isoquinolin-3-amine | $ES^+$ 323 $[M + H]^+$, Rt = 1.805 mins (Method 1) |

Preparation 106 (P106)

5-Bromo-8-fluoro-7-(2-fluoro-6-methyl-phenyl)isoquinolin-3-amine

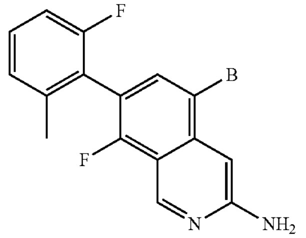

A solution of 5-bromo-8-fluoro-7-iodo-isoquinolin-3-amine (P105) (1.20 g, 3.27 mmol), $Cs_2CO_3$ (0.118 g, 0.164 mmol), Pd(dppf)$Cl_2$ (2.13 g, 6.54 mmol) and 2-(2-fluoro-6-methyl-phenyl)-4,4,5,5-tetramethyl-1,3,2-dioxaborolane (P1) (1.45 g, 6.54 mmol) in dioxane/water (20/1, 12.0 mL) was stirred at 90° C. overnight under an atmosphere of argon. The solution was filtered and the organics were extracted with EtOAc (3×10 mL). The combined organics were concentrated under reduced pressure and chromatographed [$SiO_2$, EtOAc in Pet. ether 0-25%] to give 5-bromo-8-fluoro-7-(2-fluoro-6-methyl-phenyl)isoquinolin-3-amine (P106) (0.580 g), LCMS $ES^+$ 349 $[M+H]^+$, Rt=8.883 mins (extended Method 1).

Preparation 106a (P106a)

5-Chloro-6-fluoro-7-(2-fluoro-6-methyl-phenyl)isoquinolin-3-amine

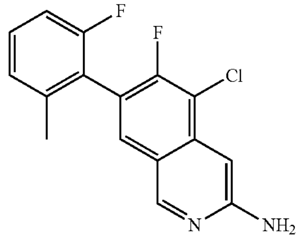

A solution of 5-chloro-6-fluoro-7-iodo-isoquinolin-3-amine (P105a) (2.00 g, 6.19 mmol), t-BuONa (2.36 g, 24.8 mmol), Pd(dppf)$Cl_2$ (2.00 g, 6.10 mmol) and 2-(2-fluoro-6-methyl-phenyl)-4,4,5,5-tetramethyl-1,3,2-dioxaborolane (P1) (5.85 g, 24.8 mmol) in dioxane/water (40/8 mL) was stirred at 70° C. for 16 hours. Further 2-(2-fluoro-6-methyl-phenyl)-4,4,5,5-tetramethyl-1,3,2-dioxaborolane (P1) (4.39 g, 18.6 mmol) was added and the solution was heated for a further 16 hours. The solution was filtered and the filtrate was concentrated under reduced pressure and chromatographed [$SiO_2$, EtOAc in Pet. ether 0-25%] to give 5-chloro-6-fluoro-7-(2-fluoro-6-methyl-phenyl)isoquinolin-3-amine (P106a) (0.900 g), LCMS $ES^+$305 $[M+H]^+$, Rt=10.42 mins (extended Method 1).

Preparation 107 (P107)

tert-Butyl 4-[[3-amino-8-fluoro-7-(2-fluoro-6-methyl-phenyl)-5-isoquinolyl]amino]piperidine-1-carboxylate

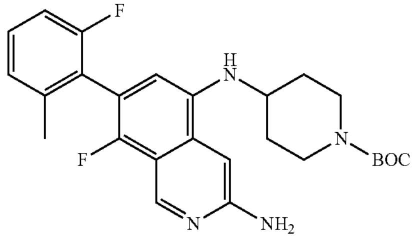 [SMILES: Cc1cccc(F)c1-c1cc(NC2CCN(C(=O)OC(C)(C)C)CC2)c2cc(N)ncc2c1F]

A solution of 5-bromo-8-fluoro-7-(2-fluoro-6-methyl-phenyl)isoquinolin-3-amine (P106) (0.100 g, 0.304 mmol), t-BuXPhos (0.012 g), $Pd_2(dba)_3$ (0.027 g), t-BuONa (0.069 g, 0.715 mmol) and tert-butyl 4-aminopiperidine-1-carboxylate (0.114 g, 0.572 mmol) in dioxane (1.0 mL) was stirred at 70° C. for 1 hour. The solution was diluted with EtOAc and the organics were extracted with EtOAc. The combined organics were washed with brine, dried over $Na_2SO_4$, filtered and concentrated under reduced pressure. The residue was purified by preparative HPLC (Method 1) to give tert-butyl 4-[[3-amino-8-fluoro-7-(2-fluoro-6-methyl-phenyl)-5-isoquinolyl]amino]piperidine-1-carboxylate (P107) (0.061 g), LCMS $ES^+$ 469 $[M+H]^+$, Rt=1.383 mins (Method 1).

The following compound was prepared in a similar manner to tert-Butyl 4-[[3-amino-8-fluoro-7-(2-fluoro-6-methyl-phenyl)-5-isoquinolyl]amino]piperidine-1-carboxylate (P107), using the appropriate intermediate:

| Preparation | Precursor | Structure | Name | LCMS Data |
|---|---|---|---|---|
| P107a | P106a | 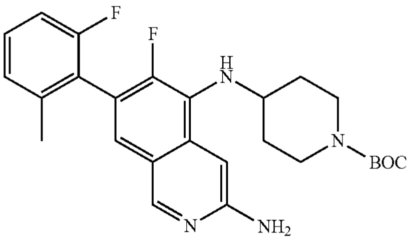 | tert-butyl 4-[[3-amino-6-fluoro-7-(2-fluoro-6-methyl-phenyl)-5-isoquinolyl]amino]piperidine-1-carboxylate | $ES^+$ 468 $[M+H]^+$, Rt = 1.405, 1.720 mins (regioisomers observed) (Method 1) |

Preparation 108 (P108)

Methyl 5-amino-2-methoxy-pyridine-4-carboxylate

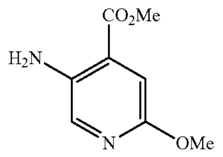 [SMILES: COC(=O)c1cc(OC)ncc1N]

5-amino-2-methoxy-pyridine-4-carboxylic acid (2.449 g, 14.57 mmol) was suspended in MeOH (50 mL) and $PhCH_3$ (150 mL). A solution of (trimethylsilyl)diazomethane (2M in $Et_2O$, 1.9 mL) was added slowly at 0° C. to the stirred solution. The solution was stirred at room temperature overnight. After this time, the mixture was diluted with water and the organics were extracted with EtOAc (2×100 mL). The combined organics were washed with brine, dried over $Na_2SO_4$ and concentrated under reduced pressure. The crude residue was chromatographed [$SiO_2$, Pet. ether:EtOAc, 5:1] to give methyl 5-amino-2-methoxy-pyridine-4-carboxylate (P108) (2.00 g), LCMS $ES^+$ 183 $[M+H]^+$, Rt=1.193 mins (Method 1).

Preparation 109 (P109)

Ethyl 6-chloro-2,4-dihydroxy-1,7-naphthyridine-3-carboxylate

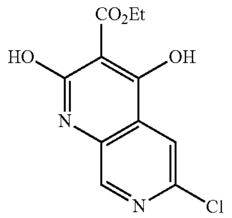 [SMILES: CCOC(=O)c1c(O)nc2cnc(Cl)cc2c1O]

To a solution of methyl 5-amino-2-methoxy-pyridine-4-carboxylate (P108) (2.10 g, 11.25 mmol) in DMF (30 mL) was added ethyl 3-chloro-3-oxo-propanoate (3.389 g, 22.50 mmol) and $K_2CO_3$ (7.774 g, 56.25 mmol). The solution was stirred at room temperature for 12 hours. After this time the solution was added to water (100.0 mL) and the organics were extracted with EtOAc (3×100 mL). The combined organics were washed with brine, dried over $Na_2SO_4$, filtered and concentrated under reduced pressure to give ethyl 6-chloro-2,4-dihydroxy-1,7-naphthyridine-3-carboxylate (P109), (1.40 g), LCMS $ES^+$269 $[M+H]^+$, Rt=1.323 mins (Method 1).

Preparation 110 (P110)

6-Chloro-1,7-naphthyridine-2,4-diol

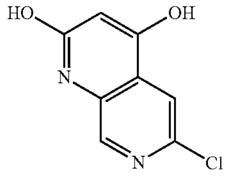 [SMILES: Oc1cc(O)c2cc(Cl)ncc2n1]

To a solution of ethyl 6-chloro-2,4-dihydroxy-1,7-naphthyridine-3-carboxylate (P109) (1.40 g, 5.21 mmol) was added HCl (3M, 20.0 mL). The solution was stirred at 100° C. for 4 hours. The solution as subsequently added to ice-water slowly and the pH was adjusted to pH=7 by addition of NaOH. A solid precipitate formed which was filtered and dried to give 6-chloro-1,7-naphthyridine-2,4-diol (P110) (0.600 g), LCMS $ES^+$197 $[M+H]^+$, Rt=1.425 mins (Method 1).

Preparation 111 (P111)

2,4,6-Trichloro-1,7-naphthyridine

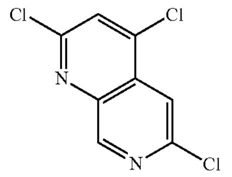 [SMILES: Clc1cc2c(Cl)cc(Cl)nc2cn1]

To a solution of 6-chloro-1,7-naphthyridine-2,4-diol (P110) (0.600 g, 3.05 mmol) was added $POCl_3$ (6.0 mL) slowly at 0° C. The solution was heated to 125° C. for 12 hours. After this time the solution was allowed to cool to room temperature before being added slowly to ice-water. The pH of the solution was adjusted to pH=8-9 by addition of NaOH (sat. aq. soln). The organics were extracted with EtOAc (3×20 mL). The combined organics were washed with brine, dried over $Na_2SO_4$, filtered and concentrated under reduced pressure to give 2,4,6-trichloro-1,7-naphthyridine (P111), (0.538 g), LCMS $ES^+$ 233 $[M+H]^+$, Rt=1.263 mins (Method 1).

Preparation 112 (P112)

4,6-Dichloro-2-(2-fluoro-6-methyl-phenyl)-1,7-naphthyridine

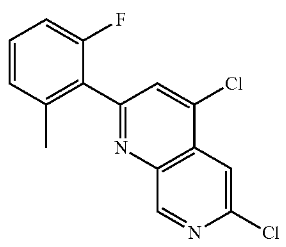 [SMILES: Cc1cccc(F)c1-c1cc(Cl)c2cc(Cl)ncc2n1]

To a solution of 2,4,6-trichloro-1,7-naphthyridine (P111) (0.538 g, 2.304 mmol) in dioxane/water (6.0 mL/0.6 mL) was added 2-(2-fluoro-6-methyl-phenyl)-4,4,5,5-tetramethyl-1,3,2-dioxaborolane (P1) (0.598 g, 2.535 mmol), $Pd(dppf)Cl_2$ (0.337 g, 0.461 mmol) and $Cs_2CO_3$ (1.501 g, 4.608 mmol). The solution was stirred at 50° C. for 12 hours. The solution was filtered through celite, washing with EtOAc. The combined organics were washed with water and brine, dried over $Na_2SO_4$ and concentrated under reduced pressure to give 4,6-dichloro-2-(2-fluoro-6-methyl-phenyl)-1,7-naphthyridine (P112) (0.320 g), LCMS $ES^+$307 $[M+H]^+$, Rt=1.475 mins (Method 1).

Preparation 113 (P113)

6-Chloro-2-(2-fluoro-6-methyl-phenyl)-N-(1-methyl-4-piperidyl)-1,7-naphthyridin-4-amine

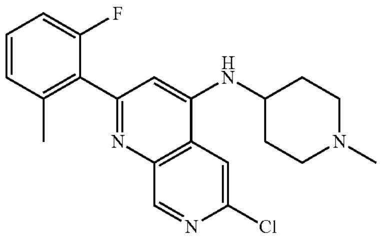 [SMILES: Cc1cccc(F)c1-c1cc(NC2CCN(C)CC2)c2cc(Cl)ncc2n1]

To a solution of 4,6-dichloro-2-(2-fluoro-6-methyl-phenyl)-1,7-naphthyridine (P112) (0.300 g, 0.977 mmol) in dry 1,4-dioxane (3.0 mL) was added 1-methylpiperidin-4-amine (0.167 g, 1.466 mmol), $Pd_2(dba)_3$ (0.030 g), RuPhos (0.030 g) and t-BuONa (0.281 g, 2.931 mmol). The solution was stirred at 50° C. for 4 hours. The solution was filtered through celite, washing with EtOAc. The organics were combined, concentrated under reduced pressure and the residue chromatographed [$SiO_2$, DCM:MeOH, 10:1] to give 6-chloro-2-(2-fluoro-6-methyl-phenyl)-N-(1-methyl-4-piperidyl)-1,7-naphthyridin-4-amine (P113) (0.177 g), LCMS $ES^+$ 385 $[M+H]^+$, Rt=0.816 mins (Method 1).

Preparation 114 (P114)

N6-Benzyl-2-(2-fluoro-6-methyl-phenyl)-N4-(1-methyl-4-piperidyl)-1,7-naphthyridine-4,6-diamine

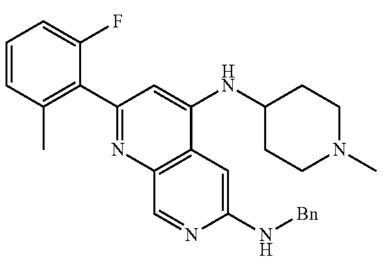 [SMILES: Cc1cccc(F)c1-c1cc(NC2CCN(C)CC2)c2cc(NCc3ccccc3)ncc2n1]

To a solution of 6-chloro-2-(2-fluoro-6-methyl-phenyl)-N-(1-methyl-4-piperidyl)-1,7-naphthyridin-4-amine (P113) (0.177 g, 0.46 mmol) in dry 1,4-dioxane (3.0 mL) was added benzylamine (0.098 g, 0.92 mmol), t-BuONa (0.088 g, 0.92 mmol), $Pd_2(dba)_3$ (0.084, 0.092 mmol) and t-BuBrettPhos (0.044 g, 0.092 mmol). The solution was stirred at 100° C. for 4 hours. The solution was filtered over celite, washing with EtOAc. The combined organics were concentrated under reduced pressure and the resulting residue was chromatographed [$SiO_2$, DCM:MeOH, 20:1] to give N6-benzyl-2-(2-fluoro-6-methyl-phenyl)-N4-(1-methyl-4-piperidyl)-1,7-naphthyridine-4,6-diamine (P114) (0.120 g), LCMS $ES^+$ 456 $[M+H]^+$, Rt=0.899 mins (Method 1).

Preparation 115 (P115)

1,7-Naphthyridine-2,4-diol

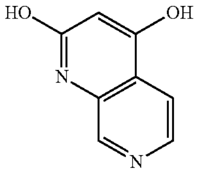

To a solution of methyl 3-aminopyridine-4-carboxylate (0.300 g, 1.972 mmol) in EtOAc (5.0 mL) was added t-BuOK (0.442 g, 13.943 mmol) at 0° C. The mixture was stirred overnight at 75° C. After this time, the solution was allowed to cool to room temperature before being diluted with water (10.0 mL). The aqueous layer was washed with EtOAc before being acidified to pH=6 using HCl (1M). A precipitate formed which was filtered, washed with water and dried under vacuum to give 1,7-naphthyridine-2,4-diol (P115) (0.055 g), LCMS $ES^+$ 163 $[M+H]^+$, Rt=0.593 mins (Method 1).

Preparation 116 (P116)

2,4-Dichloro-1,7-naphthyridine

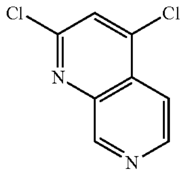 [SMILES: Clc1cc(Cl)c2ccncc2n1]

To a solution of 1,7-naphthyridine-2,4-diol (P115) (0.055 g, 10.339 mmol) in $PhCH_3$ (5.0 mL) was added $POCl_3$ (0.1 mL, 1.018 mmol). The mixture was stirred at 80° C. overnight. Further $POCl_3$ (3.0 mL) was added and the mixture was stirred at 115° C. overnight.

The mixture was added carefully to ice water. The organics were extracted with DCM, washed with brine and concentrated under reduced pressure to give 2,4-dichloro-1,7-naphthyridine (P116), (0.063 g), LCMS $ES^-$ 199 $[M+H]^+$, Rt=1.713 mins (Method 1).

Preparation 117 (P117)

4-Chloro-2-(2-fluoro-6-methyl-phenyl)-1,7-naphthyridine

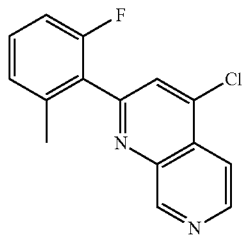 [SMILES: Cc1cccc(F)c1-c1cc(Cl)c2ccncc2n1]

To a solution of 2,4-dichloro-1,7-naphthyridine (P116) (0.340 g, 1.708 mmol) and 2-(2-fluoro-6-methyl-phenyl)-4,4,5,5-tetramethyl-1,3,2-dioxaborolane (P1) (0.403 g, 1.708 mmol), $Cs_2CO_3$ (1.11 g, 3.416 mmol) in 1,4-dioxane/water (56.0 mL/8.0 mL) was added Pd(dppf)$Cl_2$ (0.068 g). The mixture was stirred at 100° C. for 2 hours. The mixture was diluted with water and the organics were extracted with EtOAc. The combined organics were washed with brine, dried over $Na_2SO_4$, filtered and concentrated under reduced pressure. The crude residue was chromatographed [$SiO_2$, Pet. ether/EtOAc 3:1] to give 4-chloro-2-(2-fluoro-6-methyl-phenyl)-1,7-naphthyridine (P117) (0.380 g), LCMS $ES^+$ 273 $[M+H]^+$, Rt=1.763 mins (Method 1).

Preparation 118 (P118)

2-Amino-3-bromo-5-iodo-benzoic acid

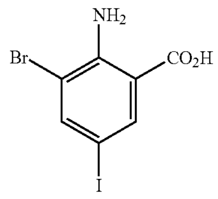

A solution of 2-amino-3-bromo-benzoic acid (0.300 g, 2.31 mmol) and N-iodosuccinimide (0.521 g, 2.31 mmol) in DCM (10.0 mL) was stirred at room temperature overnight. After this time, the mixture was filtered and concentrated under reduced pressure to give 2-amino-3-bromo-5-iodo-benzoic acid (P118) (0.600 g), LCMS $ES^+$ 342 $[M+H]^+$, Rt=1.483 mins (Method 1).

Preparation 119 (P119)

(2-Amino-3-bromo-5-iodo-phenyl)methanol

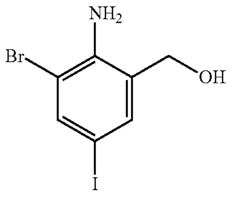 [SMILES: Nc1c(Br)cc(I)cc1CO]

To a solution of 2-amino-3-bromo-5-iodo-benzoic acid (P118) (6.10 g, 17.80 mmol) in THF (100 mL) was added $BH_3$ in THF (35.60 mL, 35.6 mmol) slowly. The solution was stirred at 50° C. for 3 hours. The solution was cooled to room temperature and concentrated under reduced pressure. EtOAc (150 mL) and brine (150 mL) were added to the mixture. The organics were extracted and washed with $NaHCO_3$ (aq. soln.). The organics were dried and concentrated under reduced pressure to give (2-amino-3-bromo-5-iodo-phenyl)methanol (P119) (6.00 g), LCMS $ES^+$328 $[M+H]^+$, Rt=1.313 mins (Method 1).

Preparation 120 (P120)

2-Amino-3-bromo-5-iodo-benzaldehyde

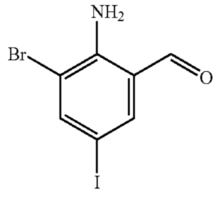 [SMILES: Nc1c(Br)cc(I)cc1C=O]

To a solution of (2-amino-3-bromo-5-iodo-phenyl)methanol (P119) (0.200 g, 0.61 mmol) in DCM (5.0 mL) and THF (0.5 mL) was added $MnO_2$ (0.319 g, 3.66 mmol) slowly. The mixture was stirred at room temperature for 15 hours. After this time, the mixture was filtered and the filtrate was concentrated under reduced pressure to give 2-amino-3-bromo-5-iodo-benzaldehyde (P120) (0.140 g), LCMS $ES^+$ 327 $[M+H]^+$, Rt=1.663 mins (Method 1).

Preparation 121 (P121)

8-Bromo-6-iodo-quinazoline

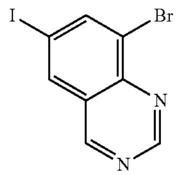

A mixture of 2-amino-3-bromo-5-iodo-benzaldehyde (P120) (0.050 g, 0.152 mmol) and formamidine acetate (0.023 g, 0.228 mmol) in DMF (2.0 mL) was stirred at 140° C. for 15 hours. The mixture was diluted with water and the organics were extracted with EtOAc (3×50 mL), dried over $Na_2SO_4$, filtered and concentrated to give 8-bromo-6-iodo-quinazoline (P121) (0.045 g), LCMS $ES^+$334 $[M+H]^+$, Rt=1.443 mins (Method 1).

Preparation 122 (P122)

8-Bromo-6-iodo-quinazolin-2-amine

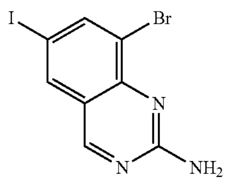

A mixture of 2-amino-3-bromo-5-iodo-benzaldehyde (P120) (0.050 g, 0.152 mmol), guanidinium carbonate (0.021 g, 0.228 mmol) in DMF (2.0 mL) was stirred at 140° C. for 15 hours. The mixture was diluted with water and the organics were extracted with EtOAc (3×50 mL). The combined organics were dried over $Na_2SO_4$, filtered and concentrated under reduced pressure to give 8-bromo-6-iodo-quinazolin-2-amine (P122) (0.040 g), LCMS $ES^+$ 349 $[M+H]^+$, Rt=1.263 mins (Method 1).

Preparation 123 (P123)

8-Bromo-6-(2-fluoro-6-methyl-phenyl)quinazoline

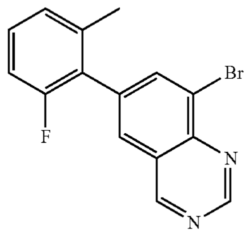 [SMILES: Cc1cccc(F)c1-c1cc(Br)c2ncncc2c1]

A mixture of 8-bromo-6-iodo-quinazoline (P121) (0.050 g, 0.149 mmol), 2-(2-fluoro-6-methyl-phenyl)-4,4,5,5-tetramethyl-1,3,2-dioxaborolane (P1) (0.070 g, 0.298 mmol), $Pd(dppf)Cl_2$ (0.011 g, 0.0149 mmol), $Cs_2CO_3$ (0.097 g, 0.298 mmol) in dioxane (3.0 mL) and water (0.3 mL) was stirred at 105° C. for 15 hours. The mixture was filtered and the solution chromatographed [$SiO_2$, Pet:Ether:EtOAc 2:1] to give 8-bromo-6-(2-fluoro-6-methyl-phenyl)quinazoline (P123) (0.032 g), LCMS $ES^+$ 319 $[M+H]^+$, Rt=1.543 mins (Method 1).

Preparation 123a (P123a)

8-Bromo-6-(2-chloro-6-methyl-phenyl)quinazoline

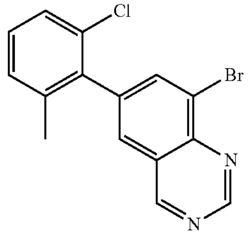 [SMILES: Cc1cccc(Cl)c1-c1cc(Br)c2ncncc2c1]

A mixture of 8-bromo-6-iodo-quinazoline (P121) (0.050 g, 0.142 mmol), 2-(2-fluoro-6-methyl-phenyl)-4,4,5,5-tetramethyl-1,3,2-dioxaborolane (P2) (0.049 g, 0.17 mmol), $Pd_2(dba)_3$ (0.013 g, 0.0142 mmol), $Cs_2CO_3$ (0.138 g, 0.438 mmol) in dioxane (2.0 mL) and water (0.5 mL) was stirred at 100° C. for 15 hours. The mixture was filtered and the solution chromatographed [$SiO_2$, Pet:Ether:EtOAc 2:1] to give 8-bromo-6-(2-chloro-6-methyl-phenyl)quinazoline (P123a) (0.020 g), LCMS $ES^+$ 333 $[M+H]^+$, Rt=1.843 mins (Method 1).

Preparation 124 (P124)

8-Bromo-6-(2-fluoro-6-methyl-phenyl)quinazolin-2-amine

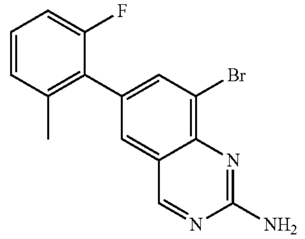

A mixture of 8-bromo-6-iodo-quinazolin-2-amine (P122) (0.050 g, 0.142 mmol), 2-(2-fluoro-6-methyl-phenyl)-4,4,5,5-tetramethyl-1,3,2-dioxaborolane (P1) (0.133 g, 0.568 mmol), $Pd_2(dba)_3$ (0.013 g) and $Cs_2CO_3$ (0.138 g, 0.426 mmol) in dioxane/water (3.0 mL/3 drops) was stirred at 105° C. for 15 hours. The mixture was filtered and the organics concentrated under reduced pressure. The residue was chromatographed [$SiO_2$, Pet. ether:EtOAc, 2:1] to give 8-bromo-6-(2-fluoro-6-methyl-phenyl)quinazolin-2-amine (P124) (0.034 g), LCMS $ES^+$ 334 $[M+H]^+$, Rt=1.413 mins (Method 1).

Preparation 124a (P124a)

8-Bromo-6-(2-chloro-6-methyl-phenyl)quinazolin-2-amine

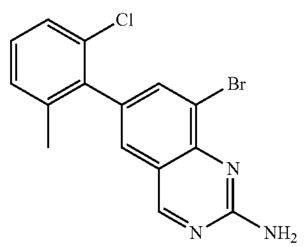

A mixture of 8-bromo-6-iodo-quinazolin-2-amine (P122) (0.040 g, 0.115 mmol), 2-(2-chloro-6-methyl-phenyl)-4,4,5,5-tetramethyl-1,3,2-dioxaborolane (P2) (0.066 g, 0.123 mmol), $Pd(PPh_3)_4$ (0.040 g) and $K_2CO_3$ (0.064 g, 0.46 mmol) in dioxane/water (2.0 mL/0.4 mL) was stirred at 90° C. for 15 hours. The mixture was filtered and the organics concentrated under reduced pressure. The residue was chromatographed [$SiO_2$, Pet. ether:EtOAc, 2:1] to give (P124a) (0.020 g), LCMS $ES^+$ 350 $[M+H]^+$, Rt=1.483 mins (Method 1).

Preparation 125 (P125)

tert-Butyl 4-[[6-(2-fluoro-6-methyl-phenyl)quinazolin-8-yl]amino]piperidine-1-carboxylate

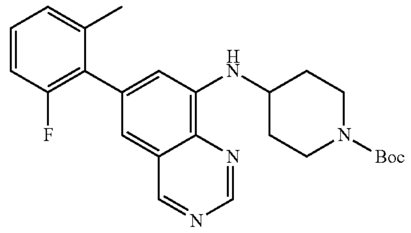 [SMILES: Cc1cccc(F)c1-c1cc(NC2CCN(C(=O)OC(C)(C)C)CC2)c2ncncc2c1]

A mixture of 8-bromo-6-(2-fluoro-6-methyl-phenyl)quinazoline (P123) (0.100 g, 0.315 mmol), tert-butyl 4-aminopiperidine-1-carboxylate (0.063 g, 0.315 mmol), $Pd_2(dba)_3$ (0.058 g, 0.063 mmol), t-BuXantphos (0.020 g) and t-BuONa (0.061 g, 0.63 mmol) in dioxane (2.0 mL) was stirred at 80° C. for 3 hours. After this time, the mixture was filtered and concentrated under reduced pressure. The residue was chromatographed [$SiO_2$, Pet. ether:EtOAc, 2:1] to give tert-butyl 4-[[6-(2-fluoro-6-methyl-phenyl)quinazolin-8-yl]amino]piperidine-1-carboxylate (P125) (0.070 g), LCMS $ES^+$ 437 $[M+H]^+$, Rt=1.963 mins (Method 1).

The following compound was prepared in a similar manner to tert-Butyl 4-[[6-(2-fluoro-6-methyl-phenyl)quinazolin-8-yl]amino]piperidine-1-carboxylate (P125) using the appropriate tert-butoxycarbonyl protected amine:

Preparation 126 (P126)

tert-Butyl 4-[[2-amino-6-(2-fluoro-6-methyl-phenyl)quinazolin-8-yl]amino]piperidine-1-carboxylate

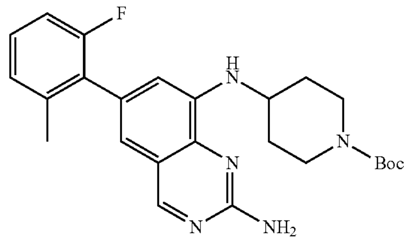

A mixture of 8-bromo-6-(2-fluoro-6-methyl-phenyl)quinazolin-2-amine (P124) (0.150 g, 0.452 mmol), tert-butyl 4-aminopiperidine-1-carboxylate (0.181 g, 0.904 mmol), $Pd_2(dba)_3$ (0.083 g, 0.090 mmol), t-BuXantphos (0.030 g) and t-BuONa (0.087 g, 0.904 mmol) in dioxane (4.0 mL) was stirred at 80° C. for 3 hours. After this time, the mixture was filtered and concentrated under reduced pressure. The residue was purified by preparative HPLC to give tert-butyl 4-[[2-amino-6-(2-fluoro-6-methyl-phenyl)quinazolin-8-yl]amino]piperidine-1-carboxylate (P126) (0.070 g), LCMS $ES^+$452 $[M+H]^+$, Rt=1.733 mins (Method 1).

The following compound was prepared in a similar manner to tert-Butyl 4-[[2-amino-6-(2-fluoro-6-methyl-phenyl)quinazolin-8-yl]amino]piperidine-1-carboxylate (P126) using the appropriate tert-butoxycarbonyl protected amine:

| Preparation | Precursor | Structure | Name | LCMS Data |
|---|---|---|---|---|
| P125a | P123a | 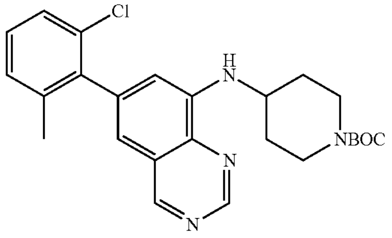 | 6-(2-chloro-6-methyl-phenyl)-N-cyclohexyl-quinazolin-8-amine | ES+ 453 [M+H]+, Rt = 2.073 mins (Method 1) |

| Preparation | Precursor | Structure | Name | LCMS Data |
|---|---|---|---|---|
| P126a | P124a | 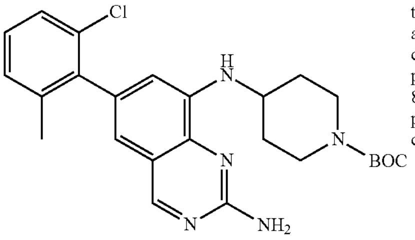 | tert-butyl 4-[[2-amino-6-(2-chloro-6-methyl-phenyl)quinazolin-8-yl]amino] piperidine-1-carboxylate | $ES^+$ 468 $[M+H]^+$, Rt = 1.843 mins (Method 1) |

Example 1 (E1)

7-(2-Fluoro-6-methyl-phenyl)-N5-(4-piperidyl)isoquinoline-3,5-diamine

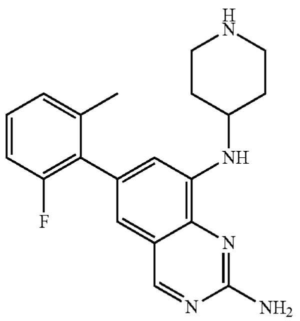

To a solution of tert-butyl 4-[[3-amino-7-(2-fluoro-6-methyl-phenyl)-5-isoquinolyl]amino]piperidine-1-carboxylate and tert-butyl 4-[[3-amino-5-(2-fluoro-6-methyl-phenyl)-7-isoquinolyl]amino]piperidine-1-carboxylate (P43) (1.200 g) in MeOH (6 mL) was added conc. HCl (3 mL). The reaction mixture was stirred at room temperature and monitored by LCMS. When the starting material had been consumed the reaction mixture was concentrated under reduced pressure and the residue purified by preparative HPLC (Method 2) to afford 7-(2-fluoro-6-methyl-phenyl)-N5-(4-piperidyl)isoquinoline-3,5-diamine (E1) (0.060 g) LCMS $ES^+$ 351 $[M+H]^+$, Rt=1.21 mins (Method 2).

$^1H$ NMR (400 MHz, MeOD): δ: ppm 8.67 (s, 1H), 7.25-7.21 (m, 1H), 7.10 (d, J=7.6 Hz, 1H), 7.03 (d, J=8.4 Hz, 2H), 6.98 (m, 1H), 6.54 (s, 1H), 3.73-3.71 (m, 1H), 3.39-3.31 (m, 2H), 3.05 (td, J=12.8, 2.4 Hz, 2H), 2.30-2.06 (m, 2H), 2.20 (s, 3H), 1.77-1.75 (m, 2H).

The following compounds were prepared in a similar manner to 7-(2-fluoro-6-methyl-phenyl)-N5-(4-piperidyl) isoquinoline-3,5-diamine (E1) using the appropriate tert-butoxycarbonyl protected amine:

| Example | Precursor | Structure | Name | LCMS Data |
|---|---|---|---|---|
| E2 | P44 | 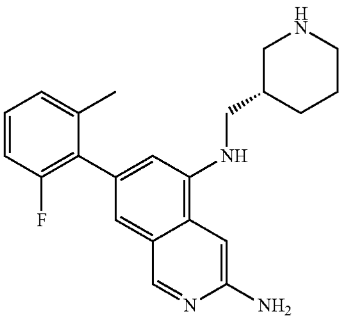 [SMILES: Cc1cccc(F)c1-c1cc(NC[C@H]2CCCNC2)c2cc(N)ncc2c1] | 7-(2-fluoro-6-methyl-phenyl)-N5-[[(3S)-3-piperidyl]methyl] isoquinoline-3,5-diamine | $ES^+$ 365 $[M+H]^+$, Rt = 1.046 mins (Method 2) |
| E3 | P45 | 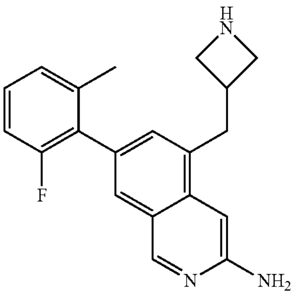 [SMILES: Cc1cccc(F)c1-c1cc(CC2CNC2)c2cc(N)ncc2c1] | N5-(azetidin-3-yl)-7-(2-fluoro-6-methyl-phenyl) isoquinoline-3,5-diamine | $ES^+$ 323 $[M+H]^+$, Rt = 1.07 mins (Method 2) |

-continued

| Example | Precursor | Structure | Name | LCMS Data |
|---|---|---|---|---|
| E4 | P46 | 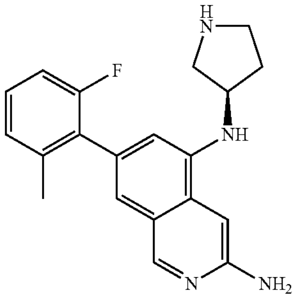 [SMILES: Cc1cccc(F)c1-c1cc(N[C@@H]2CCNC2)c2cc(N)ncc2c1] | 7-(2-fluoro-6-methyl-pheny)-N5-[(3R)-pyrrolidin-3-yl]isoquinoline-3,5-diamine | ES+ 337 [M+H]+, Rt = 1.099 mins (Method 1) |
| E5 | P67 | 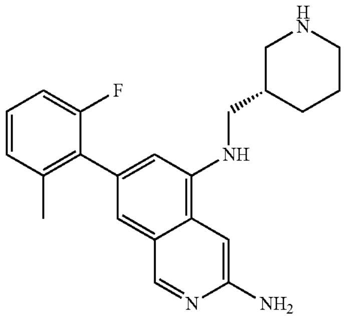 [SMILES: Cc1cccc(F)c1-c1cc(NC[C@H]2CCCNC2)c2cc(N)ncc2c1] | 7-(2-fluoro-6-methyl-phenyl)-N5-[[(2R)-2-piperidyl]methyl] isoquinoline-3,5-diamine | ES+ 365 [M+H]+, Rt = 1.183 mins (Method 2) |
| E6 | P68 | 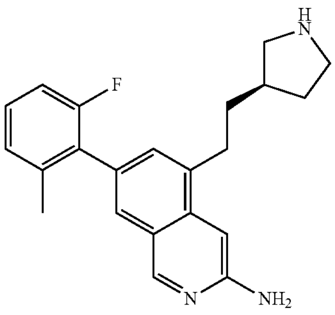 [SMILES: Cc1cccc(F)c1-c1cc(CC[C@@H]2CCNC2)c2cc(N)ncc2c1] | 7-(2-fluoro-6-methyl-phenyl)-N5-[[(3R)-pyrrolidin-3-yl]methyl] isoquinoline-3,5-diamine | ES+ 351 [M+H]+, Rt = 1.16 mins (Method 2) |
| E7 | P47 | 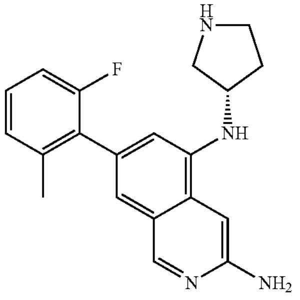 [SMILES: Cc1cccc(F)c1-c1cc(N[C@H]2CCNC2)c2cc(N)ncc2c1] | 7-(2-fluoro-6-methyl-phenyl)-N5-[(3S)-pyrrolidin-3-yl]isoquinoline-3,5-diamine | ES+ 337 [M+H]+, Rt = 0.670 mins (Method 2) |
| E8 | P48 | 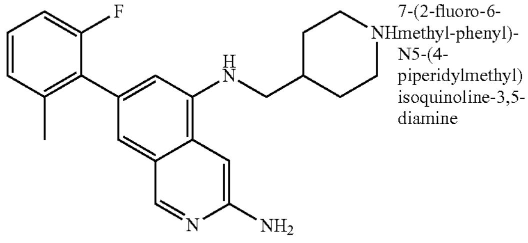 | 7-(2-fluoro-6-methyl-phenyl)-N5-(4-piperidylmethyl) isoquinoline-3,5-diamine | ES+ 365 [M+H]+, Rt = 0.820 mins (Method 1) |

-continued

| Example | Precursor | Structure | Name | LCMS Data |
|---|---|---|---|---|
| E9 | P49 | 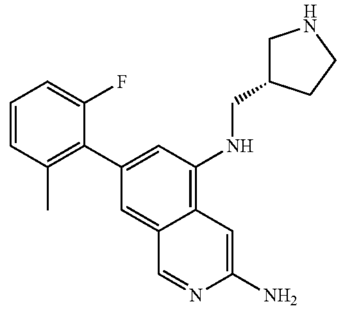 [SMILES: Cc1cccc(F)c1-c1cc(NC[C@H]2CCNC2)c2cc(N)ncc2c1] | 7-(2-fluoro-6-methyl-phenyl)-N5-[[(3S)-pyrrolidin-3-yl]methyl]isoquinoline-3,5-diamine | $ES^+$ 351 $[M+H]^+$, Rt = 0.247 mins (Method 2) |
| E10 | P50 | 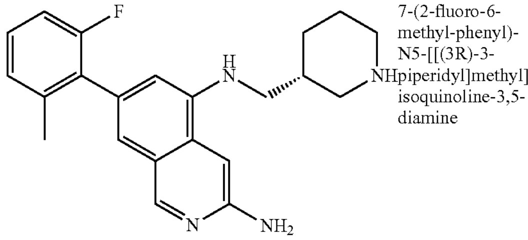 | 7-(2-fluoro-6-methyl-phenyl)-N5-[[(3R)-3-piperidyl]methyl] isoquinoline-3,5-diamine | $ES^+$ 365 $[M+H]^+$, Rt = 1.053 mins (Method 2) |
| E11 | P51 | 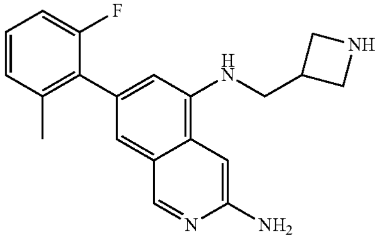 [SMILES: Cc1cccc(F)c1-c1cc(NCC2CNC2)c2cc(N)ncc2c1] | N5-(azetidin-3-ylmethyl)-7-(2-fluoro-6-methyl-phenyl) isoquinoline-3,5-diamine | $ES^+$ 337 $[M+H]^+$, Rt = 1.090 mins (Method 2) |
| E12 | P52 | 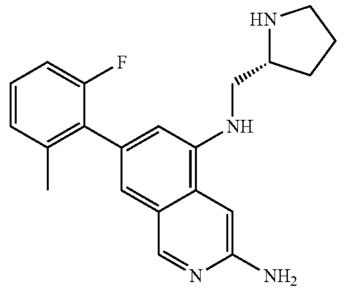 [SMILES: Cc1cccc(F)c1-c1cc(NC[C@H]2CCCN2)c2cc(N)ncc2c1] | 7-(2-fluoro-6-methyl-phenyl)-N5-[[(2R)-pyrrolidin-2-yl]methyl] isoquinoline-3,5-diamine | $ES^+$ 351 $[M+H]^+$, Rt = 1.17 mins (Method 2) |
| E13 | P53 | 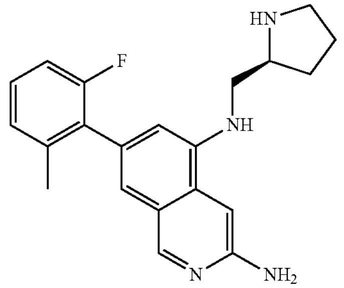 [SMILES: Cc1cccc(F)c1-c1cc(NC[C@@H]2CCCN2)c2cc(N)ncc2c1] | 7-(2-fluoro-6-methyl-phenyl)-N5-[[(2S)-pyrrolidin-2-yl]methyl] isoquinoline-3,5-diamine | $ES^+$ 351 $[M+H]^+$, Rt = 1.19 mins (Method 2) |

-continued

| Example | Precursor | Structure | Name | LCMS Data |
|---|---|---|---|---|
| E14 | P69 | 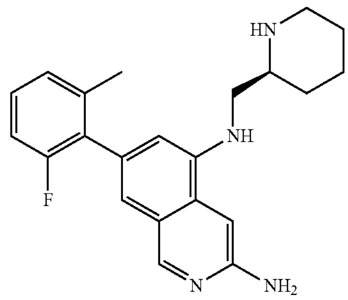 [SMILES: Cc1cccc(F)c1-c1cc(NC[C@@H]2CCCCN2)c2cc(N)ncc2c1] | 7-(2-fluoro-6-methyl-phenyl)-N5-[[(2S)-2-piperidyl]methyl]isoquinoline-3,5-diamine | $ES^+$ 365 $[M+H]^+$, Rt = 1.063 mins (Method 2) |
| E15 | P54 | 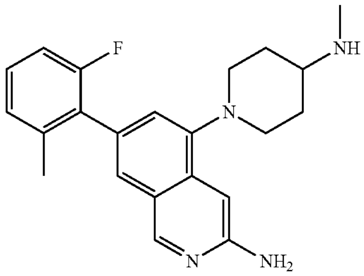 [SMILES: CNC1CCN(c2cc(-c3c(C)cccc3F)cc3cnc(N)cc23)CC1] | 7-(2-fluoro-6-methyl-phenyl)-5-[4-(methylamino)-1-piperidyl] isoquinolin-3-amine | $ES^+$ 365 $[M+H]^+$, Rt = 1.152 mins (Method 2) |
| E16 | P55 | 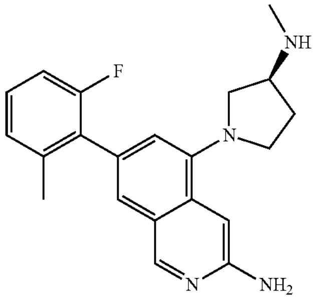 [SMILES: CN[C@H]1CCN(c2cc(-c3c(C)cccc3F)cc3cnc(N)cc23)C1] | 7-(2-fluoro-6-methyl-phenyl)-5-[(3S)-3-(methylamino) pyrrolidin-1-yl]isoquinolin-3-amine | $ES^+$ 351 $[M+H]^+$, Rt = 1.12 mins (Method 2) |
| E17 | P56 | 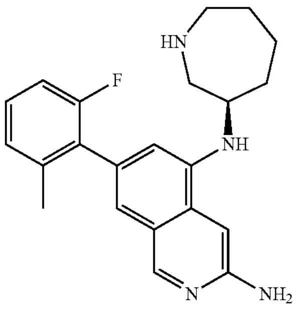 [SMILES: Cc1cccc(F)c1-c1cc(N[C@@H]2CCCCNC2)c2cc(N)ncc2c1] | N5-[(3R)-azepan-3-yl]-7-(2-fluoro-6-methyl-phenyl) isoquinoline-3,5-diamine | $ES^+$ 365 $[M+H]^+$, Rt = 1.21 mins (Method 2) |
| E18 | P57 | 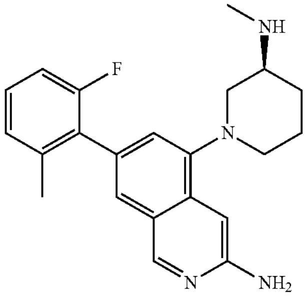 [SMILES: CN[C@H]1CCCN(c2cc(-c3c(C)cccc3F)cc3cnc(N)cc23)C1] | 7-(2-fluoro-6-methyl-phenyl)-5-[(3S)-3-(methylamino)-1-piperidyl] isoquinolin-3-amine | $ES^+$ 365 $[M+H]^+$, Rt = 1.38 mins (Method 2) |

-continued

| Example | Precursor | Structure | Name | LCMS Data |
|---|---|---|---|---|
| E19 | P70 | 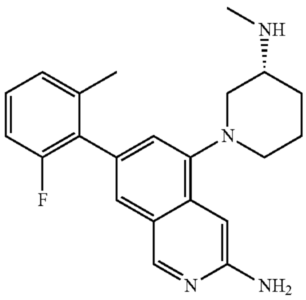 [SMILES: CN[C@@H]1CCCN(c2cc(-c3c(C)cccc3F)cc3cnc(N)cc23)C1] | 7-(2-fluoro-6-methyl-phenyl)-5-[(3R)-3-(methylamino)-1-piperidyl]isoquinolin-3-amine | ES+ 365 [M+H]+, Rt = 1.17 mins (Method 2) |
| E20 | P74 | 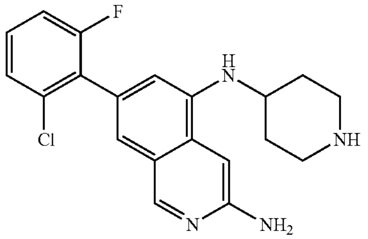 [SMILES: Nc1cc2c(NC3CCNCC3)cc(-c3c(F)cccc3Cl)cc2cn1] | 7-(2-chloro-6-fluoro-phenyl)-N5-(4-piperidyl)isoquinoline-3,5-diamine | ES+ 371,373 [M+H]+, Rt = 1.399 mins (Method 2) |
| E21 | P60 | 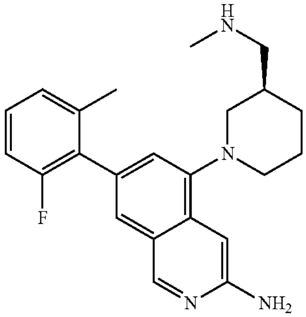 [SMILES: CNC[C@H]1CCCN(c2cc(-c3c(C)cccc3F)cc3cnc(N)cc23)C1] | 7-(2-fluoro-6-methyl-phenyl)-5-[(3R)-3-(methylamino-methyl)-1-piperidyl]isoquinolin-3-amine | ES+ 379 [M+H]+, Rt = 1.243 mins (Method 2) |
| E22 | P66 | 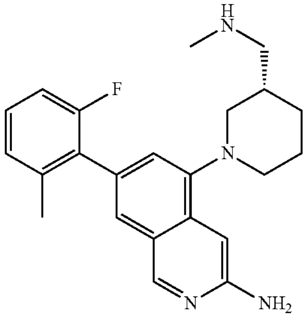 [SMILES: CNC[C@@H]1CCCN(c2cc(-c3c(C)cccc3F)cc3cnc(N)cc23)C1] | 7-(2-fluoro-6-methyl-phenyl)-5-[(3S)-3-(methylamino-methyl)-1-piperidyl]isoquinolin-3-amine | ES+ 379 [M+H]+, Rt = 1.26 mins (Method 2) |
| E23 | P71 | 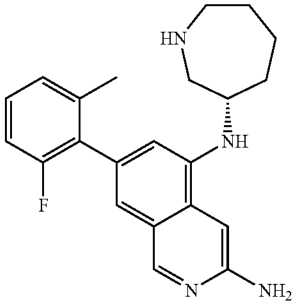 [SMILES: Cc1cccc(F)c1-c1cc(N[C@H]2CCCCNC2)c2cc(N)ncc2c1] | N5-[(3S)-azepan-3-yl]-7-(2-fluoro-6-methyl-phenyl)isoquinoline-3,5-diamine | ES+ 365 [M+H]+, Rt = 1.13 mins (Method 2) |

-continued

| Example | Precursor | Structure | Name | LCMS Data |
|---|---|---|---|---|
| E24 | P61 | 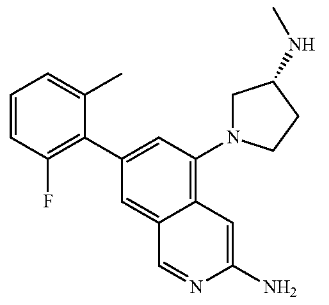 [SMILES: CN[C@@H]1CCN(c2cc(-c3c(C)cccc3F)cc3cnc(N)cc23)C1] | 7-(2-fluoro-6-methyl-phenyl)-5-[(3R)-3-(methylamino) pyrrolidin-1-yl]isoquinolin-3-amine | $ES^+$ 351 $[M+H]^+$, Rt = 1.11 mins (Method 2) |
| E25 | P62 | 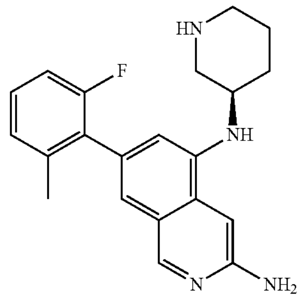 [SMILES: Cc1cccc(F)c1-c1cc(N[C@@H]2CCCNC2)c2cc(N)ncc2c1] | 7-(2-fluoro-6-methyl-phenyl)-N5-[(3R)-3-piperidyl] isoquinoline-3,5-diamine | $ES^+$ 351 $[M+H]^+$, Rt = 1.17 mins (Method 2) |
| E26 | P63 | 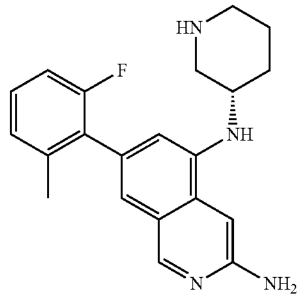 [SMILES: Cc1cccc(F)c1-c1cc(N[C@H]2CCCNC2)c2cc(N)ncc2c1] | 7-(2-fluoro-6-methyl-phenyl)-N5-[(3S)-3-piperidyl] isoquinoline-3,5-diamine | $ES^+$ 351 $[M+H]^+$, Rt = 1.226 mins (Method 2) |

Example 27 (E27)

7-(2-Fluoro-6-methyl-phenyl)-N3-methyl-N5-(4-piperidyl)isoquinoline-3,5-diamine

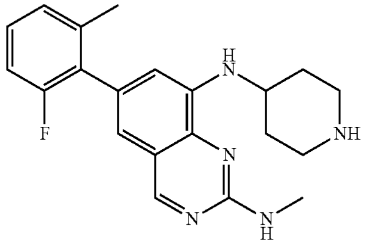

To a solution of tert-butyl 4-[[7-(2-fluoro-6-methyl-phenyl)-3-(methylamino)-5-isoquinolyl]amino]piperidine-1-carboxylate and tert-butyl 4-[[5-(2-fluoro-6-methyl-phenyl)-3-(methylamino)-7-isoquinolyl]amino]piperidine-1-carboxylate (P64) (0.054 g, 0.11 mmol) in MeOH (2 mL) was added HCl (12M, 2 mL). The solution was stirred at 45° C. for 2 hours. After this time, the mixture was concentrated under reduced pressure and chromatographed to give 7-(2-fluoro-6-methyl-phenyl)-N3-methyl-N5-(4-piperidyl)isoquinoline-3,5-diamine (E27) (0.019 g), LCMS $ES^+$ 365 $[M+H]^+$, Rt=0.91 mins (Method 2).

The following compounds were prepared in a similar manner to 7-(2-fluoro-6-methyl-phenyl)-N3-methyl-N5-(4-piperidyl)isoquinoline-3,5-diamine (E27) using the appropriate tert-butoxycarbonyl protected amine:

| Example | Precursor | Structure | Name | LCMS Data |
| --- | --- | --- | --- | --- |
| E28 | P65 | 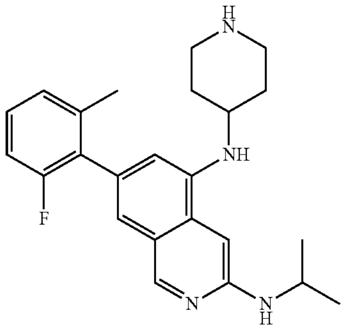 [SMILES: Cc1cccc(F)c1-c1cc(NC2CCNCC2)c2cc(NC(C)C)ncc2c1] | 7-(2-fluoro-6-methyl-phenyl)-N3-isopropyl-N5-(4-piperidyl)isoquinoline-3,5-diamine | $ES^+$ 393 $[M+H]^+$, Rt = 1.07 mins (Method 2) |

Example 29 (E29)

7-(2-Fluoro-6-methyl-phenyl)-5-[3-(methylamino)azetidin-1-yl]isoquinolin-3-amine

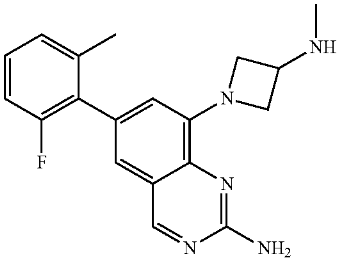

To a solution of tert-butyl N-[1-[3-amino-7-(2-fluoro-6-methyl-phenyl)-5-isoquinolyl]azetidin-3-yl]-N-methyl-carbamate (P58) (0.18 g, 0.412 mmol) in THF (5 mL) was added $LiAlH_4$ (0.165 g, 4.12 mmol) portionwise. The mixture was stirred overnight at room temperature. After this time, NaOH (1N, aq. soln.) was added to quench unreacted reagent. The resulting mixture was filtered through a pad of celite and washed with EtOAc. The organics were combined, dried over $Na_2SO_4$ and concentrated under reduced pressure. The residue was purified using preparative HPLC (Method 2) to give 7-(2-fluoro-6-methyl-phenyl)-5-[3-(methylamino)azetidin-1-yl]isoquinolin-3-amine (E29) (0.004 g), LCMS $ES^+$ 337 $[M+H]^+$, Rt=1.31 mins (Method 2).

Example 30 (E30)

7-(2-Chloro-6-methyl-phenyl)-N5-(4-piperidyl)isoquinoline-3,5-diamine

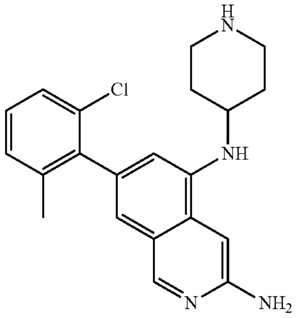

To a solution of tert-butyl 4-[[3-amino-7-(2-chloro-6-methyl-phenyl)-5-isoquinolyl]amino]piperidine-1-carboxylate and tert-butyl 4-[[3-amino-5-(2-chloro-6-methyl-phenyl)-7-isoquinolyl]amino]piperidine-1-carboxylate (P72) (0.32 g, 0.7 mmol) in MeOH (5 mL) was added HCl in EtOAc (5 mL). The mixture was stirred at room temperature overnight. The reaction mixture was concentrated under reduced pressure and the resulting residue was purified using preparative HPLC (Method 2) to give 7-(2-chloro-6-methyl-phenyl)-N5-(4-piperidyl)isoquinoline-3,5-diamine (E30) (0.012 g), LCMS $ES^+$367, 369 $[M+H]^+$, Rt=1.14 mins (Method 1).

$^1H$ NMR (400 MHz, DMSO-$d_6$): δ: ppm 8.66 (s, 1H), 7.38-7.35 (m, 1H), 7.27-7.28 (m, 2H), 6.91 (s, 1H), 6.84 (s, 1H), 6.23 (s, 1H), 5.71 (s, 2H), 5.34 (d, J=8 Hz, 1H), 3.31 (m, 1H), 2.96-2.93 (m, 2H), 2.57-2.54 (m, 2H), 2.10 (s, 3H), 1.97-1.93 (m, 2H), 1.42-1.37 (m, 2H)

The following compounds were prepared in a similar manner to 7-(2-chloro-6-methyl-phenyl)-N5-(4-piperidyl)isoquinoline-3,5-diamine (E30) using the appropriate tert-butoxycarbonyl protected amine:

| Example | Precursor | Structure | Name | LCMS Data |
|---|---|---|---|---|
| E31 | P73 | 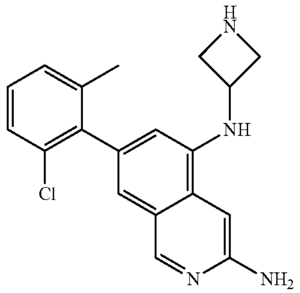 | N5-(azetidin-3-yl)-7-(2-chloro-6-methyl-phenyl)isoquinoline-3,5-diamine | $ES^+$ 339, 341 $[M+H]^+$, Rt = 1.103 mins (Method 2) |

Example 32 (E32)

3-Amino-N-(azetidin-3-yl)-7-(2-fluoro-6-methyl-phenyl)isoquinoline-4-carboxamide

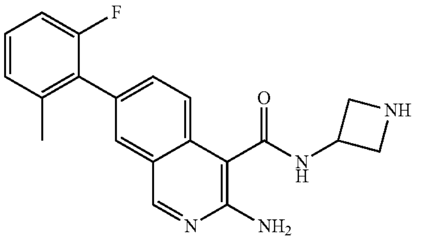

To a solution of tert-butyl 3-[[3-amino-7-(2-fluoro-6-methyl-phenyl)isoquinoline-4-carbonyl]amino]azetidine-1-carboxylate (P76) (0.070 g, 0.200 mmol) in EtOAc (4 mL) was added HCl (4N, 2 mL) and the solution was stirred overnight at room temperature. After this time, the solution was concentrated under reduced pressure and the residue was dissolved in water. The solution was subsequently neutralised using $Na_2CO_3$ (aq. soln.). The organics were extracted with EtOAc, dried over $Na_2SO_4$ and concentrated under reduced pressure. The residue was purified using preparative HPLC (Method 2) to give 3-amino-N-(azetidin-3-yl)-7-(2-fluoro-6-methyl-phenyl)isoquinoline-4-carboxamide (E32) (0.010 g), LCMS $ES^+$ 351 $[M+H]^+$, Rt=1.213 mins (Method 1).

The following compounds were prepared in a similar manner to 3-amino-N-(azetidin-3-yl)-7-(2-fluoro-6-methyl-phenyl)isoquinoline-4-carboxamide (E32) using the appropriate tert-butoxycarbonyl protected amine:

| Example | Precursor | Structure | Name | LCMS Data |
|---|---|---|---|---|
| E33 | P77 | 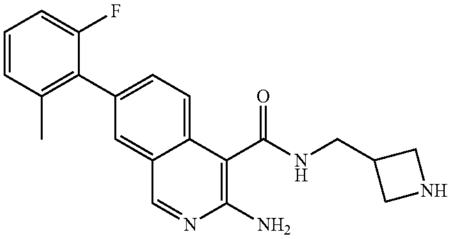 [SMILES: Cc1cccc(F)c1-c1ccc2c(C(=O)NCC3CNC3)c(N)ncc2c1] | 3-amino-N-(azetidin-3-ylmethyl)-7-(2-fluoro-6-methyl-phenyl)isoquinoline-4-carboxamide | $ES^+$ 365 $[M+H]^+$, Rt = 1.020 mins (Method 1) |
| E34 | P78 | 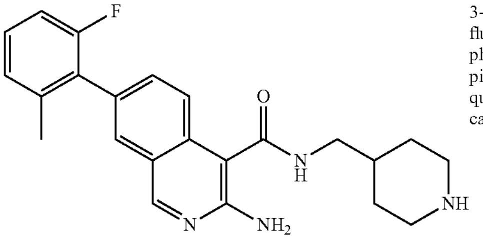 | 3-amino-7-(2-fluoro-6-methyl-phenyl)-N-(4-piperidylmethyl)isoquinoline-4-carboxamide | $ES^+$ 393 $[M+H]^+$, Rt = 1.093 mins (Method 1) |
| E35 | P79 | 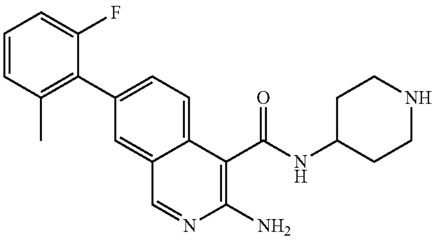 [SMILES: Cc1cccc(F)c1-c1ccc2c(C(=O)NC3CCNCC3)c(N)ncc2c1] | 3-amino-7-(2-fluoro-6-methyl-phenyl)-N-(4-piperidyl)isoquinoline-4-carboxamide | $ES^+$ 379 $[M+H]^+$, Rt = 1.023 mins (Method 1) |

-continued

| Example | Precursor | Structure | Name | LCMS Data |
|---|---|---|---|---|
| E36 | P80 | 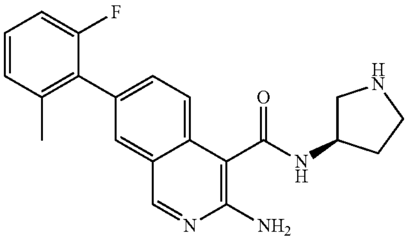 | 3-amino-7-(2-fluoro-6-methyl-phenyl)-N-[(3R)-pyrrolidin-3-yl]isoquinoline-4-carboxamide | $ES^+$ 365 $[M+H]^+$, Rt = 1.010 mins (Method 1) |
| E37 | P81 | 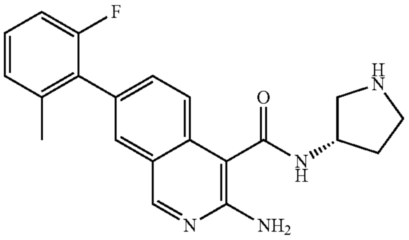 | 3-amino-7-(2-fluoro-6-methyl-phenyl)-N-[(3S)-pyrrolidin-3-yl]isoquinoline-4-carboxamide | ES+ 365 $[M+H]^+$, Rt = 1.013 mins (Method 1) |
| E38 | P82 | 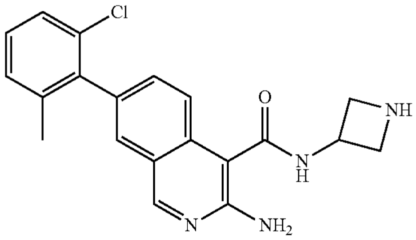 [SMILES: Cc1cccc(Cl)c1-c1ccc2c(C(=O)NC3CNC3)c(N)ncc2c1] | 3-amino-N-(azetidin-3-yl)-7-(2-chloro-6-methyl-phenyl) isoquinoline-4-carboxamide | $ES^+$ 367 $[M+H]^+$, Rt = 1.050 mins (Method 1) |
| E39 | P83 | 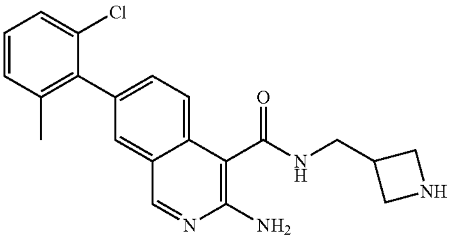 [SMILES: Cc1cccc(Cl)c1-c1ccc2c(C(=O)NCC3CNC3)c(N)ncc2c1] | 3-amino-N-(azetidin-3-ylmethyl)-7-(2-chloro-6-methyl-phenyl) isoquinoline-4-carboxamide | $ES^+$ 381 $[M+H]^+$, Rt = 0.467 mins (Method 2) |
| E40 | P84 | 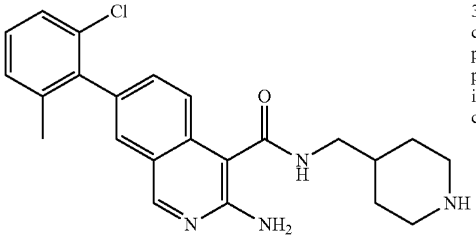 | 3-amino-7-(2-chloro-6-methyl-phenyl)-N-(4-piperidylmethyl) isoquinoline-4-carboxamide | $ES^+$ 409 $[M+H]^+$, Rt = 1.020 mins (Method 1) |
| E41 | P85 | 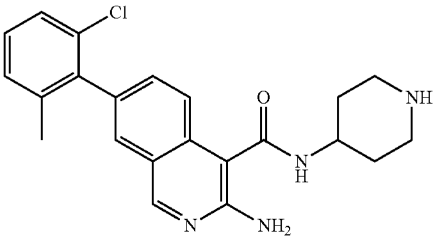 | 3-amino-7-(2-chloro-6-methyl-phenyl)-N-(4-piperidyl) isoquinoline-4-carboxamide | $ES^+$ 395 $[M+H]^+$, Rt = 1.040 mins (Method 1) |

-continued

| Example | Precursor | Structure | Name | LCMS Data |
|---|---|---|---|---|
| E42 | P86 | 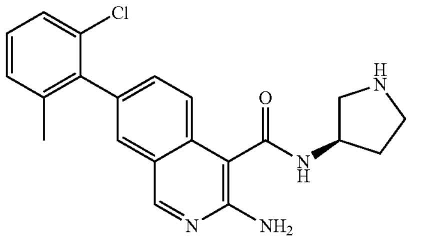 [SMILES: Cc1cccc(Cl)c1-c1ccc2c(C(=O)N[C@@H]3CCNC3)c(N)ncc2c1] | 3-amino-7-(2-chloro-6-methyl-phenyl)-N-[(3R)-pyrrolidin-3-yl]isoquinoline-4-carboxamide | $ES^+$ 381 $[M+H]^+$, Rt = 1.043 mins (Method 1) |
| E43 | P87 | 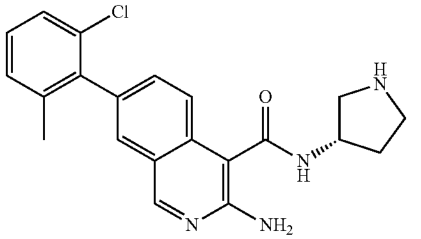 [SMILES: Cc1cccc(Cl)c1-c1ccc2c(C(=O)N[C@H]3CCNC3)c(N)ncc2c1] | 3-amino-7-(2-chloro-6-methyl-phenyl)-N-[(3S)-pyrrolidin-3-yl]isoquinoline-4-carboxamide | $ES^+$ 381 $[M+H]^+$, Rt = 1.050 mins (Method 1) |

Example 44 (E44)

N-[3-Amino-7-(2-fluoro-6-methyl-phenyl)-5-isoquinolyl]piperidine-4-carboxamide

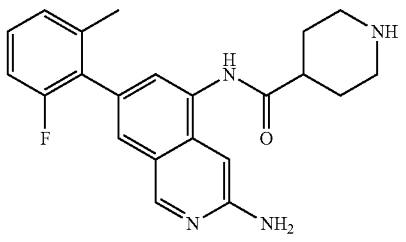 [SMILES: Cc1cccc(F)c1-c1cc(NC(=O)C2CCNCC2)c2cc(N)ncc2c1]

A solution of tert-butyl 4-[[3-amino-7-(2-fluoro-6-methyl-phenyl)-5-isoquinolyl]carbamoyl]piperidine-1-carboxylate (P89) (0.045 g, 0.089 mmol) in TFA (1.0 mL) and DCM (3.0 mL) was stirred at room temperature for 3 hours. After this time, the solution was concentrated under reduced pressure and the residue purified by preparative HPLC (Method 2) to give N-[3-amino-7-(2-fluoro-6-methyl-phenyl)-5-isoquinolyl]piperidine-4-carboxamide (E44) (0.0046 g), LCMS $ES^+$ 379 $[M+H]^+$, Rt=0.743 mins (Method 1).

The following examples were prepared in a similar manner to N-[3-amino-7-(2-fluoro-6-methyl-phenyl)-5-isoquinolyl]piperidine-4-carboxamide (E44) from the appropriate tert-butoxy-carbonyl intermediate:

| Example | Precursor | Structure | Name | LCMS Data |
|---|---|---|---|---|
| E45 | P90 | 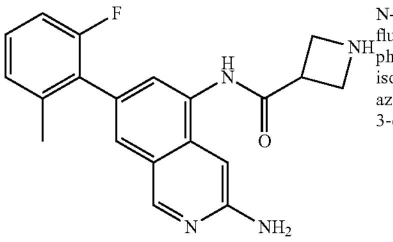 | N-[3-amino-7-(2-fluoro-6-methyl-phenyl)-5-isoquinolyl]azetidine-3-carboxamide | $ES^+$ 351 $[M+H]^+$, Rt = 0.945 mins (Method 1) |
| E136 | P90a | 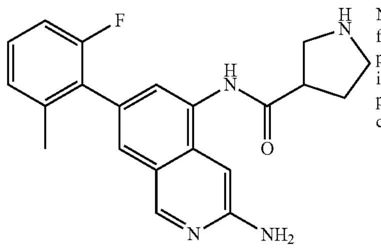 | N-[3-amino-7-(2-fluoro-6-methyl-phenyl)-5-isoquinolyl]pyrrolidine-3-carboxamide | $ES^+$ 365 $[M+H]^+$, Rt = 0.855 mins (Method 1) |

Example 46 (E46)

7-(2-Fluoro-6-methyl-phenyl)-5-(4-piperidyloxy) isoquinolin-3-amine

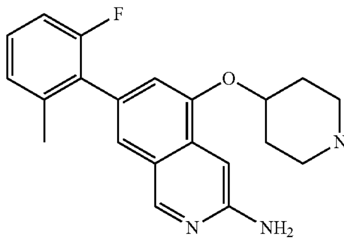

To a solution of tert-butyl 4-[[3-amino-7-(2-fluoro-6-methyl-phenyl)-5-isoquinolyl]oxy]piperidine-1-carboxylate and tert-butyl 4-[[3-amino-5-(2-fluoro-6-methyl-phenyl)-7-isoquinolyl]oxy]piperidine-1-carboxylate (P91) (0.260 g, 0.58 mmol) in MeOH (40 mL) was added HCl in EtOAc (20 mL). The mixture was stirred at room temperature for 30 minutes. The reaction mixture was neutralised with NaOH and extracted with EtOAc. The organics were dried over $MgSO_4$, filtered and concentrated under reduced pressure. The resulting residue was purified using preparative HPLC (Method 2) to give 7-(2-fluoro-6-methyl-phenyl)-5-(4-piperidyloxy)isoquinolin-3-amine (E46) (0.042 g), LCMS $ES^+$ 352 $[M+H]^+$, Rt=0.45 mins (Method 2).

The following compounds were prepared in a similar manner to 7-(2-fluoro-6-methyl-phenyl)-5-(4-piperidyloxy) isoquinolin-3-amine (E46) using the appropriate tert-butoxycarbonyl protected amine:

| Example | Precursor | Structure | Name | LCMS Data |
|---|---|---|---|---|
| E47 | P92 | 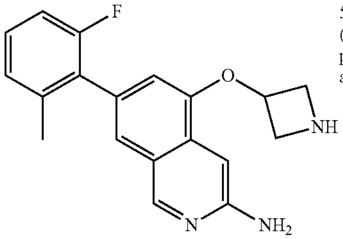 | 5-(azetidin-3-yloxy)-7-(2-fluoro-6-methyl-phenyl)isoquinolin-3-amine | $ES^+$ 324 $[M+H]^+$, Rt = 0.463 mins (Method 2) |
| E48 | P94 | 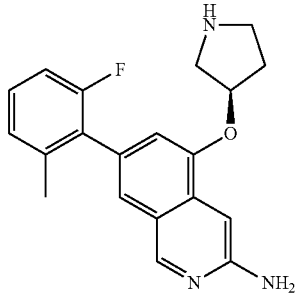 [SMILES: Cc1cccc(F)c1-c1cc(O[C@@H]2CCNC2)c2cc(N)ncc2c1] | 7-(2-fluoro-6-methyl-phenyl)-5-[(3R)-pyrrolidin-3-yl]oxy-isoquinolin-3-amine | $ES^+$ 338 $[M+H]^+$, Rt = 1.226 mins (Method 2) |

Example 49 (E49)

7-(2-Fluoro-6-methyl-phenyl)-N-(4-piperidyl)isoquinolin-5-amine

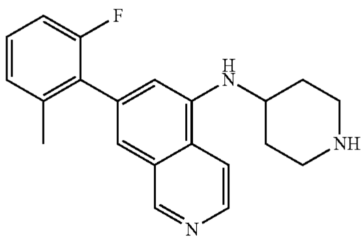

A solution of tert-butyl 4-[[7-(2-fluoro-6-methyl-phenyl)-5-isoquinolyl]amino]piperidine-1-carboxylate (P98) (0.020 g, 0.045 mmol) in DCM/TFA (3 mL/1 mL) was stirred at 35° C. for 2 hours. After this time, the solution was concentrated under reduced pressure and purified using preparative HPLC (Method 2) to give 7-(2-fluoro-6-methyl-phenyl)-N-(4-piperidyl)isoquinolin-5-amine (E49), (0.007 g), LCMS ES+ 336 [M+H]+, Rt=1.143 mins (Method 1).

The following compounds were prepared in a similar manner to 7-(2-fluoro-6-methyl-phenyl)-N-(4-piperidyl)isoquinolin-5-amine (E49) from the corresponding tert-butoxycarbonyl protected amine:

| Example | Precursor | Structure | Name | LCMS Data |
|---|---|---|---|---|
| E50 | P99 | 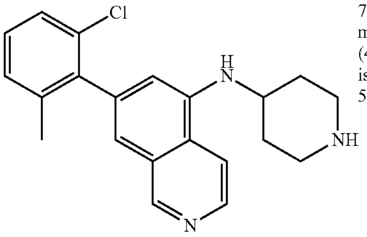 | 7-(2-chloro-6-methyl-phenyl)-N-(4-piperidyl) isoquinolin-5-amine | ES+ 352 [M+H]+, Rt = 0.743 mins (Method 1) |
| E51 | P100 | 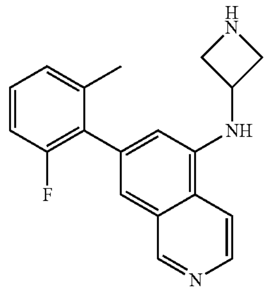 [SMILES: Cc1cccc(F)c1-c1cc(NC2CNC2)c2ccncc2c1] | N-(azetidin-3-yl)-7-(2-fluoro-6-methyl-phenyl)isoquinolin-5-amine | ES+ 308 [M+H]+, Rt = 0.893 mins (Method 1) |

Example 52 (E52)

3-Amino-7-(2-fluoro-6-methyl-phenyl)-N-(4-piperidyl)isoquinoline-5-carboxamide

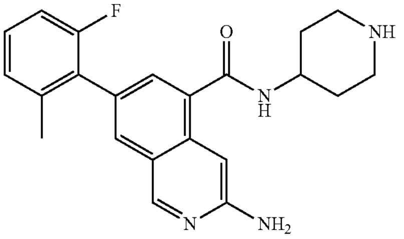

To a solution of tert-butyl 4-[[3-amino-7-(2-fluoro-6-methyl-phenyl)isoquinoline-5-carbonyl]amino]piperidine-1-carboxylate (P95) (0.055 g, 0.115 mmol) in DCM (1 mL) was added TFA (0.2 mL). The solution was stirred at room temperature for 1 hour. After this time, the solution was concentrated under reduced pressure and the resulting residue was purified by preparative HPLC (Method 2) to give 3-amino-7-(2-fluoro-6-methyl-phenyl)-N-(4-piperidyl)isoquinoline-5-carboxamide (E52) (0.020 g), LCMS ES+ 379 [M+H]+, Rt=0.963 mins (Method 1).

The following examples were prepared in a similar manner to 3-amino-7-(2-fluoro-6-methyl-phenyl)-N-(4-piperidyl)isoquinoline-5-carboxamide (E52) from the appropriate ter-butoxy-carbonyl protected amine:

| Example | Precursor | Structure | Name | LCMS Data |
|---|---|---|---|---|
| E53 | P88 | 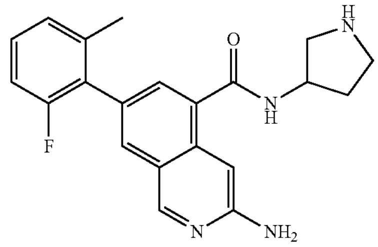 [SMILES: Cc1cccc(F)c1-c1cc(C(=O)NC2CCNC2)c2cc(N)ncc2c1] | 3-amino-7-(2-fluoro-6-methyl-phenyl)-N-pyrrolidin-3-yl-isoquinoline-5-carboxamide | $ES^+$ 365 $[M+H]^+$, Rt = 0.803 mins (Method 1) |

Example 54 (E54)

7-(2-Fluoro-6-methyl-phenyl)-N5-(1-methyl-4-piperidyl)isoquinoline-3,5-diamine

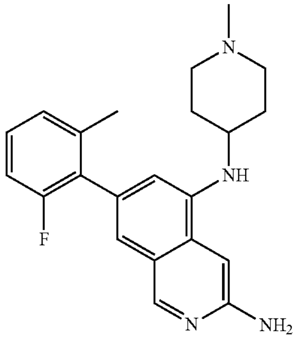

To a solution of 5-chloro-7-(2-fluoro-6-methyl-phenyl)isoquinolin-3-amine and 7-chloro-5-(2-fluoro-6-methyl-phenyl)isoquinolin-3-amine mixture (P22) (4.00 g, 13.95 mmol) in dioxane (40 mL) was added 1-methylpiperidin-4-amine (4.78 g, 41.86 mmol), t-BuONa (6.70 g, 69.76 mmol), t-BuXPhos (0.400 g), $Pd_2(dba)_3$ (0.400 g). The reaction mixture was stirred at 110° C. for 3 hours. Upon cooling the mixture was extracted with DCM/MeOH and concentrated in vacuo. The resulting residue was chromatographed [$SiO_2$] before further purification by HPLC to provide the title compound as a TFA salt. The salt was neutralised by $NH_3$/MeOH and further chromatographed to give 7-(2-fluoro-6-methyl-phenyl)-N5-(1-methyl-4-piperidyl)isoquinoline-3,5-diamine (E54) (0.230 g) as a yellow coloured solid. LCMS $ES^+$ 365 $[M+H]^+$, Rt=1.12 mins (Method 1).

$^1$H NMR (400 MHz, DMSO-$d_6$): δ: ppm 8.67 (s, 1H), 7.31-7.27 (m, 1H), 7.15-7.06 (m, 1H), 6.92 (d, J=10.4 Hz, 2H), 6.31 (s, 1H), 5.75 (br s, 2H), 5.39 (d, J=7.2 Hz, 1H), 3.29 (s, 1H), 2.75 (t, J=11.2 Hz, 2H), 2.17 (s, 3H), 2.15 (s, 3H), 2.04-1.92 (m, 4H), 1.61-1.56 (m, 2H).

The following compounds were prepared in a similar manner to 7-(2-fluoro-6-methyl-phenyl)-N5-(1-methyl-4-piperidyl)isoquinoline-3,5-diamine (E54) using 5-chloro-7-(2-fluoro-6-methyl-phenyl)isoquinolin-3-amine regioisomeric mixture (P22) and the appropriate amine coupling partner:

| Example | Structure | Name | LCMS Data |
|---|---|---|---|
| E55 | 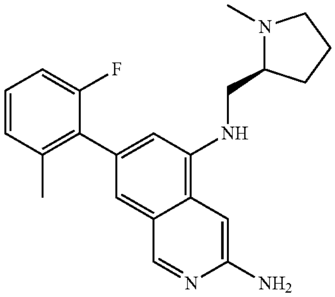 [SMILES: Cc1cccc(F)c1-c1cc(NC[C@@H]2CCCN2C)c2cc(N)ncc2c1] | 7-(2-fluoro-6-methyl-phenyl)-N5-[[(2S)-1-methylpyrrolidin-2-yl]methyl] isoquinoline-3,5-diamine | $ES^+$ 365 $[M+H]^+$, Rt = 1.386 mins. (Method 2) |
| E56 | 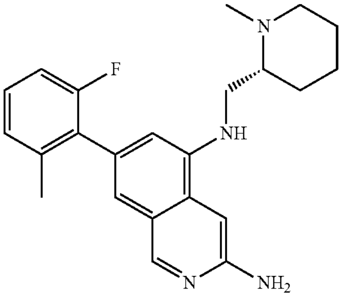 [SMILES: Cc1cccc(F)c1-c1cc(NC[C@H]2CCCCN2C)c2cc(N)ncc2c1] | 7-(2-fluoro-6-methyl-phenyl)-N5-[[(2R)-1-methyl-2-piperidyl]methyl] isoquinolin e-3,5-diamine | $ES^+$ 379 $[M+H]^+$, Rt = 1.156 mins (Method 2) |

-continued

| Example | Structure | Name | LCMS Data |
|---|---|---|---|
| E57 | 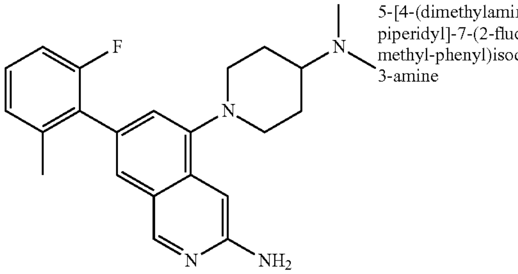 | 5-[4-(dimethylamino)-1-piperidyl]-7-(2-fluoro-6-methyl-phenyl)isoquinolin-3-amine | ES$^+$ 379 [M+H]$^+$, Rt = 1.150 mins (Method 2) |
| E58 | 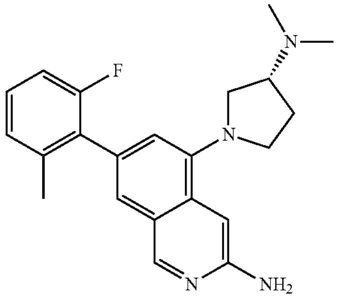 [SMILES: Cc1cccc(F)c1-c1cc(N2CC[C@@H](N(C)C)C2)c2cc(N)ncc2c1] | 5-[(3R)-3-(dimethylamino)pyrrolidin-1 -yl]-7-(2-fluoro-6-methyl-phenyl)isoquinolin-3-amine | ES$^+$ 365 [M+H]$^+$, Rt = 1.179 mins (Method 2) |
| E59 | 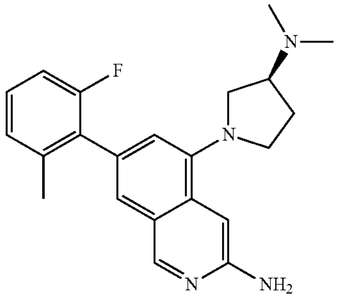 [SMILES: Cc1cccc(F)c1-c1cc(N2CC[C@H](N(C)C)C2)c2cc(N)ncc2c1] | 5-[(3S)-3-(dimethylamino)pyrrolidin-1 -yl]-7-(2-fluoro-6-methyl-phenyl)isoquinolin-3-amine | ES$^+$ 365 [M+H]$^+$, Rt = 1.296 mins (Method 2) |
| E60 | 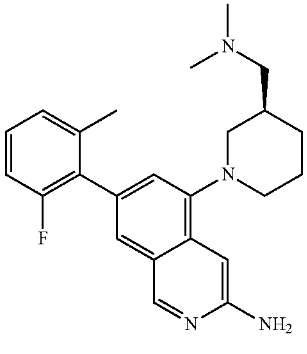 [SMILES: Cc1cccc(F)c1-c1cc(N2CCC[C@H](CN(C)C)C2)c2cc(N)ncc2c1] | 5-[(3R)-3-[(dimethylamino)methyl]-1-piperidyl]-7-(2-fluoro-6-methyl-phenyl)isoquinolin-3-amine | ES$^+$ 393 [M+H]$^+$, Rt = 1.236 mins (Method 2) |
| E61 | 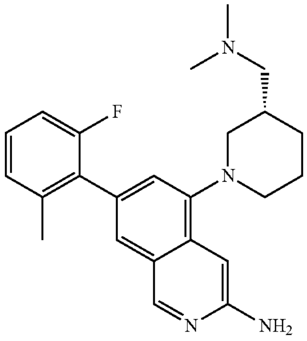 [SMILES: Cc1cccc(F)c1-c1cc(N2CCC[C@@H](CN(C)C)C2)c2cc(N)ncc2c1] | 5-[(3S)-3-[(dimethylamino)methyl]-1-piperidyl]-7-(2-fluoro-6-methyl-phenyl)isoquinolin-3-amine | ES$^+$ 393 [M+H]$^+$, Rt = 1.213 mins (Method 2) |

Example 62 (E62)

7-(2-Chloro-6-methyl-phenyl)-N5-(1-methyl-4-piperidyl)isoquinoline-3,5-diamine

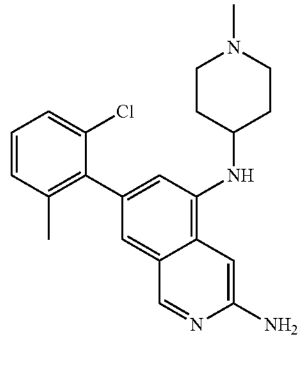

To a solution of 5-bromo-7-(2-chloro-6-methyl-phenyl) isoquinolin-3-amine and 7-bromo-5-(2-chloro-6-methyl-phenyl)isoquinolin-3-amine (P23) (0.15 g, 0.43 mmol) in 1,4-dioxane (10 mL) was added 1-methylpiperidin-4-amine (0.147 g, 1.30 mmol), t-BuONa (0.082 g, 0.86 mmol), $Pd_2(dba)_3$ (0.039 g) and t-BuXPhos (0.036 g). The mixture was stirred at 50° C. under argon for 3 hours. After this time, the mixture was concentrated under reduced pressure and purified using preparative HPLC (Method 2) to give 7-(2-chloro-6-methyl-phenyl)-N5-(1-methyl-4-piperidyl)isoquinoline-3,5-diamine (E62) (0.013 g), LCMS $ES^+$ 381 $[M+H]^+$, Rt=1.18 mins (Method 2).

The following compounds were prepared in a similar manner to 7-(2-chloro-6-methyl-phenyl)-N5-(1-methyl-4-piperidyl)isoquinoline-3,5-diamine (E62) using 5-bromo-7-(2-chloro-6-methyl-phenyl)isoquinolin-3-amine regioisomeric mixture (P23) and the appropriate amine coupling partner:

| Example | Structure | Name | LCMS Data |
|---|---|---|---|
| E63 | 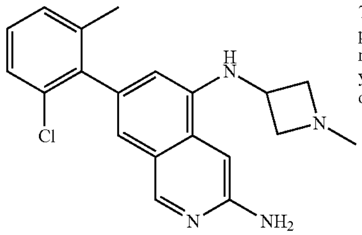 | 7-(2-chloro-6-methyl-phenyl)-N5-(1-methylazetidin-3-yl)isoquinoline-3,5-diamine | $ES^+$ 353 $[M+H]^+$, Rt = 1.083 mins (Method 2) |

Example 64 (E64)

7-(2-Chloro-6-fluoro-phenyl)-N5-(1-methyl-4-piperidyl)isoquinoline-3,5-diamine

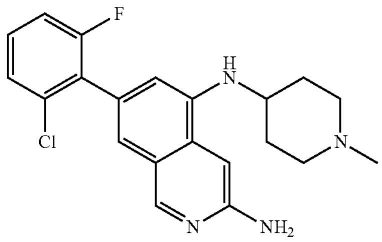 [SMILES: CN1CCC(Nc2cc(-c3c(F)cccc3Cl)cc3cnc(N)cc23)CC1]

To a solution of 7-chloro-N5-(1-methyl-4-piperidyl)isoquinoline-3,5-diamine and 5-chloro-N7-(1-methyl-4-piperidyl)isoquinoline-3,7-diamine mixture of regioisomers (P33) (0.260 g, 0.897 mmol) in 1,4-dioxane (4 mL) was added 2-(2-chloro-6-fluoro-phenyl)-4,4,5,5-tetramethyl-1,3,2-dioxaborolane (P3) (0.459 g, 1.793 mmol), $K_3PO_4$ (0.384 g, 1.793 mmol), XPhos-Pd-G2 (0.071 g, 0.089 mmol). The mixture was stirred at 100° C. overnight. The mixture was cooled to room temperature, concentrated under reduced pressure and chromatographed to give 7-(2-chloro-6-fluoro-phenyl)-N5-(1-methyl-4-piperidyl)isoquinoline-3,5-diamine (E64) (0.006 g), LCMS $ES^+$ 385, 387 $[M+H]^+$, Rt=1.389 mins (Method 2).

Example 65 (E65)

7-(2-Fluoro-6-methyl-phenyl)-N-(1-methylazetidin-3-yl)isoquinolin-5-amine

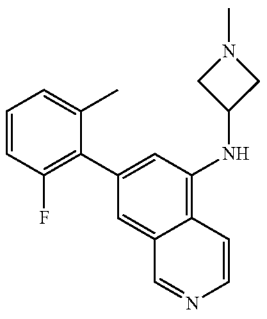

To a solution of 5-bromo-7-(2-fluoro-6-methyl-phenyl) isoquinoline (P14) (0.100 g, 0.315 mmol), 1-methylazetidin-3-amine (0.027 g, 0.315 mmol), t-BuXPhos (0.027 g, 0.063 mmol), $Pd_2(dba)_3$ (0.058 g, 0.063 mmol) in 1,4-dioxane (2 mL) was added t-BuONa (0.091 g, 0.845 mmol). The reaction mixture was heated to 100° C. for 3 hours before being cooled to room temperature, filtered, concentrated under reduced pressure and purified using preparative HPLC (Method 2) to give 7-(2-fluoro-6-methyl-phenyl)-N-(1-methylazetidin-3-yl)isoquinolin-5-amine (E65) (0.015 g), LCMS $ES^+$ 322 $[M+H]^+$, Rt=1.123 mins (Method 1).

The following compounds were prepared in a similar manner to 7-(2-fluoro-6-methyl-phenyl)-N-(1-methylazetidin-3-yl)isoquinolin-5-amine (E65) 5-bromo-7-aryl-isoquinoline regioisomeric mixture (P14) and the appropriate amine coupling partner:

| Example | Structure | Name | LCMS Data |
|---|---|---|---|
| E66 | 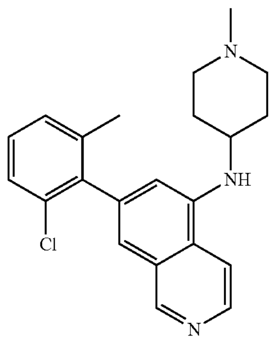 | 7-(2-chloro-6-methyl-phenyl)-N-(1-methyl-4-piperidyl)isoquinolin-5-amine | $ES^+$ 366 $[M+H]^+$, Rt = 0.703 mins (Method 1) |
| E67 | 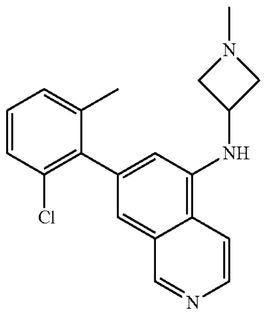 [SMILES: Cc1cccc(Cl)c1-c1cc(NC2CN(C)C2)c2ccncc2c1] | 7-(2-chloro-6-methyl-phenyl)-N-(1-methylazetidin-3-yl)isoquinolin-5-amine | $ES^+$ 338 $[M+H]^+$, Rt = 0.733 mins (Method 1) |

Example 68 (E68)

7-(2-Fluoro-6-methyl-phenyl)-N5-(1-methylazetidin-3-yl)isoquinoline-3,5-diamine

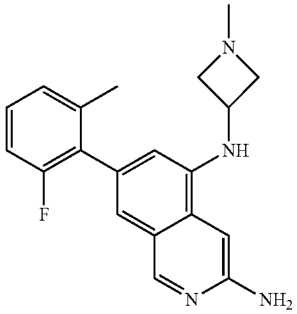 [SMILES: Cc1cccc(F)c1-c1cc(NC2CN(C)C2)c2cc(N)ncc2c1]

To a solution of N5-(azetidin-3-yl)-7-(2-fluoro-6-methyl-phenyl)isoquinoline-3,5-diamine (E3) (0.150 g, 0.46 mmol) in MeOH (10 mL) was added paraformaldehyde (0.014 g, 0.46 mmol). The mixture was stirred at room temperature for 2 hours. $NaBH_3CN$ (0.057 g, 0.92 mmol) was added and the resulting mixture was stirred at 25° C. overnight. The organics were extracted with DCM/MeOH before being concentrated under reduced pressure. The residue was purified using preparative HPLC (Method 2) to afford 7-(2-fluoro-6-methyl-phenyl)-N5-(1-methylazetidin-3-yl)isoquinoline-3,5-diamine (E68) (0.029 g), LCMS $ES^+$ 337 $[M+H]^+$, Rt=1.063 mins (Method 2).

The following compounds were prepared in a similar manner to 7-(2-fluoro-6-methyl-phenyl)-N5-(1-methylazetidin-3-yl)isoquinoline-3,5-diamine (E68) using the appropriate amine:

| Example | Precursor | Structure | Name | LCMS Data |
|---|---|---|---|---|
| E69 | E4 | 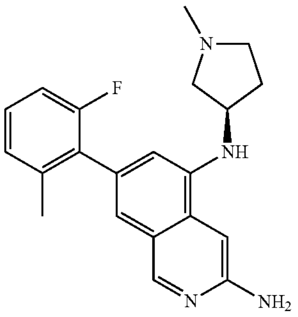 | 7-(2-fluoro-6-methyl-phenyl)-N5-[(3R)-1-methylpyrrolidin-3-yl]isoquinoline-3,5-diamine | $ES^+$ 351 $[M+H]^+$, Rt = 1.04 mins (Method 2) |
| E70 | E7 | 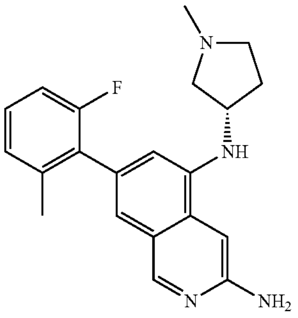 [SMILES: Cc1cccc(F)c1-c1cc(N[C@H]2CCN(C)C2)c2cc(N)ncc2c1] | 7-(2-fluoro-6-methyl-phenyl)-N5-[(3S)-1-methylpyrrolidin-3-yl]isoquinoline-3,5-diamine | $ES^+$ 351 $[M+H]^+$, Rt = 1.103 mins (Method 2) |
| E71 | E8 | 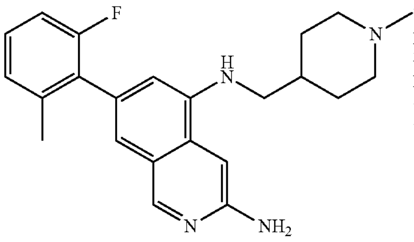 [SMILES: Cc1cccc(F)c1-c1cc(NCC2CCN(C)CC2)c2cc(N)ncc2c1] | 7-(2-fluoro-6-methyl-phenyl)-N5-[(1-methyl-4-piperidyl)methyl] isoquinoline-3,5-diamine | $ES^+$379 $[M+H]^+$, Rt = 1.113 mins (Method 2) |

-continued

| Example | Precursor | Structure | Name | LCMS Data |
|---|---|---|---|---|
| E72 | E11 | 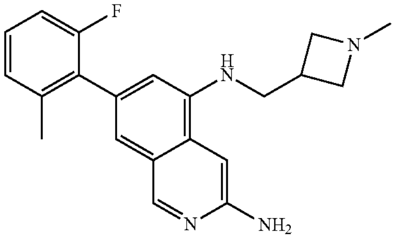 [SMILES: Cc1cccc(F)c1-c1cc(NCC2CN(C)C2)c2cc(N)ncc2c1] | 7-(2-fluoro-6-methyl-phenyl)-N5-[(1-methylazetidin-3-yl)methyl] isoquinoline-3,5-diamine | $ES^+$ 351 $[M+H]^+$, Rt = 1.156 mins (Method 2) |
| E73 | E12 | 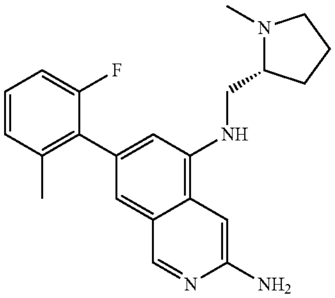 | 7-(2-fluoro-6-methyl-phenyl)-N5-[[(2R)-1-methylpyrrolidin-2-yl]methyl] isoquinoline-3,5-diamine | $ES^+$ 379 $[M+H]^+$, Rt = 1.140 mins (Method 2) |
| E74 | E6 | 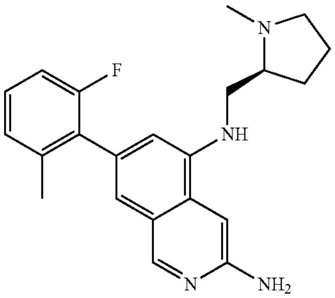 [SMILES: Cc1cccc(F)c1-c1cc(NC[C@@H]2CCCN2C)c2cc(N)ncc2c1] | 7-(2-fluoro-6-methyl-phenyl)-N5-[[(3S)-1-methylpyrrolidin-3-yl]methyl]isoquinolin e-3,5-diamine | $ES^+$ 365 $[M+H]^+$, Rt = 1.153 mins (Method 2) |
| E75 | E9 | 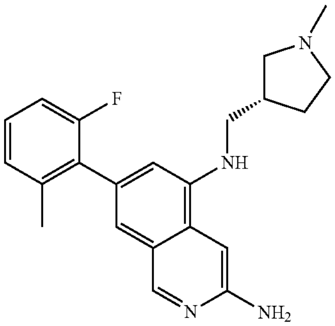 [SMILES: Cc1cccc(F)c1-c1cc(NC[C@H]2CCN(C)C2)c2cc(N)ncc2c1] | 7-(2-fluoro-6-methyl-phenyl)-N5-[[(3R)-1-methylpyrrolidin-3-yl]methyl] isoquinoline-3,5-diamine | $ES^+$ 365 $[M+H]^+$, Rt = 1.110 mins (Method 2) |
| E76 | E10 | 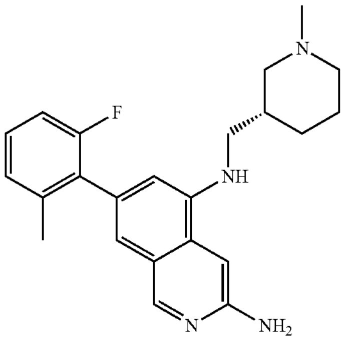 [SMILES: Cc1cccc(F)c1-c1cc(NC[C@H]2CCCN(C)C2)c2cc(N)ncc2c1] | 7-(2-fluoro-6-methyl-phenyl)-N5-[[(3S)-1-methyl-3-piperidyl]methyl]isoquinoline-3,5-diamine | $ES^+$ 379 $[M+H]^+$, Rt = 1.140 mins (Method 2) |

-continued

| Example | Precursor | Structure | Name | LCMS Data |
|---|---|---|---|---|
| E77 | E2 | 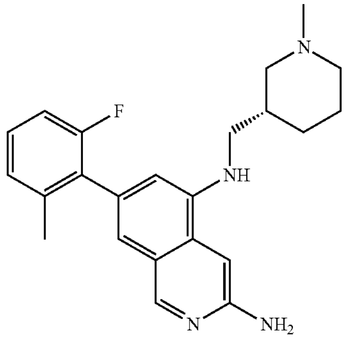 [SMILES: Cc1cccc(F)c1-c1cc(NC[C@H]2CCCN(C)C2)c2cc(N)ncc2c1] | 7-(2-fluoro-6-methyl-phenyl)-N5-[[(3R)-1-methyl-3-piperidyl]methyl] isoquinoline-3,5-diamine | $ES^+$ 379 $[M+H]^+$, Rt = 1.026 mins (Method 2) |
| E78 | E14 | 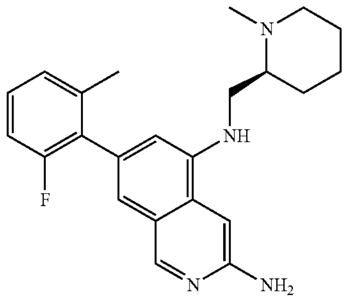 [SMILES: Cc1cccc(F)c1-c1cc(NC[C@@H]2CCCCN2C)c2cc(N)ncc2c1] | 7-(2-fluoro-6-methyl-phenyl)-N5-[[(2S)-1-methyl-2-piperidyl]methyl]isoquinoline-3,5-diamine | $ES^+$ 379 $[M+H]^+$, Rt = 1.300 mins (Method 2) |
| E79 | E29 | 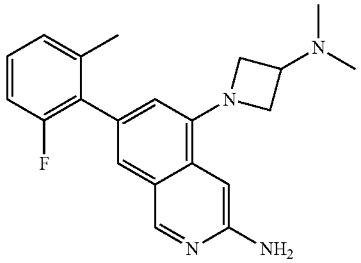 | 5-[3-(dimethylamino) azetidin-1-yl]-7-(2-fluoro-6-methyl-phenyl)isoquinolin-3-amine | $ES^+$ 365 $[M+H]^+$, Rt = 3.928 mins (extended Method 2) |
| E80 | E17 | 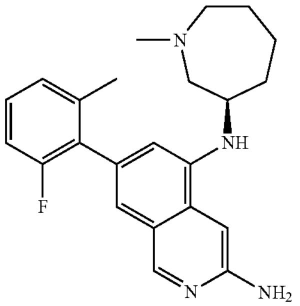 [SMILES: Cc1cccc(F)c1-c1cc(N[C@@H]2CCCCN(C)C2)c2cc(N)ncc2c1] | 7-(2-fluoro-6-methyl-phenyl)-N5-[(3R)-1-methylazepan-3-yl]isoquinoline-3,5-diamine | $ES^+$ 379 $[M+H]^+$, Rt = 3.868 mins (extended Method 2) |
| E81 | P97 | 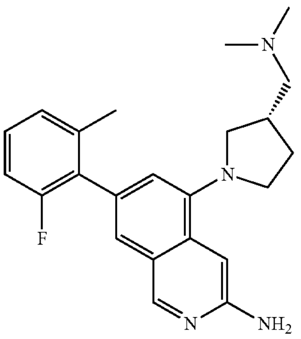 [SMILES: Cc1cccc(F)c1-c1cc(N2CC[C@@H](CN(C)C)C2)c2cc(N)ncc2c1] | 5-[(3S)-3-[(dimethylamino) methyl]pyrrolidin-1-yl]-7-(2-fluoro-6-methyl-phenyl) isoquinolin-3-amine | $ES^+$ 379 $[M+H]^+$, Rt = 1.186 mins (Method 2) |

-continued

| Example | Precursor | Structure | Name | LCMS Data |
|---|---|---|---|---|
| E82 | P96 | 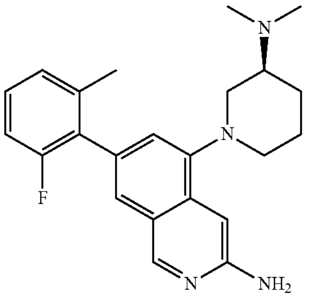 | 5-[(3S)-3-(dimethylamino)-1-piperidyl]-7-(2-fluoro-6-methyl-phenyl)isoquinolin-3-amine | $ES^+$ 379 $[M+H]^+$, Rt = 1.166 mins (Method 2) |
| E83 | E82 | 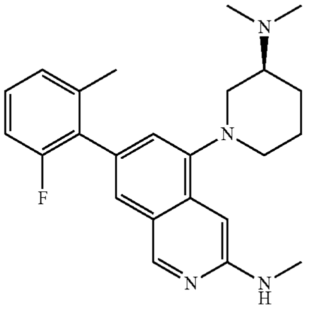 [SMILES: CNc1cc2c(N3CCC[C@H](N(C)C)C3)cc(-c3c(C)cccc3F)cc2cn1] | 5-[(3S)-3-(dimethylamino)-1-piperidyl]-7-(2-fluoro-6-methyl-phenyl)-N-methyl-isoquinolin-3-amine | $ES^+$ 393 $[M+H]^+$, Rt = 1.253 mins (Method 2) |
| E84 | E19 | 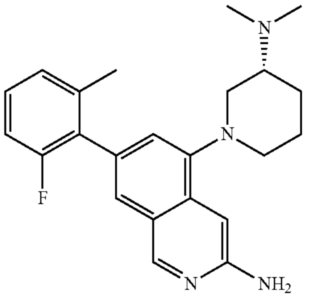 | 5-[(3R)-3-(dimethylamino)-1-piperidyl]-7-(2-fluoro-6-methyl-phenyl)isoquinolin-3-amine | $ES^+$ 379 $[M+H]^+$, Rt = 4.446 mins (extended Method 2) |
| E85 | E25 | 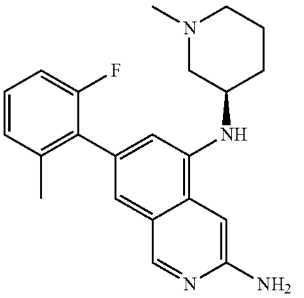 [SMILES: Cc1cccc(F)c1-c1cc(N[C@@H]2CCCN(C)C2)c2cc(N)ncc2c1] | 7-(2-fluoro-6-methyl-phenyl)-N5-[(3R)-1-methyl-3-piperidyl]isoquinoline-3,5-diamine | $ES^+$ 365 $[M+H]^+$, Rt = 1.363 mins (Method 2) |
| E86 | E26 | 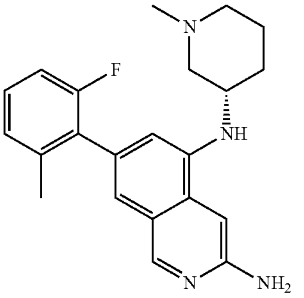 [SMILES: Cc1cccc(F)c1-c1cc(N[C@H]2CCCN(C)C2)c2cc(N)ncc2c1] | 7-(2-fluoro-6-methyl-phenyl)-N5-[(3S)-1-methyl-3-piperidyl] isoquinoline-3,5-diamine | $ES^+$ 365 $[M+H]^+$, Rt = 1.096 mins (Method 2) |

Example 87 (E87)

3-Amino-7-(2-fluoro-6-methyl-phenyl)-N-(1-methyl-4-piperidyl)isoquinoline-4-carboxamide

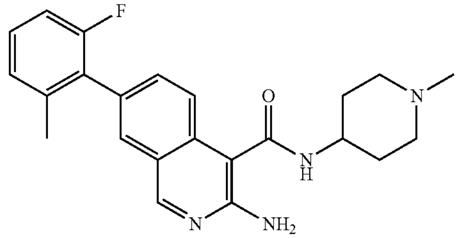 [SMILES: Cc1cccc(Cl)c1-c1ccc2c(C(=O)NC3CCN(C)CC3)c(N)ncc2c1]

To a solution of 3-amino-7-(2-fluoro-6-methyl-phenyl)isoquinoline-4-carboxylic acid (P20) (0.050 g, 0.168 mmol) in DMF (1 mL) was added 1-methylpiperidin-4-amine (0.029 g, 0.253 mmol), HATU (0.096 g, 0.253 mmol) and DIPEA (0.043 g, 0.336 mmol) and the solution was stirred overnight at room temperature. The organics were extracted with EtOAc, washed with brine, dried over $Na_2SO_4$ and concentrated under reduced pressure. The resulting residue was purified by preparative HPLC (Method 2) to give 3-amino-7-(2-fluoro-6-methyl-phenyl)-N-(1-methyl-4-piperidyl)isoquinoline-4-carboxamide (E87) (0.040 g), LCMS $ES^+$ 393 $[M+H]^+$, Rt=0.743 mins (Method 1).

The following compounds were prepared in a similar manner to 3-amino-7-(2-fluoro-6-methyl-phenyl)-N-(1-methyl-4-piperidyl)isoquinoline-4-carboxamide (E87) using the appropriate carboxylic acid and amine:

| Example | Precursor | Structure | Name | LCMS Data |
|---|---|---|---|---|
| E88 | P21 | 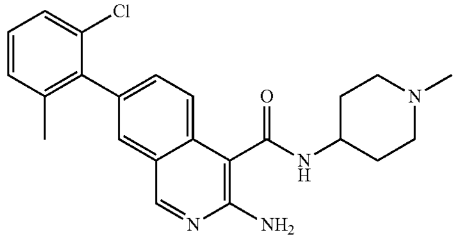 | 3-amino-7-(2-chloro-6-methyl-phenyl)-N-(1-methyl-4-piperidyl)isoquinoline-4-carboxamide | $ES^+$ 409, 411 $[M + H]^+$, Rt = 1.250 mins (Method 2) |

Example 89 (E89)

3-Amino-7-(2-fluoro-6-methyl-phenyl)-N-(1-methylazetidin-3-yl)isoquinoline-4-carboxamide

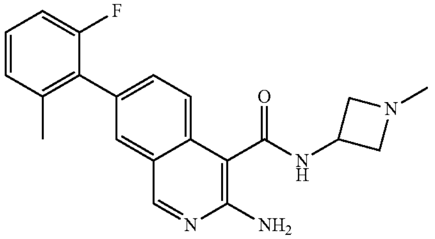 [SMILES: Cc1cccc(Cl)c1-c1ccc2c(C(=O)NC3CN(C)C3)c(N)ncc2c1]

To a solution of 3-amino-N-(azetidin-3-yl)-7-(2-fluoro-6-methyl-phenyl)isoquinoline-4-carboxamide (E32) (0.060 g, 0.171 mmol) in MeOH (2 mL) was added paraformaldehyde (0.005 g, 0.171 mmol). The mixture was stirred at room temperature for 30 minutes. $NaBH_3CN$ (0.022 g, 0.342 mmol) was added and the resulting mixture was stirred at room temperature overnight. The organics were extracted with EtOAc, washed with water, dried over $Na_2SO_4$ and concentrated under reduced pressure. The residue was purified using preparative HPLC (Method 2) to afford 3-amino-7-(2-fluoro-6-methyl-phenyl)-N-(1-methylazetidin-3-yl)isoquinoline-4-carboxamide (E89) (0.008 g), LCMS $ES^+$ 365 $[M+H]^+$, Rt=1.033 mins (Method 1).

The following compounds were prepared in a similar manner to 3-amino-7-(2-fluoro-6-methyl-phenyl)-N-(1-methylazetidin-3-yl)isoquinoline-4-carboxamide (E89) using the appropriate amine:

| Example | Precursor | Structure | Name | LCMS Data |
|---|---|---|---|---|
| E90 | E33 | 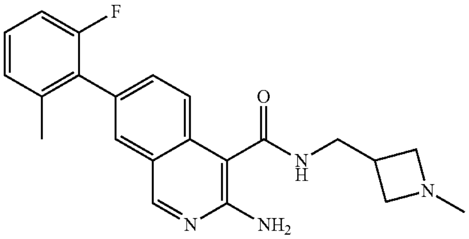 | 3-amino-7-(2-fluoro-6-methyl-phenyl)-N-[(1-methylazetidin-3-yl) methyl]isoquinoline-4-carboxamide | $ES^+$ 379 [M + H]$^+$, Rt = 0.697 mins (Method 1) |
| E91 | E34 | 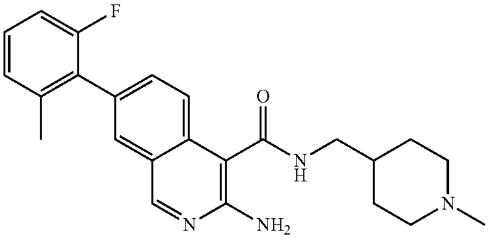 | 3-amino-7-(2-fluoro-6-methyl-phenyl)-N-[(1-methyl-4-piperidyl)methyl] isoquinoline-4-carboxamide | $ES^+$ 407 [M + H]$^+$, Rt = 1.027 mins (Method 1) |
| E92 | E36 | 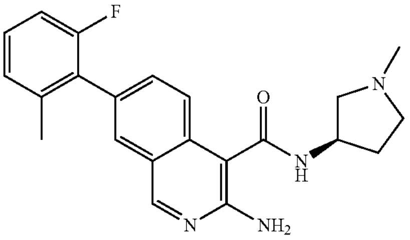 | 3-amino-7-(2-fluoro-6-methyl-phenyl)-N-[(3R)-1-methylpyrrolidin-3-yl]isoquinoline-4-carboxamide | $ES^+$ 379 [M + H]$^+$, Rt = 1.023 mins (Method 1) |
| E93 | E37 | 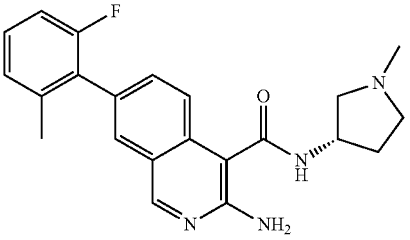 | 3-amino-7-(2-fluoro-6-methyl-phenyl)-N-[(3S)-1-methylpyrrolidin-3-yl]isoquinoline-4-carboxamide | $ES^+$ 379 [M + H]$^+$, Rt = 1.043 mins (Method 1) |
| E94 | E38 | 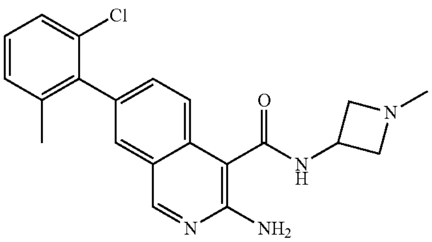 | 3-amino-7-(2-chloro-6-methyl-phenyl)-N-(1-methylazetidin-3-yl)isoquinoline-4-carboxamide | $ES^+$ 381, 383 M + H]+, Rt = 1.050 mins (Method 1) |
| E95 | E39 | 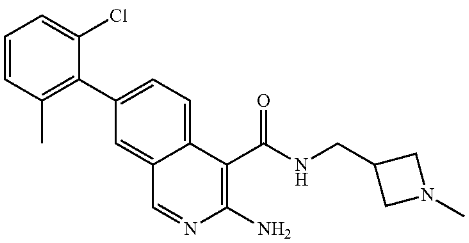 | 3-amino-7-(2-chloro-6-methyl-phenyl)-N-[(1-methylazetidin-3-yl)methyl]isoquinoline-4-carboxamide | $ES^+$ 395 [M + H]$^+$, Rt = 1.010 mins (Method 1) |

-continued

| Example | Precursor | Structure | Name | LCMS Data |
|---|---|---|---|---|
| E96 | E40 | 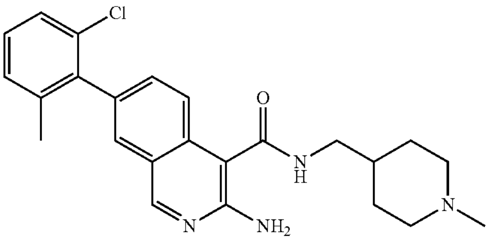 | 3-amino-7-(2-chloro-6-methyl-phenyl)-N-[(1-methyl-4-piperidyl)methyl] isoquinoline-4-carboxamide | $ES^+$ 423 $[M + H]^+$, Rt = 0.800 mins (Method 1) |
| E97 | E42 | 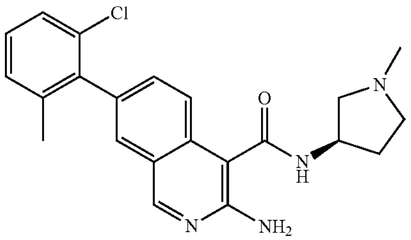 | 3-amino-7-(2-chloro-6-methyl-phenyl)-N-[(3R)-1-methylpyrrolidin-3-yl]isoquinoline-4-carboxamide | $ES^+$ 395 $[M + H]^+$, Rt = 1.067 mins (Method 1) |
| E98 | E43 | 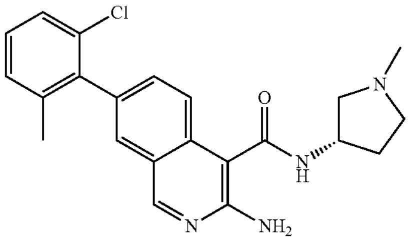 | 3-amino-7-(2-chloro-6-methyl-phenyl)-N-[(3S)-1-methylpyrrolidin-3-yl]isoquinoline-4-carboxamide | $ES^+$ 395 $[M + H]^+$, Rt = 1.047 mins (Method 1) |

Example 99 (E99)

3-Amino-7-(2-fluoro-6-methyl-phenyl)-N-(1-methylpyrrolidin-3-yl)isoquinoline-5-carboxamide

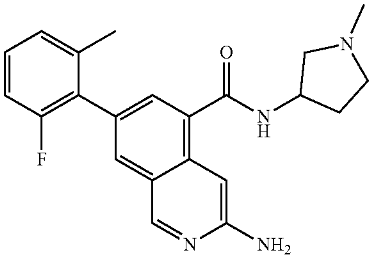 [SMILES: Cc1cccc(F)c1-c1cc(C(=O)NC2CCN(C)C2)c2cc(N)ncc2c1]

To a solution of 3-amino-7-(2-fluoro-6-methyl-phenyl) isoquinoline-5-carboxylic acid and 3-amino-5-(2-fluoro-6-methyl-phenyl)isoquinoline-7-carboxylic acid mixture of regiosiomers (P26) (0.100 g, 0.338 mmol) in MeCN (1.5 mL) was added DIPEA (0.088 g, 0.677 mmol) and HATU (0.195 g, 0.506 mmol). The solution was stirred at room temperature for 2.5 hours. Water (2.0 mL) was added and the organics were extracted with EtOAc (3×5 mL). The organics were concentrated under reduced pressure and the crude residue purified by preparative HPLC (Method 3) to give 3-amino-7-(2-fluoro-6-methyl-phenyl)-N-(1-methylpyrrolidin-3-yl)isoquinoline-5-carboxamide (E99) (0.053 g), LCMS $ES^+$ 379 $[M+H]^+$, Rt=0.813 mins (Method 1).

The following compounds were prepared in a similar manner from 3-amino-7-(2-fluoro-6-methyl-phenyl)isoquinoline-5-carboxylic acid (E99) and 3-amino-5-(2-fluoro-6-methyl-phenyl)isoquinoline-7-carboxylic acid mixture of regiosiomers (P26) and the appropriate amine:

| Example | Structure | Name | LCMS Data |
|---|---|---|---|
| E100 | 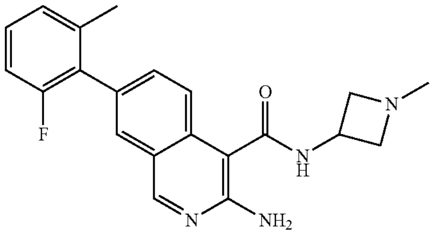 [SMILES: Cc1cccc(F)c1-c1ccc2c(C(=O)NC3CN(C)C3)c(N)ncc2c1] | 3-amino-7-(2-fluoro-6-methyl-phenyl)-N-(1-methylazetidin-3-yl)isoquinoline-5-carboxamide | $ES^+$ 365 $[M + H]^+$, Rt = 0.803 mins (Method 1) |

Example 101 (E101)

7-(2-Fluoro-6-methyl-phenyl)-5-[(1-methyl-4-piperidyl)oxy]isoquinolin-3-amine

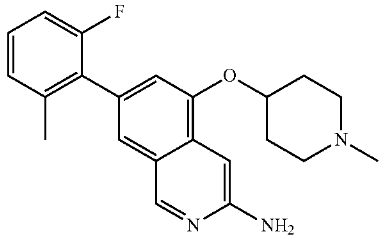 [SMILES: Cc1cccc(F)c1-c1cc(OC2CCN(C)CC2)c2cc(N)ncc2c1]

To a solution of 7-(2-fluoro-6-methyl-phenyl)-5-(4-piperidyloxy)isoquinolin-3-amine (E46) (0.020 g, 0.057 mmol) in MeOH (5 mL) was added paraformaldehyde (0.002 g, 0.057 mmol). The mixture was stirred at room temperature for 1 hour. $NaBH_3CN$ (0.001 g, 0.017 mmol) was added and the resulting mixture was stirred at room temperature for 18 hours.

The mixture was diluted with water and the organics were extracted with EtOAc. The combined organics were washed with water, dried over $MgSO_4$ and concentrated under reduced pressure. The residue was purified using preparative HPLC (Method 2) to afford 7-(2-fluoro-6-methyl-phenyl)-5-[(1-methyl-4-piperidyl)oxy]isoquinolin-3-amine (E101) (0.010 g), LCMS $ES^+$ 366 $[M+H]^+$, Rt=0.800 mins (Method 2).

The following compounds were prepared in a similar manner to 7-(2-fluoro-6-methyl-phenyl)-5-[(1-methyl-4-piperidyl)oxy]isoquinolin-3-amine (E101) using the appropriate amine:

| Example | Precursor | Structure | Name | LCMS Data |
|---|---|---|---|---|
| E102 | E47 | 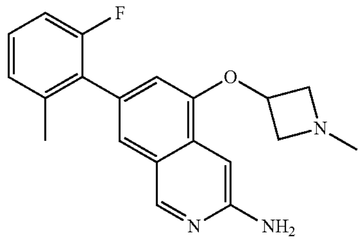 [SMILES: Cc1cccc(F)c1-c1cc(OC2CN(C)C2)c2cc(N)ncc2c1] | 7-(2-fluoro-6-methyl-phenyl)-5-(1-methylazetidin-3-yl)oxy-isoquinolin-3-amine | $ES^+$ 338 $[M + H]^+$, Rt = 0.240 mins (Method 3) |

Example 103 (E103)

7-(2-Fluoro-6-methyl-phenyl)-N-(1-methyl-4-piperidyl)isoquinolin-5-amine

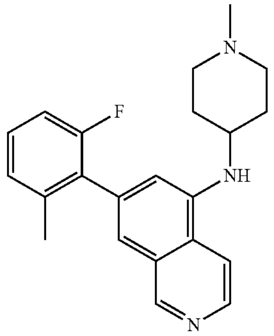 [SMILES: Cc1cccc(F)c1-c1cc(NC2CCN(C)CC2)c2ccncc2c1]

To a solution of 7-(2-fluoro-6-methyl-phenyl)isoquinolin-5-amine (P42) (0.080 g, 0.317 mmol) in MeOH (15 mL) was added 1-methylpiperidin-4-one (0.108 g, 0.952 mmol) and AcOH (0.019 g, 0.317 mmol). the mixture was stirred at room temperature for 1 hour. $NaBH_3CN$ (0.100 g, 1.59 mmol) was added and the resulting mixture was stirred at room temperature overnight. The mixture was concentrated under reduced pressure, water was added and the pH was adjusted to pH 8-9 by addition of $Na_2CO_3$. The organics were extracted using EtOAc before being concentrated and purified using preparative HPLC (Method 2) to give 7-(2-fluoro-6-methyl-phenyl)-N-(1-methyl-4-piperidyl)isoquinolin-5-amine (E103), (0.029 g), LCMS ES' 350 $[M+H]^+$, Rt=1.983 mins (Method 1).

Example 104 (E104)

1-[3-Amino-7-(2-fluoro-6-methyl-phenyl)-5-isoquinolyl]piperidin-4-ol

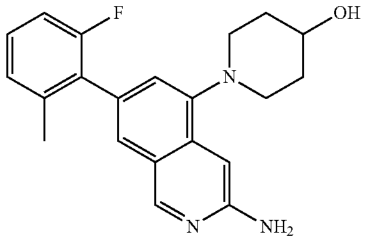 [SMILES: Cc1cccc(F)c1-c1cc(N2CCC(O)CC2)c2cc(N)ncc2c1]

To a solution of 5-chloro-7-(2-fluoro-6-methyl-phenyl) isoquinolin-3-amine and 7-chloro-5-(2-fluoro-6-methyl-phenyl)isoquinolin-3-amine mixture (P22) (0.300 g, 1.05 mmol) in 1,4-dioxane (15 mL) was added piperidin-4-ol (0.316 g, 3.14 mmol), t-BuONa (0.401 g, 4.18 mmol), $Pd_2(dba)_3$ (0.030 g) and t-BuXPhos (0.030 g). The mixture was heated to 100° C. and stirred under an atmosphere of argon overnight. Further t-BuONa (0.040 g, 0.041 mmol), $Pd2(dba)_3$ (0.015 g) and t-BuXPhos (0.015 g) was added and the mixture was stirred at 110° C. for a further 2 hours. The mixture was diluted with water and the organics were extracted with EtOAc. The organics were concentrated under reduced pressure and purified by preparative HPLC (Method 2) to give 1-[3-amino-7-(2-fluoro-6-methyl-phenyl)-5-isoquinolyl]piperidin-4-ol (E104), (0.007 g), LCMS $ES^+$352 $[M+H]^+$, Rt=1.172 mins (Method 2).

The following compounds were prepared in a similar manner to 1-[3-amino-7-(2-fluoro-6-methyl-phenyl)-5-isoquinolyl]piperidin-4-ol (E104) using 5-chloro-7-(2-fluoro-6-methyl-phenyl)isoquinolin-3-amine and 7-chloro-5-(2-fluoro-6-methyl-phenyl)isoquinolin-3-amine mixture (P22) and the appropriate amine:

| Example | Structure | Name | LCMS Data |
|---|---|---|---|
| E105 | 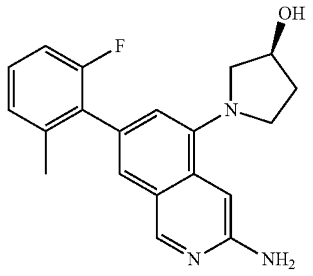 [SMILES: Cc1cccc(F)c1-c1cc(N2CC[C@H](O)C2)c2cc(N)ncc2c1] | (3S)-1-[3-amino-7-(2-fluoro-6-methyl-phenyl)-5-isoquinolyl]pyrrolidin-3-ol | $ES^+$ 338 $[M + H]^+$, Rt = 0.733 mins (Method 2) |
| E106 | 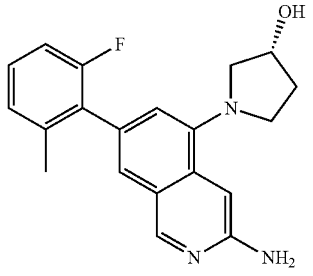 [SMILES: Cc1cccc(F)c1-c1cc(N2CC[C@@H](O)C2)c2cc(N)ncc2c1] | (3R)-1-[3-amino-7-(2-fluoro-6-methyl-phenyl)-5-isoquinolyl]pyrrolidin-3-ol | $ES^+$ 338 $[M + H]^+$, Rt = 0.756 mins (Method 2) |
| E107 | 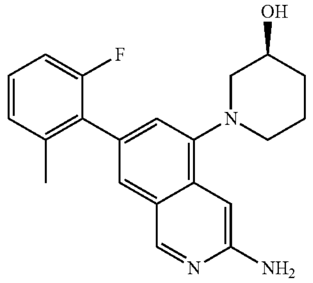 [SMILES: Cc1cccc(F)c1-c1cc(N2CCC[C@H](O)C2)c2cc(N)ncc2c1] | (3S)-1-[3-amino-7-(2-fluoro-6-methyl-phenyl)-5-isoquinolyl]piperidin-3-ol | $ES^+$ 352 $[M + H]^+$, Rt = 1.016 mins (Method 2) |

-continued

| Example | Structure | Name | LCMS Data |
|---|---|---|---|
| E108 | 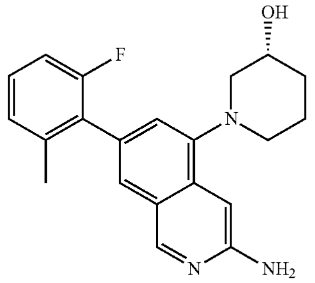 [SMILES: Cc1cccc(F)c1-c1cc(N2CCC[C@@H](O)C2)c2cc(N)ncc2c1] | (3R)-1-[3-amino-7-(2-fluoro-6-methyl-phenyl)-5-isoquinolyl]piperidin-3-ol | $ES^+$ 352 $[M + H]^+$, Rt = 0.996 mins (Method 2) |
| E109 | 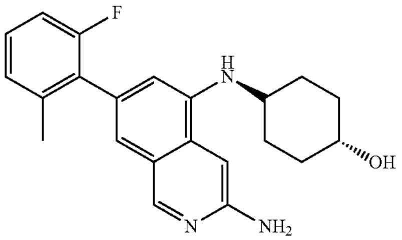 | 4-[[3-amino-7-(2-fluoro-6-methyl-phenyl)-5-isoquinolyl]amino]cyclo hexanol | $ES^+$ 366 $[M + H]^+$, Rt = 1.350 mins (Method 2) |

Example 110 (E110)

7-(2-Fluoro-6-methyl-phenyl)-N5-tetrahydropyran-4-yl-isoquinoline-3,5-diamine

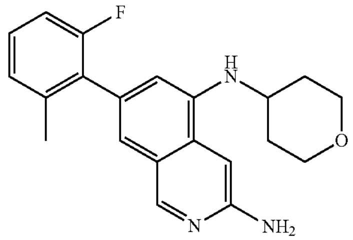 [SMILES: Cc1cccc(F)c1-c1cc(NC2CCOCC2)c2cc(N)ncc2c1]

To a solution of 5-chloro-7-(2-fluoro-6-methyl-phenyl)isoquinolin-3-amine and 7-chloro-5-(2-fluoro-6-methyl-phenyl)isoquinolin-3-amine mixture (P22) (0.300 g, 1.05 mmol) in 1,4-dioxane (3 mL) was added tetrahydropyran-4-amine (0.313 g, 3.36 mmol), t-BuONa (0.401 g, 4.18 mmol), $Pd_2(dba)_3$ (0.030 g) and t-BuXPhos (0.030 g). The mixture was stirred at 100° C. for 4 h. After this time, the organics were extracted with EtOAc, concentrated under reduced pressure and the residue chromatographed to give 7-(2-fluoro-6-methyl-phenyl)-N5-tetrahydropyran-4-yl-isoquinoline-3,5-diamine (E110), (0.008 g), LCMS $ES^+$ 352 $[M+H]^+$, Rt=1.249 mins (Method 2).

The following compounds were prepared in a similar manner to 7-(2-fluoro-6-methyl-phenyl)-N5-tetrahydropyran-4-yl-isoquinoline-3,5-diamine (E110) using 5-chloro-7-(2-fluoro-6-methyl-phenyl)isoquinolin-3-amine and 7-chloro-5-(2-fluoro-6-methyl-phenyl)isoquinolin-3-amine regioisomeric mixture (P22) and the appropriate amine:

| Example | Structure | Name | LCMS Data |
|---|---|---|---|
| E111 | 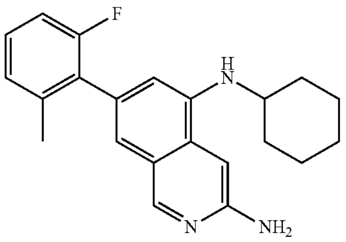 [SMILES: Cc1cccc(F)c1-c1cc(NC2CCCCC2)c2cc(N)ncc2c1] | N5-cyclohexyl-7-(2-fluoro-6-methyl-phenyl)isoquinoline-3,5-diamine | $ES^+$ 350 $[M+ H]^+$, Rt = 0.916 mins (Method 2) |

Example 112 (E112)

N-[(3S)-1-[3-Amino-7-(2-fluoro-6-methyl-phenyl)-5-isoquinolyl]pyrrolidin-3-yl]acetamide

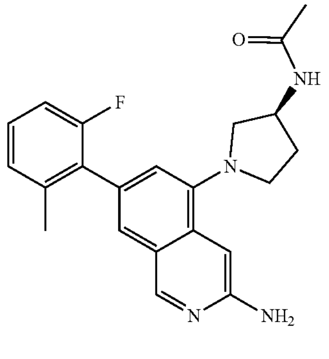 [SMILES: CC(=O)N[C@H]1CCN(c2cc(-c3c(C)cccc3F)cc3cnc(N)cc23)C1]

To a solution of 5-chloro-7-(2-fluoro-6-methyl-phenyl)isoquinolin-3-amine and 7-chloro-5-(2-fluoro-6-methyl-phenyl)isoquinolin-3-amine mixture (P22) (0.200 g, 0.78 mmol) in 1,4-dioxane (6 mL) was added N-[(3S)-pyrrolidin-3-yl]acetamide (0.268 g, 2.08 mmol), t-BuONa (0.268 g, 2.80 mmol), $Pd_2(dba)_3$ (0.020 g) and t-BuXPhos (0.020 g). The mixture was stirred at 100° C. in the microwave for 6 hours. the organics were extracted with EtOAc, washed with water and concentrated under reduced pressure. The resulting mixture was chromatographed to give N-[(3S)-1-[3-amino-7-(2-fluoro-6-methyl-phenyl)-5-isoquinolyl]pyrrolidin-3-yl]acetamide (E112) (0.024 g), LCMS $ES^+$379 $[M+H]^+$, Rt=0.740 mins (Method 2).

The following compounds were prepared in a similar manner to N-[(3S)-1-[3-amino-7-(2-fluoro-6-methyl-phenyl)-5-isoquinolyl]pyrrolidin-3-yl]acetamide (E112) using 5-chloro-7-(2-fluoro-6-methyl-phenyl)isoquinolin-3-amine and 7-chloro-5-(2-fluoro-6-methyl-phenyl)isoquinolin-3-amine regioisomeric mixture (P22) and the appropriate amine:

| Example | Structure | Name | LCMS Data |
|---|---|---|---|
| E113 | 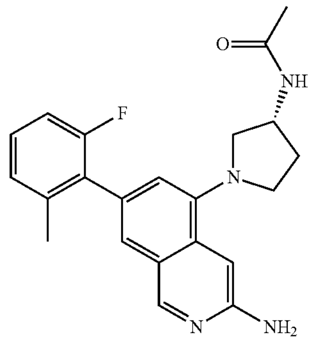 [SMILES: CC(=O)N[C@@H]1CCN(c2cc(-c3c(C)cccc3F)cc3cnc(N)cc23)C1] | N-[(3R)-1-[3-amino-7-(2-fluoro-6-methyl-phenyl)-5-isoquinolyl]pyrrolidin-3-yl]acetamide | $ES^+$ 379 $[M + H]^+$, Rt = 0.603 mins (Method 2) |
| E114 | 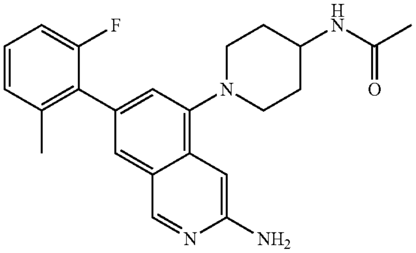 [SMILES: CC(=O)NC1CCN(c2cc(-c3c(C)cccc3F)cc3cnc(N)cc23)CC1] | N-[1-[3-amino-7-(2-fluoro-6-methyl-phenyl)-5-isoquinolyl]-4-piperidyl]acetamide | $ES^+$ 393 $[M + H]^+$, Rt = 1.163 mins (Method 2) |

Example 115 (E115)

N-[7-(2-Fluoro-6-methyl-phenyl)-5-[(1-methyl-4-piperidyl)amino]-3-isoquinolyl]acetamide

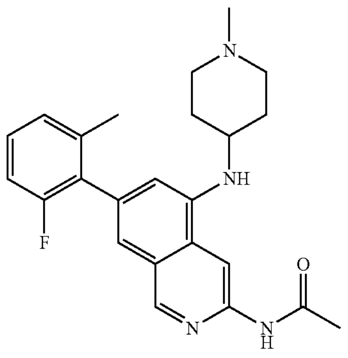 [SMILES: CC(=O)Nc1cc2c(NC3CCN(C)CC3)cc(-c3c(C)cccc3F)cc2cn1]

To a solution of 7-(2-fluoro-6-methyl-phenyl)-N5-(1-methyl-4-piperidyl)isoquinoline-3,5-diamine (E54) (0.100 g, 0.27 mmol) in THF (15 mL) at 0° C. was added NaH (0.010 g, 0.4 mmol). The mixture was stirred for 30 minutes. Acetyl chloride (0.026 g, 0.33 mmol) was added and the mixture was stirred for a further 2 hours at 0° C. The mixture was diluted with iced water (40 mL) and extracted with EtOAc (50 mL×3). The combined organics were washed with brine, dried over $Na_2SO_4$, filtered and concentrated under reduced pressure. The residue was purified by preparative HPLC (Method 2) to afford N-[7-(2-fluoro-6-methyl-phenyl)-5-[(1-methyl-4-piperidyl)amino]-3-isoquinolyl]acetamide (0.070 g), (E115), LCMS $ES^+$407 $[M+H]^+$, Rt=0.913 mins (Method 1).

Example 116 (E116)

3-Amino-7-(2-fluoro-6-methyl-phenyl)-N-(1-methyl-4-piperidyl)isoquinoline-5-carboxamide

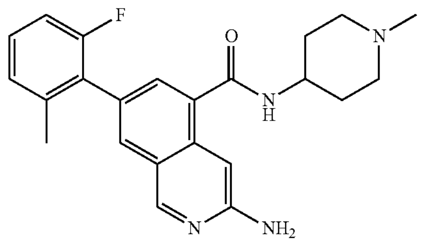

To a solution of 5-bromo-7-(2-fluoro-6-methyl-phenyl) isoquinolin-3-amine (P23) (0.300 g, 0.906 mmol) in DMF (3.0 mL) was added Pd(dppf)$Cl_2$ (0.067 g, 0.090 mmol), 1-methylpiperidin-4-amine (0.518 g, 4.53 mmol) and $Et_3N$ (0.184 g, 1.81 mmol). the solution was stirred at 115° C. under CO for 12 hours. After this time, the solution was allowed to cool to room temperature and water (3 mL) was added. The organics were extracted with EtOAc (3×5 mL), washed with brine and concentrated under reduced pressure. The crude residue was purified using preparative HPLC (Method 2) to give 3-amino-7-(2-fluoro-6-methyl-phenyl)-N-(1-methyl-4-piperidyl)isoquinoline-5-carboxamide (E116) (0.022 g), LCMS $ES^+$ 393 $[M+H]^+$, Rt=0.793 mins (Method 1).

Example 117 (E117)

7-(2-Fluoro-6-methyl-phenyl)-5-(1-methyl-4-piperidyl)isoquinolin-3-amine

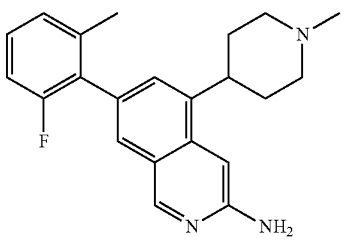

To a solution of 7-(2-fluoro-6-methyl-phenyl)-5-(1-methyl-3,6-dihydro-2H-pyridin-4-yl)isoquinolin-3-amine and 5-(2-fluoro-6-methyl-phenyl)-7-(1-methyl-3,6-dihydro-2H-pyridin-4-yl)isoquinolin-3-amine regioisomers (P101) (0.100 g, 0.288 mmol) in MeOH (2.0 mL) was added $PtO_2$ (0.030 g). The reaction was stirred overnight at room temperature under an atmosphere of $H_2$. After this time, the mixture was filtered, concentrated under reduced pressure and the residue chromatographed [$SiO_2$, DCM:MeOH, 15:1]. The resulting product was further purified using preparative HPLC (Method 2), neutralising the salt obtained with $NH_3$/MeOH to give 7-(2-fluoro-6-methyl-phenyl)-5-(1-methyl-4-piperidyl)isoquinolin-3-amine (E117), (0.0064 g), LCMS $ES^+$ 350 $[M+H]^+$, Rt=3.63 mins (extended Method 1).

Example 118 (E118)

N5-(1-Ethyl-4-piperidyl)-8-fluoro-7-(2-fluoro-6-methyl-phenyl)isoquinoline-3,5-diamine

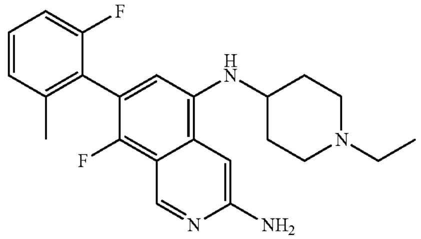

A solution of 5-bromo-8-fluoro-7-(2-fluoro-6-methyl-phenyl)isoquinolin-3-amine (P106) (0.100 g, 0.304 mmol), t-BuXPhos (0.010 g), $Pd_2(dba)_3$ (0.010 g), t-BuOK (0.068 g, 0.608 mmol) and 1-ethylpiperidin-4-amine (0.078 g, 0.608 mmol) in dioxane (1.0 mL) was stirred at 70° C. overnight. The solution was diluted with EtOAc and the organics were extracted with EtOAc. The combined organics were washed with brine, dried over $Na_2SO_4$, filtered and concentrated under reduced pressure. The residue was purified by preparative HPLC (Method 3) to give N5-(1-ethyl-4-piperidyl)-8-fluoro-7-(2-fluoro-6-methyl-phenyl)isoquinoline-3,5-diamine (E118) (0.030 g), LCMS $ES^+$ 397 $[M+H]^+$, Rt=1.063 mins (Method 1).

The following compounds were prepared in a similar manner to N5-(1-ethyl-4-piperidyl)-8-fluoro-7-(2-fluoro-6-methyl-phenyl)isoquinoline-3,5-diamine (E118) from 5-bromo-8-fluoro-7-(2-fluoro-6-methyl-phenyl)isoquinolin-3-amine (P106) and the appropriate amine:

| Example | Structure | Name | LCMS Data |
|---|---|---|---|
| E119 | 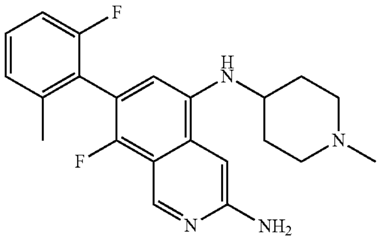 | 8-fluoro-7-(2-fluoro-6-methyl-phenyl)-N5-(1-methyl-4-piperidyl)isoquinoline-3,5-diamine | $ES^+$ 383 [M + H]$^+$, Rt = 0.920 mins (Method 1) |

Example 120 (E120)

8-Fluoro-7-(2-fluoro-6-methyl-phenyl)-N5-(4-piperidyl)isoquinoline-3,5-diamine

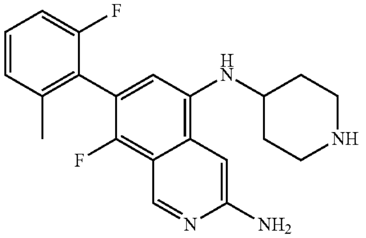

A solution of tert-butyl 4-[[3-amino-8-fluoro-7-(2-fluoro-6-methyl-phenyl)-5-isoquinolyl]amino]piperidine-1-carboxylate (P107) (0.060 g, 0.128 mmol) in DCM (1.0 mL) and TFA (0.1 mL) was stirred at room temperature for 2 hours. $NaHCO_3$ (aq. soln.) was added dropwise until pH=8-9. The organics were extracted with EtOAc (3×2 mL), washed with brine, dried over $Na_2SO_4$, filtered and concentrated under reduced pressure. The residue was purified by preparative HPLC (Method 2) to give 8-fluoro-7-(2-fluoro-6-methyl-phenyl)-N5-(4-piperidyl)isoquinoline-3,5-diamine (E120) (0.011 g), LCMS $ES^+$ 369 [M+H]$^+$, Rt=1.145 mins (Method 1).

Example 121 (E121)

2-(2-Fluoro-6-methyl-phenyl)-N4-(1-methyl-4-piperidyl)-1,7-naphthyridine-4,6-diamine

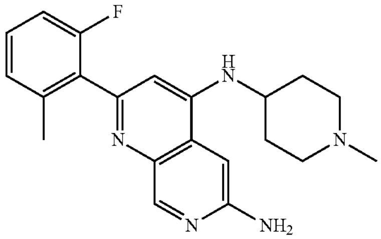 [SMILES: Cc1cccc(F)c1-c1cc(NC2CCN(C)CC2)c2cc(N)ncc2n1]

A solution of N6-benzyl-2-(2-fluoro-6-methyl-phenyl)-N4-(1-methyl-4-piperidyl)-1,7-naphthyridine-4,6-diamine (P114) (0.120 g, 0.263 mmol) in conc. $H_2SO_4$ (2.0 mL) was stirred at room temperature for 12 hours. The solution was added to ice-water slowly and the pH was adjusted to pH=8-9 by addition of NaOH (aq. soln.). The organics were extracted with EtOAc (2×10 mL). The combined organics were washed with brine, dried over $Na_2SO_4$, filtered and concentrated under reduced pressure. The crude residue was purified by preparative HPLC (Method 2) to give 2-(2-fluoro-6-methyl-phenyl)-N4-(1-methyl-4-piperidyl)-1,7-naphthyridine-4,6-diamine (E121) (0.038 g), LCMS $ES^+$ 366 [M+H]$^+$, Rt=1.646 mins (Method 3).

Example 122 (E122)

2-(2-Fluoro-6-methyl-phenyl)-N-(1-methyl-4-piperidyl)-1,7-naphthyridin-4-amine

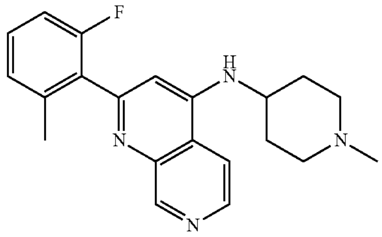 [SMILES: Cc1cccc(F)c1-c1cc(NC2CCN(C)CC2)c2ccncc2n1]

To a solution of 4-chloro-2-(2-fluoro-6-methyl-phenyl)-1,7-naphthyridine (P117) (0.330 g, 1.21 mmol) and 1-methylpiperidin-4-amine (0.416 g, 3.63 mmol) in 1,4-dioxane (20.0 mL) was added $Pd_2(dba)_3$ (0.033 g), RuPhos (0.033 g), t-BuONa (0.348 g, 3.63 mmol). The mixture was stirred at 100° C. for 3 hours. After this time, the mixture was diluted with water and the organics were extracted with EtOAc. The combined organics were dried over $Na_2SO_4$, filtered and concentrated under reduced pressure. The crude residue was chromatographed [$SiO_2$] and then further purified using preparative HPLC (Method 2) to give 2-(2-fluoro-6-methyl-phenyl)-N-(1-methyl-4-piperidyl)-1,7-naphthyridin-4-amine (P122) (0.167 g), LCMS $ES^+$ 351 [M+H]$^+$, Rt=1.896 mins (Method 3).

Example 123 (E123)

6-(2-Fluoro-6-methyl-phenyl)-N-(4-piperidyl)quinazolin-8-amine

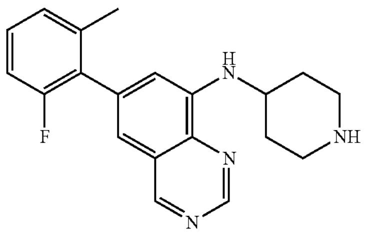 [SMILES: Cc1cccc(F)c1-c1cc(NC2CCNCC2)c2ncncc2c1]

A solution of tert-butyl 4-[[6-(2-fluoro-6-methyl-phenyl)quinazolin-8-yl]amino]piperidine-1-carboxylate (P125) (0.070 g, 0.153 mmol) in DCM (3.0 mL) and TFA (1.0 mL) was stirred at room temperature for 3 hours. After this time, the solution was concentrated under reduced pressure and the residue was purified by preparative HPLC (Method 2) to give 6-(2-fluoro-6-methyl-phenyl)-N-(4-piperidyl)quinazolin-8-amine (E123) (0.004 g), LCMS $ES^{+}337$ $[M+H]^{+}$, Rt=0.803 mins (Method 1).

The following compounds were prepared in a similar manner to 6-(2-fluoro-6-methyl-phenyl)-N-(4-piperidyl)quinazolin-8-amine (E123) from the appropriate tert-butoxycarbonyl protected intermediate:

| Example | Precursor | Structure | Name | LCMS Data |
|---|---|---|---|---|
| E124 | P126 | 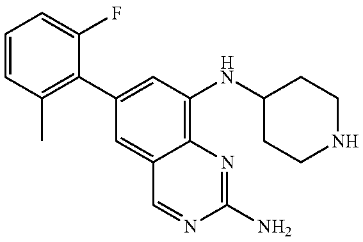 | 6-(2-fluoro-6-methyl-phenyl)-N8-(4-piperidyl)quinazoline-2,8-diamine | $ES^{+}$ 352 $[M + H]^{+}$, Rt = 0.793 mins (Method 1) |
| E137 | P126a | 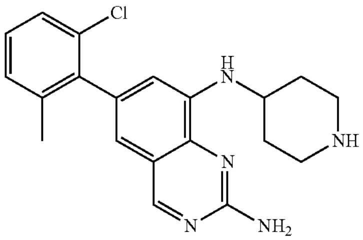 [SMILES: Cc1cccc(Cl)c1-c1cc(NC2CCNCC2)c2nc(N)ncc2c1] | 6-(2-chloro-6-methyl-phenyl)-N8-(4-piperidyl)quinazoline-2,8-diamine | $ES^{+}$ 368 $[M + H]^{+}$, Rt = 0.850 mins (Method 1) |
| E138 | P125a | 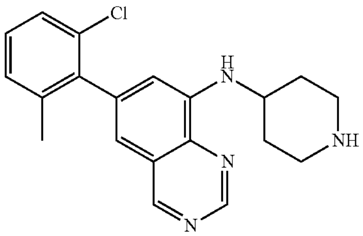 [SMILES: Cc1cccc(Cl)c1-c1cc(NC2CCNCC2)c2ncncc2c1] | 6-(2-chloro-6-methyl-phenyl)-N-(4-piperidyl)quinazolin-8-amine | $ES^{+}$ 353 $[M + H]^{+}$, Rt = 0.853 mins (Method 1) |

Example 125 (E125)

6-(2-Fluoro-6-methyl-phenyl)-N-(1-methyl-4-piperidyl)quinazolin-8-amine

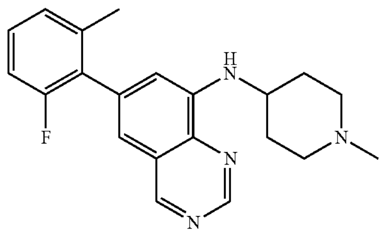 [SMILES: Cc1cccc(F)c1-c1cc(NC2CCN(C)CC2)c2ncncc2c1]

A mixture of 8-bromo-6-(2-fluoro-6-methyl-phenyl)quinazoline (P123) (0.020 g, 0.063 mmol), 1-methylpiperidin-4-amine (0.015 g, 0.126 mmol), $Pd_2(dba)_3$ (0.012 g, 0.0126 mmol), RuPhos (0.005 g) and t-BuONa (0.012 g, 0.126 mmol) in dioxane (2.0 mL) was stirred at 80° C. for 3 hours. After this time, the mixture was filtered and concentrated under reduced pressure. The crude residue was purified by preparative HPLC (Method 2) to give 6-(2-fluoro-6-methyl-phenyl)-N-(1-methyl-4-piperidyl)quinazolin-8-amine (E125) (0.003 g), LCMS $ES^+351$ $[M+H]^+$, Rt=0.793 mins. (Method 1).

The following compounds were prepared in a similar manner to 6-(2-fluoro-6-methyl-phenyl)-N-(1-methyl-4-piperidyl)quinazolin-8-amine (E125) from 8-bromo-6-(2-fluoro-6-methyl-phenyl)quinazoline (P123) and the appropriate amine:

| Example | Structure | Name | LCMS Data |
|---|---|---|---|
| E126 | 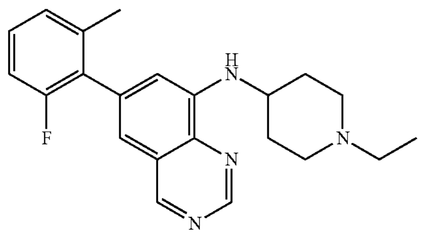 [SMILES: CCN1CCC(Nc2cc(-c3c(C)cccc3F)cc3cncnc23)CC1] | N-(1-ethyl-4-piperidyl)-6-(2-fluoro-6-methyl-phenyl)quinazolin-8-amine | $ES^+$ 365 $[M + H]^+$, Rt = 0.803 mins (Method 1) |

Example 127 (E127)

N8-(1-Ethyl-4-piperidyl)-6-(2-fluoro-6-methyl-phenyl)quinazoline-2,8-diamine

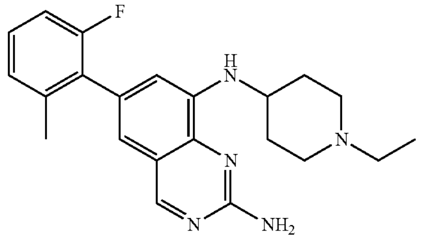

To a solution of 8-bromo-6-(2-fluoro-6-methyl-phenyl) quinazolin-2-amine (P124) (0.021 g, 0.063 mmol), 1-ethylpiperidin-4-amine (0.016 g, 0.126 mmol), $Pd_2(dba)_3$ (0.012 g, 0.0126 mmol), t-BuXantphos (0.005 g) and t-BuONa (0.012 g, 0.126 mmol) in dioxane (2.0 mL) was stirred at 80° C. for 3 hours. After this time, the solution was filtered and the filtrate was concentrated under reduced pressure. The residue was chromatographed $[SiO_2]$ to give N8-(1-ethyl-4-piperidyl)-6-(2-fluoro-6-methyl-phenyl)quinazoline-2,8-diamine (E127) (0.002 g), LCMS $ES^+380$ $[M+H]^+$, Rt=0.813 mins (Method 1).

The following compounds were prepared in a similar manner to N8-(1-Ethyl-4-piperidyl)-6-(2-fluoro-6-methyl-phenyl)quinazoline-2,8-diamine (E127) from the appropriate precursor and amine:

| Example | Precursor | Structure | Name | LCMS Data |
|---|---|---|---|---|
| E128 | P124a | 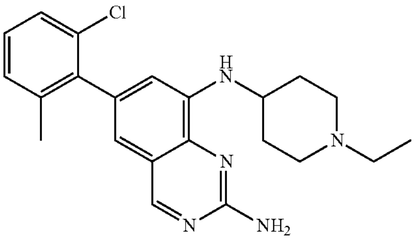 | 6-(2-chloro-6-methyl-phenyl)-N8-(1-ethyl-4-piperidyl)quinazoline-2,8-diamine | $ES^+$ 396 $[M + H]^+$, Rt = 0.86 mins (Method 1) |
| E129 | P124a | 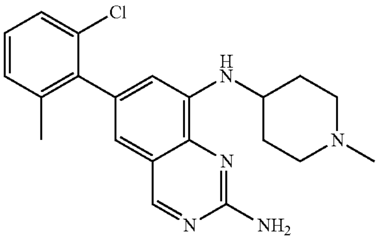 [SMILES: Cc1cccc(Cl)c1-c1cc(NC2CCN(C)CC2)c2nc(N)ncc2c1] | 6-(2-chloro-6-methyl-phenyl)-N8-(1-methyl-4-piperidyl)quinazoline-2,8-diamine | $ES^+$ 382 $[M + H]^+$, Rt = 0.803 mins (Method 1) |
| E130 | P123a | 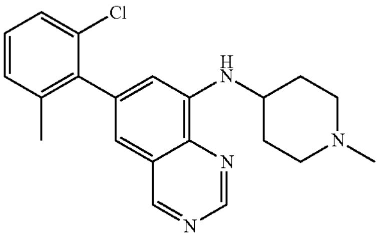 [SMILES: Cc1cccc(Cl)c1-c1cc(NC2CCN(C)CC2)c2ncncc2c1] | 6-(2-chloro-6-methyl-phenyl)-N-(1-methyl-4-piperidyl)quinazolin-8-amine | $ES^+$ 367 $[M + H]^+$, Rt = 1.060 mins (Method 1) |
| E131 | P123a | 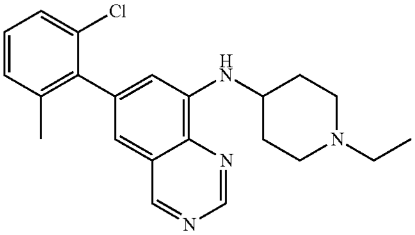 [SMILES: CCN1CCC(Nc2cc(-c3c(C)cccc3Cl)cc3cncnc23)CC1] | 6-(2-chloro-6-methyl-phenyl)-N-(1-ethyl-4-piperidyl)quinazolin-8-amine | $ES^+$ 381 $[M + H]^+$, Rt = 0.833 mins (Method 1) |
| E132 | P124 | 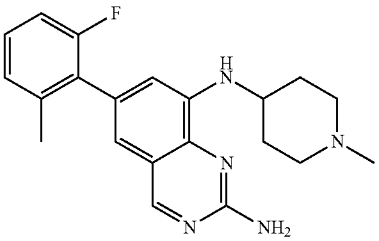 | 6-(2-fluoro-6-methyl-phenyl)-N8-(1-methyl-4-piperidyl)quinazoline-2,8-diamine | $ES^+$ 366 $[M + H]^+$, Rt = 0.823 mins (Method 1) |

Example 133 (E133)

3-Amino-7-(2-fluoro-6-methyl-phenyl)-5-(4-piperidylamino)isoquinoline-4-carbonitrile

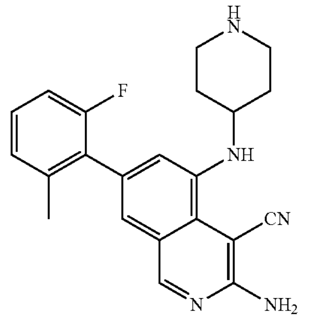 [SMILES: Cc1cccc(F)c1-c1cc(NC2CCNCC2)c2c(C#N)c(N)ncc2c1]

To a solution of tert-butyl 4-[[3-amino-4-cyano-7-(2-fluoro-6-methyl-phenyl)-5-isoquinolyl]amino]piperidine-1-carboxylate (P75a) (0.030 g, 0.063 mmol) in DCM (0.5 mL) was added TFA dropwise (0.2 mL). The solution was stirred at room temperature for 1.5 hours. After this time, $NaHCO_3$ (aq.) was added until pH=8-9. The organics were extracted with EtOAc (3×1.0 mL) and washed with brine. The combined organics were concentrated under reduced pressure and the obtained residue purified by preparative HPLC (Method x) to give 3-amino-7-(2-fluoro-6-methyl-phenyl)-5-(4-piperidylamino)isoquinoline-4-carbonitrile (E133) (0.009 g), LCMS $ES^+$ 376 $[M+H]^+$, Rt=0.900 mins (Method 1).

Example 134 (E134)

6-Fluoro-7-(2-fluoro-6-methyl-phenyl)-N5-(4-piperidyl)isoquinoline-3,5-diamine

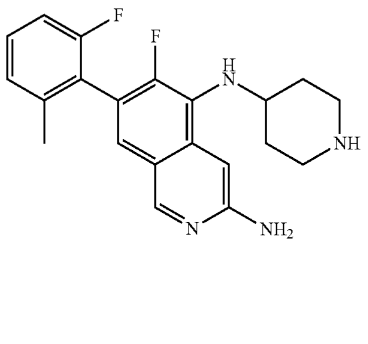

A solution of tert-butyl 4-[[3-amino-6-fluoro-7-(2-fluoro-6-methyl-phenyl)-5-isoquinolyl]amino]piperidine-1-carboxylate (P107a) (0.100 g, 0.214 mmol) and TFA (1.0 mL) in DCM (2.0 mL) was stirred at room temperature for 16 hours. The reaction mixture was concentrated under reduced pressure and the residue purified by preparative HPLC to afford 6-fluoro-7-(2-fluoro-6-methyl-phenyl)-N5-(4-piperidyl)isoquinoline-3,5-diamine (E134) (0.060 g), LCMS $ES^+$ $[M+H]^+$, Rt=0.985 mins (Method 1).

Example 135 (E135)

6-Fluoro-7-(2-fluoro-6-methyl-phenyl)-N5-(1-methyl-4-piperidyl)isoquinoline-3,5-diamine

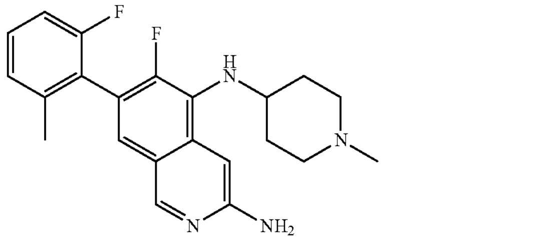

A solution of 6-fluoro-7-(2-fluoro-6-methyl-phenyl)-N5-(4-piperidyl)isoquinoline-3,5-diamine (E121) (0.030 g, 0.082 mmol) in DCM/MeOH (3 mL/3 mL) was added formaldehyde (0.007 g, 0.098 mmol) and AcOH (1 drop) at 0° C. The solution was stirred at 0° C. for 30 minutes. After this time, $NaBH_3CN$ (0.015 g, 0.246 mmol) was added and the resulting mixture was stirred at 0° C. for a further 2 hours. The reaction mixture was poured into $Na_2CO_3$ (aq. soln.). The organics were extracted into EtOAc (10 mL×2). The combined organics were washed with brine (10 mL) and concentrated under reduced pressure. The residue was purified by preparative HPLC (Method 3) to give 6-fluoro-7-(2-fluoro-6-methyl-phenyl)-N5-(1-methyl-4-piperidyl)isoquinoline-3,5-diamine (E135) (0.015 g) LCMS $ES^+$ 383 $[M+H]^+$, Rt=0.783 mins (Method 1).

Biology

Materials and Methods

SIK2, SIK1, SIK3, Abl, Src and EPHA2 Kinase Assays

SIK2, SIK1, SIK3, Abl, Src and EPHA2 assays were performed using an IMAP fluorescence polarization assay format (Molecular Devices Inc.). 0.6-13 nM of each kinase (Life Technologies) was incubated for 60 min at room temperature with 100 nM of either FAM-Abltide, FAM-Srctide or FAM-HDAC protein derived peptide (synthesized by Alta Biosciences, Birmingham UK). Assays were carried out in the presence of 50 or 100 μM ATP in either 20 mM Tris buffer (pH 7.2) containing 4 mM $MgCl_2$, 0.2% BSA and 2 mM DTT (SIK2, SIK1, SIK3, Abl, Src); or 20 mM Tris buffer (pH 8.5) containing 20 mM $MgCl_2$, 0.5% BSA, 0.2% Triton and 5 mM DTT (EPHA2). Typically, dose response analyses were performed over concentration ranges from 0.00005-1 μM. Reactions were stopped by adding 2 assay volumes of 0.25% (v/v) IMAP binding reagent in either an 85:15 ratio (SIK2, SIK1, SIK3, Abl, EPHA2) or 30:70 ratio (Src) of IMAP binding buffers A and B (Molecular Devices). After incubation to allow the detection reagents to bind to the phosphorylated peptide, fluorescence polarization was measured on a Tecan Infinite plate reader at excitation (470 nm) and emission (530 nm) wavelengths. Inhibition was calculated using no inhibitor and no enzyme controls as 0 and 100% inhibition, respectively.

Table 3 provides details of the inhibitory constant (nM) of compounds of the invention at SIK1, SIK2 and SIK3 and other kinases.

TABLE 3

| Example No. | SIK1 - AVERAGE Ki (nM) | SIK2 - AVERAGE Ki (nM) | SIK3 - AVERAGE Ki (nM) | Abl - AVERAGE Ki (nM) | EPHA2 - AVERAGE Ki (nM) | Src - AVERAGE Ki (nM) |
|---|---|---|---|---|---|---|
| 1 | 0.3641 | 0.05180 | 0.3523 | 16.30 | 122.0 | 152.7 |
| 2 | 0.5238 | 0.1799 | 1.370 | 11.12 | 64.64 | 157.4 |
| 3 | 0.8083 | 0.1426 | 0.6426 | 20.38 | 877.6 | 330.0 |
| 4 | 0.3538 | 0.07030 | 0.2309 | 7.788 | 643.8 | 138.4 |
| 5 | 1.742 | 0.3758 | 8.931 | 74.09 | >1000 | 261.2 |
| 6 | 0.3103 | 0.05170 | 0.5699 | 0.2979 | 49.54 | 144.9 |
| 7 | 0.4143 | 0.04960 | 0.3246 | 5.550 | 199.0 | 192.7 |
| 8 | 0.5465 | 0.1076 | 1.020 | 1.396 | 5.150 | 16.53 |
| 9 | 0.3161 | 0.04110 | 0.2690 | 0.6869 | 166.2 | 216.7 |
| 10 | 0.5355 | 0.1005 | 0.9655 | 4.834 | 47.65 | 32.08 |
| 11 | 0.4168 | 0.06720 | 0.1947 | 0.9210 | 95.12 | 23.54 |
| 12 | 1.070 | 0.3293 | 3.103 | 22.95 | 216.4 | 167.4 |
| 13 | 0.5014 | 0.1912 | 1.012 | 3.287 | 144.2 | 24.30 |
| 14 | 0.6007 | 0.09690 | 2.431 | 8.009 | 59.53 | 67.76 |
| 15 | 1.011 | 0.1554 | 1.944 | 19.41 | 155.9 | 396.5 |
| 16 | 2.004 | 0.2243 | 4.695 | 41.63 | 277.7 | 924.3 |
| 17 | 0.4627 | 0.09600 | 1.647 | 2.551 | >1000 | >1000 |
| 18 | 0.6558 | 0.1957 | 7.090 | 1.877 | 100.1 | 53.40 |
| 19 | 0.4760 | 0.1130 | 4.449 | 24.57 | >1000 | 305.7 |
| 20 | NT | 26.11 | NT | NT | NT | NT |
| 21 | 0.5939 | 0.2736 | 9.362 | 10.54 | 41.51 | 50.43 |
| 22 | 1.673 | 0.5629 | 13.64 | 46.60 | 227.4 | 304.0 |
| 23 | 0.2869 | 0.04880 | 0.1712 | 3.749 | 24.58 | 15.90 |
| 24 | 2.336 | 0.4016 | 7.501 | 34.00 | 148.5 | 327.2 |
| 25 | 0.5465 | 0.1324 | 1.281 | 4.963 | >1000 | >1000 |
| 26 | 0.3025 | 0.03950 | 0.08380 | 0.3410 | 24.57 | 163.2 |
| 27 | 0.4286 | 0.07480 | 0.3494 | 22.87 | 215.7 | 218.5 |
| 28 | 1.392 | 0.1547 | 0.5039 | 14.76 | >1000 | 412.7 |
| 29 | 0.3814 | 0.05600 | 0.4474 | 19.28 | 164.7 | 97.40 |
| 30 | 0.4741 | 0.3347 | 2.916 | 36.09 | 65.50 | 96.25 |
| 31 | 2.595 | 0.9682 | 9.521 | 182.0 | >1000 | 315.1 |
| 32 | NT | 27.25 | NT | 487.4 | NT | 723.2 |
| 33 | NT | 11.82 | NT | NT | NT | NT |
| 34 | NT | 41.47 | NT | NT | NT | NT |
| 35 | NT | 11.37 | NT | 445.5 | NT | 563.7 |
| 36 | NT | 18.16 | NT | NT | NT | NT |
| 37 | NT | 7.743 | NT | NT | NT | NT |
| 38 | NT | 11.34 | NT | 88.48 | 763.7 | 137.4 |
| 39 | NT | 19.59 | NT | NT | NT | NT |
| 40 | NT | 39.52 | NT | NT | NT | NT |
| 41 | 6.066 | 3.747 | 61.69 | 190.1 | NT | 58.42 |
| 42 | 17.00 | 6.555 | 100.4 | 339.8 | 173.3 | 201.6 |
| 43 | NT | 6.541 | NT | 344.8 | NT | 135.9 |
| 44 | 15.43 | 5.906 | 36.85 | 85.22 | 638.5 | 290.6 |
| 45 | 17.85 | 5.482 | 35.40 | 83.99 | 924.3 | 883.5 |
| 46 | 0.1916 | 0.02030 | 0.1254 | 3.633 | 39.19 | 95.82 |
| 47 | 1.011 | 0.1681 | 2.066 | 13.49 | 1076 | 731.5 |
| 48 | 0.3380 | 0.08900 | 0.2978 | 22.64 | 227.2 | 320.1 |
| 49 | 0.4963 | 0.1159 | 0.7781 | >1000 | 174.5 | 219.3 |
| 50 | 1.270 | 0.9828 | 3.232 | 66.15 | 18.90 | 98.03 |
| 51 | 2.808 | 0.5320 | 3.164 | 24.92 | 242.2 | 220.5 |
| 52 | 5.445 | 3.090 | 11.54 | 12.09 | 23.87 | 60.00 |
| 53 | 12887 | 2773 | >100000 | 5525 | >100000 | >100000 |
| 54 | 0.4176 | 0.04660 | 0.8827 | 16.12 | 194.7 | 102.7 |
| 55 | 0.9536 | 0.2200 | 3.846 | 9.105 | 183.2 | 56.99 |
| 56 | 1.058 | 0.5782 | 6.299 | 47.98 | 238.3 | 228.5 |
| 57 | 1.134 | 0.1467 | 2.449 | 59.90 | 150.4 | 303.2 |
| 58 | 5.368 | 1.109 | 8.640 | 107.3 | >1000 | 1401 |
| 59 | 15.30 | 2.873 | 27.42 | 211.1 | >1000 | 2166 |
| 60 | 7.970 | 1.459 | 42.36 | 223.4 | >1000 | 797.8 |
| 61 | 3.233 | 1.082 | 39.54 | 27.72 | 198.7 | 226.0 |
| 62 | 0.4924 | 0.1334 | 2.937 | 209.1 | 199.4 | 312.6 |
| 63 | 2.007 | 0.998 | 10.09 | 103.6 | 220.2 | 150.8 |
| 64 | NT | 11.73 | NT | >10000 | NT | 2418.8 |
| 65 | 3.727 | 0.7161 | 4.572 | 35.94 | 263.7 | 284.8 |
| 66 | 0.5280 | 0.6457 | 1.145 | 58.71 | 54.94 | 104.5 |

TABLE 3-continued

| Example No. | SIK1 - AVERAGE Ki (nM) | SIK2 - AVERAGE Ki (nM) | SIK3 - AVERAGE Ki (nM) | Abl - AVERAGE Ki (nM) | EPHA2 - AVERAGE Ki (nM) | Src - AVERAGE Ki (nM) |
|---|---|---|---|---|---|---|
| 67 | 10.36 | 11.817 | 27.18 | 92.94 | 50.40 | 248.8 |
| 68 | 0.5323 | 0.1004 | 0.9926 | 17.80 | 322.8 | 160.3 |
| 69 | 0.2997 | 0.09720 | 0.9862 | 5.140 | >1000 | 35.80 |
| 70 | 0.4391 | 0.1109 | 4.145 | 9.940 | 74.56 | 84.81 |
| 71 | 1.169 | 0.4861 | 5.668 | 15.60 | >1000 | 148.6 |
| 72 | 0.6270 | 0.1175 | 1.289 | 1.834 | 153.2 | 40.07 |
| 73 | 0.4984 | 0.06930 | 0.5280 | 6.454 | 251.1 | 98.11 |
| 74 | 0.4609 | 0.1005 | 0.7647 | 0.5051 | 66.15 | >1000 |
| 75 | 0.6183 | 0.1902 | 1.995 | 10.30 | 120.0 | 45.20 |
| 76 | 0.5163 | 0.1877 | 1.638 | 1.998 | 16.60 | 12.68 |
| 77 | 1.134 | 0.3025 | 3.744 | 26.50 | 80.07 | 196.6 |
| 78 | 0.4328 | 0.09350 | 1.597 | 6.847 | 118.9 | 43.34 |
| 79 | 0.7465 | 0.1011 | 2.239 | 12.66 | 84.11 | 105.8 |
| 80 | 0.9050 | 0.4478 | 4.898 | 15.18 | >1000 | 48.62 |
| 81 | NT | 7.68 | NT | 296.3 | NT | 1351.6 |
| 82 | 1.254 | 0.2686 | 10.28 | 10.36 | >1000 | 93.89 |
| 83 | 0.5504 | 0.3162 | 7.347 | 9.379 | >1000 | 97.84 |
| 84 | 0.4087 | 0.08190 | 2.226 | 49.43 | >1000 | 274.5 |
| 85 | 0.6109 | 0.09110 | 1.623 | 7.382 | 257.6 | 40.25 |
| 86 | 0.6564 | 0.08380 | 1.979 | 6.717 | 22.26 | 34.32 |
| 87 | NT | 9.986 | NT | 666.8 | NT | 574.1 |
| 88 | 6.205 | 4.414 | 72.52 | 355.1 | 124.3 | 193.0 |
| 89 | 53.23 | 5.310 | 129.8 | 83.72 | 1852 | 1041 |
| 90 | NT | 32.33 | NT | NT | NT | NT |
| 91 | NT | 47.64 | NT | NT | NT | NT |
| 92 | NT | 16.82 | NT | NT | NT | NT |
| 93 | NT | 26.82 | NT | NT | NT | NT |
| 94 | NT | 14.41 | NT | NT | NT | NT |
| 95 | NT | 31.59 | NT | NT | NT | NT |
| 96 | NT | 54.50 | NT | NT | NT | NT |
| 97 | NT | 13.00 | NT | NT | NT | NT |
| 98 | NT | 12.78 | NT | 480.8 | NT | 317.4 |
| 99 | 5.621 | 2.914 | 38.83 | 3.042 | 29.25 | 32.85 |
| 100 | 11.77 | 4.411 | 61.39 | 3.648 | 131.4 | 41.35 |
| 101 | 0.6603 | 0.05390 | 0.9155 | 59.13 | >100 | 133.7 |
| 102 | 1.455 | 0.2191 | 5.273 | 24.65 | >1000 | 273.6 |
| 103 | 2.215 | 0.2958 | 5.013 | 97.16 | 188.7 | 142.7 |
| 104 | 43.39 | 4.373 | 176.1 | 45.40 | >1000 | >1000 |
| 105 | NT | 38.09 | NT | 169.3 | NT | >10000 |
| 106 | 123.2 | 19.49 | 552.6 | 28.80 | >10000 | >10000 |
| 107 | 24.57 | 4.460 | 201.3 | 56.37 | >1000 | 616.9 |
| 108 | 29.71 | 2.392 | 130.3 | 100.7 | 2285 | 1876 |
| 109 | 3.760 | 1.602 | 14.94 | 74.82 | >1000 | 3333 |
| 110 | 55.52 | 6.974 | 78.06 | 55.95 | >1000 | >10000 |
| 111 | NT | 83.48 | NT | NT | NT | NT |
| 112 | 91.64 | 14.65 | 430.7 | 124.4 | >10000 | >10000 |
| 113 | 74.93 | 9.815 | 234.4 | 88.94 | >10000 | 1077.7 |
| 114 | 11.99 | 0.6171 | 20.27 | 16.44 | >1000 | 1602 |
| 115 | 0.1826 | 0.02740 | 0.3008 | 0.2433 | 1.076 | 0.9741 |
| 116 | 8.533 | 4.929 | 13.78 | 16.71 | 47.38 | 80.18 |
| 117 | 0.6783 | 0.05460 | 0.4733 | 12.27 | >1000 | >1000 |
| 118 | 10.20 | 6.199 | 77.00 | >10000 | >10000 | >10000 |
| 119 | 4.296 | 3.106 | 24.96 | >1000 | >1000 | >1000 |
| 120 | 3.549 | 2.426 | 22.08 | >1000 | >1000 | >1000 |
| 121 | 178.1 | 45.95 | 488.2 | >10000 | 2647.3 | >10000 |
| 122 | 266.0 | 121.1 | 531.3 | >10000 | >10000 | >10000 |
| 123 | 2.722 | 1.864 | 6.919 | >1000 | 215.8 | >1000 |
| 124 | 0.3381 | 0.04720 | 0.3545 | 6.132 | 48.56 | 17.11 |
| 125 | 2.990 | 1.372 | 4.995 | >1000 | 243.9 | >1000 |
| 126 | 2.952 | 3.014 | 6.350 | 92.69 | 302.1 | 538.9 |
| 127 | 0.6471 | 0.1677 | 1.215 | 7.161 | 149.1 | 30.75 |
| 128 | 0.4091 | 0.1839 | 1.458 | 26.38 | 19.96 | 27.38 |
| 129 | 0.1762 | 0.0784 | 0.3393 | 17.45 | 18.15 | 19.29 |
| 130 | 5.531 | 2.869 | 17.25 | >10000 | 85.32 | 549.2 |
| 131 | 5.395 | 5.59 | 20.91 | 236.6 | 75.61 | 284.8 |
| 132 | 0.3166 | 0.0399 | 0.4497 | 8.626 | 58.84 | 46.32 |
| 133 | 0.348 | 0.0609 | 0.2712 | 1.134 | 34.79 | 6.322 |
| 134 | 0.5579 | 0.1316 | 0.4516 | 1.942 | 25.14 | 12.28 |
| 135 | 0.3608 | 0.0936 | 0.3125 | 7.99 | 30.69 | 65.26 |
| 136 | 1.896 | 1.1 | 8.893 | 27.55 | 259.9 | 147.2 |
| 137 | 0.296 | 0.0693 | 0.5099 | 22.54 | 9.217 | 18.73 |
| 138 | 3.703 | 3.123 | 15.65 | 544.8 | 93.42 | 332.9 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

REFERENCES

1. Ahmed A A, Lu Z, Jennings N B, Etemadmoghadam D, Capalbo L, Jacamo R O, et al. SIK2 is a centrosome kinase required for bipolar mitotic spindle formation that provides a potential target for therapy in ovarian cancer. Cancer Cell 2010; 18:109-21.
2. Dentin R, Liu Y, Koo S H, Hedrick S, Vargas T, Heredia J, et al. Insulin modulates gluconeogenesis by inhibition of the coactivator TORC2. Nature 2007; 449:366-9.
3. Horike N, Kumagai A, Shimono Y, Onishi T, Itoh Y, Sasaki T, et al. Downregulation of SIK2 expression promotes the melanogenic program in mice. Pigment Cell Melanoma Res 2010; 23:809-19.
4. Sasaki T, Takemori H, Yagita Y, Terasaki Y, Uebi T, Horike N, et al. SIK2 is a key regulator for neuronal survival after ischemia via TORC1-CREB. Neuron 2011; 69:106-19.
5. Bricambert J, Miranda J, Benhamed F, Girard J, Postic C, Dentin R. Salt inducible kinase 2 links transcriptional coactivator p300 phosphorylation to the prevention of ChREBP-dependent hepatic steatosis in mice. J Clin Invest 2010; 120:4316-31.
6. Nagel S, Leich E, Quentmeier H, Meyer C, Kaufmann M, Zaborski M, et al. Amplification at 11q23 targets protein kinase SIK2 in diffuse large B-cell lymphoma. Leuk Lymphoma 2010; 51:881-91.
7. Imielinski M, Berger A H, Hammerman P S, Hernandez B, Pugh T J, Hodis E, et al. Mapping the hallmarks of lung adenocarcinoma with massively parallel sequencing. Cell 2012; 150:1107-20.
8. Bon H, Wadhwa K, Schreiner A, Osborne M, Carroll T, Ramos-Montoya A, et al. Salt-inducible kinase 2 regulates mitotic progression and transcription in prostate cancer. Mol Cancer Res 2015; 13:620-35.
9. Charoenfuprasert S, Yang Y Y, Lee Y C, Chao K C, Chu P Y, Lai C R, et al. Identification of salt-inducible kinase 3 as a novel tumor antigen associated with tumorigenesis of ovarian cancer. *Oncogene* (2011) 30:3570-84. doi: 10.1038/onc.2011.77
10. Cheng H, Liu P, Wang Z C, Zou L, Santiago S, Garbitt V, et al. SIK1 couples LKB1 to p53-dependent anoikis and suppresses metastasis. *Sci Signal*. (2009) 2:ra35. doi: 10.1126/scisignal.2000369
11. Imielinski M, Berger A H, Hammerman P S, Hernandez B, Pugh T J, Hodis E, et al. Mapping the hallmarks of lung adenocarcinoma with massively parallel sequencing. *Cell* (2012) 150:1107-20. doi: 10.1016/j.cell.2012.08.029
12. Miranda F, Mannion D, Liu S, Zheng Y, Mangala L S, Redondo C, et al. Salt-inducible kinase 2 couples ovarian cancer cell metabolism with survival at the adipocyte-rich metastatic niche. *Cancer Cell* (2016) 30:273-89. doi: 10.1016/j.ccell.2016.06.020
13. Tarumoto Y, Lu B, Somerville T D D, Huang Y H, Milazzo J P, Wu X S, et al. LKB1, Salt-inducible kinases, and MEF2C are linked dependencies in acute myeloid leukemia. *Mol Cell* (2018) 69:1017-27 e6. doi: 10.1016/j.molcel.2018.02.011
14. Patra K C, Kato Y, Mizukami Y, Widholz S, Boukhali M, Revenco I, et al. Mutant GNAS drives pancreatic tumourigenesis by inducing PKA-mediated SIK suppression and reprogramming lipid metabolism. *Nat Cell Biol*. (2018) 20:811-22. doi: 10.1038/s41556-018-0122-3

The invention claimed is:

1. A compound of formula (IVa), (IVb) or (IVc), or a salt or solvate thereof:

(IVa)

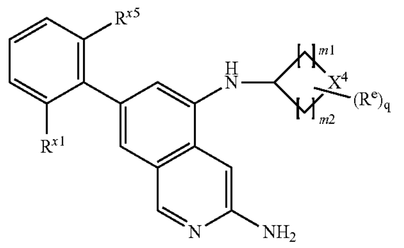

(IVb)

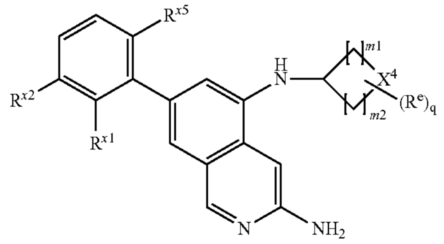

(IVc)

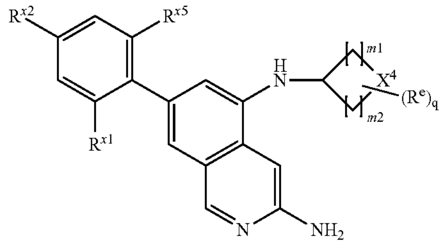

wherein $X^4$ is nitrogen;

m1 and m2 are numbers independently selected from 1, 2, 3 and 4;

q is a number independently selected from 1, 2 and 3;

$R^e$ is selected from hydrogen, halogen, CN, =O, $(CH_2)_y$OH, $C_{1-6}$ alkyl, $(CH_2)_yC_{1-6}$ alkoxy, $(CH_2)_yC_{1-6}$ haloalkyl, $(CH_2)_yC_{1-6}$ haloalkoxy, $(CH_2)_yNH_2$, $(CH_2)_yNHR^q$, $(CH_2)_yN(R^q)_2$, $(CH_2)_yNHCO(R^q)$, $(CH_2)_yCONH_2$, $(CH_2)_yCONH(R^q)$, and $(CH_2)_yCON(R^q)_2$, and where each $R^q$ is independently selected from $C_{1-4}$ alkyl which is optionally substituted with one or more groups selected from halogen, OH, $NH_2$, NHMe, $NMe_2$, and $C_{1-3}$ alkoxy; and where $_y$ is a number between 0 and 3;

$R^{x1}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl —C(=O)$R^h$, —C(=O)O$R^j$, —C(=O)N$R^jR^k$, —C(O)C(=O)$R^h$, —N$R^jR^k$, —N$R^j$C(=O)$R^h$, —N$R^j$C(=O)O$R^k$, —N$R^j$C(=O) N$R^jR^k$, —O$R^j$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$, —S(=O)$_2$N$R^jR^k$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl; and $R^{x2}$ is selected from hydroxyl, halogen, CN, $C_{1-6}$ haloalkyl, $C_{1-6}$ haloalkoxy, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl-C(=O)$R^h$, —C(=O)O$R^j$, —C(O)C(=O)$R^h$, —N$R^jR^k$, —N$R^j$C(=O)O$R^k$, —S$R^j$, —OC(=O)$R^h$, —OC(=O)N$R^jR^k$, —OC(=O)O$R^j$, —S(=O)$_2R^h$, —S(=O)$R^h$, —OS(=O)$R^h$, —OS(=O)$_2R^h$, —OS(=O)$_2$O$R^j$, —S(=O)N$R^jR^k$, —OS(=O)$_2$N$R^jR^k$; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, halogen, =O, CN, $C_{1-6}$ haloalkyl, $C_{1-6}$ haloalkoxy, $C_{3-6}$ cycloalkyl, N$R^jR^k$, $C_{1-6}$ alkyl, O—$C_{1-6}$ alkyl, and phenyl;

where each $R^h$, $R^j$ and $R^k$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from halogen, CN, $C_{1-6}$ alkyl, $C_{1-6}$ alkoxy, $NH_2$, NH ($C_{1-3}$ alkyl) and N ($C_{1-3}$ alkyl)$_2$; or $R^j$ and $R^k$ when attached to the same atom and together with the atom to which they are attached combine to provide a 3-7 membered heterocycloalkyl which is optionally substituted by one or more groups selected from halogen, hydroxy, $C_{1-3}$ alkyl, $C_{1-3}$ alkoxy, =O and CN; or a compound selected from:

| Example | Structure |
|---|---|
| E2 | 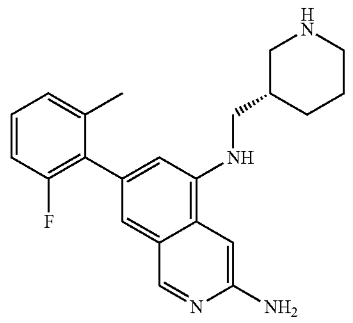 [SMILES: Cc1cccc(F)c1-c1cc(NC[C@H]2CCCNC2)c2cc(N)ncc2c1] |
| E5 | 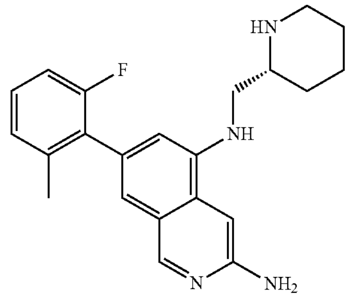 [SMILES: Cc1cccc(F)c1-c1cc(NC[C@H]2CCCCN2)c2cc(N)ncc2c1] |
| E6 | 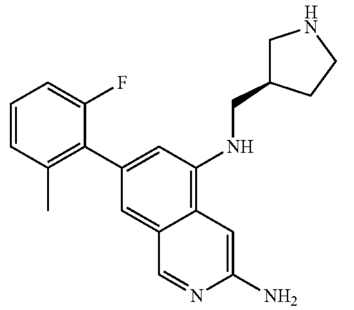 [SMILES: Cc1cccc(F)c1-c1cc(NC[C@@H]2CCNC2)c2cc(N)ncc2c1] |
| E8 | 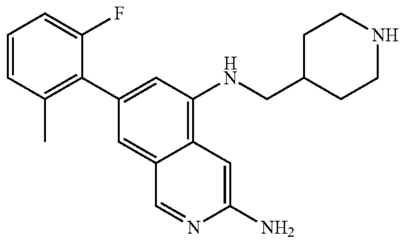 |
| E9 | 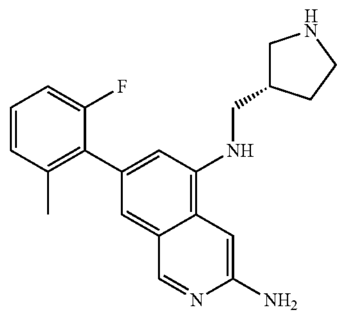 [SMILES: Cc1cccc(F)c1-c1cc(NC[C@H]2CCNC2)c2cc(N)ncc2c1] |

-continued
E10
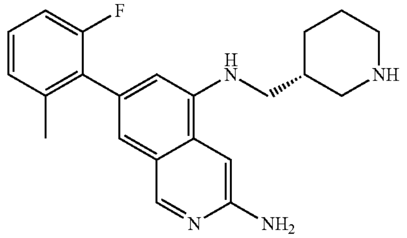 [SMILES: Cc1cccc(F)c1-c1cc(NC[C@@H]2CCCNC2)c2cc(N)ncc2c1]
E11
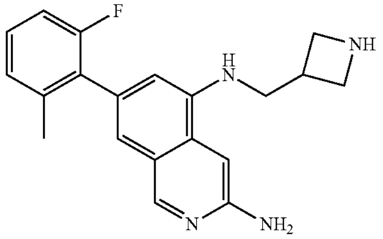
E12
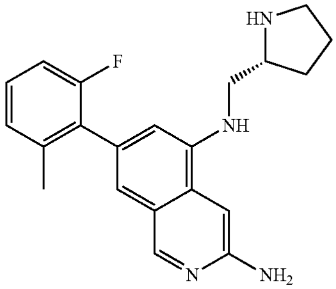 [SMILES: Cc1cccc(F)c1-c1cc(NC[C@H]2CCCN2)c2cc(N)ncc2c1]
E13
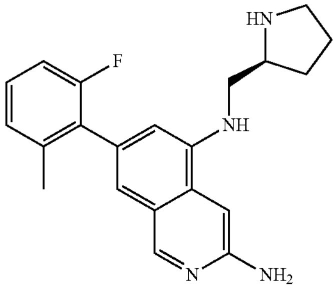 [SMILES: Cc1cccc(F)c1-c1cc(NC[C@@H]2CCCN2)c2cc(N)ncc2c1]
E14
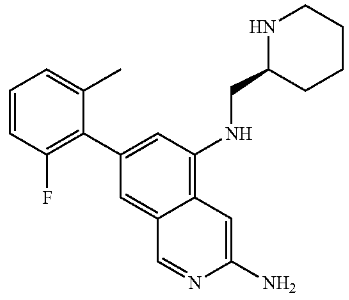 [SMILES: Cc1cccc(F)c1-c1cc(NC[C@@H]2CCCCN2)c2cc(N)ncc2c1]
E15
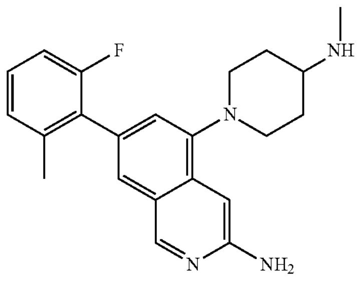 [SMILES: CNC1CCN(c2cc(-c3c(C)cccc3F)cc3cnc(N)cc23)CC1]
-continued
E16
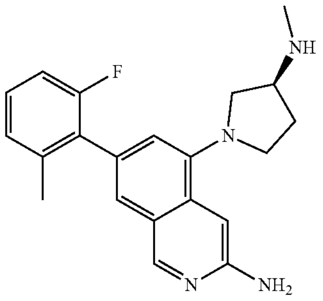 [SMILES: CN[C@H]1CCN(c2cc(-c3c(C)cccc3F)cc3cnc(N)cc23)C1]
E18
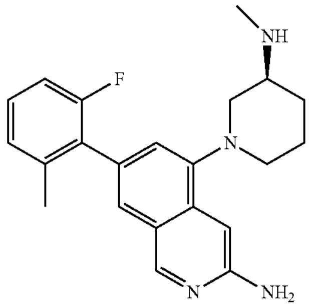 [SMILES: CN[C@H]1CCCN(c2cc(-c3c(C)cccc3F)cc3cnc(N)cc23)C1]
E19
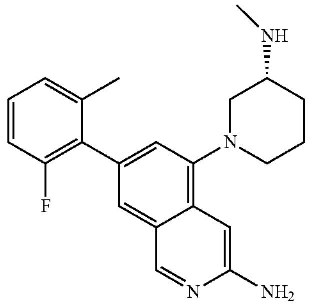 [SMILES: CN[C@@H]1CCCN(c2cc(-c3c(C)cccc3F)cc3cnc(N)cc23)C1]
E21
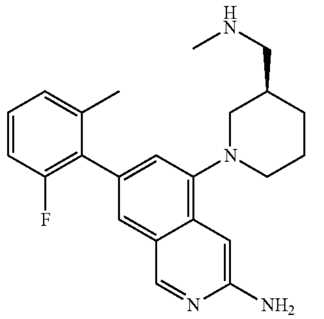 [SMILES: CNC[C@H]1CCCN(c2cc(-c3c(C)cccc3F)cc3cnc(N)cc23)C1]
E22
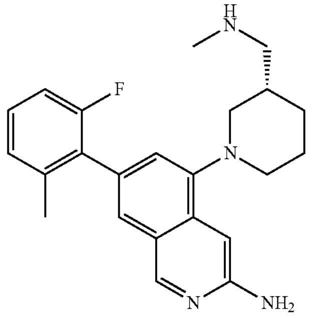

-continued
E24
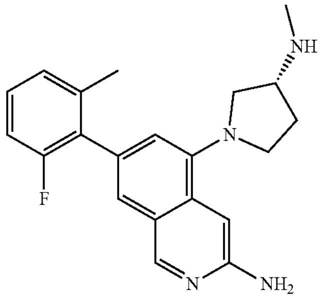 [SMILES: CN[C@@H]1CCN(c2cc(-c3c(C)cccc3F)cc3cnc(N)cc23)C1]
E27
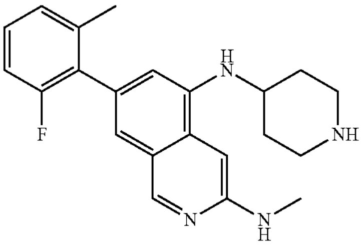 [SMILES: CNc1cc2c(NC3CCNCC3)cc(-c3c(C)cccc3F)cc2cn1]
E28
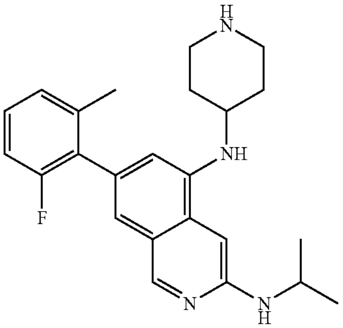 [SMILES: Cc1cccc(F)c1-c1cc(NC2CCNCC2)c2cc(NC(C)C)ncc2c1]
E29
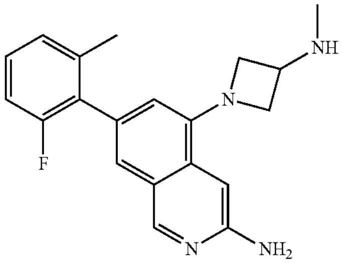 [SMILES: CNC1CN(c2cc(-c3c(C)cccc3F)cc3cnc(N)cc23)C1]
E44
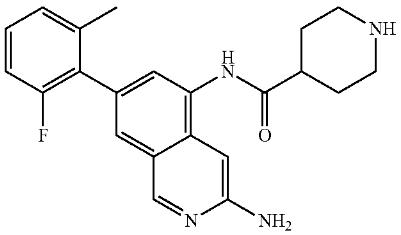 [SMILES: Cc1cccc(F)c1-c1cc(NC(=O)C2CCNCC2)c2cc(N)ncc2c1]
E45
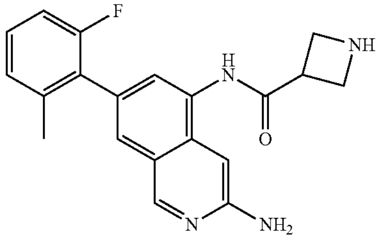 [SMILES: Cc1cccc(F)c1-c1cc(NC(=O)C2CNC2)c2cc(N)ncc2c1]
-continued
E46
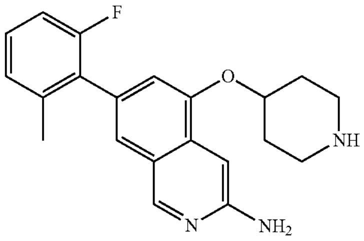 [SMILES: Cc1cccc(F)c1-c1cc(OC2CCNCC2)c2cc(N)ncc2c1]
E47
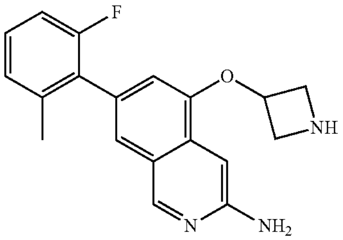 [SMILES: Cc1cccc(F)c1-c1cc(OC2CNC2)c2cc(N)ncc2c1]
E48
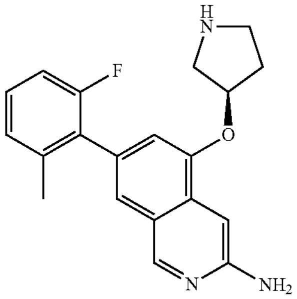 [SMILES: Cc1cccc(F)c1-c1cc(O[C@@H]2CCNC2)c2cc(N)ncc2c1]
E52
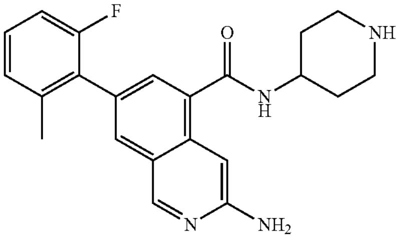
E55
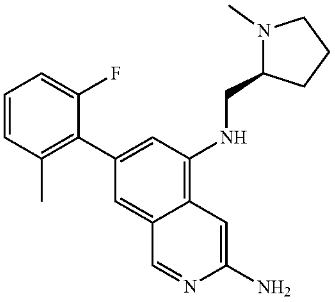 [SMILES: Cc1cccc(F)c1-c1cc(NC[C@@H]2CCCN2C)c2cc(N)ncc2c1]
E56
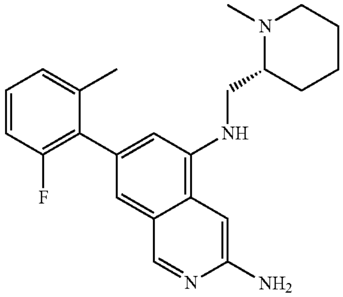 [SMILES: Cc1cccc(F)c1-c1cc(NC[C@H]2CCCCN2C)c2cc(N)ncc2c1]

-continued
E57
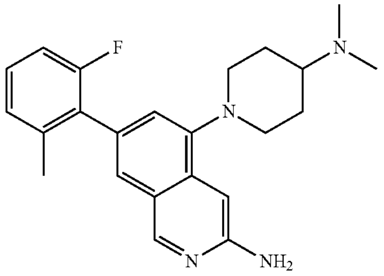 [SMILES: Cc1cccc(F)c1-c1cc(N2CCC(N(C)C)CC2)c2cc(N)ncc2c1]
E58
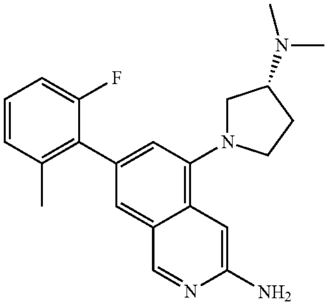 [SMILES: Cc1cccc(F)c1-c1cc(N2CC[C@@H](N(C)C)C2)c2cc(N)ncc2c1]
E59
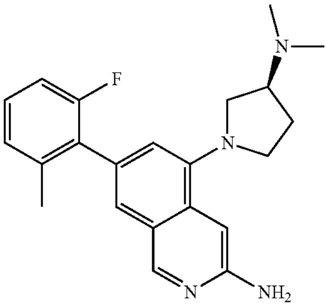 [SMILES: Cc1cccc(F)c1-c1cc(N2CC[C@H](N(C)C)C2)c2cc(N)ncc2c1]
E60
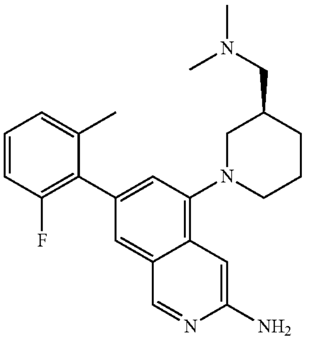 [SMILES: Cc1cccc(F)c1-c1cc(N2CCC[C@H](CN(C)C)C2)c2cc(N)ncc2c1]
E61
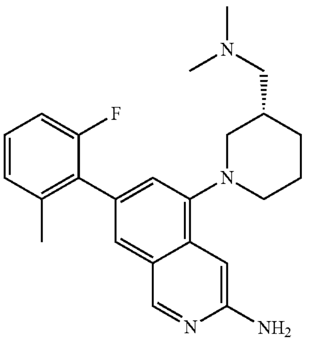 [SMILES: Cc1cccc(F)c1-c1cc(N2CCC[C@@H](CN(C)C)C2)c2cc(N)ncc2c1]
-continued
E71
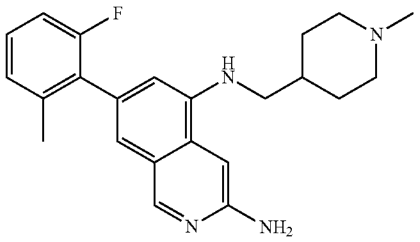 [SMILES: Cc1cccc(F)c1-c1cc(NCC2CCN(C)CC2)c2cc(N)ncc2c1]
E72
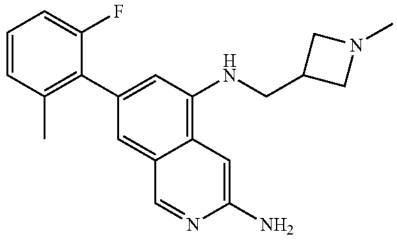 [SMILES: Cc1cccc(F)c1-c1cc(NCC2CN(C)C2)c2cc(N)ncc2c1]
E73
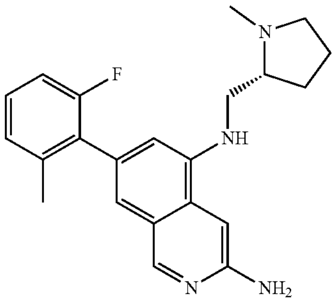 [SMILES: Cc1cccc(F)c1-c1cc(NC[C@H]2CCCN2C)c2cc(N)ncc2c1]
E74
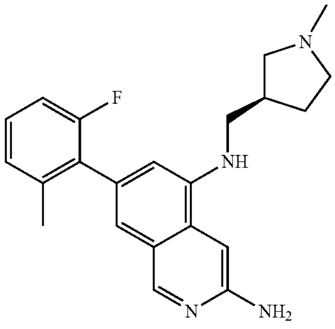 [SMILES: Cc1cccc(F)c1-c1cc(NC[C@@H]2CCN(C)C2)c2cc(N)ncc2c1]
E75
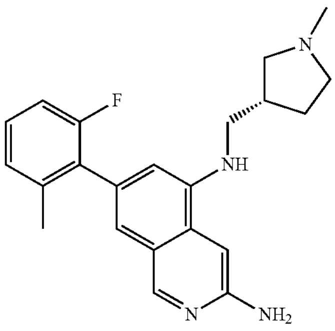 [SMILES: Cc1cccc(F)c1-c1cc(NC[C@H]2CCN(C)C2)c2cc(N)ncc2c1]

-continued
E76
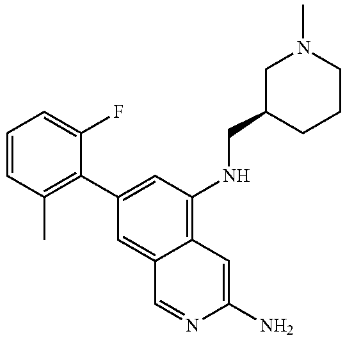 [SMILES: Cc1cccc(F)c1-c1cc(NC[C@@H]2CCCN(C)C2)c2cc(N)ncc2c1]
E77
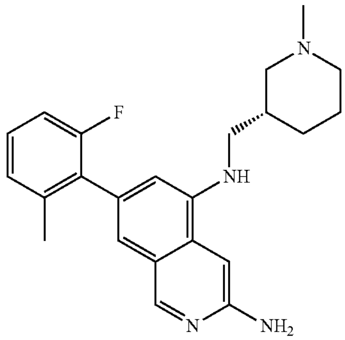 [SMILES: Cc1cccc(F)c1-c1cc(NC[C@H]2CCCN(C)C2)c2cc(N)ncc2c1]
E78
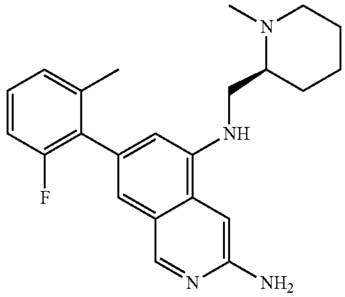 [SMILES: Cc1cccc(F)c1-c1cc(NC[C@@H]2CCCCN2C)c2cc(N)ncc2c1]
E79
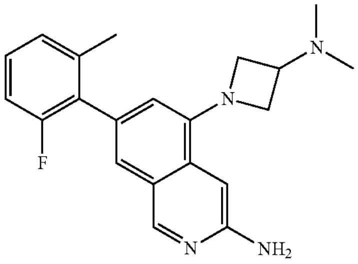 [SMILES: Cc1cccc(F)c1-c1cc(N2CC(N(C)C)C2)c2cc(N)ncc2c1]
E81
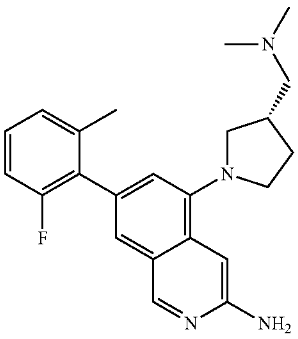 [SMILES: Cc1cccc(F)c1-c1cc(N2CC[C@@H](CN(C)C)C2)c2cc(N)ncc2c1]
-continued
E82
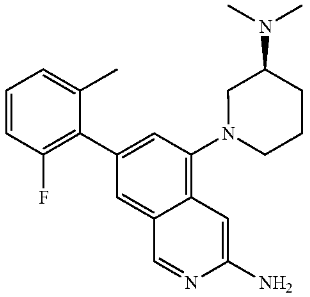 [SMILES: Cc1cccc(F)c1-c1cc(N2CCC[C@H](N(C)C)C2)c2cc(N)ncc2c1]
E83
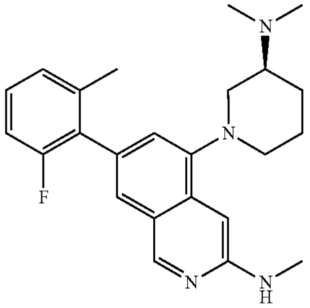 [SMILES: CNc1cc2c(N3CCC[C@H](N(C)C)C3)cc(-c3c(C)cccc3F)cc2cn1]
E84
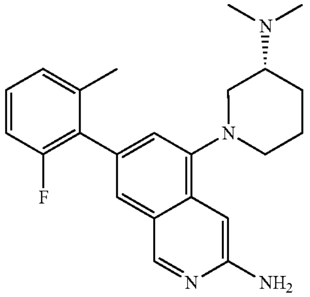 [SMILES: Cc1cccc(F)c1-c1cc(N2CCC[C@@H](N(C)C)C2)c2cc(N)ncc2c1]
E99
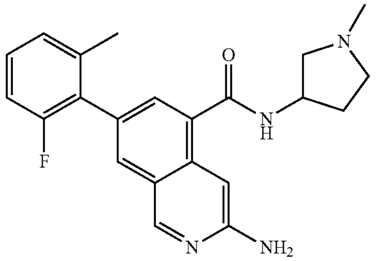 [SMILES: Cc1cccc(F)c1-c1cc(C(=O)NC2CCN(C)C2)c2cc(N)ncc2c1]
E100
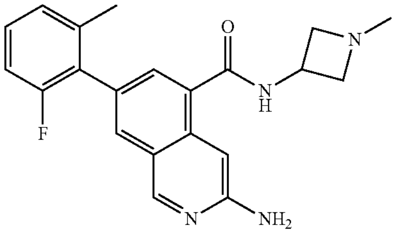 [SMILES: Cc1cccc(F)c1-c1cc(C(=O)NC2CN(C)C2)c2cc(N)ncc2c1]
E101
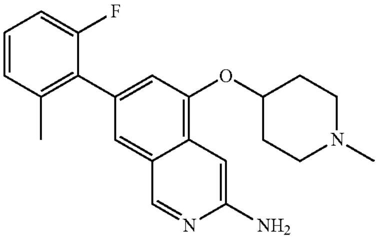

-continued
E102
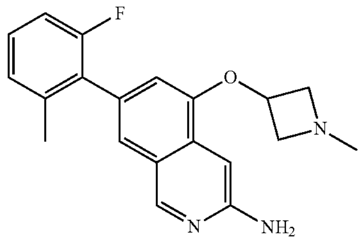 [SMILES: Cc1cccc(F)c1-c1cc(OC2CN(C)C2)c2cc(N)ncc2c1]
E104
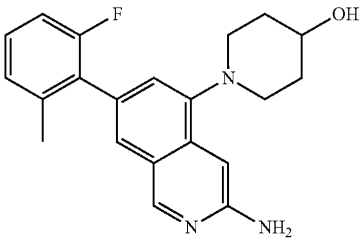 [SMILES: Cc1cccc(F)c1-c1cc(N2CCC(O)CC2)c2cc(N)ncc2c1]
E105
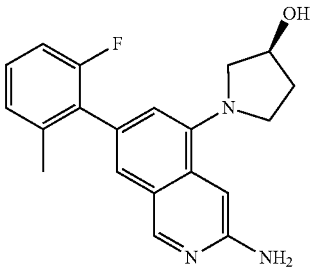 [SMILES: Cc1cccc(F)c1-c1cc(N2CC[C@H](O)C2)c2cc(N)ncc2c1]
E106
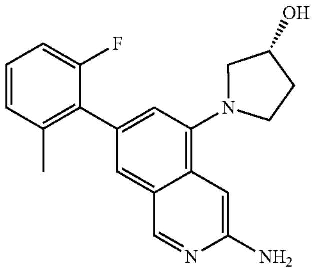 [SMILES: Cc1cccc(F)c1-c1cc(N2CC[C@@H](O)C2)c2cc(N)ncc2c1]
E107
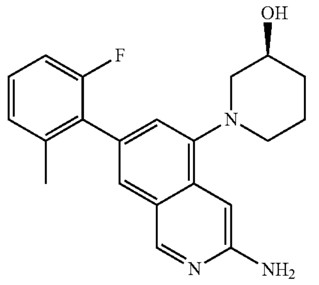 [SMILES: Cc1cccc(F)c1-c1cc(N2CCC[C@H](O)C2)c2cc(N)ncc2c1]
E108
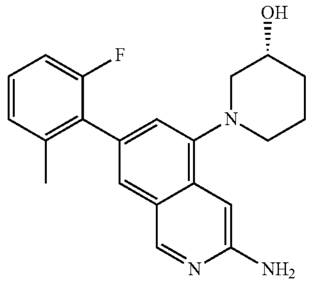 [SMILES: Cc1cccc(F)c1-c1cc(N2CCC[C@@H](O)C2)c2cc(N)ncc2c1]
-continued
E109
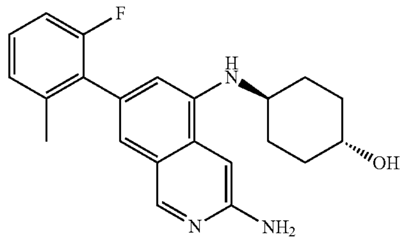 [SMILES: Cc1cccc(F)c1-c1cc(N[C@H]2CC[C@H](O)CC2)c2cc(N)ncc2c1]
E110
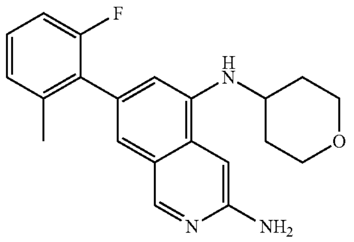 [SMILES: Cc1cccc(F)c1-c1cc(NC2CCOCC2)c2cc(N)ncc2c1]
E111
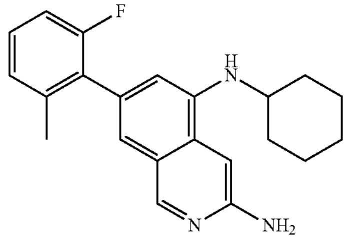 [SMILES: Cc1cccc(F)c1-c1cc(NC2CCCCC2)c2cc(N)ncc2c1]
E112
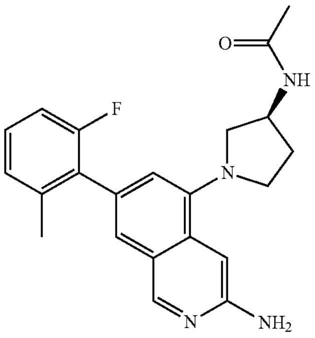 [SMILES: CC(=O)N[C@H]1CCN(c2cc(-c3c(C)cccc3F)cc3cnc(N)cc23)C1]
E113
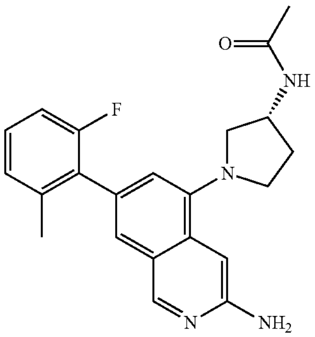 [SMILES: CC(=O)N[C@@H]1CCN(c2cc(-c3c(C)cccc3F)cc3cnc(N)cc23)C1]
E114
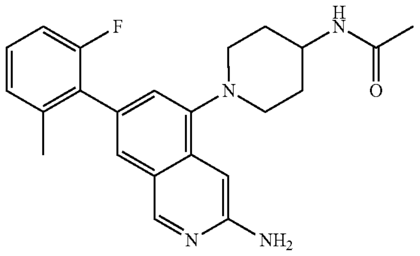 [SMILES: CC(=O)NC1CCN(c2cc(-c3c(C)cccc3F)cc3cnc(N)cc23)CC1]

-continued

E116

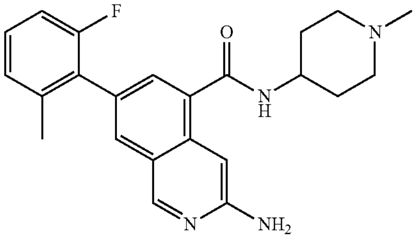

E118

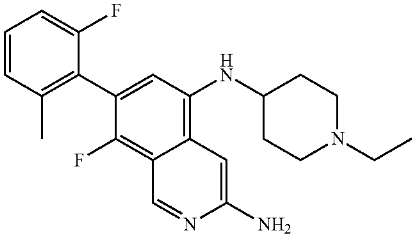

E119

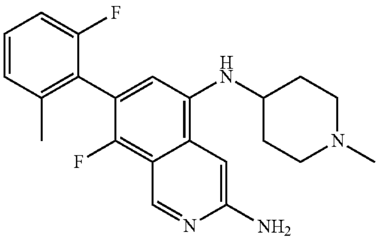

E120

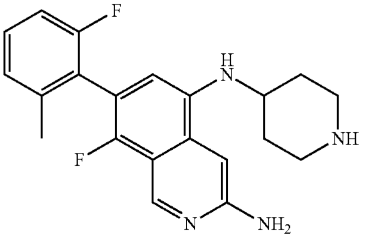 [SMILES: Cc1cccc(F)c1-c1cc(NC2CCNCC2)c2cc(N)ncc2c1F]

E134

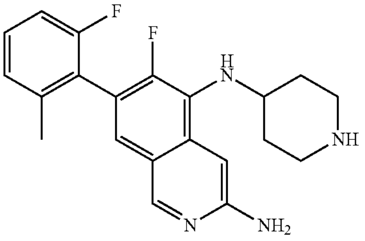

E135

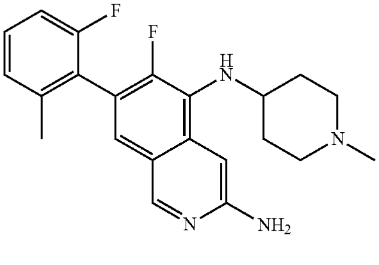

-continued

E133

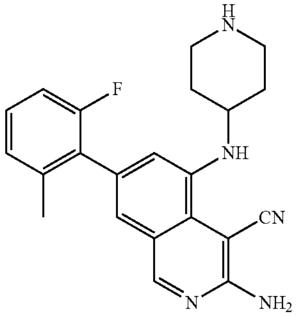 [SMILES: Cc1cccc(F)c1-c1cc(NC2CCNCC2)c2c(C#N)c(N)ncc2c1]

E136

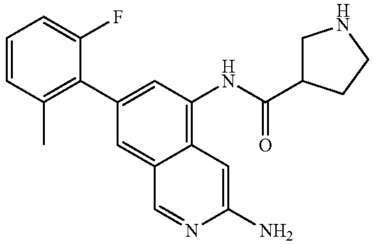 [SMILES: Cc1cccc(F)c1-c1cc(NC(=O)C2CCNC2)c2cc(N)ncc2c1]

| Example | Name |
|---|---|
| E2 | 7-(2-fluoro-6-methyl-phenyl)-N5-[[(3S)- 3-piperidyl]methyl]isoquinoline-3,5-diamine |
| E5 | 7-(2-fluoro-6-methyl-phenyl)-N5-[[(2R)- 2-piperidyl]methyl]isoquinoline-3,5-diamine |
| E6 | 7-(2-fluoro-6-methyl-phenyl)-N5-[[(3R)- pyrrolidin-3-yl]methyl]isoquinoline-3,5-diamine |
| E8 | 7-(2-fluoro-6-methyl-phenyl)-N5-(4- piperidylmethyl)isoquinoline-3,5-diamine |
| E9 | 7-(2-fluoro-6-methyl-phenyl)-N5-[[(3S)- pyrrolidin-3-yl]methyl]isoquinoline-3,5-diamine |
| E10 | 7-(2-fluoro-6-methyl-phenyl)-N5-[[(3R)- 3-piperidyl]methyl]isoquinoline-3,5-diamine |
| E11 | N5-(azetidin-3-ylmethyl)-7-(2-fluoro-6- methyl-phenyl)isoquinoline-3,5-diamine |
| E12 | 7-(2-fluoro-6-methyl-phenyl)-N5-[[(2R)- pyrrolidin-2-yl]methyl]isoquinoline-3,5-diamine |
| E13 | 7-(2-fluoro-6-methyl-phenyl)-N5-[[(2S)- pyrrolidin-2-yl]methyl]isoquinoline-3,5-diamine |
| E14 | 7-(2-fluoro-6-methyl-phenyl)-N5-[[(2S)- 2-piperidyl]methyl]isoquinoline-3,5-diamine |
| E15 | 7-(2-fluoro-6-methyl-phenyl)-5-[4- (methylamino)-1-piperidyl]isoquinolin-3-amine |
| E16 | 7-(2-fluoro-6-methyl-phenyl)-5-[(3S)-3-(methylamino)pyrrolidin-1-yl]isoquinolin-3-amine |
| E18 | 7-(2-fluoro-6-methyl-phenyl)-5-[(3S)-3- (methylamino)-1-piperidyl]isoquinolin-3-amine |
| E19 | 7-(2-fluoro-6-methyl-phenyl)-5-[(3R)-3- (methylamino)-1-piperidyl]isoquinolin-3-amine |
| E21 | 7-(2-fluoro-6-methyl-phenyl)-5-[(3R)-3-(methylaminomethyl)-1-piperidyl]isoquinolin-3-amine |
| E22 | 7-(2-fluoro-6-methyl-phenyl)-5-[(3S)-3- (methylaminomethyl)-1-piperidyl]isoquinolin-3-amine |
| E24 | 7-(2-fluoro-6-methyl-phenyl)-5-[(3R)-3-(methylamino)pyrrolidin-1-yl]isoquinolin-3-amine |
| E27 | 7-(2-fluoro-6-methyl-phenyl)-N3-methyl- N5-(4-piperidyl)isoquinoline-3,5-diamine |
| E28 | 7-(2-fluoro-6-methyl-phenyl)-N3- isopropyl-N5-(4-piperidyl)isoquinoline-3,5-diamine |
| E29 | 7-(2-fluoro-6-methyl-phenyl)-5-[3- (methylamino)azetidin-1-yl]isoquinolin-3-amine |
| E44 | N-[3-amino-7-(2-fluoro-6-methyl- phenyl)-5-isoquinolyl]piperidine-4-carboxamide |
| E45 | N-[3-amino-7-(2-fluoro-6-methyl- phenyl)-5-isoquinolyl]azetidine-3-carboxamide |
| E46 | 7-(2-fluoro-6-methyl-phenyl)-5-(4- piperidyloxy)isoquinolin-3-amine |
| E47 | 5-(azetidin-3-yloxy)-7-(2-fluoro-6- methyl-phenyl)isoquinolin-3-amine |
| E48 | 7-(2-fluoro-6-methyl-phenyl)-5-[(3R)- pyrrolidin-3-yl]oxy-isoquinolin-3-amine |
| E52 | 3-amino-7-(2-fluoro-6-methyl-phenyl)-N- (4-piperidyl)isoquinoline-5-carboxamide |
| E55 | 7-(2-fluoro-6-methyl-phenyl)-N5-[[(2S)- 1-methylpyrrolidin-2-yl]methyl]isoquinoline-3,5-diamine |

-continued

| | |
|---|---|
| E56 | 7-(2-fluoro-6-methyl-phenyl)-N5-[[(2R)- 1-methyl-2-piperidyl]methyl]isoquinoline-3,5-diamine |
| E57 | 5-[4-(dimethylamino)-1-piperidyl]-7-(2- fluoro-6-methyl-phenyl)isoquinolin-3-amine |
| E58 | 5-[(3R)-3-(dimethylamino)pyrrolidin-1- yl]-7-(2-fluoro-6-methyl-phenyl)isoquinolin-3-amine |
| E59 | 5-[(3S)-3-(dimethylamino)pyrrolidin-1- yl]-7-(2-fluoro-6-methyl-phenyl)isoquinolin-3-amine |
| E60 | 5-[(3R)-3-[(dimethylamino)methyl]-1- piperidyl]-7-(2-fluoro-6-methyl-phenyl)isoquinolin-3-amine |
| E61 | 5-[(3S)-3-[(dimethylamino)methyl]-1- piperidyl]-7-(2-fluoro-6-methyl-phenyl)isoquinolin-3-amine |
| E71 | 7-(2-fluoro-6-methyl-phenyl)-N5-[(1- methyl-4-piperidyl)methyl]isoquinoline-3,5-diamine |
| E72 | 7-(2-fluoro-6-methyl-phenyl)-N5-[(1- methylazetidin-3-yl)methyl]isoquinoline-3,5-diamine |
| E73 | 7-(2-fluoro-6-methyl-phenyl)-N5-[[(2R)- 1-methylpyrrolidin-2-yl]methyl]isoquinoline-3,5-diamine |
| E74 | 7-(2-fluoro-6-methyl-phenyl)-N5-[[(3S)- 1-methylpyrrolidin-3-yl]methyl]isoquinoline-3,5-diamine |
| E75 | 7-(2-fluoro-6-methyl-phenyl)-N5-[[(3R)- 1-methylpyrrolidin-3-yl]methyl]isoquinoline-3,5-diamine |
| E76 | 7-(2-fluoro-6-methyl-phenyl)-N5-[(3S)- 1-methyl-3-piperidyl]methyl]isoquinoline-3,5-diamine |
| E77 | 7-(2-fluoro-6-methyl-phenyl)-N5-[[(3R)- 1-methyl-3-piperidyl]methyl]isoquinoline-3,5-diamine |
| E78 | 7-(2-fluoro-6-methyl-phenyl)-N5-[[(2S)- 1-methyl-2-piperidyl]methyl]isoquinoline-3,5-diamine |
| E79 | 5-[3-(dimethylamino)azetidin-1-yl]-7-(2- fluoro-6-methyl-phenyl)isoquinolin-3-amine |
| E81 | 5-[(3S)-3- [(dimethylamino)methyl]pyrrolidin-1-yl]-7-(2-fluoro-6-methyl-phenyl)isoquinolin-3-amine |
| E82 | 5-[(3S)-3-(dimethylamino)-1-piperidyl]- 7-(2-fluoro-6-methyl-phenyl)isoquinolin-3-amine |
| E83 | 5-[(3S)-3-(dimethylamino)-1-piperidyl]- 7-(2-fluoro-6-methyl-phenyl)-N-methyl-isoquinolin-3-amine |
| E84 | 5-[(3R)-3-(dimethylamino)-1-piperidyl]- 7-(2-fluoro-6-methyl-phenyl)isoquinolin-3-amine |
| E99 | 3-amino-7-(2-fluoro-6-methyl-phenyl)-N- (1-methylpyrrolidin-3-yl)isoquinoline-5-carboxamide |
| E100 | 3-amino-7-(2-fluoro-6-methyl-phenyl)-N- (1-methylazetidin-3-yl)isoquinoline-5-carboxamide |
| E101 | 7-(2-fluoro-6-methyl-phenyl)-5-[(1- methyl-4-piperidyl)oxy]isoquinolin-3-amine |
| E102 | 7-(2-fluoro-6-methyl-phenyl)-5-(1- methylazetidin-3 -yl)oxy-isoquinolin-3-amine |
| E104 | 1-[3-amino-7-(2-fluoro-6-methyl-phenyl)- 5-isoquinolyl]piperidin-4-ol |
| E105 | (3S)-1-[3-amino-7-(2-fluoro-6-methyl- phenyl)-5-isoquinolyl]pyrrolidin-3-ol |
| E106 | (3R)-1-[3-amino-7-(2-fluoro-6-methyl- phenyl)-5-isoquinolyl]pyrrolidin-3-ol |
| E107 | (3S)-1-[3-amino-7-(2-fluoro-6-methyl- phenyl)-5-isoquinolyl]piperidin-3-ol |
| E108 | (3R)-1-[3-amino-7-(2-fluoro-6-methyl- phenyl)-5-isoquinolyl]piperidin-3-ol |
| E109 | 4-[[3-amino-7-(2-fluoro-6-methyl- phenyl)-5-isoquinolyl]amino]cyclohexanol |
| E110 | 7-(2-fluoro-6-methyl-phenyl)-N5- tetrahydropyran-4-yl-isoquinoline-3,5-diamine |
| E111 | N5-cyclohexyl-7-(2-fluoro-6-methyl- phenyl)isoquinoline-3,5-diamine |
| E112 | N-[(3S)-1-[3-amino-7-(2-fluoro-6- methyl-phenyl)-5-isoquinolyl]pyrrolidin-3-yl]acetamide |
| E113 | N-[(3R)-1-[3-amino-7-(2-fluoro-6- methyl-phenyl)-5-isoquinolyl]pyrrolidin-3-yl]acetamide |
| E114 | N-[1-[3-amino-7-(2-fluoro-6-methyl- phenyl)-5-isoquinolyl]-4-piperidyl]acetamide |
| E116 | 3-amino-7-(2-fluoro-6-methyl-phenyl)-N- (1-methyl-4-piperidyl)isoquinoline-5-carboxamide |
| E118 | N5-(1-ethyl-4-piperidyl)-8-fluoro-7-(2- fluoro-6-methyl-phenyl)isoquinoline-3,5-diamine |
| E119 | 8-fluoro-7-(2-fluoro-6-methyl-phenyl)- N5-(1-methyl-4-piperidyl)isoquinoline-3,5-diamine |
| E120 | 8-fluoro-7-(2-fluoro-6-methyl-phenyl)- N5-(4-piperidyl)isoquinoline-3,5-diamine |
| E134 | 6-fluoro-7-(2-fluoro-6-methyl-phenyl)- N5-(4-piperidyl)isoquinoline-3,5-diamine |
| E135 | 6-fluoro-7-(2-fluoro-6-methyl-phenyl)- N5-(1-methyl-4-piperidyl)isoquinoline-3,5-diamine |
| E133 | 3-amino-7-(2-fluoro-6-methyl-phenyl)-5- (4-piperidylamino)isoquinoline-4-carbonitrile |
| E136 | N-[3-amino-7-(2-fluoro-6-methyl- phenyl)-5-isoquinolyl]pyrrolidine-3-carboxamide; |

or a salt or solvate of any one thereof.

2. The compound according to claim 1 which is selected from compounds of formula (IVa), (IVb) and (IVc):

(IVa)

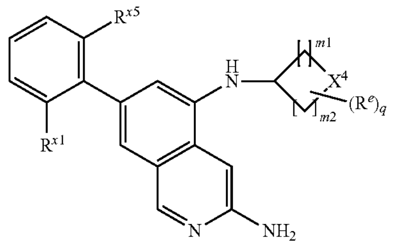

(IVb)

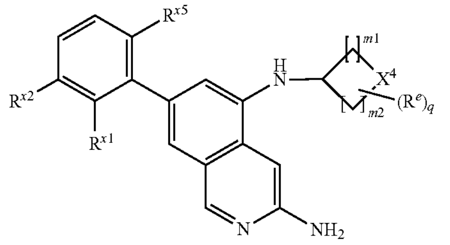

(IVc)

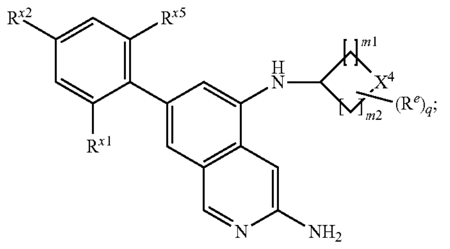

or a salt or solvate thereof.

3. The compound according to claim 1 selected from compounds of sub-formulae (IVb) and (IVc);

or a salt or solvate thereof.

4. The compound of claim 1 selected from compounds of sub-formula (IVa); or a salt or solvate thereof.

5. The compound according to claim 1, or a salt or solvate thereof, wherein m1 and m2 are numbers independently selected from 1, 2 and 3.

6. The compound according to claim 1, or a salt or solvate thereof, wherein m1 and m2 are both 2.

7. The compound according to claim 1, or a salt or solvate thereof, wherein q is 1.

8. The compound according to claim 1, or a salt or solvate thereof, wherein $R^e$ is selected from hydrogen, $C_{1-4}$ alkyl, $NH_2$, NH ($C_{1-4}$ alkyl), and N ($C_{1-4}$ alkyl)$_2$.

9. The compound according to claim 1, or a salt or solvate thereof, wherein $R^e$ is selected from hydrogen, methyl, ethyl, $NH_2$, NHMe, and $NMe_2$.

10. The compound according to claim 1, or a salt or solvate thereof, wherein $R^{x1}$ and $R^{x5}$ are independently selected from hydroxyl, halogen, CN, $C_{1-6}$ haloalkyl, $C_{1-6}$ haloalkoxy, $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl, alkylheteroaryl, —$NR^jR^k$, —$NR^jC$(═O) $OR^k$, —$OR^j$, —$SR^j$, —OC(═O)$R^h$, —OC(═O) $NR^jR^k$, —OC(═O)$OR^j$; where said $C_{1-6}$ alkyl, $C_{1-6}$ alkoxy, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl;

wherein $R^{x2}$ is selected from hydroxyl, halogen, CN, $C_{1-6}$ haloalkyl, $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl, alkylheteroaryl; where said $C_{1-6}$ alkyl, $C_{3-6}$ cycloalkyl, 3-10 membered heterocycloalkyl, alkylheterocycloalkyl, $C_{6-11}$ aryl, alkylaryl, heteroaryl and alkylheteroaryl are optionally substituted with one or more groups selected from hydroxyl, $C_{1-6}$ haloalkyl, $C_{1-6}$ haloalkoxy, $C_{3-6}$ cycloalkyl, $NR^jR^k$, $C_{1-6}$ alkyl, O—$C_{1-6}$ alkyl, and phenyl; and where each $R^h$, $R^j$ and $R^k$ are independently selected from hydrogen, $C_{1-6}$ haloalkyl, $C_{3-6}$ cycloalkyl, phenyl, benzyl, 5-6 membered heteroaryl, 4-7 membered heterocycloalkyl, and $C_{1-6}$ alkyl wherein said $C_{3-6}$ cycloalkyl, phenyl, benzyl, 5-6 membered heteroaryl, 4-7 membered heterocycloalkyl and $C_{1-6}$ alkyl are optionally substituted with one or more groups selected from $C_{1-6}$ alkyl, $C_{1-6}$ alkoxy, $NH_2$, $NH(C_{1-3}$ alkyl) and $N(C_{1-3}$ alkyl$)_2$; or $R^j$ and $R^k$ when attached to the same atom and together with the atom to which they are attached combine to provide a 3-7 membered heterocycloalkyl which is optionally substituted by one or more groups selected from hydroxy, $C_{1-3}$ alkyl, and $C_{1-3}$ alkoxy.

11. The compound according to claim 1, or a salt or solvate thereof, wherein $R^{x1}$ and $R^{x5}$ are independently selected from halogen, CN, $C_{1-6}$ alkyl and $C_{1-6}$ alkoxy.

12. The compound according to claim 1 or a salt or solvate thereof, wherein $R^{x1}$ and $R^{x5}$ are independently selected from halogen and $C_{1-6}$ alkyl.

13. The compound according to claim 1 or a salt or solvate thereof, wherein $R^{x1}$ and $R^{x5}$ are independently selected from fluoro, chloro and methyl.

14. The compound according to claim 1 which is selected from:

| Example | Structure | Name |
|---|---|---|
| E1 | 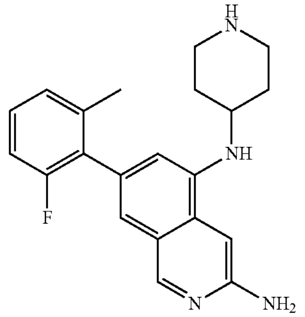 | 7-(2-fluoro-6-methyl-phenyl)-N5-(4-piperidyl)isoquinoline-3,5-diamine |
| E2 | 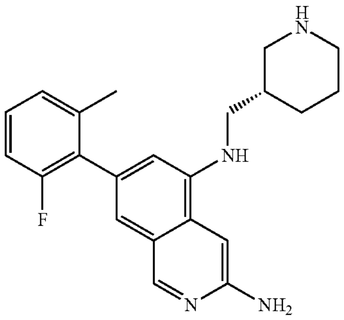 [SMILES: Cc1cccc(F)c1-c1cc(NC[C@H]2CCCNC2)c2cc(N)ncc2c1] | 7-(2-fluoro-6-methyl-phenyl)-N5-[[(3S)-3-piperidyl]methyl]isoquinoline-3,5-diamine |
| E3 | 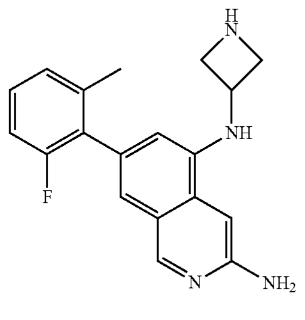 | N5-(azetidin-3-yl)-7-(2-fluoro-6-methyl-phenyl)isoquinoline-3,5-diamine |

-continued

| Example | Structure | Name |
| --- | --- | --- |
| E4 | 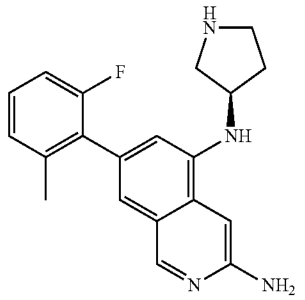 | 7-(2-fluoro-6-methyl-phenyl)-N5-[(3R)-pyrrolidin-3-yl]isoquinoline-3,5-diamine |
| E5 | 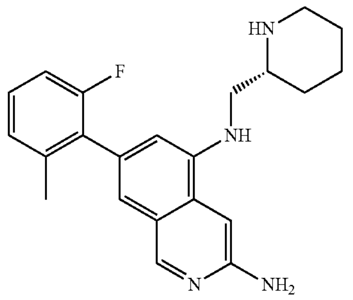 [SMILES: Cc1cccc(F)c1-c1cc(NC[C@H]2CCCCN2)c2cc(N)ncc2c1] | 7-(2-fluoro-6-methyl-phenyl)-N5-[[(2R)-2-piperidyl]methyl]isoquinoline-3,5-diamine |
| E6 | 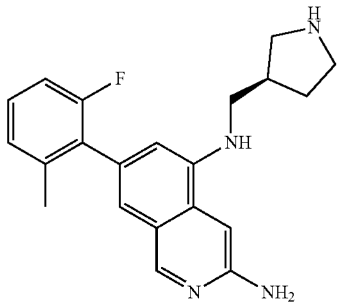 [SMILES: Cc1cccc(F)c1-c1cc(NC[C@@H]2CCNC2)c2cc(N)ncc2c1] | 7-(2-fluoro-6-methyl-phenyl)-N5-[[(3R)-pyrrolidin-3-yl]methyl]isoquinoline-3,5-diamine |
| E7 | 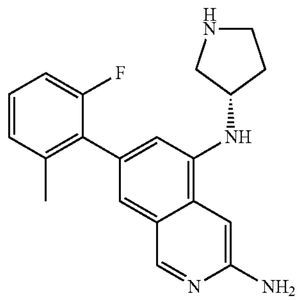 [SMILES: Cc1cccc(F)c1-c1cc(N[C@H]2CCNC2)c2cc(N)ncc2c1] | 7-(2-fluoro-6-methyl-phenyl)-N5-[(3S)-pyrrolidin-3-yl]isoquinoline-3,5-diamine |
| E8 | 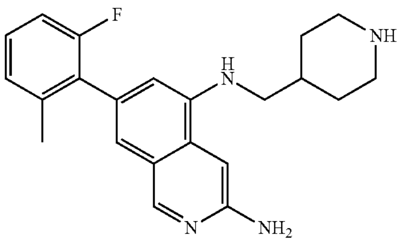 [SMILES: Cc1cccc(F)c1-c1cc(NCC2CCNCC2)c2cc(N)ncc2c1] | 7-(2-fluoro-6-methyl-phenyl)-N5-(4-piperidylmethyl)isoquinoline-3,5-diamine |

-continued

| Example | Structure | Name |
|---|---|---|
| E9 | 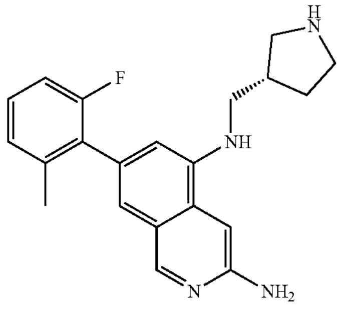 [SMILES: Cc1cccc(F)c1-c1cc(NC[C@H]2CCNC2)c2cc(N)ncc2c1] | 7-(2-fluoro-6-methyl-phenyl)-N5-[[(3S)-pyrrolidin-3-yl]methyl]isoquinoline-3,5-diamine |
| E10 | 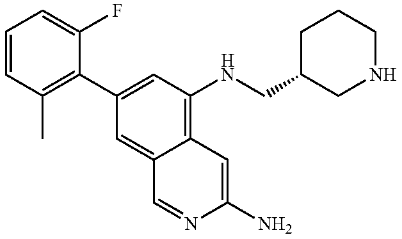 [SMILES: Cc1cccc(F)c1-c1cc(NC[C@@H]2CCCNC2)c2cc(N)ncc2c1] | 7-(2-fluoro-6-methyl-phenyl)-N5-[[(3R)-3-piperidyl]methyl]isoquinoline-3,5-diamine |
| E11 | 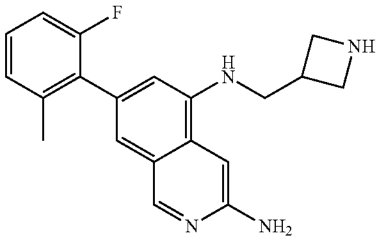 | N5-(azetidin-3-ylmethyl)-7-(2-fluoro-6-methyl-phenyl)isoquinoline-3,5-diamine |
| E12 | 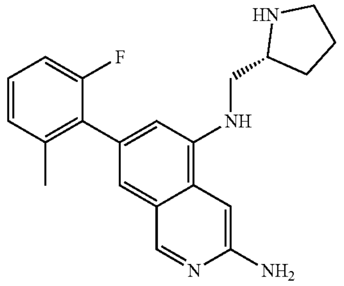 [SMILES: Cc1cccc(F)c1-c1cc(NC[C@H]2CCCN2)c2cc(N)ncc2c1] | 7-(2-fluoro-6-methyl-phenyl)-N5-[[(2R)-pyrrolidin-2-yl]methyl]isoquinoline-3,5-diamine |
| E13 | 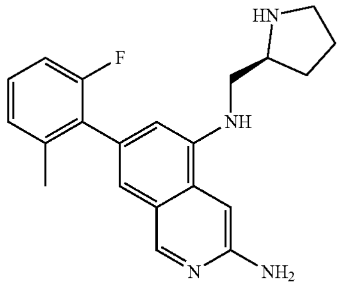 [SMILES: Cc1cccc(F)c1-c1cc(NC[C@@H]2CCCN2)c2cc(N)ncc2c1] | 7-(2-fluoro-6-methyl-phenyl)-N5-[[(2S)-pyrrolidin-2-yl]methyl]isoquinoline-3,5-diamine |

-continued

| Example | Structure | Name |
|---|---|---|
| E14 | 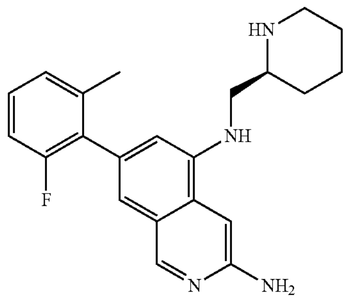 [SMILES: Cc1cccc(F)c1-c1cc(NC[C@@H]2CCCCN2)c2cc(N)ncc2c1] | 7-(2-fluoro-6-methyl-phenyl)-N5-[[(2S)-2-piperidyl]methyl]isoquinoline-3,5-diamine |
| E15 | 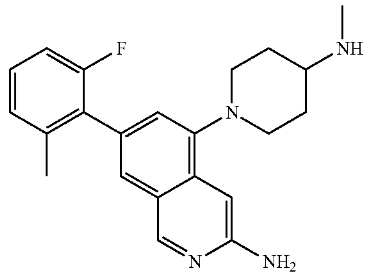 [SMILES: CNC1CCN(c2cc(-c3c(C)cccc3F)cc3cnc(N)cc23)CC1] | 7-(2-fluoro-6-methyl-phenyl)-5-[4-(methylamino)-1-piperidyl]isoquinolin-3-amine |
| E16 | 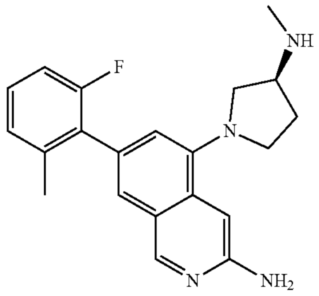 [SMILES: CN[C@H]1CCN(c2cc(-c3c(C)cccc3F)cc3cnc(N)cc23)C1] | 7-(2-fluoro-6-methyl-phenyl)-5-[(3S)-3-(methylamino)pyrrolidin-1-yl]isoquinolin-3-amine |
| E17 | 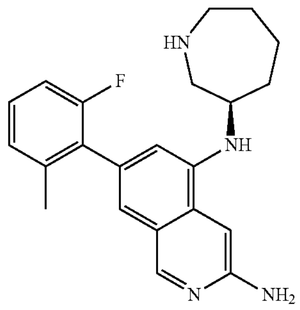 | N5-[(3R)-azepan-3-yl]-7-(2-fluoro-6-methyl-phenyl)isoquinoline-3,5-diamine |
| E18 | 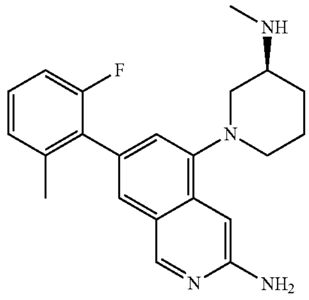 | 7-(2-fluoro-6-methyl-phenyl)-5-[(3S)-3-(methylamino)-1-piperidyl]isoquinolin-3-amine |

-continued

| Example | Structure | Name |
| --- | --- | --- |
| E19 | 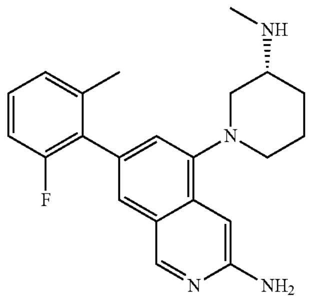 | 7-(2-fluoro-6-methyl-phenyl)-5-[(3R)-3-(methylamino)-1-piperidyl]isoquinolin-3-amine |
| E20 | 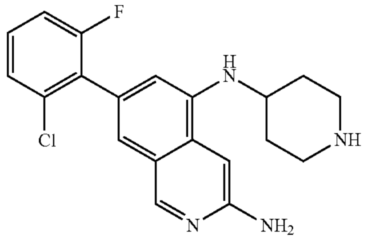 | 7-(2-chloro-6-fluoro-phenyl)-N5-(4-piperidyl)isoquinoline-3,5-diamine |
| E21 | 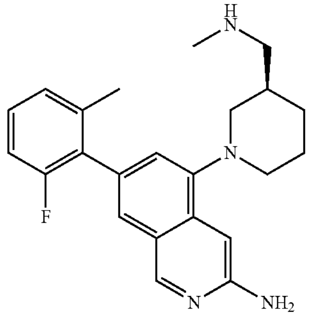 [SMILES: CNC[C@H]1CCCN(c2cc(-c3c(C)cccc3F)cc3cnc(N)cc23)C1] | 7-(2-fluoro-6-methyl-phenyl)-5-[(3R)-3-(methylaminomethyl)-1-piperidyl]isoquinolin-3-amine |
| E22 | 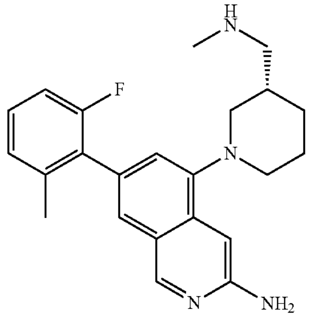 [SMILES: CNC[C@@H]1CCCN(c2cc(-c3c(C)cccc3F)cc3cnc(N)cc23)C1] | 7-(2-fluoro-6-methyl-phenyl)-5-[(3S)-3-(methylaminomethyl)-1-piperidyl]isoquinolin-3-amine |
| E23 | 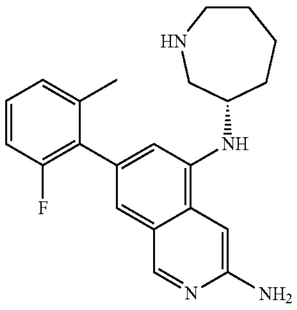 [SMILES: Cc1cccc(F)c1-c1cc(N[C@H]2CCCCNC2)c2cc(N)ncc2c1] | N5-[(3S)-azepan-3-yl]-7-(2-fluoro-6-methyl-phenyl)isoquinoline-3,5-diamine |

-continued
| Example | Structure | Name |
|---|---|---|
| E24 | 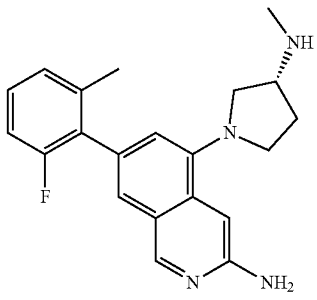 [SMILES: CN[C@@H]1CCN(c2cc(-c3c(C)cccc3F)cc3cnc(N)cc23)C1] | 7-(2-fluoro-6-methyl-phenyl)-5-[(3R)-3-(methylamino)pyrrolidin-1-yl]isoquinolin-3-amine |
| E25 | 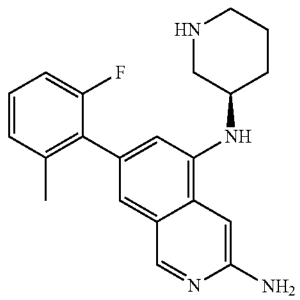 | 7-(2-fluoro-6-methyl-phenyl)-N5-[(3R)-3-piperidyl]isoquinoline-3,5-diamine |
| E26 | 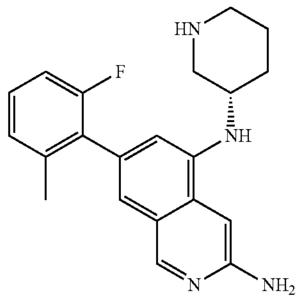 | 7-(2-fluoro-6-methyl-phenyl)-N5-[(3S)-3-piperidyl]isoquinoline-3,5-diamine |
| E27 | 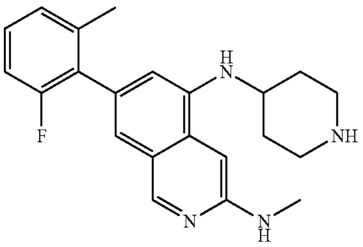 | 7-(2-fluoro-6-methyl-phenyl)-N3-methyl-N5-(4-piperidyl)isoquinoline-3,5-diamine |
| E28 | 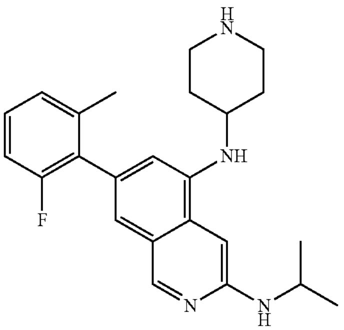 [SMILES: Cc1cccc(F)c1-c1cc(NC2CCNCC2)c2cc(NC(C)C)ncc2c1] | 7-(2-fluoro-6-methyl-phenyl)-N3-isopropyl-N5-(4-piperidyl)isoquinoline-3,5-diamine |

-continued
| Example | Structure | Name |
|---|---|---|
| E29 | 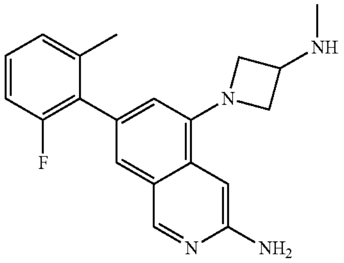 [SMILES: CNC1CN(c2cc(-c3c(C)cccc3F)cc3cnc(N)cc23)C1] | 7-(2-fluoro-6-methyl-phenyl)-5-[3-(methylamino)azetidin-1-yl]isoquinolin-3-amine |
| E30 | 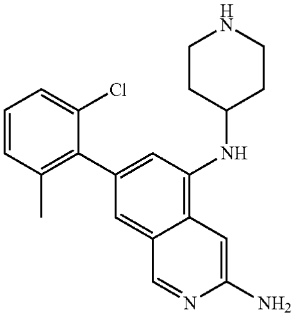 | 7-(2-chloro-6-methyl-phenyl)-N5-(4-piperidyl)isoquinoline-3,5-diamine |
| E31 | 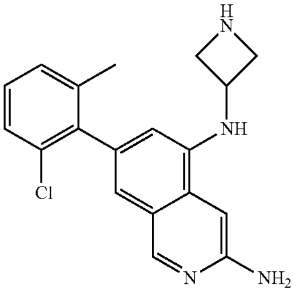 [SMILES: Cc1cccc(Cl)c1-c1cc(NC2CNC2)c2cc(N)ncc2c1] | N5-(azetidin-3-yl)-7-(2-chloro-6-methyl-phenyl)isoquinoline-3,5-diamine |
| E44 | 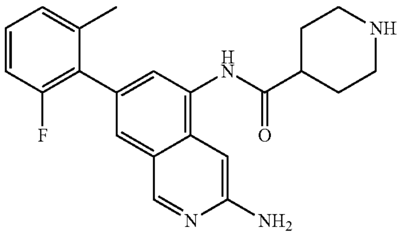 [SMILES: Cc1cccc(F)c1-c1cc(NC(=O)C2CCNCC2)c2cc(N)ncc2c1] | N-[3-amino-7-(2-fluoro-6-methyl-phenyl)-5-isoquinolyl]piperidine-4-carboxamide |
| E45 | 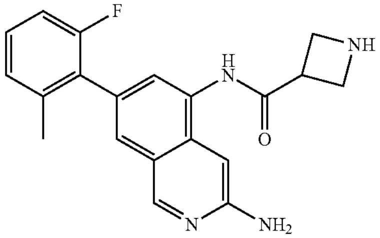 | N-[3-amino-7-(2-fluoro-6-methyl-phenyl)-5-isoquinolyl]azetidine-3-carboxamide |

-continued
| Example | Structure | Name |
|---|---|---|
| E46 | 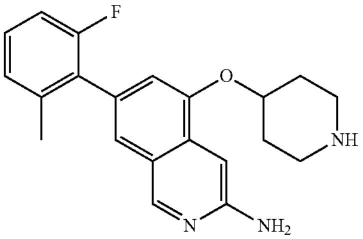 | 7-(2-fluoro-6-methyl-phenyl)-5-(4-piperidyloxy)isoquinolin-3-amine |
| E47 | 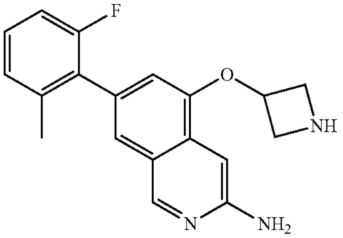 [SMILES: Cc1cccc(F)c1-c1cc(OC2CNC2)c2cc(N)ncc2c1] | 5-(azetidin-3-yloxy)-7-(2-fluoro-6-methyl-phenyl)isoquinolin-3-amine |
| E48 | 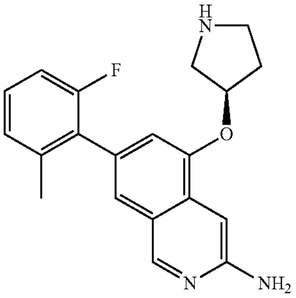 | 7-(2-fluoro-6-methyl-phenyl)-5-[(3R)-pyrrolidin-3-yl]oxy-isoquinolin-3-amine |
| E52 | 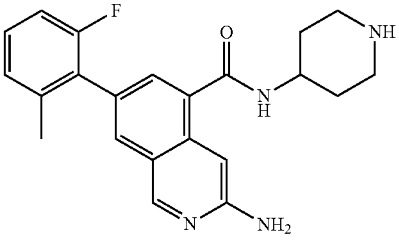 | 3-amino-7-(2-fluoro-6-methyl-phenyl)-N-(4-piperidyl)isoquinoline-5-carboxamide |
| E54 | 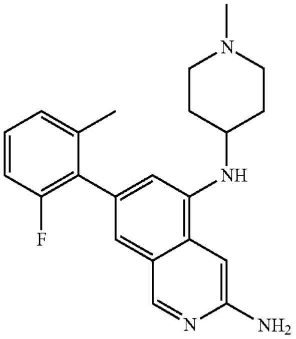 | 7-(2-fluoro-6-methyl-phenyl)-N5-(1-methyl-4-piperidyl)isoquinoline-3,5-diamine |

-continued

| Example | Structure | Name |
| --- | --- | --- |
| E55 | 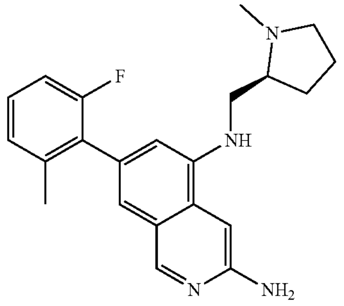 [SMILES: Cc1cccc(F)c1-c1cc(NC[C@@H]2CCCN2C)c2cc(N)ncc2c1] | 7-(2-fluoro-6-methyl-phenyl)-N5-[[(2S)-1-methylpyrrolidin-2-yl]methyl]isoquinoline-3,5-diamine |
| E56 | 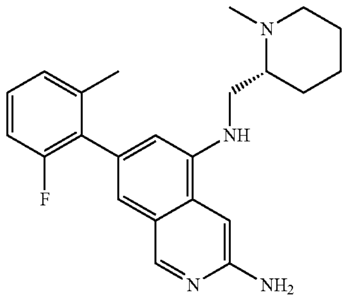 [SMILES: Cc1cccc(F)c1-c1cc(NC[C@H]2CCCCN2C)c2cc(N)ncc2c1] | 7-(2-fluoro-6-methyl-phenyl)-N5-[[(2R)-1-methyl-2-piperidyl]methyl]isoquinoline-3,5-diamine |
| E57 | 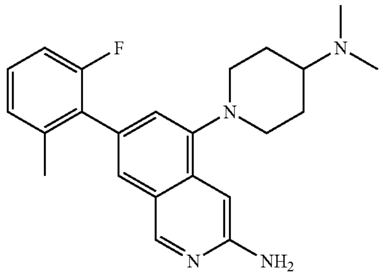 [SMILES: Cc1cccc(F)c1-c1cc(N2CCC(N(C)C)CC2)c2cc(N)ncc2c1] | 5-[4-(dimethylamino)-1-piperidyl]-7-(2-fluoro-6-methyl-phenyl)isoquinolin-3-amine |
| E58 | 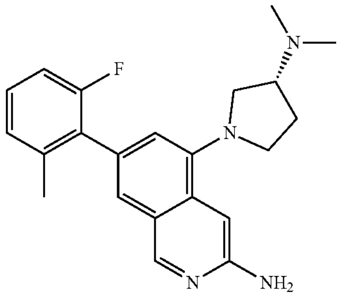 [SMILES: Cc1cccc(F)c1-c1cc(N2CC[C@@H](N(C)C)C2)c2cc(N)ncc2c1] | 5-[(3R)-3-(dimethylamino)pyrrolidin-1-yl]-7-(2-fluoro-6-methyl-phenyl)isoquinolin-3-amine |
| E59 | 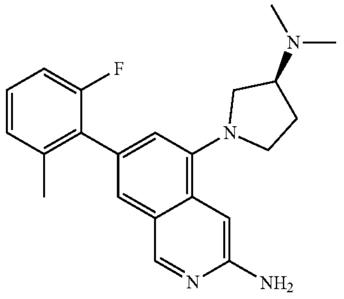 [SMILES: Cc1cccc(F)c1-c1cc(N2CC[C@H](N(C)C)C2)c2cc(N)ncc2c1] | 5-[(3S)-3-(dimethylamino)pyrrolidin-1-yl]-7-(2-fluoro-6-methyl-phenyl)isoquinolin-3-amine |

-continued

| Example | Structure | Name |
|---|---|---|
| E60 | 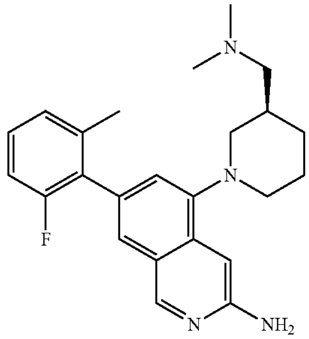 [SMILES: Cc1cccc(F)c1-c1cc(N2CCC[C@H](CN(C)C)C2)c2cc(N)ncc2c1] | 5-[(3R)-3-[(dimethylamino)methyl]-1-piperidyl]-7-(2-fluoro-6-methyl-phenyl)isoquinolin-3-amine |
| E61 | 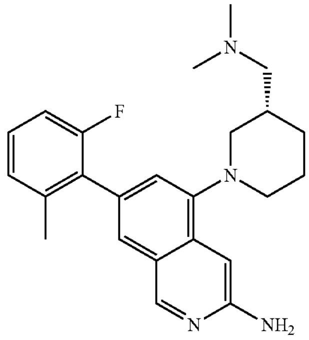 [SMILES: Cc1cccc(F)c1-c1cc(N2CCC[C@@H](CN(C)C)C2)c2cc(N)ncc2c1] | 5-[(3S)-3-[(dimethylamino)methyl]-1-piperidyl]-7-(2-fluoro-6-methyl-phenyl)isoquinolin-3-amine |
| E62 | 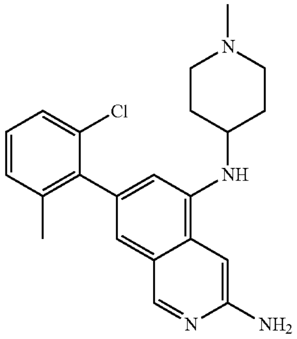 [SMILES: Cc1cccc(Cl)c1-c1cc(NC2CCN(C)CC2)c2cc(N)ncc2c1] | 7-(2-chloro-6-methyl-phenyl)-N5-(1-methyl-4-piperidyl)isoquinoline-3,5-diamine |
| E63 | 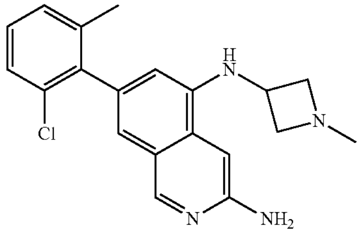 [SMILES: Cc1cccc(Cl)c1-c1cc(NC2CN(C)C2)c2cc(N)ncc2c1] | 7-(2-chloro-6-methyl-phenyl)-N5-(1-methylazetidin-3-yl)isoquinoline-3,5-diamine |
| E64 | 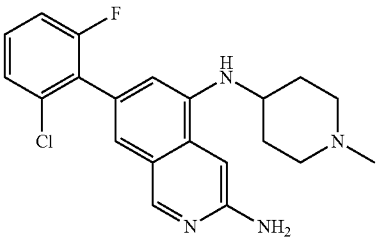 | 7-(2-chloro-6-fluoro-phenyl)-N5-(1-methyl-4-piperidyl)isoquinoline-3,5-diamine |

-continued

| Example | Structure | Name |
|---|---|---|
| E68 | 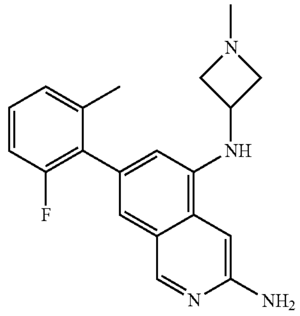 [SMILES: Cc1cccc(F)c1-c1cc(NC2CN(C)C2)c2cc(N)ncc2c1] | 7-(2-fluoro-6-methyl-phenyl)-N5-(1-methylazetidin-3-yl)isoquinoline-3,5-diamine |
| E69 | 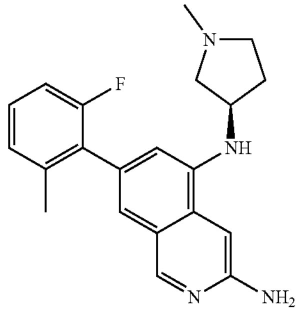 [SMILES: Cc1cccc(F)c1-c1cc(N[C@@H]2CCN(C)C2)c2cc(N)ncc2c1] | 7-(2-fluoro-6-methyl-phenyl)-N5-[(3R)-1-methylpyrrolidin-3-yl]isoquinoline-3,5-diamine |
| E70 | 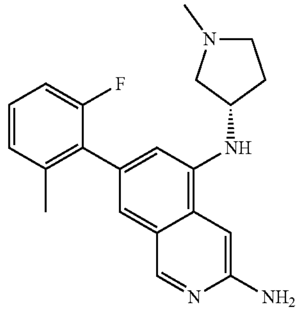 [SMILES: Cc1cccc(F)c1-c1cc(N[C@H]2CCN(C)C2)c2cc(N)ncc2c1] | 7-(2-fluoro-6-methyl-phenyl)-N5-[(3S)-1-methylpyrrolidin-3-yl]isoquinoline-3,5-diamine |
| E71 | 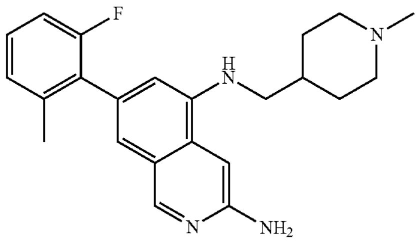 [SMILES: Cc1cccc(F)c1-c1cc(NCC2CCN(C)CC2)c2cc(N)ncc2c1] | 7-(2-fluoro-6-methyl-phenyl)-N5-[(1-methyl-4-piperidyl)methyl]isoquinoline-3,5-diamine |
| E72 | 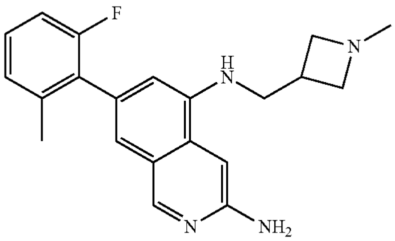 [SMILES: Cc1cccc(F)c1-c1cc(NCC2CN(C)C2)c2cc(N)ncc2c1] | 7-(2-fluoro-6-methyl-phenyl)-N5-[(1-methylazetidin-3-yl)methyl]isoquinoline-3,5-diamine |

-continued
| Example | Structure | Name |
| --- | --- | --- |
| E73 | 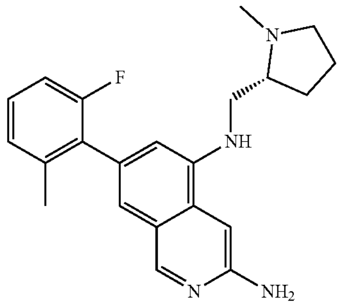 [SMILES: Cc1cccc(F)c1-c1cc(NC[C@H]2CCCN2C)c2cc(N)ncc2c1] | 7-(2-fluoro-6-methyl-phenyl)-N5-[[(2R)-1-methylpyrrolidin-2-yl]methyl]isoquinoline-3,5-diamine |
| E74 | 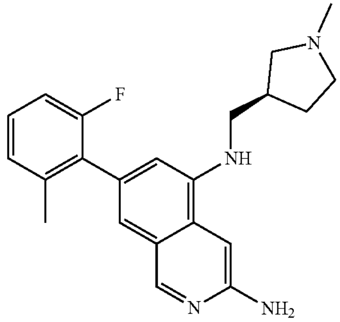 [SMILES: Cc1cccc(F)c1-c1cc(NC[C@@H]2CCN(C)C2)c2cc(N)ncc2c1] | 7-(2-fluoro-6-methyl-phenyl)-N5-[[(3S)-1-methylpyrrolidin-3-yl]methyl]isoquinoline-3,5-diamine |
| E75 | 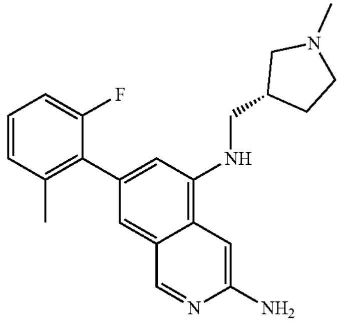 [SMILES: Cc1cccc(F)c1-c1cc(NC[C@H]2CCN(C)C2)c2cc(N)ncc2c1] | 7-(2-fluoro-6-methyl-phenyl)-N5-[[(3R)-1-methylpyrrolidin-3-yl]methyl]isoquinoline-3,5-diamine |
| E76 | 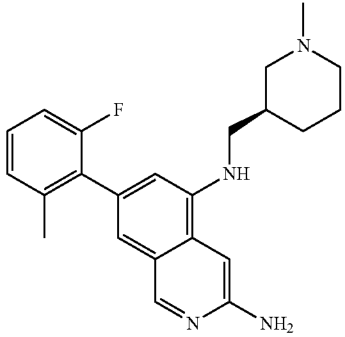 [SMILES: Cc1cccc(F)c1-c1cc(NC[C@@H]2CCCN(C)C2)c2cc(N)ncc2c1] | 7-(2-fluoro-6-methyl-phenyl)-N5-[[(3S)-1-methyl-3-piperidyl]methyl]isoquinoline-3,5-diamine |

-continued

| Example | Structure | Name |
|---|---|---|
| E77 | 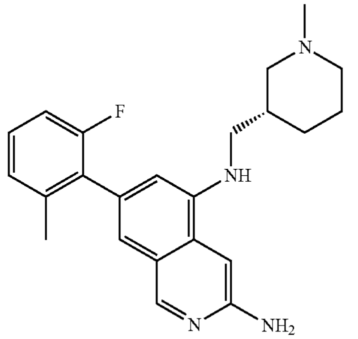 [SMILES: Cc1cccc(F)c1-c1cc(NC[C@H]2CCCN(C)C2)c2cc(N)ncc2c1] | 7-(2-fluoro-6-methyl-phenyl)-N5-[[(3R)-1-methyl-3-piperidyl]methyl]isoquinoline-3,5-diamine |
| E78 | 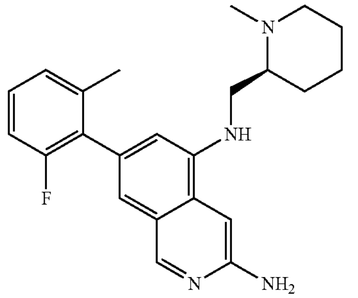 [SMILES: Cc1cccc(F)c1-c1cc(NC[C@@H]2CCCCN2C)c2cc(N)ncc2c1] | 7-(2-fluoro-6-methyl-phenyl)-N5-[[(2S)-1-methyl-2-piperidyl]methyl]isoquinoline-3,5-diamine |
| E79 | 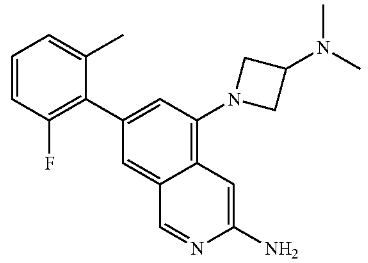 [SMILES: Cc1cccc(F)c1-c1cc(N2CC(N(C)C)C2)c2cc(N)ncc2c1] | 5-[3-(dimethylamino)azetidin-1-yl]-7-(2-fluoro-6-methyl-phenyl)isoquinolin-3-amine |
| E80 | 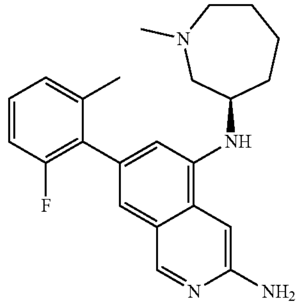 | 7-(2-fluoro-6-methyl-phenyl)-N5-[(3R)-1-methylazepan-3-yl]isoquinoline-3,5-diamine |
| E81 | 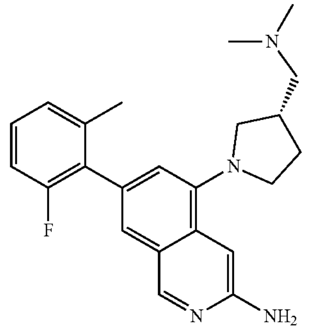 [SMILES: Cc1cccc(F)c1-c1cc(N2CC[C@@H](CN(C)C)C2)c2cc(N)ncc2c1] | 5-[(3S)-3-[(dimethylamino)methyl]pyrrolidin-1-yl]-7-(2-fluoro-6-methyl-phenyl)isoquinolin-3-amine |

-continued

| Example | Structure | Name |
|---|---|---|
| E82 | 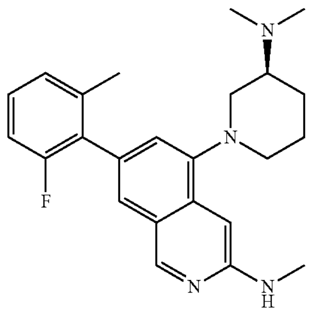 [SMILES: CNc1cc2c(N3CCC[C@H](N(C)C)C3)cc(-c3c(C)cccc3F)cc2cn1] | 5-[(3S)-3-(dimethylamino)-1-piperidyl]-7-(2-fluoro-6-methyl-phenyl)isoquinolin-3-amine |
| E83 | 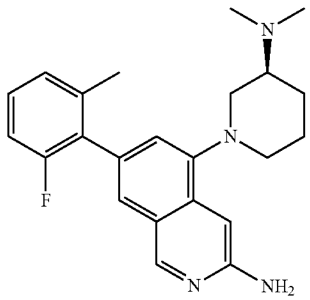 | 5-[(3S)-3-(dimethylamino)-1-piperidyl]-7-(2-fluoro-6-methyl-phenyl)-N-methyl-isoquinolin-3-amine |
| E84 | 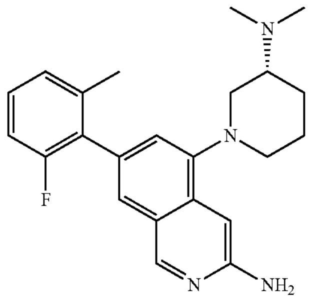 [SMILES: Cc1cccc(F)c1-c1cc(N2CCC[C@@H](N(C)C)C2)c2cc(N)ncc2c1] | 5-[(3R)-3-(dimethylamino)-1-piperidyl]-7-(2-fluoro-6-methyl-phenyl)isoquinlin-3-amine |
| E85 | 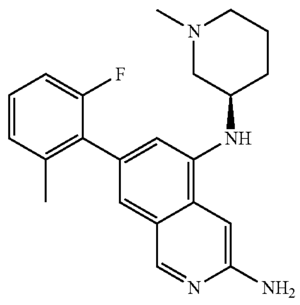 | 7-(2-fluoro-6-methyl-phenyl)-N5-[(3R)-1-methyl-3-piperidyl]isoquinoline-3,5-diamine |
| E86 | 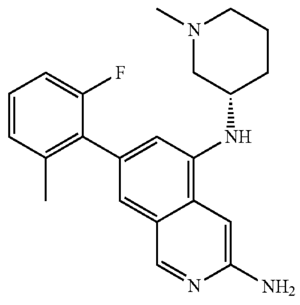 [SMILES: Cc1cccc(F)c1-c1cc(N[C@H]2CCCN(C)C2)c2cc(N)ncc2c1] | 7-(2-fluoro-6-methyl-phenyl)-N5-[(3S)-1-methyl-3-piperidyl]isoquinoline-3,5-diamine |

-continued

| Example | Structure | Name |
|---|---|---|
| E99 | 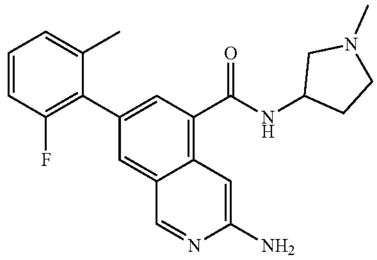 [SMILES: Cc1cccc(F)c1-c1cc(C(=O)NC2CCN(C)C2)c2cc(N)ncc2c1] | 3-amino-7-(2-fluoro-6-methyl-phenyl)-N-(1-methylpyrrolidin-3-yl)isoquinoline-5-carboxamide |
| E100 | 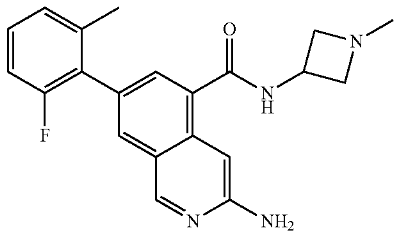 | 3-amino-7-(2-fluoro-6-methyl-phenyl)-N-(1-methylazetidin-3-yl)isoquinoline-5-carboxamide |
| E101 | 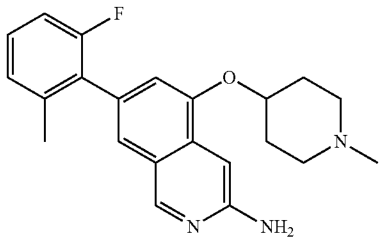 [SMILES: Cc1cccc(F)c1-c1cc(OC2CCN(C)CC2)c2cc(N)ncc2c1] | 7-(2-fluoro-6-methyl-phenyl)-5-[(1-methyl-4-piperidyl)oxy]isoquinolin-3-amine |
| E102 | 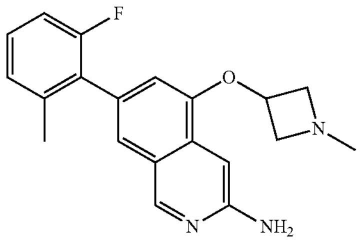 [SMILES: Cc1cccc(F)c1-c1cc(OC2CN(C)C2)c2cc(N)ncc2c1] | 7-(2-fluoro-6-methyl-phenyl)-5-(l-methylazetidin-3-yl)oxy-isoquinolin-3-amine |
| E104 | 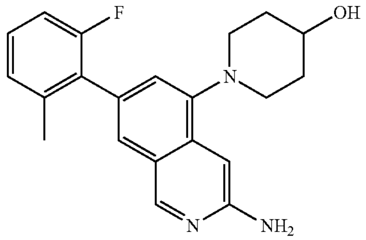 [SMILES: Cc1cccc(F)c1-c1cc(N2CCC(O)CC2)c2cc(N)ncc2c1] | 1-[3-amino-7-(2-fluoro-6-methyl-phenyl)-5-isoquinolyl]piperidin-4-ol |
| E105 | 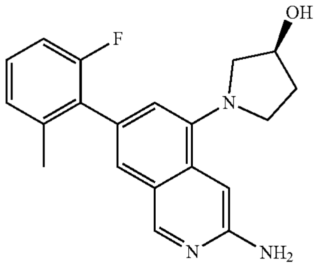 [SMILES: Cc1cccc(F)c1-c1cc(N2CC[C@H](O)C2)c2cc(N)ncc2c1] | (3S)-1-[3-amino-7-(2-fluoro-6-methyl-phenyl)-5-isoquinolyl]pyrrolidin-3-ol |

-continued

| Example | Structure | Name |
|---|---|---|
| E106 | 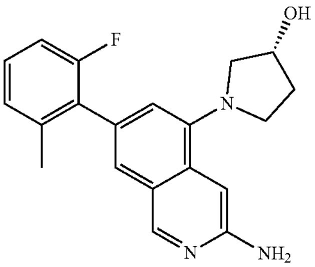 [SMILES: Cc1cccc(F)c1-c1cc(N2CC[C@@H](O)C2)c2cc(N)ncc2c1] | (3R)-1-[3-amino-7-(2-fluoro-6-methyl-phenyl)-5-isoquinolyl]pyrrolidin-3-ol |
| E107 | 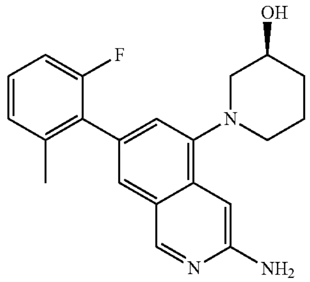 [SMILES: Cc1cccc(F)c1-c1cc(N2CCC[C@H](O)C2)c2cc(N)ncc2c1] | (3S)-1-[3-amino-7-(2-fluoro-6-methyl-phenyl)-5-isoquinolyl]piperidin-3-ol |
| E108 | 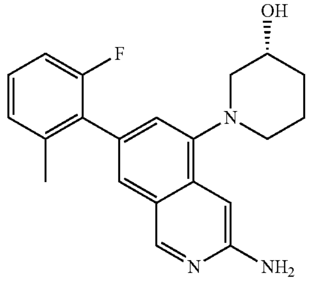 [SMILES: Cc1cccc(F)c1-c1cc(N2CCC[C@@H](O)C2)c2cc(N)ncc2c1] | (3R)-1-[3-amino-7-(2-fluoro-6-methyl-phenyl)-5-isoquinolyl]piperidin-3-ol |
| E109 | 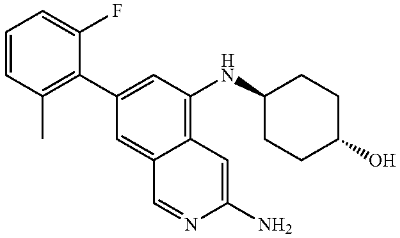 | 4-[[3-amino-7-(2-fluoro-6-methyl-phenyl)-5-isoquinolyl]amino]cyclohexanol |
| E110 | 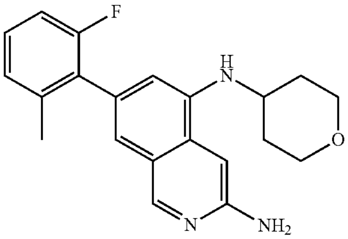 [SMILES: Cc1cccc(F)c1-c1cc(NC2CCOCC2)c2cc(N)ncc2c1] | 7-(2-fluoro-6-methyl-phenyl)-N5-tetrahydropyran-4-yl-isoquinoline-3,5-diamine |
| E111 | 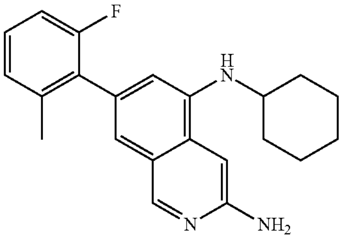 [SMILES: Cc1cccc(F)c1-c1cc(NC2CCCCC2)c2cc(N)ncc2c1] | N5-cyclohexyl-7-(2-fluoro-6-methyl-phenyl)isoquinoline-3,5-diamine |

-continued

| Example | Structure | Name |
|---|---|---|
| E112 | 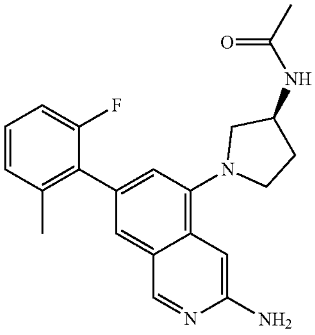 [SMILES: CC(=O)N[C@H]1CCN(c2cc(-c3c(C)cccc3F)cc3cnc(N)cc23)C1] | N-[(3S)-1-[3-amino-7-(2-fluoro-6-methyl-phenyl)-5-isoquinolyl]pyrrolidin-3-yl]acetamide |
| E113 | 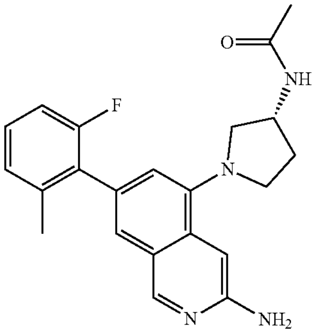 [SMILES: CC(=O)N[C@@H]1CCN(c2cc(-c3c(C)cccc3F)cc3cnc(N)cc23)C1] | N-[(3R)-1-[3-amino-7-(2-fluoro-6-methyl-phenyl)-5-isoquinolyl]pyrrolidin-3-yl]acetamide |
| E114 | 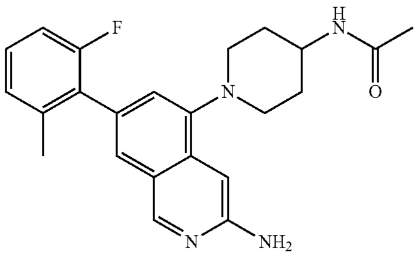 [SMILES: CC(=O)NC1CCN(c2cc(-c3c(C)cccc3F)cc3cnc(N)cc23)CC1] | N-[1-[3-amino-7-(2-fluoro-6-methyl-phenyl)-5-isoquinolyl]-4-piperidyl]acetamide |
| E116 | 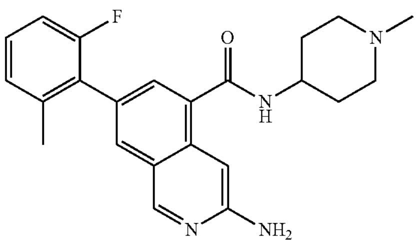 | 3-amino-7-(2-fluoro-6-methyl-phenyl)-N-(1-methyl-4-piperidyl)isoquinoline-5-carboxamide |
| E118 | 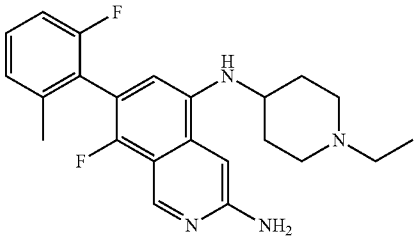 [SMILES: CCN1CCC(Nc2cc(-c3c(C)cccc3F)c(F)c3cnc(N)cc23)CC1] | N5-(1-ethyl-4-piperidyl)-8-fluoro-7-(2-fluoro-6-methyl-phenyl)isoquinoline-3.5-diamine |

-continued

| Example | Structure | Name |
|---|---|---|
| E119 | 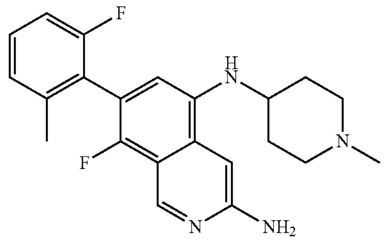 [SMILES: Cc1cccc(F)c1-c1cc(NC2CCN(C)CC2)c2cc(N)ncc2c1F] | 8-fluoro-7-(2-fluoro-6-methyl-phenyl)-N5-(1-methyl-4-piperidyl)isoquinoline-3,5-diamine |
| E120 | 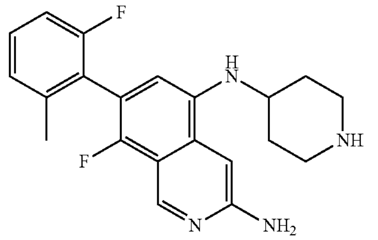 [SMILES: Cc1cccc(F)c1-c1cc(NC2CCNCC2)c2cc(N)ncc2c1F] | 8-fluoro-7-(2-fluoro-6-methyl-phenyl)-N5-(4-piperidyl)isoquinoline-3,5-diamine |
| E134 | 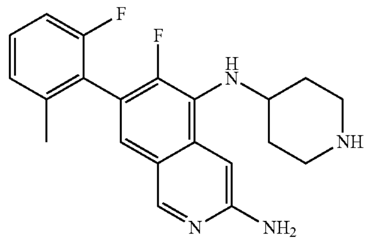 | 6-fluoro-7-(2-fluoro-6-methyl-phenyl)-N5-(4-piperidyl)isoquinoline-3,5-diamine |
| E135 | 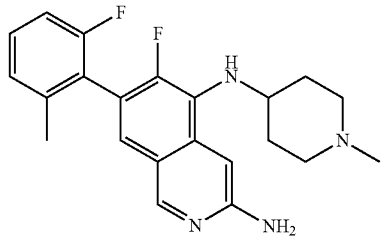 | 6-fluoro-7-(2-fluoro-6-methyl-phenyl)-N5-(1-methyl-4-piperidyl)isoquinoline-3,5-diamine |
| E133 | 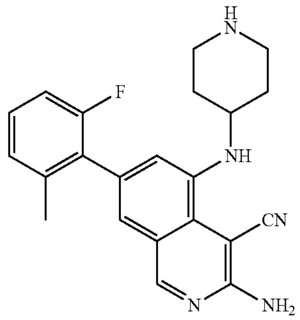 [SMILES: Cc1cccc(F)c1-c1cc(NC2CCNCC2)c2c(C#N)c(N)ncc2c1] | 3-amino-7-(2-fluoro-6-methyl-phenyl)-5-(4-piperidylamino)isoquinoline-4-carbonitrile |

-continued

| Example | Structure | Name |
|---|---|---|
| E136 | 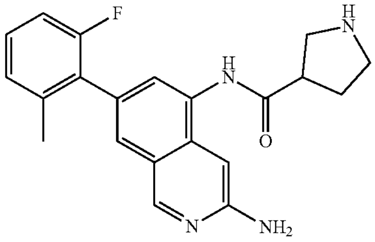 [SMILES: Cc1cccc(F)c1-c1cc(NC(=O)C2CCNC2)c2cc(N)ncc2c1] | N-[3-amino-7-(2-fluoro-6-methyl-phenyl)-5-isoquinolyl]pyrrolidine-3-carboxamide; |

or a salt or solvate of any one thereof.

15. The compound according to claim 1 selected from:

| Example | Structure | Name |
|---|---|---|
| E26 | 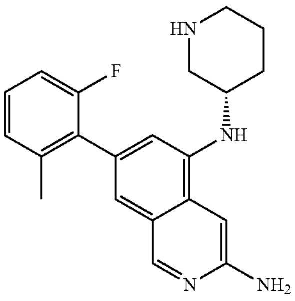 | 7-(2-fluoro-6-methyl-phenyl)-N5-[(3S)-3-piperidyl]isoquinoline-3,5-diamine |
| E54 | 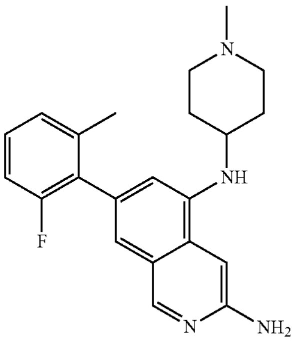 | 7-(2-fluoro-6-methyl-phenyl)-N5-(1-methyl-4-piperidyl)isoquinoline-3,5-diamine |
| E23 | 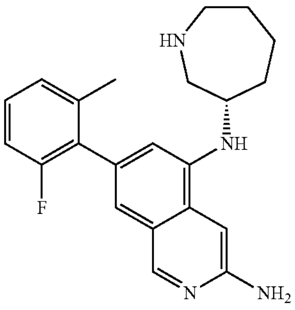 [SMILES: Cc1cccc(F)c1-c1cc(N[C@H]2CCCCNC2)c2cc(N)ncc2c1] | N5-[(3S)-azepan-3-yl]-7-(2-fluoro-6-methyl-phenyl)isoquinoline-3,5-diamine |

-continued
| Example | Structure | Name |
|---|---|---|
| E7 | 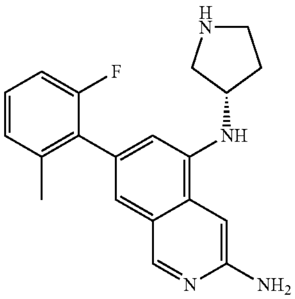 [SMILES: Cc1cccc(F)c1-c1cc(N[C@H]2CCNC2)c2cc(N)ncc2c1] | 7-(2-fluoro-6-methyl-phenyl)-N5-[(3S)-pyrrolidin-3-yl]isoquinoline-3,5-diamine |
| E1 | 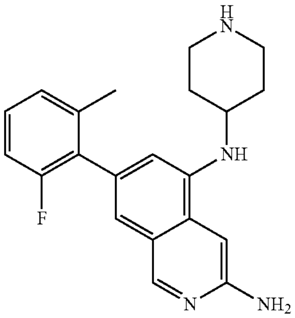 | 7-(2-fluoro-6-methyl-phenyl)-N5-(4-piperidyl)isoquinoline-3,5-diamine |
| E4 | 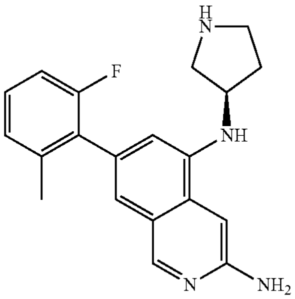 | 7-(2-fluoro-6-methyl-phenyl)-N5-[(3R)-pyrrolidin-3-yl]isoquinoline-3,5-diamine |
| E86 | 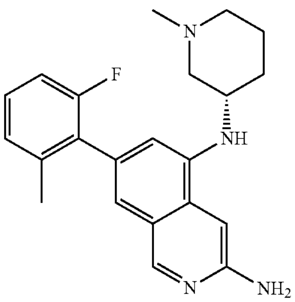 | 7-(2-fluoro-6-methyl-phenyl)-N5-[(3S)-1-methyl-3-piperidyl]isoquinoline-3,5-diamine |
| E85 | 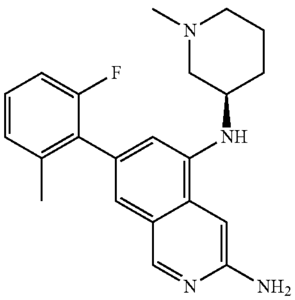 | 7-(2-fluoro-6-methyl-phenyl)-N5-[(3R)-1-methyl-3-piperidyl]isoquinoline-3,5-diamine |

-continued
| Example | Structure | Name |
|---|---|---|
| E17 | 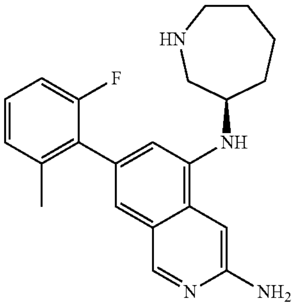 [SMILES: Cc1cccc(F)c1-c1cc(N[C@@H]2CCCCNC2)c2cc(N)ncc2c1] | N5-[(3R)-azepan-3-yl]-7-(2-fluoro-6-methyl-phenyl)isoquinoline-3,5-diamine |
| E69 | 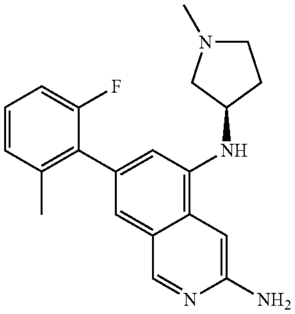 | 7-(2-fluoro-6-methyl-phenyl)-N5-[(3R)-1-methylpyrrolidin-3-yl]isoquinoline-3,5-diamine |
| E68 | 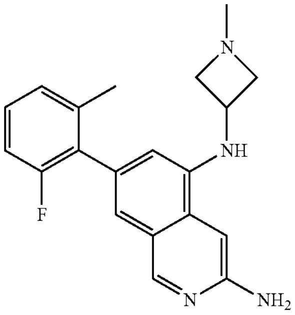 [SMILES: Cc1cccc(F)c1-c1cc(NC2CN(C)C2)c2cc(N)ncc2c1] | 7-(2-fluoro-6-methyl-phenyl)-N5-(1-methylazetidin-3-yl)isoquinoline-3,5-diamine |
| E70 | 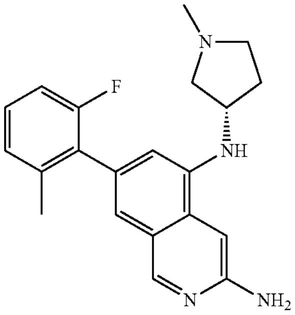 [SMILES: Cc1cccc(F)c1-c1cc(N[C@H]2CCN(C)C2)c2cc(N)ncc2c1] | 7-(2-fluoro-6-methyl-phenyl)-N5-[(3S)-1-methylpyrrolidin-3-yl]isoquinoline-3,5-diamine |
| E25 | 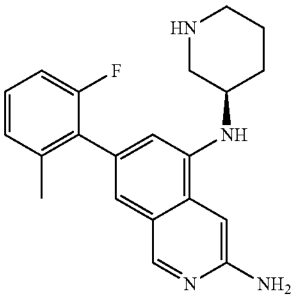 | 7-(2-fluoro-6-methyl-phenyl)-N5-[(3R)-3-piperidyl]isoquinoline-3,5-diamine |

-continued
| Example | Structure | Name |
|---|---|---|
| E62 | 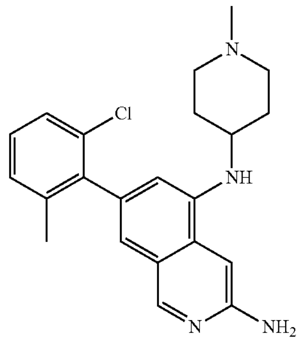 | 7-(2-chloro-6-methyl-phenyl)-N5-(l-methyl-4-piperidyl)isoquinoline-3,5-diamine |
| E3 | 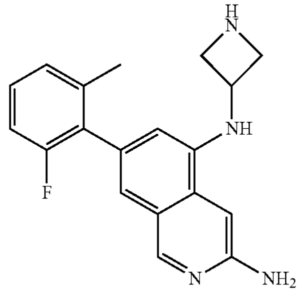 | N5-(azetidin-3-yl)-7-(2-fluoro-6-methyl-phenyl)isoquinoline-3,5-diamine |
| E30 | 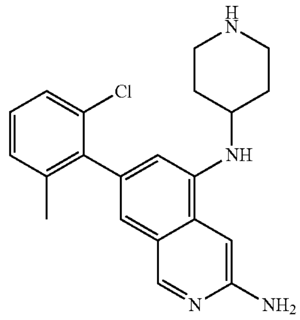 | 7-(2-chloro-6-methyl-phenyl)-N5-(4-piperidyl)isoquinoline-3,5-diamine |
| E80 | 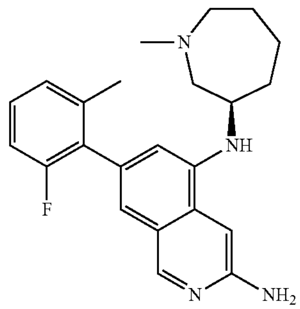 [SMILES: Cc1cccc(F)c1-c1cc(N[C@@H]2CCCCN(C)C2)c2cc(N)ncc2c1] | 7-(2-fluoro-6-methyl-phenyl)-N5-[(3R)-1-methylazepan-3-yl]isoquinoline-3,5-diamine |
| E31 | 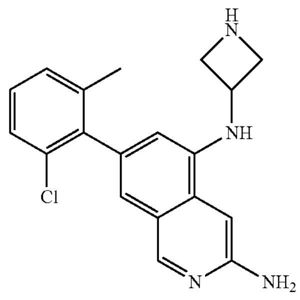 | N5-(azetidin-3-yl)-7-(2-chloro-6-methyl-phenyl)isoquinoline-3,5-diamine |

-continued

| Example | Structure | Name |
|---|---|---|
| E63 | 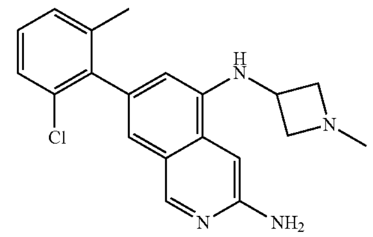 [SMILES: Cc1cccc(Cl)c1-c1cc(NC2CN(C)C2)c2cc(N)ncc2c1] | 7-(2-chloro-6-methyl-phenyl)-N5-(1-methylazetidin-3-yl)isoquinoline-3,5-diamine |
| E64 | 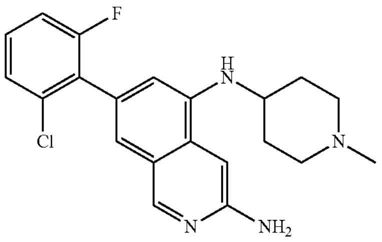 | 7-(2-chloro-6-fluoro-phenyl)-N5-(1-methyl-4-piperidyl)isoquinoline-3,5-diamine |
| E20 | 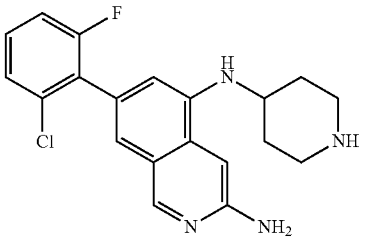 | 7-(2-chloro-6-fluoro-phenyl)-N5-(4-piperidyl)isoquinoline-3,5-diamine; |

or a salt or solvate of any one thereof.

16. The compound according claim 1 as a pharmaceutically acceptable salt or solvate.

17. A pharmaceutical composition comprising the compound according to claim 1, or a pharmaceutically acceptable salt of solvate thereof, and a pharmaceutically acceptable excipient.

18. A combination comprising the compound according to claim 1, or a pharmaceutically acceptable salt of solvate thereof, and one or more additional therapeutic agents.

* * * * *